(12) United States Patent
Ruben et al.

(10) Patent No.: US 7,169,565 B2
(45) Date of Patent: Jan. 30, 2007

(54) ANTIBODIES TO HASAV70 POLYPEPTIDE

(75) Inventors: Steven M. Ruben, Brookeville, MD (US); Craig A. Rosen, Laytonsville, MD (US); Reinhard Ebner, Gaithersburg, MD (US); Yanggu Shi, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/960,251

(22) Filed: Oct. 8, 2004

(65) Prior Publication Data

US 2005/0089911 A1    Apr. 28, 2005

Related U.S. Application Data

(63) Continuation of application No. 10/143,090, filed on May 13, 2002, now abandoned, which is a continuation of application No. 09/154,707, filed on Sep. 17, 1998, now abandoned, which is a continuation-in-part of application No. PCT/US98/05311, filed on Mar. 19, 1998, now abandoned.

(60) Provisional application No. 60/060,862, filed on Oct. 2, 1997, provisional application No. 60/056,370, filed on Aug. 19, 1997, provisional application No. 60/054,804, filed on Aug. 5, 1997, provisional application No. 60/048,094, filed on May 30, 1997, provisional application No. 60/048,350, filed on May 30, 1997, provisional application No. 60/048,188, filed on May 30, 1997, provisional application No. 60/048,135, filed on May 30, 1997, provisional application No. 60/050,937, filed on May 30, 1997, provisional application No. 60/048,187, filed on May 30, 1997, provisional application No. 60/048,099, filed on May 30, 1997, provisional application No. 60/048,352, filed on May 30, 1997, provisional application No. 60/048,186, filed on May 30, 1997, provisional application No. 60/048,069, filed on May 30, 1997, provisional application No. 60/048,095, filed on May 30, 1997, provisional application No. 60/048,131, filed on May 30, 1997, provisional application No. 60/048,096, filed on May 30, 1997, provisional application No. 60/048,355, filed on May 30, 1997, provisional application No. 60/048,160, filed on May 30, 1997, provisional application No. 60/048,351, filed on May 30, 1997, provisional application No. 60/048,154, filed on May 30, 1997, provisional application No. 60/041,276, filed on Mar. 21, 1997, provisional application No. 60/041,277, filed on Mar. 21, 1997, provisional application No. 60/041,281, filed on Mar. 21, 1997, provisional application No. 60/042,344, filed on Mar. 21, 1997, now abandoned.

(51) Int. Cl.
*G01N 33/53*    (2006.01)
*C12N 5/12*    (2006.01)
*C12N 1/20*    (2006.01)
*C12N 5/06*    (2006.01)
*C12N 5/16*    (2006.01)
*C12N 5/22*    (2006.01)
*C07K 16/00*    (2006.01)
*C07K 16/18*    (2006.01)
*C12P 21/08*    (2006.01)

(52) U.S. Cl. .................... 435/7.1; 435/325; 435/252.3; 435/326; 435/343.1; 435/346; 530/387.1; 530/388.1

(58) Field of Classification Search ..................... None
See application file for complete search history.

(56) References Cited

U.S. PATENT DOCUMENTS

| 5,536,637 | A | 7/1996 | Jacobs ........................... 435/6 |
| 5,871,970 | A | 2/1999 | Hillman et al. ............. 435/69.1 |
| 5,976,801 | A | 11/1999 | Bandman et al. ............... 435/6 |

FOREIGN PATENT DOCUMENTS

| WO | WO-90/14432 | 11/1990 |
| WO | WO-96/17925 | 6/1996 |
| WO | WO-97/04097 | 2/1997 |
| WO | WO-97/07198 A2 | 2/1997 |
| WO | WO-98/44114 | 10/1998 |
| WO | WO-99/07849 | 2/1999 |
| WO | WO-99/63088 | 12/1999 |
| WO | WO-00/53753 | 9/2000 |

OTHER PUBLICATIONS

Bonaldo, et al., *Genome Res.*, 6:791 (1996).
Egeo et al., "Identification and characterization of a new human cDNA from chromosome 21q22.3 encoding a basic nuclear protein," *Hum. Genet.*, 102:289-293 (1998).
Genbank Accession No. BAA07896 (2000).
Genbank Accession No. D42073 (1999).
Genbank Accession No. R66471 (1995).

(Continued)

*Primary Examiner*—James Martinell
(74) *Attorney, Agent, or Firm*—Human Genome Sciences, Inc.

(57) ABSTRACT

The present invention relates to 87 novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

25 Claims, No Drawings

OTHER PUBLICATIONS

Genbank Accession No. H74164 (1995).
Genbank Accession No. H04035 (1995).
Genbank Accession No. H08241 (1995).
Genbank Accession No. AI478733 (1999).
Genbank Accession No. AA875665 (1999).
Genbank Accession No. CAA05100 (1999).
Genbank Accession No. BAA07670 (1999).
Genbank Accession No. AI797684 (1999).
Genbank Accession No. D30965 (1995).
Genbank Accession No. D31176 (1995).
Genbank Accession No. H73236 (1995).
Genbank Accession No. R34003 (1995).
Genbank Accession No. R88485 (1995).
Genbank Accession No. AA003043 (1996).
Genbank Accession No. AA028649 (1996).
Genbank Accession No. AA041304 (1996).
Genbank Accession No. AA041328 (1996).
Genbank Accession No. W14868 (1996).
Genbank Accession No. W41218 (1996).
Genbank Accession No. W42572 (1996).
Genbank Accession No. W56939 (1996).
Genbank Accession No. W64383 (1996).
Genbank Accession No. W70681 (1996).
Genbank Accession No. W70707 (1996).
Genbank Accession No. W91002 (1996).
Genbank Accession No. W95460 (1996).
Genbank Accession No. W95567 (1996).
Genbank Accession No. W98300 (1996).
Genbank Accession No. W98572 (1996).
Genbank Accession No. AA232452 (1997).
Genbank Accession No. AA239568 (1997).
Genbank Accession No. AA405402 (1997).
Genbank Accession No. AA427487 (1997).
Genbank Accession No. AA427646 (1997).
Genbank Accession No. AA456267 (1997).
Genbank Accession No. AA594137 (1997).
Genbank Accession No. AA688740 (1997).
Genbank Accession No. AAC53316 (1997).
Genbank Accession No. W12808 (1997).
Genbank Accession No. AA788855 (1998).
Genbank Accession No. AAC17216 (1998).
Genbank Accession No. CAA16492 (1998).
Genbank Accession No. AI341112 (1999).
Geneseq Accession No. AAT20523, Matsubara et al., "Human Gene Signature HUMGS01734" (Jul. 22, 1996).
Genseq Accession No. Y53640 (2000).
Genseq Accession No. Y13382 (1999).
Genseq Accesion No. Y11533 (1999).
Genseq Accession No. Y00916 (1999).
Genseq Accession No. Y00917 (1999).
Jacobs, et al., *J. of Cell. Biochem. Suppl.*, p. 19, abstract No. C1-207 (1995).
Ozawa, *J. Biochem.*, 118:154-160 (1995).
Ozawa, et al., *J. of Biol. Chem.*, 268(1):699-705 (1993).
Stryer, *Biochemistry*, 3$^{rd}$ Ed., W.H. Freeman and Co., pp. 16-17 (1988).
Zubay, Biochemistry, Addison-Wesley Publishing Co., p. 7 (1983).

ANTIBODIES TO HASAV70 POLYPEPTIDE

CROSS REFERENCE TO RELATED APPLICATIONS

This application is a continuation of U.S. patent application Ser. No. 10/143,090 (filed May 13, 2002), now abandoned which is a continuation of U.S. patent application Ser. No. 09/154,707 (filed Sep. 17, 1998; now abandoned), which is a continuation-in-part of International Patent Application No. PCT/US98/05311 (filed Mar. 19, 1998) now abandoned which claims benefit under 35 U.S.C. § 119(e) of U.S. Provisional Applications Nos. 60/041,277 (filed Mar. 21, 1997), 60/042,344 (filed Mar. 21, 1997), 60/041,276 (filed Mar. 21, 1997), 60/041,281 (filed Mar. 21, 1997), 60/048,094 (filed May 30, 1997), 60/048,350 (filed May 30, 1997), 60/048,188 (filed May 30, 1997), 60/048,135 (filed May 30, 1997), 60/050,937 (filed May 30, 1997), 60/048,187 (filed May 30, 1997), 60/048,099 (filed May 30, 1997), 60/048,352 (filed May 30, 1997), 60/048,186 (filed May 30, 1997), 60/048,069 (filed May 30, 1997), 60/048,095 (filed May 30, 1997), 60/048,131 (filed May 30, 1997), 60/048,096 (filed May 30, 1997), 60/048,355 (filed May 30, 1997), 60/048,160 (filed May 30, 1997), 60/048,35 1 (filed May 30, 1997), 60/048,154 (filed May 30, 1997), 60/054,804 (filed Aug. 5, 1997), 60/056,370 (filed Aug. 19, 1997), and 60/060,862 (filed Oct. 2, 1997). Each of the above-identified applications is hereby incorporated herein by reference in its entirety.

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence.

Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may-be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity,- and most preferably, not more than about three-fold less activity relative to the polypeptide of the present invention.)

Polynucleotides and Polypeptides of the Invention

Features of Protein Encoded by Gene No: 1

The translation product of this gene shares sequence homology with nucleolin, which is thought to be important in macromolecule binding, as well as some membrane proteins. Preferred polypeptide fragments comprise the amino acid sequence:

DPEAADSGEPQNKRTPDLPEEEYVKEEIQENEEA (SEQ ID NO:231)

VKKMLVEATREFEEVVVDES;

QKLKRKAEEDPEAADSGEPQNKRTPDLPEEEYVK (SEQ ID NO:232)

EEIQENEEAVKKMLVEATREFEEVVVDES;

KAMEKSSLTQHSWQSLKDRYLKHLRGQEHKYLLG (SEQ ID NO:233)

DAPVSPSSQKLKRKAEEDPEAADSGEPQNKRTPD

LPEEEYVKEEIQENEEAVKKMLVEATREFEEVVV

DESPPDFEIHI.

Also preferred are the polynucleotide fragments encoding these polypeptide fragments. This gene maps to chromosome 16, and therefore can be used as a marker in linkage analysis for chromosome 16.

This gene is expressed primarily in brain and kidney and-to a lesser extent in wide range of tissues.

Therefore, polynucleotides and polypeptides of the invention are useful as reagents for differential identification of the tissue(s) or cell type(s) present in a biological sample and for diagnosis of diseases and conditions, which include, but are not limited to, cell-cell interaction or cell-matrix interaction. Similarly, polypeptides and antibodies directed to these polypeptides are useful in providing immunological probes for differential identification of the tissue(s) or cell type(s). For a number of disorders of the above tissues or cells, particularly of the brain and kidney, expression of this gene at significantly higher or lower levels may be routinely detected in certain tissues or cell types (e.g., brain and other tissue of the nervous system, and kidney, and cancerous and wounded tissues) or bodily fluids (e.g., serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 121 as residues: Met-1 to Trp-10.

The tissue distribution in brain and kidney combined with the homology to nucleolin indicates that polynucleotides and polypeptides corresponding to this gene are useful for treatment/diagnosis of diseases involving cell-cell interaction or cell-extracellular matrix interaction. Protein, as well as, antibodies directed against the protein may show utility as a tissue-specific marker and/or immunotherapy target for the above listed tissues. Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1665 of SEQ ID NO:11, b is an integer of 15 to 1679, where both a and b correspond to the positions of nucleotide residues shown in SEQ ID NO:11, and where the b is greater than or equal to a +14.

Features of Protein Encoded by Gene No: 2

The translation product of this gene shares sequence homology with a porcine zona pellucida protein ZPDS. 1711. (See Accession No. R39356.) These two proteins have weak homology with *Drosophila* commissureless and metal homeostasis proteins which are thought to be important in controlling growth cone guidance across the CNS midline and protecting cells against reactive oxygen toxicity. Thus, based on homology, it is likely that this gene may also be involved in development. Preferred polypeptide fragments comprise the amino acid sequence: LPSYDEAERTKAE-ATIPLVPGRDEDF VGRDDFDDADQLRIGNDGIFMLT-FFMAFLFNWIGFFLSFCLTTSAAGRYGAISG FGLS-LIKWILIVRFSTYFPGYFDGQYWLWWVFLVLGFLLF-LRGFINYAKVRKM PETFSNLPRTRVLFI (SEQ ID NO:234); and/or AGRYGAISGFGLSLIKWILIVRFS (SEQ ID NO:235). Also preferred are polynucleotide fragments encoding these polypeptide fragments. The gene that encodes the disclosed cDNA is thought to reside on chromosome 5. Accordingly, polynucleotides related to this invention are useful as a marker in linkage analysis for chromosome 5.

This gene is expressed primarily in kidney, adrenal gland, brain, fetal and reproductive tissues, and to a lesser extent in wide range of tissues.

Therefore, polynucleotides and polypeptides of the invention are useful as reagents for differential identification of the tissue(s) or cell type(s) present in a biological sample and for diagnosis of diseases and conditions, which include, but are not limited to, fertilization control or tissue damage by metabolites or other toxic agents. Similarly, polypeptides and antibodies directed to these polypeptides are useful in providing immunological probes for differential identification of the tissue(s) or cell type(s). For a number of disorders of the above tissues or cells, particularly of the reproductive, urogenital or renal system, expression of this gene at significantly higher or lower levels may be routinely detected in certain tissues or cell types (e.g. reproductive, kidney, adrenal gland, and brain and other tissue of the nervous system, and cancerous and wounded tissues) or—bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in reproductive tissues combined with the homology to zona pellucida protein indicates that polynucleotides and polypeptides corresponding to this gene are useful for fertility control such as contraceptive development. The homology with metal homeostasis and commissureless genes indicates the gene's function in spermatozoa guidance and protection. It would also be useful for the treatment/diagnosis of tissue damages caused by toxic metabolites and other agents since the gene product is also expressed in urosecretive tissues. Protein, as well as, antibodies directed against the protein may show utility as a tissue-specific marker and/or immunotherapy target for the above listed tissues. Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1949 of SEQ ID NO:12, b is an integer of 15 to 1963, where both a and b correspond to the positions of nucleotide residues shown in SEQ ID NO:12, and where the b is greater than or equal to a +14.

Features of Protein Encoded by Gene No: 3

This gene is expressed primarily in liver and to a lesser extent in placenta. Preferred polypeptide fragments comprise the amino acid sequence: MKHLSAVJFT KLTFLQL-WVEI FEGSVENCQTLTSYSKLQIKYTFSRGSTFYI (SEQ ID NO:236). Also preferred are polynucleotide fragments encoding these polypeptide fragments.

Therefore, polynucleotides and polypeptides of the invention are useful as reagents for differential identification of the tissue(s) or cell type(s) present in a biological sample and for diagnosis of diseases and conditions, which include, but are not limited to, digestive, metabolic, developmental, and nutrient transport/utilization disorders. Similarly, polypeptides and antibodies directed to these polypeptides are useful in providing immunological probes for differential identification of the tissue(s) or cell type(s). For a number of disorders of the above tissues or cells, particularly of the digestive and circulatory system, expression of this gene at significantly higher or lower levels may be routinely detected in certain tissues or cell types (e.g., liver, and placenta, and cancerous and wounded tissues) or bodily fluids (e.g., amniotic fluid, lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in liver and placenta indicates that the protein product is either an extracellular enzyme or a molecule carrier. Therefore, polynucleotides and polypeptides corresponding to this gene are useful for diagnosis/ treatment of digestive and nutrient transport/utilization disorders, including malabsorption and malnutrition. Protein, as well as, antibodies directed against the protein may show utility as a tissue-specific marker and/or immunotherapy target for the above listed tissues. Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1198 of SEQ ID NO:13, b is an integer of 15 to 1212, where both a and b correspond to the positions of nucleotide residues shown in SEQ ID NO:13, and where the b is greater than or equal to a +14.

Features of Protein Encoded by Gene No: 4

This gene shares homology with the sap47 gene of *Drosophila melanogaster*, a gene which codes for a conserved neuronal protein associated with synaptic terminals. (See Mol. Brain Res. 32:45–54 (1995); see also, Accession No. 929571.) Thus, based on homology, the gene of the present invention also should be associated with synaptic terminals. Preferred polypeptide fragments comprise the amino acid sequence: FSSDFRTSPWESRRVESKAT-SARCGLWGSGPRRRPASGMFRGLSSWLGLQQP VAGGGQPNGDAPPEQPSETVAE-SAEEELQQAGDQELLHQAKDFGNYLFNFASA ATK-KITESVAETAQTIKKSVEEGKIDGIHDK-TIIGDFQKEQKKFVEEQHTKKSEA AVPPWVDTNDEETIQQQILALSADKRN-FLRDPPAGVQFNFDFDQMYPVALVML (SEQ ID NO:237); MRFALVPKLVKEEVFWRNYFYRVS-LIKQSAQLTALAAQQQA AGKGGEEQ (SEQ ID NO:238); STSPGVSEFVSDAFDACNLNQEDLRKE-MEQL VLDKKQEETAVLEEDSADWEKELQQELQ-EYEVVTESEKRDENWDK (SEQ ID NO:239); SPWESR-RVESKATSARCGLWGSGPRRRPASGMFRGLSSWLGL-QQ PVAGGGQPNGDAPPEQPS (SEQ ID NO:240); PVAGGGQPNGDAPPEQPSETV ESAEEELQQAGDQELLHQAKDFGNYLFN-FASAATKKrrESVAE (SEQ ID NO: 241); and/or FQKEQKKFVEEQHTKKSEAAVPPWVDT-NDEETIQQQILALSADKR NFLRDPPAGVQFNFD-FDQMYPVALVML (SEQ ID NO:242). Also preferred are polynucleotide fragments encoding these polypeptide fragments. Contact of cells with supernatant expressing the product of this gene increases the permeability of the plasma membrane of aortic smooth muscle cells to calcium. Thus, it is likely that the product of this gene is involved in a signal transduction pathway that is initiated when the product binds a receptor on the surface of the aortic smooth muscle cells. Thus, polynucleotides and polypeptides have uses which include, but are not limited to, activating aortic smooth muscle cells.

This gene is expressed primarily in kidney pyramids and to a lesser extent in lung and other tissues of various types. This gene fluxes calcium in human aortic smooth muscle cells, and therefore is involved in signal transduction.

Therefore, polynucleotides and polypeptides of the invention are useful as reagents for differential identification of the tissue(s) or cell type(s) present in a biological sample and for diagnosis of diseases and conditions, which include, but are not limited to, renal, developmental, vascular, and nervous disorders. Similarly, polypeptides and antibodies directed to these polypeptides are useful in providing immunological probes for differential identification of the tissue(s) or cell type(s). For a number of disorders of the above tissues or cells, particularly of the kidney and/or nervous system, expression of this gene at significantly higher or lower levels may be routinely detected in certain tissues or cell types (e.g., kidney, lung, brain and other tissue of the nervous system, developmental, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in kidney and lung and homology with sap47 indicates that the protein product has regulatory or direct functions in molecular exchange with body fluids and nervous system signaling. Polynucleotides and polypeptides corresponding to this gene are useful for treatment of disorders in kidney and nervous system. The activity of the translation product of this gene in activating aortic smooth muscle cells supports the notion that this protein is involved in regulatory or direct functions in molecular exchange with body fluids. This clone would be useful for the dignosis and treatment of disorders in kidney and the nervous system. Protein, as well as, antibodies directed against the protein may show utility as a tissue-specific marker and/or immunotherapy target for the above listed tissues. Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2047 of SEQ ID NO:14, b is an integer of 15 to 2061, where both a and b correspond to the positions of nucleotide residues shown in SEQ ID NO:14, and where the b is greater than or equal to a +14.

Features of Protein Encoded by Gene No: 5

The translation product of this gene shares sequence homology with the mouse Ly-9.2 antigen which is thought to be an important cell surface marker in lymphoids, myeloids and hematopoietic progenitors. (See Accession No. gi1198932.) Preferred polypeptide fragments comprise the amino acid sequence: PFICVARNPVSRNFSSPI LARKLCEGAA (SEQ ID NO:243); and/or KED-PANTVYSTVEIPKKMENPHSLLT MPDTPRL (SEQ ID NO:244). Also preferred are polynucleotide fragments encoding these polypeptide fragments. Based on homology, it is likely that this gene is also a cell surface marker, involved in hematopoiesis.

This gene is expressed primarily in activated macrophages, monocytes and T-cells and to a lesser extent in spleen and bone marrow.

Therefore, polynucleotides and polypeptides of the invention are useful as reagents for differential identification of the tissue(s) or cell type(s) present in a biological sample and for diagnosis of diseases and conditions, which include, but are not limited to, immune and hematopoietic disorders. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may be routinely detected in certain tissues or cell types (e.g. immune, blood cells, and bone marrow, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 125 as residues: Lys-26 to Tyr-33, Arg-44 to Ile-49, Ser-53 to Lys-71, Lys-86 to Pro-91.

The tissue distribution in immune tissue combined with the homology to a protein within the Ly-9.2 surface immunoglobulin family indicates that polynucleotides and polypeptides corresponding to this gene are useful for diagnosis of immune and hematopoietic disorders. Polypeptides and polynucleotides corresponding to this gene are also be used as a marker for leukemia or a modulator of the functions of the cells of macrophage/monocyte or T-cell types. Expression of this gene product in immune cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1398 of SEQ ID NO:15, b is an integer of 15 to 1412, where both a and b correspond to the positions of nucleotide residues shown in SEQ ID NO:15, and where the b is greater than or equal to a +14.

Features of Protein Encoded by Gene No: 6

The translation product of this gene shares sequence homology with the *Drosophila* glutactin gene which is thought to be important in cell-cell interaction or cell-extracellular matrix contact. The gene encoding the disclosed cDNA is thought to reside on chromosome 16. Accordingly, polynucleotides related to this invention are useful as a marker in linkage analysis for chromosome 16.

This gene is expressed primarily in colon tissue, aorta endothelial cells and to a lesser extent in skin, breast tissue and T-cells.

Therefore, polynucleotides and polypeptides of the invention are useful as reagents for differential identification of these tissue(s) or cell type(s) present in a biological sample and for diagnosis of diseases and conditions, which include, but are not limited to, diseases of the gastrointestinal tract, vascular system or T-cell development. Similarly, polypeptides and antibodies directed to these polypeptides are useful in providing immunological probes for differential identification of these tissue(s) or cell type(s). For a number of disorders of the above tissues or cells, particularly of the digestive system, cardiovascular system, and immune system, expression of this gene at significantly higher or lower levels may be routinely detected in certain tissues or cell types (e.g., colon, endothelial, cardiovascular tissue, skin, mammary tissue, and blood cells, and cancerous and wounded tissues) or bodily fluids (e.g., lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to glutactin indicates that polynucleotides and polypeptides corresponding to this gene are useful for the development and maintenance of the integrity of the basal membrane in the gastrointestinal tract, or vasculature in the cardiovascular system. The expression in T-cells also indicates the protein may be involved in T-cell adhesion, cell-cell interaction and development. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1038 of SEQ ID NO:16, b is an integer of 15 to 1052, where both a and b correspond to the positions of nucleotide residues shown in SEQ ID NO:16, and where the b is greater than or equal to a +14.

Features of Protein Encoded by Gene No: 7

The translation product of this gene shares sequence homology with MURF4 protein, an ATPase homolog, which is thought to be important in ATP hydrolysis.

This gene is expressed primarily in breast tissue.

Therefore, polynucleotides and polypeptides of the invention are useful as reagents for differential identification of the tissue(s) or cell type(s) present in a biological sample and for diagnosis of diseases and conditions, which include, but are not limited to, breast cancer and non-neoplastic breast diseases. Similarly, polypeptides and antibodies directed to these polypeptides are useful in providing immunological probes for differential identification of these tissue(s) or cell type(s). For a number of disorders of the above tissues or cells, particularly of the breast tissue, expression of this gene at significantly higher or lower levels may be routinely detected in certain tissues or cell types (e.g., mammary tissue, and cancerous and wounded tissues) or bodily fluids (e.g., breast milk, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in breast tissue combined with the homology to the MURF4 gene indicates that polynucleotides and polypeptides corresponding to this gene are useful for diagnosis and treatment of neoplastic or non-neoplastic breast diseases because ATPase like protein may be involved in changed metabolic states of the breast. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 669 of SEQ ID NO:17, b is an integer of 15 to 683, where both a and b correspond to the positions of nucleotide residues shown in SEQ ID NO:17, and where the b is greater than or equal to a +14.

Features of Protein Encoded by Gene No: 8

This gene shares homology to the alcohol dehydrogenase gene. Preferred polypeptide fragments comprise the amino acid sequence: ASAVLLDLPNSG GEAQAKKLGNNCV-FAPADVTSEKDVQTALALAKGKFGRVD-VAVNCAGIAVAS KTYNLKKGQTHTLEDFQRVLDVN-LMGTFNVIRLVAGEMGQNEPDQGGQRGVI INTASVAAFEGQVGQAAYSASKGGIVG-MTLPIARDLAPIGIRVMTIAPGLFGTPL LTSLPEKVCN-FLASQVPFPSRLGDPAEYAHLVQAIIEN-PFLNGEVIRLDGAIRMQ P (SEQ ID NO:245); SVAAFEGQVGQAAYSASKGGIVGMTtPIA (SEQ ID NO:246). and/or SVAAFEGQVGQAAYSASKGGIVG-MTLPIA (SEQ ID NO:247). Polynucleotides encoding these fragments are also encompassed by the invention. Other groups have also recently cloned this gene, recognizing its homology to alcohol dehydrogenase. (See Accession No. 1778355.) Moreover, a second group recently cloned the mouse homologue of this gene. (See Accession No. 2078284.) They found that the mouse homologue binds to amyloid beta-peptide and mediates neurotoxicity in Alzheimer's disease, calling the protein ERAB. This gene maps to chromosome X, and therefore can be used in linkage analysis as a marker for chromosome X. Therefore, mutations in the translated product of this gene may be involved in Alzheimer's disease in humans, as well as other sex linked diseases. This gene can be used as a diagnostic marker for these diseases.

It has been discovered that this gene is expressed primarily in breast cancer tissue, infant brain, and to a lesser extent in fetal liver tissue.

Therefore, nucleic acids of the invention are useful as reagents for differential identification of the tissue(s) or cell type(s) present in a biological sample and for diagnosis of the following diseases and conditions: neurodegenerative diseases, breast cancer, non-neoplastic breast diseases, or developmental disorders. Similarly, polypeptides and antibodies directed to those polypeptides are useful to provide immunological probes for differential identification of these tissue(s) or cell type(s). For a number of disorders of the above tissues or cells, particularly of the brain and CNS, and breast tissue, expression of this gene at significantly higher or lower levels may be detected in certain tissues or cell types (e.g. brain, breast, metabolic, developmental, immune, hematopoietic, cancerous and wounded tissues) or bodily fluids (e.g., lymph, amniotic fluid, serum, plasma, urine, synovial fluid or spinal fluid) taken from an individual having such a disorder, relative to the standard gene expression level, i.e., the expression level in healthy tissue from an individual not having the disorder. Preferred epitopes include those comprising a sequence shown in SEQ ID NO. 128 as residues: Arg-45 to Ser-53.

The tissue distribution in neural tissue combined with the homology to the ERAB mouse gene suggests that the protein product of this clone would be useful for the diagnosis and treatment of Alzheimers and related neurodegenerative diseases. Mutations in the translated product of this gene may be involved in Alzheimer's disease in humans, as well as other sex linked diseases. This gene can be used as a diagnostic marker for these diseases. Furthermore, the tissue distribution suggests that this gene may also be involved in neoplastic or non-neoplastic breast diseases in humans. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1040 of SEQ ID NO:18, b is an integer of 15 to 1054, where both a and b correspond to the positions of nucleotide residues shown in SEQ ID NO:18, and where the b is greater than or equal to a +14.

Features of Protein Encoded by Gene No: 9

The translation product of this gene shares week sequence homology with rat N-methyl-D-aspartate receptor subunit and other proline-rich proteins which are thought to be important in neurotransmission or protein-protein intereaction.

This gene is expressed primarily in synovial hypoxia and to a lesser extent in ovary, senescent cells and brain.

Therefore, polynucleotides and polypeptides of the invention are useful as reagents for differential identification of the tissue(s) or cell type(s) present in a biological sample and for diagnosis of diseases and conditions, which include, but are not limited to, synovial hypoxia, reproductive, or neural disorders. Similarly, polypeptides and antibodies directed to these polypeptides are useful in providing immunological probes for differential identification of the tissue(s) or cell type(s). For a number of disorders of the above tissues or cells, particularly of the synovia and brain, expression of this gene at significantly higher or lower levels may be routinely detected in certain tissues or cell types (e.g., synovial tissue, ovary and other reproductive tissue, and brain and other tissue of the nervous system, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in synovial hypoxia and nerve tissues, and homology to N-methyl-D-aspartate receptor subunit and other proline-rich proteins indicates that polynucleotides and polypeptides corresponding to this gene are useful for diagnosis and intervention of synovial-hypoxia and other synovial disorders, particularly disorders involving nitric oxide signaling. Protein, as well as, antibodies directed against the protein may show utility as a tissue-specific marker and/or immunotherapy target for the above listed tissues. Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1379 of SEQ ID NO:19, b is an integer of 15 to 1393, where both a and b correspond to the positions of nucleotide residues shown in SEQ ID NO:19, and where the b is greater than or equal to a +14.

Features of Protein Encoded by Gene No: 10

This gene is expressed primarily in prostate and keratinocytes, and to a lesser extent in placenta, ovary and primary dendritic cells.

Therefore, polynucleotides and polypeptides of the invention are useful as reagents for differential identification of the tissue(s) or cell type(s) present in a biological sample and for diagnosis of diseases and conditions, which include, but are not limited to, male and female infertility, cancer, skin disorders, and other hyperproliferative disorders. Similarly, polypeptides and antibodies directed to these polypeptides are useful in providing immunological probes for differential identification of these tissue(s) or cell type(s). For a number of disorders of the above tissues or cells, particularly of the reproductive system, skin, and neoplasia, expression of this gene at significantly higher or lower levels may be routinely detected in certain tissues or cell types (e.g., prostate, skin, placenta, ovary and other reproductive tissue, and cancerous and wounded tissues) or bodily fluids (e.g., arnuiotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 130 as residues: Pro-17 to Met-23, Ala-30 to Trp-38, Ile-49 to Trp-54, Lys-68 to Gly-74, Thr-93 to Gly-99, Met-126 to Glu-132, Gly-173 to Ser-178, Lys-205 to Tyr-214.

The tissue distribution of this gene in the prostate, placenta and ovary indicates that this gene product is useful for treatment/diagnosis of male or female infertility, endocrine disorders, fetal deficiencies, ovarian failure, amenorrhea, ovarian cancer, benign prostate hyperplasia, prostate cancer, and other forms of cancer of the reproductive system. The tissue distribution also suggests that the protein product of this clone would be useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althietes foot, and ringworm). Protein, as well as, antibodies directed against the protain may show utility as a tissue-specific marker and/or immnuntherapy target for the above-listed tissues. Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1201 of SEQ ID NO:20, b is an integer of 15 to 1215, where both a and b correspond to the positions of nucleotide residues shown in SEQ ID NO:20, and where the b is greater than or equal to a +14.

Features of Protein Encoded by Gene No: 11

This gene is expressed primarily in the thyroid and to a lesser extent in the pineal gland. The gene encoding the disclosed cDNA is thought to reside on chromosome 10. Accordingly, polynucleotides related to this invention are useful as a marker in linkage analysis for chromosome 10.Preferred polypeptide fragments comprise the amino acid sequence: HPIEWAINAATLSQFY (SEQ ID NO:248); CWIKYCLTLMQN AQLSMQDNIG (SEQ ID NO:249); KVSYLRPLDFEEARELF LLGQHYVF (SEQ ID NO:250); MERRCKMHKR EPLTVDLNPQ (SEQ ID NO:251); and/or SHIV KKNNLNKSALKYYQLFLD (SEQ ID NO:252). Also preferred are polynucleotides encoding these polypeptide fragments.

Therefore, polynucleotides and polypeptides of the invention are useful as reagents for differential identification of the tissue(s) or cell type(s) present in a biological sample and for diagnosis of diseases and conditions, which include, but are not limited to, immune, thyroid and pineal gland disorders. Similarly, polypeptides and antibodies directed to these polypeptides are useful in providing immunological probes for differential identification of these tissue(s) or cell type(s). For a number of disorders of the above tissues or cells, particularly of the immune and endocrine systems, expression of this gene at significantly higher or lower levels may be routinely detected in certain tissues or cell types (e.g. immune, thyroid and pineal gland, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 131 as residues: Ser-2 to Ser-8, Thr-38 to Arg-44.

The tissue distribution indicates that polynucleotides and polypeptides corresponding to this gene are useful for treating/detecting immune disorders such as arthritis, asthma, immune deficiency diseases (e.g., AIDS), and leukemia, as well as treating/detecting thymus disorders (e.g., Graves Disease, lymphocytic thyroiditis, hyperthyroidism, and hypothyroidism), and treating/detecting pineal gland disorders (e.g., circadian rhythm disturbances associated with shift work, jet lag, blindness, insomnia and old age). Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2028 of SEQ ID NO:21, b is an integer of 15 to 2042, where both a and b correspond to the positions of nucleotide residues shown in SEQ ID NO:21, and where the b is greater than or equal to a +14.

Features of Protein Encoded by Gene No: 12

The gene encoding the disclosed cDNA is thought to reside on chromosome 9.

Accordingly, polynucleotides related to this invention are useful as a marker in linkage analysis for chromosome 9.

It has been discovered that this gene is expressed primarily in colon and brain tissue, and to a lesser extent in lung and tonsils.

Therefore, polynucleotides and polypeptides of the invention are useful as reagents for differential identification of the tissue(s) or cell type(s) present in a biological sample and for diagnosis of diseases and conditions, which include, but are not limited to, pulmonary or immune disorders. Similarly, polypeptides and antibodies directed to these polypeptides are useful in providing immunological probes for differential identification of these tissue(s) or cell type(s). For a number of disorders of the above tissues or cells, particularly of the pulmonary and immune systems, expression of this gene at significantly higher or lower levels may be routinely detected in certain tissues or cell types (e.g., immune, brain, pulmonary tissue, and tonsils, and cancerous and wounded tissues) or bodily fluids (e.g., lymph, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 132 as residues: Glu-28 to Gly-49.

The tissue distribution of this gene only in lung indicates that it could play a role in the treatment/detection of lung lymphoma or sarcoma formation, pulmonary edema and embolism, bronchitis and cystic fibrosis. Its expression in tonsils indicates a potential role in the treatment/detection of immune disorders such as arthritis, asthma, immune deficiency diseases (e.g., AIDS), and leukemia, in addition to the treatment/detection of tonsillitis. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1858 of SEQ ID NO:22, b is an integer of 15 to 1872, where both a and b correspond to the positions of nucleotide residues shown in SEQ ID NO:22, and where the b is greater than or equal to a +14.

Features of Protein Encoded by Gene No: 13

This gene is expressed primarily in progenitor cells (CD34 cells) of lymphoid, myeloid and erythroid cells.

Therefore, polynucleotides and polypeptides of the invention are useful as reagents for differential identification of the tissue(s) or cell type(s) present in a biological sample and for diagnosis of diseases and conditions, which include, but are not limited to, hematopoietic and immune disorders. Similarly, polypeptides and antibodies directed to these polypeptides are useful in providing immunological probes for differential identification of these tissue(s) or cell type(s).

For a number of disorders of the above tissues or cells, particularly of the hematopoietic and immune systems, expression of this gene at significantly higher or lower levels may be routinely detected in certain tissues or cell types (e.g., immune, blood cells, myeloid cells, and bone marrow, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The predominant tissue distribution of this gene in hematopoietic cell types indicates that the gene could be important for the treatment or detection of immune or hematopoietic disorders including arthritis, asthma, immunodeficiency diseases and leukemia Preferred embodiments of the present invention are polypeptide fragments comprising the amino acid sequence: FTIHLSTCLLSLLLVRMSGFLLLARASPSI CALDSSCFVEYCSSYSSSCFLHQFPSLLDHLCQ (SEQ ID NO:253); or FLLL ARASPSICALDSSCFVQEY (SEQ ID NO:254). Also preferred are polynucleotide fragments encoding these polypeptide fragments. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 275 of SEQ ID NO:23, b is an integer of 15 to 289, where both a and b correspond to the positions of nucleotide residues shown in SEQ ID NO:23, and where the b is greater than or equal to a +14.

Features of Protein Encoded by Gene No: 14

This gene is homologous to the *Drosophila Regena* (Rga) gene. (See Accession No. 1658504.) This *Drosophila* gene is thought to be a homolog of the global negative transcriptional regulator NOT2 (CDC36) from yeast, which modifies gene expression and suppresses position effect variegation. Preferred polypeptide fragments comprise the amino acid sequence: PDGRVTNIPQGMVTDQFGMIGLLTHRAAETDPGMVHL ALGSDLTTLGLNLNS (SEQ ID NO:255); VBLALGSDLTTLGLNLNSPENLYP (SEQ ID NO:257); EDLLFYLYYMNGGDVLQLLAAVELFNRDWRYHKEERVWI TR (SEQ ID NO:256); EDLLFYLYYMNGGDVLQLLAAVELFNRDWRYH KEERVWITR (SEQ ID NO:258); and/or HNEDFPALPGS (SEQ ID NO:259).

This gene is expressed primarily in placenta and to a lesser extent in infant brain.

Therefore, polynucleotides and polypeptides of the invention are useful as reagents for differential identification of the tissue(s) or cell type(s) present in a biological sample and for diagnosis of diseases and conditions, which include, but are not limited to, neurodegenerative and developmental disorders. Similarly, polypeptides and antibodies directed to these polypeptides are useful in providing immunological probes for differential identification of the tissue(s) or cell type(s). For a number of disorders of the above tissues or cells, particularly of the neurological system, expression of this gene at significantly higher or lower levels may be routinely detected in certain tissues or cell types (e.g., placenta, and brain and other tissue of the nervous system, reproductive, developmental tissues, and cancerous and wounded tissues) or bodily fluids (e.g., amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 134 as residues: Leu-9 to Tyr-15, Asp-34 to Gln-46, Pro-51 to Asp-57, Gly-88 to Thr-104, Thr-123 to Ser-128.

The tissue distribution of this gene in neural tissue indicates that it could be used in the detection and/or treatment of neurological disorders such as such as Alzheimer's Disease, Parkinson's Disease, Huntington's Disease, schizophrenia, mania, dementia, paranoia, obsessive compulsive disorder, and panic disorder. Similarly, expression within fetal and other cellular sources marked by proliferating cells, combined with the homology to a transcriptional regulator suggests that this protein may play a role in the regulation of cellular division, and may show utility in the diagnosis and treatment of cancer and other proliferative disorders. Similarly, embryonic development also involves decisions involving cell differentiation and/or apoptosis in pattern formation.

Thus this protein may also be involved in apoptosis or tissue differentiation and could again be useful in cancer therapy. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present-invention are one or more polynucleotides comprising a nucleotide sequence described by the general formula of a-b, where a is any integer between 1 to 3519 of SEQ ID NO:24, b is an integer of 15 to 3533, where both a and b correspond to the positions of nucleotide residues shown in SEQ ID NO:24, and where the b is greater than or equal to a +14.

Features of Protein Encoded by Gene No: 15

This gene is expressed primarily in adrenal gland tumor and osteoclastoma.

Therefore, polynucleotides and polypeptides of the invention are useful as reagents for differential identification of the tissue(s) or cell type(s) present in a biological sample and for diagnosis of diseases and conditions, which include, but are not limited to, endocrine and bone disorders. Similarly, polypeptides and antibodies directed to these polypeptides are useful in providing immunological probes for differential identification of the tissue(s) or cell type(s). For a number of disorders of the above tissues or cells, particularly of the endocrine system and in bone, expression of this gene at significantly higher or lower levels may be routinely detected in certain tissues or cell types (e.g., adrenal gland, and bone, skeletal tissues, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 135 as residues: Ile-52 to Trp-57.

The tissue distribution of this gene in endocrine tissue indicates that it may be involved in the treatment and/or detection of adrenal gland tumors, osteosarcomas, endocrine disorders and bone disorders, particularly osteoporosis. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1134 of SEQ ID NO:25, b is an integer of 15 to 1148, where both a and b correspond to the positions of nucleotide residues shown in SEQ ID NO:25, and where the b is greater than or equal to a +14.

Features of Protein Encoded by Gene No: 16

The translation product of this gene shares sequence homology with the FK506 binding protein, a protein which plays an important role in immunosupression. (See Accession No. M75099.) Specifically, a 12-kDa FK506-binding protein (FKBP-12) is a cytosolic receptor for the immunosuppressants FK506 and rapamycin. (See, Proc. Natl. Acad. Sci. 88: 6677–6681 (1991).) Thus, based on homology, it is likely that this gene also has immunosuppression activity or may be involved in other activities related to calcium dependent regulation. Preferred polypeptides comprise the amino acid sequence: GRIIDTSLTRDPLVIELGQKQVEP-GLEQSLLDMCVGEKRRAIIPSH LAYGKRGFPPSVPA-DAVVQYDVELIALIR (SEQ ID NO:260); and/or IHYTGSLV DGR IIDTS (SEQ ID NO:261). Also preferred are the polynucleotide fragments encoding these polypeptides.

This gene is expressed primarily in melanocytes. Furthermore, northern analysis demonstrated that this gene is also abundant in fetal liver and kidney. In adult tissues, it is expressed relatively highly in spleen, placenta, and thymus, and at a low level in other tissues.

Therefore, polynucleotides and polypeptides of the invention are useful as reagents for differential identification of the tissue(s) or cell type(s) present in a biological sample and for diagnosis of diseases and conditions, which include, but are not limited to, developmental conditions, or cancer and other hyperproliferative disorders. Similarly, polypeptides and antibodies directed to these polypeptides are useful in providing immunological probes for differential identification of the tissue(s) or cell type(s). For a number of disorders of the above tissues or cells, particularly of the immune system and cancer, expression of this gene at significantly higher or lower levels may be routinely detected in certain tissues or cell types (e.g. immune, melanocytes, developmental, integumentary, hepatic, renal, and cancerous and wounded tissues) or bodily fluids (e.g., amniotic fluid, lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 136 as residues: Ala-118 to Phe-124, Arg-178 to Lys-201.

The tissue distribution in developing tissues combined with the homology to the FK506 binding proteins which are believed to a role in immunosupression mediated by the immunosupressant drugs rapamycin and cyclosporin, indicates that this gene could serve as a novel target for the identification of novel immunosupressant drugs. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 703 of SEQ ID NO:26, b is an integer of 15 to 717, where both a and b correspond to the positions of nucleotide residues shown in SEQ ID NO:26, and where the b is greater than or equal to a +14.

Features of Protein Encoded by Gene No: 17

The translation product of this gene shares sequence homology with the rat calcium-activated potassium channel rSK3, which is thought to be important in regulating vascular tone. (See Accession No. gil2564072, gil1575663, and gil1575661.) Although homologous to these proteins, this gene contains an 18 amino acid insert, not previously identified in the homologs. Preferred polypeptide fragments comprise the amino acid sequence: CESPESPAQPSGSS-LPAWYH (SEQ ID NO:262). Also preferred are the polynucleotide fragments encoding these polypeptides.

This gene is expressed primarily in B-cells, frontal cortex and endothelial cells.

Therefore, polynucleotides and polypeptides of the invention are useful as reagents for differential identification of the tissue(s) or cell type(s) present in a biological sample and for diagnosis of diseases and conditions, which include, but are not limited to, immune, cardiovascular (hyper/hypotension, asthma, pulmonary edema, pneumonia, heart disease, restenosis, atherosclerosis, stoke, angina and thrombosis) or neurological disorders. Similarly, polypeptides and antibodies directed to these polypeptides are useful in providing immunological probes for differential identification of the tissue(s) or cell type(s). For a number of disorders of the above tissues or cells, particularly of the cardiovascular and nervous systems, expression of this gene at significantly higher or lower levels may be routinely detected in certain tissues or cell types (e.g. cardiac, blood cells, immune, brain and other tissues of the nervous system, and endothelium, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 137 as residues: Glu-72 to Gly-82, His-90 to Val-95, Gln-168 to Lys-174, Val-202 to Ser-212.

The tissue distribution in endothelial cells combined with the homology to calcium-activated potassium channels indicates that polynucleotides and polypeptides corresponding to this gene are useful for the diagnosis and treatment of vascular disorders (hyper/hypotension, athesma, pulmonary edema, pneumonia, heart disease, restenosis, atherosclerosis, stoke, angina and thrombosis). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1085 of SEQ ID NO:27, b is an integer of 15 to 1099, where both a and b correspond to the positions of nucleotide residues shown in SEQ ID NO:27, and where the b is greater than or equal to a +14.

Features of Protein Encoded by Gene No: 18

This gene is expressed primarily in smooth muscle and hematopoietic cells and to a lesser extent in brain (amygdala, corpus colosum, hippocampus).

Therefore, polynucleotides and polypeptides of the invention are useful as reagents for differential identification of the tissue(s) or cell type(s) present in a biological sample and for diagnosis of diseases and conditions, which include, but are not limited to, cardiovascular (hypertension, heart disease, athesma, pulmonary edema, restenosis, atherosclerosis, stoke, angina, thrombosis, and wound healing), immune, or neurological disorders. Similarly, polypeptides and antibodies directed to these polypeptides are useful in providing immunological probes for differential identification of the tissue(s) or cell type(s). For a number of disorders of the above tissues or cells, particularly of the cardiovascular and neurological systems, expression of this gene at significantly higher or lower levels may be routinely detected in certain tissues or cell types (e.g. immune, smooth muscle, vascular, and brain and other tissue of the nervous system, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 138 as residues: Lys-43 to Arg-49, Tyr-58 to Glu-65.

The tissue distribution in smooth muscle indicates that polynucleotides and polypeptides corresponding to this gene are useful for the treatment and diagnosis of cadiovascular disorders (hypertension, heart disease, athesma, pulmonary edema, restenosis, atherosclerosis, stoke, angina, thrombosis, and wound healing). Expression in brain indicates a role in the treatment and diagnosis of behavioral or neurological disorders, such as depression, schizophrenia, Alzheimer's disease, mania, dementia, paranoia, and addictive behavior. Expression of this gene product in hematopietic cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 927 of SEQ ID NO:28, b is an integer of 15 to 941, where both a and b correspond to the positions of nucleotide residues shown in SEQ ID NO:28, and where the b is greater than or equal to a +14.

Features of Protein Encoded by Gene No: 19

This gene is expressed primarily in T-cells (Jurkats, resting, activated, and anergic T-cells), endothelial cells, pineal gland, and to a lesser extent in a variety of other tissues and cell types. Preferred polypeptide fragments comprise the amino acid sequence: EEAGAGRRCSHG-GARPAGLGNEGLGLGGDPDHTDTGSRSKQRINN WKESKHKVIMASASARGNQDKDAHFP-PPSKQSLLFCPKSKLHIHRAEISK (SEQ ID NO:263); and/or SKQRINNWKESKHKVIMASASAR (SEQ ID NO:264). Also preferred are the polynucleotide fragments encoding these polypeptides.

Therefore, polynucleotides and polypeptides of the invention are useful as reagents for differential identification of the tissue(s) or cell type(s) present in a biological sample and for diagnosis of diseases and conditions, which include, but are not limited to immune disorders, such as, inflammation, immunodeficiencies, or cardiovascular disorders. Similarly, polypeptides and antibodies directed to these polypeptides are useful in providing immunological probes for differential identification of these tissue(s) or cell type(s). For a number of disorders of the above tissues or cells, particularly of the immune, neurological and vascular systems, expression of this gene at significantly higher or lower levels may be routinely detected in certain tissues or cell types (e.g., T-cells and other blood cells, endothelial cells, and pineal gland, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 139 as residues: Phe-71 to Arg-76, Pro-82 to His-87, Glu-103 to Ala-111.

The tissue distribution in T-cells indicates that polynucleotides and polypeptides corresponding to this gene are useful for the diagnosis and treatment of immune disorders including: leukemias, lymphomas, auto-immune, immuno-supressive (e.g. transplantation) and immunodeficiencies (e.g. AIDS) and hematopoietic disorders. In addition, expression in the pineal gland might suggest a role in the diagnosis of specific brain tumors and treatment of neurological disorders. Endothelial cell expression might suggest a role in cadiovascular or respiratory/pulmonary disorders or infections (athesma, pulmonary edema, pneumonia). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 742 of SEQ ID NO:29, b is an integer of 15 to 756, where both a and b correspond to the positions of nucleotide residues shown in SEQ ID NO:29, and where the b is greater than or equal to a +14.

Features of Protein Encoded by Gene No: 20

The gene encoding the disclosed cDNA is thought to reside on chromosome 15. Accordingly, polynucleotides related to this invention are useful as a marker in linkage analysis form chromosome 15.

This gene is expressed primarily in brain and embryo and to a lesser extent in leukocytes.

Therefore, polynucleotides and polypeptides of the invention are useful as reagents for differential identification of the tissue(s) or cell type(s) present in a biological sample and for diagnosis of diseases and conditions, which include, but are not limited to, developmental, immune, and neurological disorders. Similarly, polypeptides and antibodies directed to these polypeptides are useful in providing immunological probes for differential identification of the tissue(s) or cell type(s). For a number of disorders of the above tissues or cells, particularly of the central nervous and immune systems, expression of this gene at significantly higher or lower levels may be routinely detected in certain tissues or cell types (e.g., brain, immune, cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 140 as residues: Met-1 to Gly-8.

The tissue distribution in immune tissues indicates that polynucleotides and polypeptides corresponding to this gene are useful for the treatment and diagnosis of immune disorders including: leukemias, lymphomas, auto-immune, immuno-supressive (e.g. transplantation) and immunodeficiencies (e.g. AIDS) and hematopoietic disorders. The expression in the brain—and in particular the fetal brain—would suggest a possible role in the treatment and diagnosis of developmental and neurodegenerative diseases of the brain and nervous system (depression, schizophrenia, Alzheimer's disease, mania, dementia, paranoia, and addictive behavior). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2086 of SEQ ID NO:30, b is an integer of 15 to 2100, where both a and b correspond to the positions of nucleotide residues shown in SEQ ID NO:30, and where the b is greater than or equal to a +14.

Features of Protein Encoded by Gene No: 21

The gene encoding the disclosed cDNA is thought to reside on chromosome 17. Accordingly, polynucleotides related to this invention are useful as a marker in linkage analysis for chromosome 17.

This gene is expressed primarily in brain, kidney, lung, liver, spleen, and a variety of leukocytes (especially T-cells) and to a lesser extent in a variety of other tissues and cell types.

Therefore, polynucleotides and polypeptides of the invention are useful as reagents for differential identification of the tissue(s) or cell type(s) present in a biological sample and for diagnosis of diseases and conditions, which include, but are not limited to, leukemias, lymphomas, autoimmune, immunosuppressive, and immunodeficiencies, hematopoietic disorders, as well as renal disorders, and neoplasms. Similarly, polypeptides and antibodies directed to these polypeptides are useful in providing immunological probes for differential identification of the tissue(s) or cell type(s). For a number of disorders of the above tissues or cells, particularly of the renal, pulmonary, immune, and central nervous systems, expression of this gene at significantly higher or lower levels may be routinely detected in certain tissues or cell types (e.g., brain and other tissue of the nervous system, renal, pulmonary tissue, liver, spleen, and blood cells, and cancerous and wounded tissues) or bodily fluids (e.g., lymph, bile, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in immune tissue indicates that polynucleotides and polypeptides corresponding to this gene are useful for the treatment and diagnosis of renal conditions, such as acture renal failure, kidney fibrosis, and kidney tubule regeneration. The expression in leukocytes and other immune tissues indicates a role in immune disorders including: leukemias, lymphomas, auto-immune, immuno-supressive (e.g. transplantation) and immunodeficiencies (e.g. AIDS) and hematopoietic disorders. The expression in the brain—and in particular the fetal brain—indicates a possible role in the treatment and diagnosis of developmental and neurodegenerative diseases of the brain and nervous system (depression, schizophrenia, Alzheimer's disease, mania, dementia, paranoia, and addictive behavior). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1434 of SEQ ID NO:31, b is an integer of 15 to 1448, where both a and b correspond to the positions of nucleotide residues shown in SEQ ID NO:31, and where the b is greater than or equal to a +14.

Features of Protein Encoded by Gene No: 22

The gene encoding the disclosed cDNA is thought to reside on chromosome 19. Accordingly, polynucleotides related to this invention are useful as a marker in linkage analysis for chromosome 19.

This gene is expressed primarily in skin (fetal epithelium, keratinocytes and skin).

Therefore, polynucleotides and polypeptides of the invention are useful as reagents for differential identification of the tissue(s) or cell type(s) present in a biological sample and for diagnosis of-diseases and conditions, which include, but are not limited to, skin cancers (e.g., melanomas), eczema, psoriasis or other disorders of the integumentary system. Similarly, polypeptides and antibodies directed to these polypeptides are useful in providing immunological probes for differential identification of these tissue(s) or cell type(s). For a number of disorders of the above tissues or cells, particularly of the skin, expression of this gene at significantly higher or lower levels may be routinely detected in certain tissues or cell types (e.g., keratinocytes, epithelium, integumentary, endothelial and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 142 as residues: Pro-28 to Glu-35, Ser-39 to Phe-44, Ala-94 to Gln-99.

The tissue distribution in integumentary tissue, suggests that the protein product of this clone would be useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, athletes foot, and ringworm). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 442 of SEQ ID NO:32, b is an integer of 15 to 456, where both a and b correspond to the positions of nucleotide residues shown in SEQ ID NO:32, and where the b is greater than or equal to a +14.

Features of Protein Encoded by Gene No: 23

This gene maps to chromosome 11. Another group recently isolated this same gene, associating the sequence to the region thought to harbor the gene involved in Multiple Endocrine Neoplasia Type 1, or MEN 1. (See Accession No. 2529721 and Genome Res. 7(7), 725–735 (1997), incorporated herein by reference in its entirety.) Preferred polypeptide fragments comprise the amino acid sequence: LFHWACLNERA AQLPRNTAXAGYQCPSCNGPS (SEQ ID NO:265).

This gene is expressed primarily in epididymus, pineal gland, T-cells, as well as fetal epithelium, lung and kidney.

Therefore, polynucleotides and polypeptides of the invention are useful as reagents for differential identification of the tissue(s) or cell type(s) present in a biological sample and for diagnosis of diseases and conditions, which include, but are not limited to, immune, metabolic mediated disorders, reproductive, endocrine, and MEN. Similarly, polypeptides and antibodies directed to these polypeptides are useful in providing immunological probes for differential identification of the tissue(s) or cell type(s). For a number of disorders of the above tissues or cells, particularly of the immune, renal, neurological and pulmonary systems, expression of this gene at significantly higher or lower levels may be routinely detected in certain tissues or cell types (e.g., immune, epididymus and other reproductive tissue, pineal gland, T-cells and other blood cells, epithelium, lung, and kidney, and cancerous and wounded tissues) or bodily fluids (e.g., seminal fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in fetal tissues indicates that polynucleotides and polypeptides corresponding to this gene are useful for the treatment and diagnosis of developmental deficiencies or abnormalities as well as a host of different disorders which arise as a result of conditions in the indicated tissues or cell types. An area of particular interest is in the treatment and diagnosis of immune disorders including: leukemias, lymphomas, auto-immune, immuno-supressive (e.g. transplantation) and immunodeficiencies (e.g. AIDS) and hematopoietic disorders. The expression in the brain, and in particular the fetal brain, would suggest a possible role in the treatment and diagnosis of developmental and neurodegenerative diseases of the brain and nervous system (depression, schizophrenia, Alzheimer's disease, mania, dementia, paranoia, and addictive behavior). Respiratory/pulmonary disorders, such as athesma, pulmonary edema are also potential therapeutic areas, as well as renal conditions such as acute renal failure, kidney fibrosis and kidney tubule regeneration. Moreover, this gene can be used in the treatment and/or detection of MEN I. Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1312 of SEQ ID NO:33, b is an integer of 15 to 1326, where both a and b correspond to the positions of nucleotide residues shown in SEQ ID NO:33, and where the b is greater than or equal to a +14.

Features of Protein Encoded by Gene No: 24

This gene is expressed primarily in fetal spleen.

Therefore, polynucleotides and polypeptides of the invention are useful as reagents for differential identification of the tissue(s) or cell type(s) present in a biological sample and for diagnosis of diseases and conditions, which include, but are not limited to developmental, leukemia, lymphoma, AIDS, hematopoeitic disorders. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may be routinely detected in certain tissues or cell types (e.g. immune, spleen, developmental, hepatic, hematopoietic, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in fetal spleen indicates that polynucleotides and polypeptides corresponding to this gene are useful for the treatment and diagnosis of immune disorders including: leukemias, lymphomas, auto-immune, immunosupressive (e.g. transplantation) and immunodeficiencies (e.g. AIDS) and hematopoietic disorders. Expression of this gene product in fetal spleen suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 696 of SEQ ID NO:34, b is an integer of 15 to 710, where both a and b correspond to the positions of nucleotide residues shown in SEQ ID NO:34, and where the b is greater than or equal to a +14.

Features of Protein Encoded by Gene No: 25

A closely related homolog of this gene was recently cloned by another group, calling the gene CDO, an oncogene-, serum-, and anchorage-regulated member of the Ig/fibronectin type III repeat family. (See Accession No. 2406628, and J. Cell Biol. 138(1): 203–213 (1997), herein incorporated by reference in its entirety.) Preferred polypeptide fragments comprise the amino acid sequence: FYTYYRPDSDNDSDYKK DMVEGDKYWHSISHLQ-PETSYDIKMQCFNEGGESEFSNVMICETKARKS SGQP GRLPPPTLAPPQPPLPETIERPVGTGAM-VARSSDLPYLIVGVVLGSWLIPVFIPF CLWRAW-SKQKHTTDLGFPRSALPPSCPYTMVPLG-GLPGHQAVDSPTSVASVD GPVLM (SEQ ID NO:266); or YIYYRPDSDNDSDYKKDMVEGDKYWHSISHLQ PETSYDIKMQCFNEGGESEFSNVMICETKARKS (SEQ ID NO:267).

This gene is expressed primarily in fetal lung and kidney, human embryo and osteoclastoma stromal cells and to a lesser extent in a variety of other tissues and cell types.

Therefore, polynucleotides and polypeptides of the invention are useful as reagents for differential identification of the tissue(s) or cell type(s) present in a biological sample and for diagnosis of diseases and conditions, which include, but are not limited to, developmental disorders and cancers, as well as pulmonary and renal disorders. Similarly, polypeptides and antibodies directed to these polypeptides are useful in providing immunological probes for differential identification of the tissue(s) or cell type(s). For a number of disorders of the above tissues or cells, particularly of the respiratory/pulmonary, skeletal and renal systems, expression of this gene at significantly higher or lower levels may be routinely detected in certain tissues or cell types (e.g., lung, kidney, embryonic tissue, and bone cells, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 145 as residues: Thr-5 to Pro-18, Ala-76 to Thr-84.

The tissue distribution in fetal tissues indicates that polynucleotides and polypeptides corresponding to this gene are useful for the detection and treatment of osteoperosis, fractures, osteosarcoma, ossification, and osteonecrosis, as well as respiratory/pulmonary disorders, such as athesma, pulmonary edema, and renal conditions such as acute renal failure, kidney fibrosis and kidney tubule regeneration. Alternatively, this gene may function in a tumor suppression capacity, and it may be down-regulated by tumor cells or proto-oncogenes. Expression of this gene may be important in the prevention of tumor growth or metastasis. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1174 of SEQ ID NO:35, b is an integer of 15 to 1188, where both a and b correspond to the positions of nucleotide residues shown in SEQ ID NO:35, and where the b is greater than or equal to a +14.

Features of Protein Encoded by Gene No: 26

This gene is homologous to the HIV envelope glycoprotein. (See Accession No.2641463.) Preferred polypeptide fragments comprise the amino acid sequence: NVRALL-HRMPEPPKINTAKFNNNKRKNLSL (SEQ ID NO:268).

This gene is expressed primarily in pineal gland and skin, and to a lesser extent in lung.

Therefore, polynucleotides and polypeptides of the invention are useful as reagents for differential identification of the tissue(s) or cell type(s) present in a biological sample and for diagnosis of diseases and conditions, which include, but are not limited to, neurological and behavior disorders; respiratory/pulmonary disorders, such as athesma, pulmonary edema; skin conditions such as eczema, psoriasis, acne and skin cancer, as well as AIDS. Similarly, polypeptides and antibodies directed to these polypeptides are useful in providing immunological probes for differential identification of the tissue(s) or cell type(s). For a number of disorders of the above tissues or cells, particularly of the central nervous and respiratory systems, as well as skin and AIDS, expression of this gene at significantly higher or lower levels may be routinely detected in certain tissues or cell types (e.g., blood cells, pineal gland, integumentary, endocrine, epidermis, and pulmonary tissue, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 146 as residues: Gln-15 to Gln-20.

The tissue distribution in integumentary tissues indicates that polynucleotides and polypeptides corresponding to this gene are useful for the treatment and diagnosis of conditions which affect the above tissues, such as skin cancer, eczema, psoriasis, acne, athesma, pulmonary edema, neuro-degenerative or developmental disorders such as Alzheimer's, depression, schizophrenia, dementia, and AIDS. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 942 of SEQ ID NO:36, b is an integer of 15 to 956, where both a and b correspond to the positions of nucleotide residues shown in SEQ ID NO:36, and where the b is greater than or equal to a +14.

Features of Protein Encoded by Gene No: 27

Preferred polypeptide encoded by this gene comprise the following amino acid sequence: NTNQREALQYAKNFQP-FALNHQKDIQVLMGSLVYLRQGIENSPYVHL LDAN-QWADICDWNACALLGLSVESPLSVSF-SAGCVALPALINKAVIEQRQC TGVWNQKDELPIEVDLGKKCWYHSI-FACPILRQQTTDNNPPMKLVCGHIISRD ALNKMFNG-SKLKCPYCPMEQSPGDAKQIFF (SEQ ID NO:269). Polynucleotides encoding such polypeptides are also provided as are complementary polynucleotides thereto. The gene encoding the disclosed cDNA is thought to reside on chromosome 2. Accordingly, polynucleotides related to this invention are useful as a marker in linkage analysis for chromosome 2. Contact of cells with supernatant expressing the product of this gene increases the permeability of the plasma membranes of both astrocytes and monocytes to calcium. Thus, it is likely that the product of this gene is involved in signal transduction pathway(s) which are initiated when the product binds a receptor(s) on the surface of both astrocytes and monocytes. Thus, polynucleotides have uses which include, but are not limited to, activating astrocytes and monocytes.

This gene is expressed primarily in liver (adult and fetal) and spleen tissue, and to a lesser extent in placenta, T helper cells, kidney tumor, ovarian tumor, melanocytes and fetal heart.

Therefore, polynucleotides and polypeptides of the invention are useful as reagents for differential identification of the tissue(s) or cell type(s) present in a biological sample and for diagnosis of diseases and conditions, which include, but are not limited to, immune and developmental diseases and disorders and liver diseases such as liver cancer. Similarly, polypeptides and antibodies directed to these polypeptides are useful in providing immunological probes for differential identification of the tissue(s) or cell type(s). For a number of disorders of the above tissues or cells, particularly of the immune, circulatory and hematopoietic systems, expression of this gene at significantly higher or lower levels may be routinely detected in certain tissues or cell types (e.g., liver, spleen, placenta, blood cells, developmental, kidney, ovary and other reproductive tissue, melanocytes, and heart, and cancerous and wounded tissues) or bodily fluids (e.g., lymph, amniotic fluid, bile, serum,-plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in immune cells indicates that the protein products of this gene are useful for study, diagnosis and treatment of growth, hematopoietic and immune system disorders particularly related to the liver. Expression of this gene product in hematopoietic cells suggests a role in the regulation of the proliferation;

survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1589 of SEQ ID NO:37, b is an integer of 15 to 1603, where both a and b correspond to the positions of nucleotide residues shown in SEQ ID NO:37, and where the b is greater than or equal to a +14.

Features of Protein Encoded by Gene No: 28

The translation product of this gene shares sequence homology with prostaglandin transporter which is thought to be important in metabolic and endocrine disorders. See, for example, Gastroenterology Oct: 109(4):1274–1282 (1995). Preferred polypeptides encoded by this gene comprise the following amino acid sequence: SYLSACFAGCNSTNLT-GCACLTTVPAENATVVPGKCPSPGC-QEAFLTFLCVMCI CSLIGAMARHP (SEQ ID NO:270); and/or PSVIlLIRTVSPELKSYALGVLFLLLRL LGFIPP-PLIFGAGIDSTCLFWSTFCGEQGACV-LYDNVVYRYLYVSIAIALKSFAFI (SEQ ID NO:271).

This gene is expressed primarily in hematopoietic and brain tissues.

Therefore, polynucleotides and polypeptides of the invention are useful as reagents for differential identification of the tissue(s) or cell type(s) present in a biological sample and for diagnosis of diseases and conditions, which include, but are not limited to, metabolic, immune and endocrine diseases and disorders. Similarly, polypeptides and antibodies directed to these polypeptides are useful in providing immunological probes for differential identification of the tissue(s) or cell type(s). For a number of disorders of the above tissues or cells, particularly of the metabolic, immune and endocrine systems, expression of this gene at significantly higher or lower levels may be routinely detected in certain tissues or cell types (e.g., immune, endocrine tissue, hematopoietic tissue, and brain and other tissue of the nervous system, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in hematopoietic cells combined with the homology to a prostaglandin (and anion) transporter indicates that polynucleotides and polypeptides corresponding to this gene are useful for study, diagnosis and treatment of endocrine, metabolic, immune and kidney disorders. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1075 of SEQ ID NO:38, b is an integer of 15 to 1089, where both a and b correspond to the positions of nucleotide residues shown in SEQ ID NO:38, and where the b is greater than or equal to a +14.

Features of Protein Encoded by Gene No: 29

This gene is expressed primarily in early stage human lung.

Therefore, polynucleotides and polypeptides of the invention are useful as reagents for differential identification of the tissue(s) or cell type(s) present in a biological sample and for diagnosis of diseases and conditions, which include, but are not limited to, growth and respiratory disorders. Similarly, polypeptides and antibodies directed to these polypeptides are useful in providing immunological probes for differential identification of the tissue(s) or cell type(s). For a number of disorders of the above tissues or cells, particularly of the developmental and respiratory systems, expression of this gene at significantly higher or lower levels may be routinely detected in certain tissues or cell types (e.g., pulmonary tissue, developmental, and cancerous and wounded tissues) or bodily fluids (e.g., amniotic fluid, lymph, pulmonary, surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 149 as residues: Val-50 to Trp-55.

The tissue distribution in fetal lung indicates that the protein products of this gene are useful for study, diagnosis and treatment of respiratory and growth diseases and disorders. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 615 of SEQ ID NO:39, b is an integer of 15 to 629, where both a-and b correspond to the positions of nucleotide residues shown in SEQ ID NO:39, and where the b is greater than or equal to a +14.

Features of Protein Encoded by Gene No: 30

The translation product of this gene shares sequence homology with human DNA helicase which is thought to be important in accurate and complete DNA replication in creation of new cells. Preferred polypeptides encoded by this gene comprise the following amino acid sequence: QSLFTRFVRVGVPTVDLDAQGRAR, SLCX-aYNYKLGNLPHVQLLPEFSTANAGLLYD-FQLIDFQGVGESEPN PYFYQNLGEAEYVVALFMYM-CLLGYPADKISILTTYNGQKHLIRDUNRCGNN PLIGRPNKVTTVDRFQGQQNDY-ILLSLVRTPVGHLRDVRRLVWAMSRAR (SEQ ID NO:272); and/or LVKEAKIL-AMTCTHAALKRHDLVKLGFKYDNILMEE AAQLEET-FIPLLLQNPQDGFSRLKRWMGDHHQLPPVI (SEQ ED NO:273). The gene encoding the disclosed cDNA is thought to reside on chromosome 15. Accordingly, polynucleotides related to this invention are useful as a marker in linkage analysis for chromosome 15.

This gene is expressed primarily in testes tumor and to a lesser extent in adrenal gland tumor and placenta.

Therefore, polynucleotides and polypeptides of the invention are useful as reagents for differential identification of the tissue(s) or cell type(s) present in a biological sample and for diagnosis of diseases and conditions, which include, but are not limited to, reproductive disorders, cancers and endocrine/growth disorders. Similarly, polypeptides and antibodies directed to these polypeptides are useful in providing immunological probes for differential identification of the tissue(s) or cell type(s). For a number of disorders of the above tissues or cells, particularly of the endocrine, developmental, and reproductive systems, expression of this gene at significantly higher or lower levels may be routinely detected in certain tissues or cell types (e.g., testes and other reproductive tissue, adrenal gland, and placenta, and cancerous and wounded tissues) or bodily fluids (e.g., seminal fluid, serum, plasma, urine, synovial fluid or spinal fluid) or another tissue or cell sample taken from an individual having such a disorder, relative to the standard gene expression level, i.e. the expression level in healthy tissue or bodily fluid from an individual not having the disorder.

The tissue distribution in testes combined with the homology to a DNA helicase indicates that the protein products of this gene are useful for study treatment, and diagnosis of many cancer types, including testicular cancer; as well as disorders involving endocrine function and normal growth and development. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1950 of SEQ ID NO:40, b is an integer of 15 to 1964, where both a and b correspond to the positions of nucleotide residues shown in SEQ ID NO:40, and where the b is greater than or equal to a +14.

Features of Protein Encoded by Gene No: 31

The translation product of this gene shares sequence homology with BID-apoptotic death gene (mouse), Genbank accession no. PID g1669514, which is thought to be important in programmed cell death.

This gene is expressed primarily in jurkat membrane bound polysomes and activated neutrophils and to a lesser extent in endothelial cells and human cerebellum.

Therefore, polynucleotides and polypeptides of the invention are useful as reagents for differential identification of the tissue(s) or cell type(s) present in a biological sample and for diagnosis of diseases and conditions, which include, but are not limited to, cancers and other proliferative disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g. immune, blood cells, hematopoietic, endothelium, and brain and other tissue of the nervous system, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 151 as residues: Glu-4 to Leu-l 1, Cys-28 to Arg-35, Gln-50 to His-66, Glu-73 to Gln-79, Gly-94 to Ser-100, Arg-I 14 to Asp-126, Pro-139 to Lys-146.

The tissue distribution in immune cells combined with the homology to the BID-apoptotic death gene indicates that the protein products of this gene are useful for study of cell death, and treatment and diagnosis of proliferative disorders and cancers. Apoptosis—programmed cell death—is a physiological mechanism involved in the deletion of peripheral T lymphocytes of the immune system, and its dysregulation can lead to a number of different pathogenic processes. Diseases associated with increased cell survival, or the inhibition of apoptosis, include cancers (such as follicular lymphomas, carcinomas with p53 mutations, and hormone-dependent tumors, such as breast cancer, prostrate cancer, Kaposifs sarcoma and ovarian cancer); autoimmune disorders (such as systemic lupus erythematosus and immune-related glomerulonephritis rheumatoid arthritis) and viral infections (such as herpes viruses, pox viruses and adenoviruses), inflammation; graft vs. host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, the invention provides a method of enhancing apoptosis in an individual by treating the individual with a polypeptide encoded by this gene. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1508 of SEQ ID NO:41, b is an integer of 15 to 1522, where both a and b correspond to the positions of nucleotide residues shown in SEQ ID NO:41, and where the b is greater than or equal to a +14.

Features of Protein Encoded by Gene No: 32

The translation product of this gene shares sequence homology with human fructose transporter which is thought to be important in normal metabolic function and activity.

This gene is expressed primarily in T-cell lymphoma.

Therefore, polynucleotides and polypeptides of the invention are useful as reagents for differential identification of the tissue(s) or cell type(s) present in a biological sample and for diagnosis of diseases and conditions, which include, but are not limited to, leukemia and other cancers, and metabolic disorders. Similarly, polypeptides and antibodies directed to these polypeptides are useful in providing immunological probes for differential identification of the tissue(s) or cell type(s). For a number of disorders of the above tissues or cells, particularly of the hematopoietic, lymph and metabolic systems, expression of this gene at significantly higher or lower levels may be routinely detected in certain tissues or cell types (e.g. immune, brain, T-cells and other blood cells, metabolic tissues, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 152 as residues: Pro-22 to Gly-48, Ser-54 to Pro-61.

The tissue distribution in T-cell lymphoma indicates that the protein products of this gene are useful for study of mechanisms leading to cancer, treatment and diagnosis of cancerous and pre-cancerous conditions; as well as the study and treatment of various metabolic diseases and disorders. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 861 of SEQ ID NO:42, b is an integer of 15 to 875, where both a and b correspond to the positions of nucleotide residues shown in SEQ ID NO:42, and where the b is greater than or equal to a +14.

Features of Protein Encoded by Gene No: 33

This gene is expressed primarily in human meningima and placental tissues.

Therefore, polynucleotides and polypeptides of the invention are useful as reagents for differential identification of the tissue(s) or cell type(s) present in a biological sample and for diagnosis of diseases and conditions, which include, but are not limited to, inflammation and other disorders of the CNS. Similarly, polypeptides and antibodies directed to these polypeptides are useful in providing immunological probes for differential identification of the tissue(s) or cell type(s). For a number of disorders of the above tissues or cells, particularly of the CNS and immune systems, expression of this gene at significantly higher or lower levels may be routinely detected in certain tissues or cell types (e.g. immune, meningima, developmental, proliferating, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 153 as residues: Asn-23 to Pro-31.

The tissue distribution in neural tissue indicates that the protein products of this gene are useful for study, diagnosis and treatment of disorders of the CNS and inflammatory responses. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 829 of SEQ ID NO:43, b is an integer of 15 to 843, where both a and b correspond to the positions of nucleotide residues shown in SEQ ID NO:43, and where the b is greater than or equal to a +14.

Features of Protein Encoded by Gene No: 34

This gene is expressed primarily in activated monocytes and wound healing tissues and to a lesser extent in fetal epithelium.

Therefore, polynucleotides and polypeptides of the invention are useful as reagents for differential identification of the tissue(s) or cell type(s) present in a biological sample and for diagnosis of diseases and conditions, which include, but are not limited to, immune and inflammatory disorders and wound healing and tissue repair dysfunctions. Similarly, polypeptides and antibodies directed to these polypeptides are useful in providing immunological probes for differential identification of the tissue(s) or cell type(s). For a number of disorders of the above tissues or cells, particularly of the immune, epithelial and gastrointestinal systems, and healing wounds, expression of this gene at significantly higher or lower levels may be routinely detected in certain tissues or cell types (e.g. immune, keratinocytes, monocytes, integumentary, developmental, and other blood cells, and epithelium, and cancerous and wounded tissues) or bodily fluids (e.g., amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 154 as residues: Ala-28 to Ala-33, Gly-35 to Glu-45.

The tissue distribution in immune cells indicates that the protein products of this gene are useful for diagnosis, study and treatment of immune and inflammatory disorders and wound healing dysfunctions. Expression of this gene product in immune cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 475 of SEQ ID NO:44, b is an integer of 15 to 489, where both a and b correspond to the positions of nucleotide residues shown in SEQ ID NO:44, and where the b is greater than or equal to a +14.

Features of Protein Encoded by Gene No: 35

This gene is expressed primarily in human osteosarcoma and prostate cancer.

Therefore, polynucleotides and polypeptides of the invention are useful as reagents for differential identification of the tissue(s) or cell type(s) present in a biological sample and for diagnosis of diseases and conditions, which include, but are not limited to, skeletal and neoplastic conditions such as bone and prostate cancer. Similarly, polypeptides and antibodies directed to these polypeptides are useful in providing immunological probes for differential identification of the tissue(s) or cell type(s). For a number of disorders of the above tissues or cells, particularly of the immune and skeletal systems, expression of this gene at significantly higher or lower levels may be routinely detected in certain tissues or cell types (e.g., immune, bone, prostate, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 155 as residues: Ser-14-to Gly-22, Leu-37 to Gln-43.

The tissue distribution in skeletal cells indicates that the protein products of this gene are useful for diagnosis and treatment of skeletal disorders and cancer. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 520 of SEQ ID NO:45, b is an integer of 15 to 534, where both a and b correspond to the positions of nucleotide residues shown in SEQ ID NO:45, and where the b is greater than or equal to a +14.

Features of Protein Encoded by Gene No: 36

This gene encodes a protein which is highly homologous to a protein called congenital heart disease protein 5, presumably implicated in-congenital heart disease (see Genbank PID g2810996).

This gene is expressed primarily in Hodgkin's lymphoma, erythroleukemia cells, and TNF activated synovial fibroblasts, to a lesser extent in ovarian cancer, cerebellum, spleen, fetal liver and placenta and finally to a lesser extent in various other mesenchymal tissues.

Therefore, polynucleotides and polypeptides of the invention are useful as reagents for differential identification of the tissue(s) or cell type(s) present in a biological sample and for diagnosis of diseases and conditions, which include, but are not limited to, cancer, immune, hematopoietic and cardiovascular disorders. Similarly, polypeptides and antibodies directed to these polypeptides are useful in providing immunological probes for differential identification of the tissue(s) or cell type(s). For a number of disorders of the above tissues or cells, particularly of the immune, hematopoietic and cardiovascular systems, expression of this gene at significantly higher or lower levels may be routinely detected in certain tissues or cell types (e.g., heart and other cardiovascular tissue, immune, lymphoid tissue, blood cells, bone marrow, ovary and other reproductive tissue, brain and other tissue of the nervous system, spleen, liver, and mesenchymal tissue, and cancerous and wounded tissues) or bodily fluids (e.g., lymph, bile, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 156 as residues: Lys-41 to Met-49, Gln-54 to Glu-59, Glu-76 to Thr-88.

The homology of this gene and translation product to congenital heart disease protein 5 indicates a role for this protein in the diagnosis, prognosis and/or treatment of heart disease or other cardiovascular related disorders. In addition, predominant expression in cells associated with the immune and hematopoetic system indicates a role for this protein in the treatment, diagnosis and/or prognosis of immune and autoimmune diseases, such as lupus, transplant rejection, allergic reactions, arthritis, asthma, immunodeficiency diseases, leukemia, AIDS, thymus disorders such as Graves Disease, lymphocytic thyroiditis, hyperthyroidism and hypothyroidism, graft versus host reaction, graft versus host disease, transplant rejection, myelogenous leukemia, bone marrow fibrosis, and myeloproliferative disease. The protein could also be used to enhance or protect proliferation, differentiation and functional activation of hematopoietic progenitor cells such as bone marrow cells, which could be useful for cancer patients undergoing chemotherapy or patients undergoing bone marrow transplantation. The protein may also be useful to increase the proliferation of peripheral blood leukocytes, which could be useful in the combat of a range of hematopoietic disorders including immunodeficiency diseases, leukemia, and septicemia. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1360 of SEQ ID NO:46, b is an integer of 15 to 1374, where both a and b correspond to the positions of nucleotide residues shown in SEQ ID NO:46, and where the b is greater than or equal to a +14.

Features of Protein Encoded by Gene No: 37

This gene is expressed primarily in ovarian cancer.

Therefore, polynucleotides and polypeptides of the invention are useful as reagents for differential identification of the tissue(s) or cell type(s) present in a biological sample and for diagnosis of diseases and conditions, which include, but are not limited to, urogenital neoplasias, reproductive, or endocrine disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., ovary and other reproductive tissue, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy-tissue or bodily fluid from an individual not having the disorder. Preferred epitopes include those comprising a sequence shown in SEQ ID NO. 157 as residues: Asn-22 to Asn-27.

The tissue distribution in ovarian tissues indicates that polynucleotides and polypeptides corresponding to this gene are useful for study, diagnosis and treatment of ovarian and other tumors. Protein, as well as, antibodies directed against the protein may show utility as a tumor marker and/or immunotherapy targets for the above listed tissues. Many polynucleotide sequences, such as EST,sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 582 of SEQ ID NO:47, b is an integer of 15 to 596, where both a and b correspond to the positions of nucleotide residues shown in SEQ ID NO:47, and where the b is greater than or equal to a +14.

Features of Protein Encoded by Gene No: 38

The translation product of this gene shares sequence homology with zinc finger proteins, which are small DNA-binding molecules noted for their occurrence in a large number of eukaryotic transcription factors.

This gene is expressed primarily in fetal, cancer, and endothelial lines.

Therefore, polynucleotides and polypeptides of the invention are useful as reagents for differential identification of the tissue(s) or cell type(s) present in a biological sample and for diagnosis of diseases and conditions, which include, but are not limited to, immune and growth disorders. Similarly, polypeptides and antibodies directed to these polypeptides are useful in providing immunological probes for differential identification of the tissue(s) or cell type(s). For a number of disorders of the above tissues or cells, particularly of the cardiovascular system, expression of this gene at significantly higher or lower levels may be routinely detected in certain tissues or cell types (e.g. immune, fetal tissue, and endothelial cells, and cancerous and wounded tissues) or bodily fluids (e.g., lymph, bile, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in fetal tissue indicates that the protein products of this gene are useful for study, diagnosis and treatment of immune and developmental conditions and cancer. The homology to zinc finger proteins suggests that this protein may play a role in the transcriptional regulation of certain cancer genes. Protein, as well as, antibodies directed against the protein may show utility as a tissue-specific marker and/or immunotherapy target for the above listed tissues. Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 837 of SEQ ID NO:48, b is an integer of 15 to 851, where both a and b correspond to the positions of nucleotide residues shown in SEQ ID NO:48, and where the b is greater than or equal to a +14.

Features of Protein Encoded by Gene No: 39

This gene is expressed primarily in fetal, infant, and adult brain and to a lesser extent in other brain and endocrine organs and blastomas.

Therefore, polynucleotides and polypeptides of the invention are useful as reagents for differential identification of the tissue(s) or cell type(s) present in a biological sample and for diagnosis of diseases and conditions, which include, but are not limited to, brain tumors and neurodegenerative conditions, in addition to developmental disorders. Similarly, polypeptides and antibodies directed to these polypeptides are useful in providing immunological probes for differential identification of the tissue(s) or cell type(s). For a number of disorders of the above tissues or cells, particularly of the nervous and endocrine systems, expression of this gene at significantly higher or lower levels may be routinely detected in certain tissues or cell types (e.g., brain and other tissue of the nervous system, endocrine tissue, and cancerous and wounded tissues) or bodily fluids (e.g., amniotic fluid, lymph, serum, plasma, urine, synovial fluid or spinal fluid) or another tissue or cell sample taken from an individual having such a disorder, relative to the standard gene expression level, i.e., the expression level-in healthy tissue or bodily fluid from an individual not having the disorder.

The tissue distribution in neural tissue indicates that the protein products of this gene are useful for the study, diagnosis and treatment of brain cancer and other neurological disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2006 of SEQ ID NO:49, b is an integer of 15 to 2020, where both a and b correspond to the positions of nucleotide residues shown in SEQ ID NO:49, and where the b is greater than or equal to a +14.

Features of Protein Encoded by Gene No: 40

The translation product of this gene shares sequence homology with vesicular glycoproteins and lectins. Preferred polypeptides encoded by this gene comprise the following amino acid sequence: DTYPNEEKQQERVF-PXXSAMVNNGSLSYDHER DGRPTELGGCXA VRNL-HYDTFLVIRYVKRHLTIMMIDGKHEWRDCIEVPGV RLPRGYYFGTSSITGDLSDNHDVIS-LKLFELTVERTPEEE (SEQ ID NO:274); and/or LKREH-SLSKPYQGVGTGSSSLWNLMGNAM-VMTQYIRLTPDMQSKQGA LWNRVPCFLRDWELQVHFKIHGQGKKNL-HGDGLAIWYT (SEQ ID NO:275). The gene encoding the disclosed cDNA is thought to reside on chromosome 2. Accordingly, polynucleotides related to this invention are useful as a marker in linkage analysis for chromosome 2. When tested against U937 myeloid cell lines and Jurkat T-cell lines, supernatants removed from cells containing this gene activated the GAS pathway. Thus, it is likely that this gene activates myeloid cells and T-cells through the Jaks-STAT signal transduction pathway. The Gamma Activating Sequence (GAS) is a promoter element found upstream of many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the GAS element, can be used to indicate proteins involved in the proliferation and differentiation of cells. When tested against sensory neuron cell lines, supernatants removed from cells containing this gene activated the EGR1 pathway. Thus, it is likely that this gene activates sensory neuron cells through a signal transduction pathway induced by the EGR1 promoter. The Early Growth Response Gene 1 (EGR1) is a separate signal transduction pathway in which the EGR1 promoter induces various tissues and cell types upon activation, leading the cells to undergo differentiation and proliferation.

This gene is expressed primarily in infant brain and to a lesser extent in various normal and transformed neural, endocrine, and immune organs.

Therefore, polynucleotides and polypeptides of the invention are useful as reagents for differential identification of the tissue(s) or cell type(s) present in a biological sample and for diagnosis of diseases and conditions, which include, but are not limited to, neurological and neurodevelopmental conditions. Similarly, polypeptides and antibodies directed to these polypeptides are useful in providing immunological probes for differential identification of the tissue(s) or cell type(s). For a number of disorders of the above tissues or cells, particularly of the nervous and hormonal systems, expression of this gene at significantly higher or lower levels may be routinely detected in certain tissues (e.g., brain and other tissue of the nervous system, endocrine tissue, and tissue and cells of the immune system, developmental disorders, and cancerous and wounded tissues) or bodily fluids (e.g., amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 160 as residues: Pro-64 to Gly-71, Gly-94 to Leu-100, Thr-110 to Pro-116, Thr-135 to Arg-145, Glu-164 to Glu-171, Asp-204 to Asp-21 1, Arg-253 to His-261, Asn-312 to Tyr-323.

The tissue distribution in neural tissue indicates that the protein products of this gene are useful for the study, diagnosis and treatment of mental retardation and other neurological disorders and neoplasias. The activity of this gene seen in various biological assays indicates that this gene is involved in a number of signal transduction assays, which further suggests that this gene could be important in cell proliferation and differentiation. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2418 of SEQ ID NO:50, b is an integer of 15 to 2432, where both a and b correspond to the positions of nucleotide residues shown in SEQ ID NO:50, and where the b is greater than or equal to a +14.

Features of Protein Encoded by Gene No: 41

This gene displays homology to the glycosyltransferase family, which catalyze the addition of sialic acids to carbohydrate groups which are present on glycoproteins and glycolipids.

This gene is expressed primarily in smooth muscle and to a lesser extent in pineal gland, fetal liver, and infant brain.

Therefore, polynucleotides and polypeptides of the invention are useful as reagents for differential identification of the tissue(s) or cell type(s) present in a biological sample and for diagnosis of diseases and conditions, which include, but are not limited to, gastrointestinal injury, inflammatory and neurodegenerative conditions, endocrine, hematopoietic, hepatic or developmental disorders. Similarly, polypeptides and antibodies directed to these polypeptides are useful in providing immunological probes for differential identification of the tissue(s) or cell type(s). For a number of disorders of the above tissues or cells, particularly of the immune and nervous systems, expression of this gene at significantly higher or lower levels may be routinely detected in certain tissues or cell types (e.g., smooth muscle, pineal gland, liver, and brain and other tissue of the nervous system, and cancerous and wounded tissues) or bodily fluids (e.g., amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 161 as residues: Ser-12 to Trp-21, Arg-24 to Pro-32, Asp-73 to Lys-82, Lys-90 to Ala-97.

The tissue distribution in neural and fetal tissue indicates that the protein products of this gene are useful for the study, diagnosis and treatment of neurodegenerative and growth disorders and gastrointestinal repair. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2326 of SEQ ID NO:51, b is an integer of 15 to 2340, where both a and b correspond to the positions of nucleotide residues shown in SEQ ID NO:51, and where the b is greater than or equal to a +14.

Features of Protein Encoded by Gene No: 42

The translation product of this gene shares sequence similarity with metallothionein polypeptides. See, for example, Proc. Natl. Acad. Sci. U S A 1992 July 15:89(14): 6333–6337. Metallothioneins are believed to inhibit neuronal survival among other biological functions. Based on the sequence similarity (especially the conserved cysteine motifs characteristic of the metallothionein family) the translation product of this gene is expected to share certain biological activities with other members of the metallothionein polypeptide family. Preferred polypeptides encoded by this gene comprise the following amino acid sequence: PGTLQCSALHHDPGCANCSRFCRD CSPPACQC (SEQ ID NO:276).

This gene is expressed exclusively in placenta and fetal liver, and to a lesser extent in osteoblast and bone marrow cells.

Therefore, polynucleotides and polypeptides of the invention are useful as reagents for differential identification of the tissue(s) or cell type(s) present in a biological sample and for diagnosis of diseases and conditions, which include, but are not limited to, hematopoietic and immune disorders and hepatic or skeletal system conditions. Similarly, polypeptides and antibodies directed to these polypeptides are useful in providing immunological probes for differential identification of the tissue(s) or cell type(s). For a number of disorders of the above tissues or cells, particularly of the reproductive and immune systems, expression of this gene at significantly higher or lower levels may be routinely detected in certain tissues or cell types (e.g., immune, placenta, liver, brain and other tissue of the nervous system, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in immune cells and homology to metallothionien indicates that the protein products of this gene are useful for diagnosis and treatment of immune and hematopoietic system disorders and neurological diseases, especially in fetal development. Expression of this gene product in hematopoietic cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 587 of SEQ ID NO:52, b is an integer of 15 to 601, where both a and b correspond to the positions of nucleotide residues shown in SEQ ID NO:52, and where the b is greater than or equal to a +14.

Features of Protein Encoded by Gene No: 43

Preferred polypeptides encoded by this gene comprise the following amino acid sequence: FLYDVLMXHEAVM-RTHQIQLPDPEFPS (SEQ ID NO:277).

This gene is expressed primarily in T-cells and synovial tissue.

Therefore, polynucleotides and polypeptides of the invention are useful as reagents for differential identification of the tissue(s) or cell type(s) present in a biological sample and for diagnosis of diseases and conditions, which include, but are not limited to, immune system disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain-tissues or cell types (e.g., synovial tissue, and T-cells and other blood cells, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that the protein products of this gene are useful for treatment and diagnosis of disorders of the immune system. Expression of this gene product in immune cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukernia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 345 of SEQ ID NO:53, b is an integer of 15 to 359, where both a and b correspond to the positions of nucleotideresidues shown in SEQ ID NO:53, and where the b is greater than or equal to a +14.

Features of Protein Encoded by Gene No: 44

The translation product of this gene shares sequence similarity with several methyltransferases (e.g., see Gen-bank gil1065505) which suggests this protein would be important in normal developmental and cellular processes.

This gene is expressed primarily in ovary, thymus, infant adrenal gland, tissues of the nervous system and the hematopoietic tissue, and to a lesser extent in adipose tissue and other tissues.

Therefore, polynucleotides and polypeptides of the invention are useful as reagents for differential identification of the tissue(s) or cell type(s) present in a biological sample and for diagnosis of diseases and conditions, which include, but are not limited to, disorders of the reproductive system, the endocrine system, the hematopoietic system and the CNS. Similarly, polypeptides and antibodies directed to these polypeptides are useful in providing immunological probes for differential identification of the tissue(s) or cell type(s). For a number of disorders of the above tissues or cells, particularly of the immune, endocrine, CNS and reproductive system, expression of this gene at significantly higher or lower levels may be routinely detected in certain tissues or cell types (e.g., ovary and other reproductive tissue, thymus, adrenal gland, brain and other tissue of the nervous system, hematopoietic tissue, and adipose tissue, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 164 as residues: Ser-3 to Gly-12, Asp-19 to Arg-31, Tyr-70 to Tyr-77, Asn-130 to Lys-140, Pro-165 to Gln-170, Pro-192 to Lys-199, Leu-216 to Glu-227, Glu-254 to Phe-281.

The tissue distribution in hematopoietic cells and homology to methyltransferase indicates that the protein products of this gene are useful for diagnosis and treatment of disorders of the CNS, the hematopoietic system and reproductive organs and tissues. For example, the abundant expression in the ovary may indicate that the gene product can be used as a hormone with either systemic or reproductive functions; as growth factors for germ cell maintenance and in vitro culture; as a fertility control agent; remedy for sexual dysfunction or sex development disorders; diagnostics/treatment for ovarian tumors, such as serous adenocarcinoma, dysgerminoma, embryonal carcinoma, choriocarcinoma, teratoma, etc; The expression in thymus may indicate its utility in T-cell development and thus its applications in immune related medical conditions, such as infection, allergy, immune deficiency, tissue/organ transplantation, etc. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence would be cumbersome. Accordingly, preferably excluded from the present invention are one or more-polynucleotides comprising a nucleotide sequence described by the general formula of a-b, where a is any integer between 1 to 1127 of SEQ ID NO:54, b is an integer of 15 to 1141, where both a and b correspond to the positions of nucleotide residues shown in SEQ ID NO:54, and where the b is greater than or equal to a +14.

Features of Protein Encoded by Gene No: 45

The translation product of this gene shares sequence homology with cytochrome C oxidase which is thought to be important in the metabolic function of cells. This gene has now recently been published as estrogen response gene. See Genbank accession no. AB007618 and Mol. Cell. Biol. 18 (1), 442–449 (1998). See also J Immunol. March 1:154(5): 2384–2392 (1995), where the mouse homologue was published and implicated in siliocis. In specific embodiments, polypeptides of the invention comprise the following amino acid sequence: PADXKPVVSTEAPPIIFATPTKLTSD-STVY DYAGKNKVPELQK-FFQKADGVPVYLKRGLPDQMLYRTT-MALTVGGTIYCLIAL YMASQPKNK (SEQ ID NO:278) or SFSGAVALAADAGSRTLGVMYYKFSGFTQ KLA-GAWASEAYSPQDCSLWFPQKHHLSYLPHQLN (SEQ ID NO:279). Polynucleotides encoding these polypeptides are also encompassed by the invention. The gene encoding the disclosed cDNA is believed to reside on chromosome 2. Accordingly, polynucleotides related to this invention are useful as a marker in linkage analysis for chromosome 2.

This gene is expressed primarily in adipose tissue, kidney and fetal brain and to a lesser extent in other tissues and organs.

Therefore, polynucleotides and polypeptides of the invention are useful as reagents for differential identification of the tissue(s) or cell type(s) present in a biological sample and for diagnosis of diseases and conditions, which include, but are not limited to, metabolic diseases involving especially adipose tissue, brain and kidney. Similarly, polypeptides and antibodies directed to these polypeptides are useful in providing immunological probes for differential identification of the tissue(s) or cell type(s). For a number of disorders of the above tissues or cells, particularly of the CNS and vascular system, expression of this gene at significantly higher or lower levels may be routinely detected in certain tissues or cell types (e.g., adipose tissue, kidney, brain and other tissue of the nervous system, and cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 165 as residues: Thr-8 to Ser-13, Ser-29 to Ala-34, Pro-64 to Lys-77.

The tissue distribution and homology to cytochrome C oxidase, estrogen response gene product and siliocis related gene product indicates that the protein products of this gene are useful for diagnosis and treatment of metabolic disorders in the CNS, adipose tissue and kidney, particularly siliocis. Expression within fetal suggests that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1546 of SEQ ID NO:55, b is an integer of 15 to 1560, where both a and b correspond to the positions of nucleotide residues shown in SEQ ID NO:55, and where the b is greater than or equal to a +14.

Features of Protein Encoded by Gene No: 46

The translation product of this gene shares sequence homology with reticulocalbin. See, for example, J. Biochem. 117 (5), 1113–1119 (1995). Based on the sequence similarity, the translation product of this gene is expected to share certain biological activities with reticulocalbin, e.g., Ca++ binding activities. This gene product is sometimes hereinafter referred to as "Reticulocalbin-2". When tested against Jurkat T-cell lines, supernatants removed from cells containing this gene activated the GAS pathway. Thus, it is likely that this gene activates T-cells through the Jaks-STAT signal transduction pathway. The Gamma Activating Sequence (GAS) is a promoter element found upstream of many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the GAS element, can be used to indicate proteins involved in the proliferation and differentiation of cells. When tested against K562 leukemia cell lines, supernatants removed from cells containing this gene activated the ISRE pathway. Thus, it is likely that this gene activates leukemia cells through a signal transduction pathway induced by the ISRE promoter. The Interferon-Sensitive Responsive Element (ISRE) is a promoter element found upstream in many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the ISRE element, can be used to indicate proteins involved in the proliferation and differentiation of cells This gene is expressed primarily in breast, endothelial cells, synovial, heart and smooth muscle cells.

Therefore, polynucleotides and polypeptides of the invention are useful as reagents for differential identification of the tissue(s) or cell type(s) present in a biological sample and for diagnosis of diseases and conditions, which include, but are not limited to, diseases of the breast, vascular, skeletal/cardiac muscular system as well as the integumentary system. Similarly, polypeptides and antibodies directed to these polypeptides are useful in providing immunological probes for differential identification of the tissue(s) or cell type(s). For a number of disorders of the above tissues or cells, particularly of the breast, vascular and skeleto-muscular system, expression of this gene at significantly higher or lower levels may be routinely detected in certain tissues and cell types (e.g., mammary tissue, endothelial cells, synovial tissue, heart and other cardiovascular tissue, smooth muscle, integumentary, and cancerous and wounded tissues) or bodily fluids (e.g.lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 166 as residues:

Gly-16 to Arg-32, Ala-42 to Asn-50, Glu-66 to Gln-76, Arg-85 to Gly-94, Thr-108 to Asp-115, Trp-121 to Gly-130, Leu-137 to His-144, Glu-155 to Lys-161, Asp-175 to Ser-180, Glu-209 to Gly-217, Glu-232 to Glu-237, Thr-243 to Asp-261, Glu-287 to Arg-295.

The tissue distribution in smooth muscle cells indicates that the protein products of this gene are useful for diagnosis and treatment of diseases of the vascular and skeletal/cardiac muscular system. The homology of the gene with reticulocalbin indicates its biological function in regulating calcium store, a particularly important function in muscular cell types. The gene expression in the heart may indicate its utilities in diagnosis and remedy in heart failure, ischemic heart diseases, cardiomyopathy, hypertension, arrhythmia, etc. The abundant expression in the breast may indicate its applications in breast neoplasia and breast cancers, such as fibroadenoma, papillary carcinoma, ductal carcinoma, Pagetfs disease, medullary carcinoma, mucinous carcinoma, tubular carcinoma, secretory carcinoma and apocrine carcinoma; juvenile hypertrophy and gynecomastia, mastitis and abscess, duct ectasia, fat necrosis and fibrocystic diseases, etc. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1493 of SEQ ID NO:56, b is an integer of 15 to 1507, where both a and b correspond to the positions of nucleotide residues shown in SEQ ID NO:56, and where the b is greater than or equal to a +14.

Features of Protein Encoded by Gene No: 47

The translation product of this gene shares weak sequence homology with H+-transporting ATP synthase which is thought to be important in cell metabolism or signal transduction.

This gene is expressed only in testis.

Therefore, polynucleotides and polypeptides of the invention are useful as reagents for differential identification of the tissue(s) or cell type(s) present in a biological sample and for diagnosis of some types of diseases and conditions. Similarly, polypeptides and antibodies directed to these polypeptides are useful in providing immunological probes for differential identification of the tissue(s) or cell type(s). For a number of disorders of the above tissues or cells, particularly of the brain and hematopoietic tissues, expression of this gene at significantly higher or lower levels may be routinely detected in certain tissues and cell types (e.g., testes and other reproductive tissue, and cancerous and wounded tissues) or bodily fluids (e.g.lymph, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Since only one out of about a million expressed sequence tags are found in testes, it is reasonable to suggest that the expression of this gene is selective for testes. Since some of the genes only expressed in testes are usually expressed in brain or in certain induced hematopoietic cells/tissues, it is speculated that this gene will be expressed in brain or hematopoietic cells/tissues and is useful for diagnosis and treatment of disorders of these systems. Similarly, the secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g.for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory, activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed-tissues. Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 436 of SEQ ID NO:57, b is an integer of 15 to 450, where both a and b correspond to the positions of nucleotide residues shown in SEQ ID NO:57, and where the b is greater than or equal to a +14.

Features of Protein Encoded by Gene No: 48

The translation product of this gene shares sequence homology with human polymeric immunoglobulin receptor (accession No.X73079) which is thought to be important in antibody recognition and immune defenses. In one embodiment, polypeptides of the invention comprise the sequence GWYWCG (SEQ ID NO:280). Polynucleotides encoding these polypeptides are also encompassed by the invention. The gene encoding the disclosed cDNA is believed to reside on chromosome 1. Accordingly, polynucleotides related to this invention are useful as a marker in linkage analysis for chromosome 1.

This gene is expressed primarily in placenta and to a lesser extent in corpus callosum and fetal liver and spleen.

Therefore, polynucleotides and polypeptides of the invention are useful as reagents for differential identification of the tissue(s) or cell type(s) present in a biological sample and for diagnosis of diseases and conditions, which include, but are not limited to, disorders of the immune system, e.g. autoimmune diseases and immunodeficiency, in addition to developmental disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g., placenta, liver, and spleen, developmental tissues, and cancerous and wounded tissues) or bodily fluids (e.g.lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder Preferred epitope&include those comprising a sequence shown in SEQ ID NO. 168 as residues: Tyr-37 to Cys-49, Gly-51 to Tyr-56, Lys-88 to Trp-93, Leu-130 to Glu-136.

The tissue distribution in fetal liver and spleen combined with the homology to human polymeric immunoglobulin receptor indicates that polynucleotides and polypeptides corresponding to this gene are useful for diagnosis and treatment of immune disorders, e.g. autoimmune diseases and immunodeficiencies. Expression within fetal tissues and other cellular sources marked by proliferating cells suggests that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor-marker and/or immunotherapy targets for the above listed tissues. Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1133 of SEQ ID NO:58, b is an integer of 15 to 1147, where both a and b correspond to the positions of nucleotide residues shown in SEQ ID NO:58, and where the b is greater than or equal to a +14.

Features of Protein Encoded by Gene No: 49

This gene is expressed in thymus.

Therefore, polynucleotides and polypeptides of the invention are useful as reagents for differential identification of the tissue(s) or cell type(s) present in a biological sample and for diagnosis of diseases and conditions, which include, but are not limited to, immune disorders, such as inflammation or immunodeficiencies. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues (e.g.immune, hematopoietic, thymus and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in thymus indicates that polynucleotides and polypeptides corresponding to this gene are useful for diagnosis and treatment of immune disorders, such as autoimmunity and immunodeficiency disorders. Similarly, this gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 763 of SEQ ID NO:59, b is an integer of 15 to 777, where both a and b correspond to the positions of nucleotide residues shown in SEQ ID NO:59, and where the b is greater than or equal to a +14.

Features of Protein Encoded by Gene No: 50

Preferred polypeptide encoded by this gene comprise the following amino acid sequence: MKVGARIRVKMSVN-KAHPVVSTHWRWPAEWPQMFLHAQEPRTE VKSR-PLGLAGFIRQDSKI RKPLEQETIMSAADTALWPYGH-GNREHQENELQKY LQYKDMHLLDSGQSLGHTHTLQGSHNLTALNI (SEQ ED NO:281). Polynucleotides encoding this polypeptide are also provided as are complementary polynucleotides thereto.

This gene is expressed primarily in adrenal gland, pituitary, T helper cells, and breast cells and to a lesser extent in a wide variety of tissues.

Therefore, polynucleotides and polypeptides of the invention are useful as reagents for differential identification of the tissue(s) or cell type(s) present in a biological sample and for diagnosis of the some diseases and conditions. Similarly, polypeptides and antibodies directed to these polypeptides are useful in providing immunological probes for differential identification of the tissue(s) or cell type(s). For a number of disorders of the above tissues or cells, particularly of the immune and endocrine systems, expression of this gene at significantly higher or lower levels may be routinely detected in certain tissues and cell types (e.g., adrenal gland, pituitary, T-cells and other blood cells, and mammary tissue, and cancerous and wounded tissues) or bodily fluids (e.g.-.lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 170 as residues: Gln-39 to Ser-47, Arg-57 to Glu-67, Tyr-82 to Gln-95.

The tissue distribution in immune tissues indicates that polynucleotides and polypeptides corresponding to this gene are useful for diagnosis and treatment of a wide range of disorders, such as immune and endocrine disorders. Similarly, the secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g.for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1177 of SEQ ID NO:60, b is an integer of 15 to 1191, where both a and b correspond to the positions of nucleotide residues shown in SEQ ID NO:60, and where the b is greater than or equal to a +14.

Features of Protein Encoded by Gene No: 51

The translation product of this gene shares sequence homology with human Sop2p-like protein which is important in cytoskeleton structure. In one embodiment, polypeptides of the invention comprise the sequence SLHKNSVSQISVLSGGKAKCS QFCTTGMDGGMSIWDVKSLESALKDLKI (SEQ ID NO:282). Polynucleotides encoding this polypeptide are also encompassed by the invention. This gene maps to chromosome 7. Therefore, polynucleotides of the invention can be used in linkage analysis as a marker for chromosome 7.

This gene is expressed primarily in immune and hematopoietic tissues/cells and to a lesser extent in other tissues.

Therefore, polynucleotides and polypeptides of the invention are useful as reagents for differential identification of the tissue(s) or cell type(s) present in a biological sample and for diagnosis of diseases and conditions, which include, but are not limited to, immunological and hematopoietic disorders and inflammation. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may be routinely detected in certain tissues and cell types (e.g., immune and hematopoietic tissue/cells, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 171 as residues: Lys-49 to Gln-54, Ala-61 to Arg-66, Lys-82 to Lys-87, Glu-126 to Val-133, His-136 to Ee-141, Glu-175 to Ser-187, Asp-286 to Leu-296, Ala-298 to Ser-310.

The tissue distribution in immune tissues indicates that polynucleotides and polypeptides corresponding to this gene are useful for diagnosis and treatment of immunological, hematopoietic, and inflammatory disorders, e.g, immunodeficiency, autoimmunity, inflammation. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1566 of SEQ ID NO:61, b is an integer of 15 to 1580, where both a and b correspond to the positions of nucleotide residues shown in SEQ ID NO:61, and where the b is greater than or equal to a +14.

Features of Protein Encoded by Gene No: 52

The translation product of this gene shares sequence homology with Caenorhabditis elegans R53.5 gene encoding a putative secreted protein.

This gene is expressed primarily in endothelial cells, brain and several highly vascularized, and tumor tissues and to a lesser extent in other tissues.

Therefore, polynucleotides and polypeptides of the invention are useful as reagents for differential identification of the tissue(s) or cell type(s) present in a biological sample and for diagnosis of diseases and conditions, which include, but are not limited to, aberrant angiogensis and tumorigenesis. Similarly, polypeptides and antibodies directed to these polypeptides are useful in providing immunological probes for differential identification of the tissue(s) or cell type(s). For a number of disorders of the above tissues or cells, particularly of the vascular and neural systems, expression of this gene at significantly higher or lower levels may be routinely detected in certain tissues and cell types (e.g., endothelial cells, brain and other tissue of the nervous system, and vascular tissue, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 172 as residues: Thr-43 to Asn-60, Thr-106 to Phe-115, Asp-122 to Arg-133, Arg-186 to Asp-192, Leu-211 to Lys-216.

The tissue distribution in vascular tissue combined with the homology to a C. elegans secreted protein indicates that polynucleotides and polypeptides corresponding to this gene are useful for diagnosis or treatment of disorders of the vascular or central nervous system, e.g. aberrant angiogenesis, ischemia, neurodegeneration, stroke, etc. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1103 of SEQ ID NO:62, b is an integer of 15 to 1117, where both a and b correspond to the positions of nucleotide residues shown in SEQ ID NO:62, and where the b is greater than or equal to a +14.

Features of Protein Encoded by Gene No: 53

In one embodiment, polypeptides of the invention comprise the sequence EASKSSHAGLDLFSVAACHRF (SEQ ID NO:283). Polynucleotides encoding this polypeptide are also encompassed by the invention. When tested against Jurkat T-cell lines, supernatants removed from cells containing this gene activated the GAS pathway. Thus, it is likely that this gene activates T-cells through the Jaks-STAT signal transduction pathway. The Gamma Activating Sequence (GAS) is a promoter element found upstream of many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the GAS element, can be used to indicate proteins involved in the proliferation and differentiation of cells.

This gene is expressed primarily in T-cells and to a lesser extent in brain.

Therefore, polynucleotides and polypeptides of the invention are useful as reagents for differential identification of the tissue(s) or cell type(s) present in a biological sample and for diagnosis of diseases and conditions, which include, but are not limited to, lymphocytic disorders. Similarly, polypeptides and antibodies directed to these polypeptides are useful in providing immunological probes for differential identification of the tissue(s) or cell type(s). For a number of disorders of the above tissues or cells, particularly of the lymphoid system, expression of this gene at significantly higher or lower levels may be routinely detected in certain tissues and cell types (e.g.immune, T-cells, or other blood cells, brain and other tissue of the nervous system, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 173 as residues: Pro-3 to Thr-8, Arg-37 to Asp-46.

The tissue distribution in T-cells indicates that polynucleotides and polypeptides corresponding to this gene are useful for diagnosis, treatment, and cure of lymphocytic disorders. Alternatively, expression within neural tissue suggests that the protein product of this clone would be useful for the detection/treatment of neurodegenerative disease states, behavioural disorders, or inflamatory conditions such as Alzheimers Disease, Parkinsons Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 347 of SEQ ID NO:63, b is an integer of 15 to 361, where both a and b correspond to the positions of nucleotide residues shown in SEQ ID NO:63, and where the b is greater than or equal to a +14.

Features of Protein Encoded by Gene No: 54

The translation product of this gene shares sequence homology with secreted cartilage matrix protein, a major component of the extracellular matrix of nonarticular cartilage which is thought to be important in cartilage structure. In specific embodiments, polypeptides of the invention comprise the sequence: RCKKCTEGPI DLVFVIDGSKSL-GEENFEVVKQF (SEQ ID NO:292); VTGIIDSLTISP-KAARVGL LQYSTQVH (SEQ ID NO:285); TEFTLRN-FNSAKDMKKAVAHMKYM (SEQ ID NO:286); GKGSMTGLALKHMFERSFTQGEGARPF (SEQ ID NO:287); STRVP RAAIVFTDGRAQDDVSEWASKA-KANGITMYAVGVGKAIE (SEQ ID NO:288); EELQE-IASEPTNKHLFYAEDFSTMDEISEKLKKGICEALEDS (SEQ ID NO:289); TQRLEEMTQRM (SEQ ID NO:290); PQGCPEQPLH (SEQ ID NO:291); YMGKGSMTGLA-LKHMFERSFT (SEQ ID NO:284), GWETLPKKDVCKST HHGCEHICVNNGNSYICKCSXGFV-LAEDGRRCKKCTEGPIDLVFVIDGSKSLG EENFE-VVKQFVTGIIDSLTISP-KAARVGLLQYSTQVHTEFTLRNFNSAKDMKKA VAHMKYMGKGSMTGLALKHMFERS-
FTQGEGARPFPQGCPEQPLCSPTDGLR MTSPSGPVK-
PRPMVSLCMLLG (SEQ ID NO:293), or
KFYPRRRGQALSTRVP RAAIVFIGRAQDDVSE-
WASKAKANGITMYAVGVGKAIEEELQEIASEPTNKH
LFYAEDFSTMDEISEKLKKGICEALEDS-
DGRQDSPAGELPKTVQQPTVQHRYLF EEDNLL-
RSTQKLSHSTKPSGSPLEEKHDQCKCEN-
LIMFQNLANEEVRKLTQRLE
EMTQRMEALENRLRYR (SEQ ID NO:294). Polynucleotides encoding these polypeptides are also encompassed by the invention. The gene encoding the disclosed cDNA is believed to reside on chromosome 8. Accordingly, polynucleotides related to this invention are useful as a marker in linkage analysis for chromosome 8.

This gene is expressed primarily in placenta, infant brain, prostate, fetal lung and to a lesser extent in endometrium and fetal tissues.

Therefore, polynucleotides and polypeptides of the invention are useful as reagents for differential identification of the tissue(s) or cell type(s) present in a biological sample and for diagnosis of diseases and conditions, which include, but are not limited to, abnormal placenta and pregnancy, disorder and injury in brain, prostate, and vasculature. Similarly, polypeptides and antibodies directed to these polypeptides are useful in providing immaunological probes for differential identification of the tissue(s) or cell type(s). For a number of disorders of the above tissues or cells, particularly of the reproduction, neuronal, and vascular systems, expression of this gene at significantly higher or lower levels may be routinely detected in certain tissues or cell types (e.g.developing, placenta, brain and other tissue of the nervous system, prostate, lung and endometrium, and cancerous and wounded tissues) or bodily fluids (e.g.amniotic fluid, seminal fluid, pulmonary surfactant, or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in placental tissues indicates that polynucleotides and polypeptides corresponding to this gene are useful for diagnosis, treatment, and cure of abnormalities in placenta and pregnancy, disorder and injury in brain, prostate, and vasculature. Similarly, the homology to the cartilage matrix protein suggests that the protein product of this clone would be useful for the treatment, diagnosis, and/or prevention of various skin disorders including congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Moreover, the protein product of this clone may also be useful for the treatment or diagnosis of various connective tissue disorders such as arthritis, trauma, tendonitis, chrondomalacia and inflammation, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related-to SEQ ID NO:64 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1654 of SEQ ID NO:64, b is an integer of 15 to 1668, where both a and b correspond to the positions of nucleotide residues shown in SEQ ID NO:64, and where the b is greater than or equal to a +14.

Features of Protein Encoded by Gene No: 55

The translation product of this gene is the human ortholog of bovine and hamster CII-3, a succinate-ubiquinone oxidoreductase complex II membrane-intrinsic subunit, which is thought to be important in mitochondrial electron transport chain during metabolism. In specific embodiments, the polypeptides of the invention compriseMAALLLRH-
VGRHCLRABIFSPQLCIRNAVPLGTTA-
KEEMERFWNKNIG SNRPLSPHITIYS (SEQ ID NO:295); VFPLMYHTWNGIRHLMWDLGKGLKIPQL YQSG (SEQ ID NO:296); MAALLLRHVGRHCLRAH (SEQ ID NO:297); VKSLCL GPALIHTAKFAL (SEQ ID NO:298); VFPLMYHTWNGIRHLMWDLGKGL (SEQ ID NO:299).

This gene is expressed in 8-week old early stage human.

Therefore, polynucleotides and polypeptides of the invention are useful as reagents for differential identification of the tissue(s) or cell type(s) present in a biological sample and for diagnosis of diseases and conditions, which include, but are not limited to, metabolic or developmental disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., developmental, metabolic, cancerous and wounded tissues) or bodily fluids (e.g., lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in fetal tissue combined with the homology to a metabolic protein indicates that polynucleotides and polypeptides corresponding to this gene are useful for diagnosis, treatment, and cure of metabolism disorders. Similarly, expression within embryonic tissue and other cellular sources marked by proliferating cells suggests that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1339 of SEQ ID NO:65, b is an integer of 15 to 1353, where both a and b correspond to the positions of nucleotide residues shown in SEQ ID NO:65, and where the b is greater than or equal to a +14.

Features of Protein Encoded by Gene No: 56

This gene is expressed primarily in umbilical vein endothelial cells, human ovarian tumor cells, human meningima cells, and human Jurkat membrane bound polysomes. In specific embodiments, polypeptides of the invention comprise the amino acid sequence: RVWDVRPFAPKER-CVKIFQGNV (SEQ ID NO:300); HNFEKNLL RCSWSP-DGSKLAAGSADRFVYV (SEQ ID NO:301); WDTTSRRILYKLPG HAGSINEVAFHPDEPI (SEQ ID NO:302), YQGLGLRQNKLTYTMRGHADSVTG LSLS-SEGSYLLSNAMDNTVRVWDVRPFAPKER-CVKIFQGNVHNFFKNLLRCS WSPDGSKIAAG-SADRFVYVWDTTSRRILYKLPGHAGSINEVAFHIPD-EPHISASS DKRLYMGEIQ (SEQ ID NO:303), or RKKAAIQTFQNTYQVLAVTFNDTSD QIISG-GIDNDIKVWDCARTS (SEQ ID NO:304). Polynucleotides encoding these polypeptides are also encompassed by the invention.

Therefore, polynucleotides and polypeptides of the invention are useful as reagents for differential identification of the tissue(s) or cell type(s) present in a biological sample and for diagnosis of diseases and conditions, which include, but are not limited to, inflammation, immune and cardiovascular disorders and urogenital neoplasias, and developmental disorders. Similarly, polypeptides and antibodies directed to these polypeptides are useful in providing immunological probes for differential identification of these tissue(s) or cell type(s). For a number of disorders of the above tissues or cells, particularly of the immune, neurological, urogenital, reproductive system and vascular systems, expression of this gene at significantly higher or lower levels may be routinely detected in certain tissues and cell types (e.g., blood cells, cells, endothelial cells, ovary and other reproductive tissue, developmental, meningima, and cancerous and wounded tissues).or bodily fluids (e.g.amniotic fluid, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:143 as residues: Phe-71 to Arg-76, Pro-82 to His-87, Glu-103 to Ala-111.

The tissue distribution in immune cells indicates that polynucleotides and polypeptides corresponding to this gene are useful for the diagnosis and treatment of immune disorders including: leukemias, lymphomas, auto-immune, immuno-supressive (e.g. transplantation) and immunodeficiencies (e.g. AIDS) and hematopoietic disorders. In addition, expression in ovarian tumor cells suggests that polynucleotides and polypeptides corresponding to this gene are useful for study, diagnosis, and treatment of ovarian tumors, and other tumors and neoplasias. Further, endothelial cell expression suggests a role in cadiovascular or respiratory/pulmonary disorders or infections (asthma, pulmonary edema, pneumonia). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 997 of SEQ ID NO:66, b is an integer of 15 to 1011, where both a and b correspond to the positions of nucleotide residues shown in SEQ ID NO:66, and where the b is greater than or equal to a +14.

Features of Protein Encoded by Gene No: 57

The translation product of this gene shares sequence homology with type I collagen. In specific embodiments, the polypeptides of the invention comprise the sequence: GRI-PAPAPSVPAGPDSR (SEQ ID NO:308); VRGRTVLR-PGLDAEPE LSPE (SEQ ID NO:305); EQRVLERKLK-KERKKEERQ (SEQ ID NO:306); ARRSG AELAWDYLCRWAQKHKNWRFQK-TRQTWLLHMYDSDKVPDEHFSTLLAYLE GLQGR (SEQ ID NO:309); and/or RLREAGLVAQHPP (SEQ ID NO:307). Polynucleotides encoding these polypeptides are also encompassed by the invention. Polynucleotides of the invention do not comprise the nucleic acid sequence shown as Genbank Accession No. gb|L07392|HUMRETPIGA, which is hereby incorporated herein by reference.

This gene is expressed primarily in epididymus, prostate cell line (LNCAP), and pituitary gland; and to a lesser extent in many other tissues.

Therefore, polynucleotides and polypeptides of the invention are useful as reagents for differential identification of the tissue(s) or cell type(s) present in a biological sample and for diagnosis of diseases and conditions, which include, but are not limited to, abnormalities of the epididymus, prostate (especially prostate cancer), pituitary gland, or other reproductive, urogenital, or endocrine disorders. Similarly, polypeptides and antibodies directed to these polypeptides are useful in providing immunological probes for differential identification of the tissue(s) or cell type(s). For a number of disorders of the above tissues or cells, particularly of the male reproductive system and neuroendocrine system, expression of this gene at significantly higher or lower levels may be routinely detected in certain tissues and cell types (e.g., epididymus and other reproductive tissue, prostate, and pituitary gland, and cancerous and wounded tissues) or bodily fluids (e.g.seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to type I collagen, indicates that polynucleotides and polypeptides corresponding to this gene are useful for diagnosis and treatment of abnormalities of the epididymus, prostate (especially prostate cancer), and pituitary gland. Similarly, the protein product of this clone may also be useful for the treatment or diagnosis of various connective tissue disorders such as arthritis, trauma, tendonitis, chrondomalacia and inflammation, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b where a is any integer between 1 to 1179 of SEQ ID NO:67, b is an integer of 15 to 1193, where both a and b correspond to the positions of nucleotide residues shown in SEQ ID NO:67, and where the b is greater than or equal to a +14.

Features of Protein Encoded by Gene No: 58

This gene is expressed primarily in the frontal cortex of the brain from a schizophrenic individual.

Therefore, polynucleotides and polypeptides of the invention are useful as reagents for differential identification of the tissue(s) or cell type(s) present in a biological sample and for diagnosis of diseases and conditions, which include, but are not limited to, neural disorders, particularly neurodegenerative disorders such as schizophrenia. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues and cell types (e.g., brain and other tissue of the nervous system, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for the detection/treatment of neurodegenerative disease states, behavioural disorders, or inflammatory conditions such as Alzheimers Disease, Parkinsons Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 546 of SEQ ID NO:68, b is an integer of 15 to 560, where both a and b correspond to the positions of nucleotide residues shown in SEQ ID NO:68, and where the b is greater than or equal to a +14.

Features of Protein Encoded by Gene No: 59

The polypeptide encoded by Gene 59 is homologous to human surface 4 integral membrane protein. In specific embodiments, the polypeptides of the invention comprise the sequence: TGCVLVLSRNFVQYACFGLFGIIALQ-TIAYSILWDLKF LMRN (SEQ ID NO:310); SRSEGKSM-FAGVPTMSSPKQYMQLGGRVLLVLMFMTLLH FDAS-FFSIVQNIVG (SEQ ID NO:311); GTAEDFADQFLRVTKQYLP HVARLCLIST FLEDG-IRMFQWSEQRDYIDT WNCGYLLAS (SEQ ID NO:312); LMRNESRS (SEQ ID NO:314); ASFLLSRTSWGTA (SEQ ID NO:315); ASFLLSRTSW GTALMIL (SEQ ID NO:313), ASFLLSRTSWGTALMIL (SEQ ID NO:316), PSFTL TPASFLLSRTSWGTALMILVAIGFKTK-LAALTLVVWLFAINVYFNAFWTIPVYK PMHDFLKY-DFFQT (SEQ ID NO:317), RTEPPPGTSCGGRSGCGR-RRARASE RASEPSRASRRRHGPERPDGHGRGLR-RPVPPCHKAVPAPRGAPLSDQHLPGG RHPYV-VPVERAARLHRHHLELRLPAGLVLR-LPQLAGTXTGCVLVLSRNFVQYA CFGLFGIIALQTIAYSILWDLKFLMRN-LALGGGLLLLLAESRSEGKSMFAGVPT MRESSP-KQYMQLGGRVLLVLMFMTLLHFDASFF-SIVQNIVGHSSDDFSGHWF (SEQ ID NO:318), GXSRRRALPVEAAAGAGADGREPASER-ASRAEPPAVAMGQ NDLMGTAEDFADQFLRVT-KQYLPHVARLCLISTFLEDGIWFQWSEQRDYIDT TWNCGYLLASSFVFLNLLGX (SEQ ID NO:319), or WVFLFLLALGGLGP DSGRCLCREGRJSGIYQLI-LAKQFLRFFCFMWETDLNLILCCILYLSCV (SEQ ID NO:320). Polynucleotides encoding these polypeptides are also encompassed by the invention. The gene encoding the disclosed cDNA is believed to reside on chromosome 9. Accordingly, polynucleotides related to this invention are useful as a marker in linkage analysis for chromosome 9.

This gene is expressed primarily in Hodgkin's lymphoma and lung; and to a lesser extent in many other human tissues.

Therefore, polynucleotides and polypeptides of the invention are useful as reagents for differential identification of the tissue(s) or cell type(s) present in a biological sample and for diagnosis of diseases and conditions, which include, but are not limited to, immune discorders, particularly Hodgkin's lymphoma, tumors or other abnormalities of the lung. Similarly, polypeptides and antibodies directed to these polypeptides are useful in providing immunological probes for differential identification of the tissue(s) or cell type(s). For a number of disorders of the above tissues or cells, particularly of the immune and respiratory systems, expression of this gene at significantly higher or lower levels may be routinely detected in certain tissues or cell types (e.g.hematopoietic, lymphoid tissue, and pulmonary tissue, and cancerous and wounded tissues) or bodily fluids (e.g- .lymph, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 179 as residues: Met-20 to Trp-27.

The tissue distribution in immune tissue indicates that polynucleotides and polypeptides corresponding to this gene are useful for diagnosis and treatment of Hodgkin's lymphoma, tumors or other abnormalities of the lung. Similarly, expression of this clone within immune tissues, particularly Hodgkin's lymphoma, suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1643 of SEQ ID NO:69, b is an integer of 15 to 1657, where both a and b correspond to the positions of nucleotide residues shown in SEQ ID NO:69, and where the b is greater than or equal to a +14.

Features of Protein Encoded by Gene No: 60

The gene encoding the disclosed cDNA is believed to reside on chromosome 17. Accordingly, polynucleotides related to this invention are useful as a marker in linkage analysis for chromosome 17.

This gene is expressed primarily in bone cancer and stomach cancer, and to a lesser extent in many other tissues.

Therefore, polynucleotides and polypeptides of the invention are useful as reagents for differential identification of the tissue(s) or cell type(s) present in a biological sample and for diagnosis of diseases and conditions, which include, but are not limited to, bone cancer and stomach cancer. Similarly, polypeptides and antibodies directed to these polypeptides are useful in providing immunological probes for differential identification of the tissue(s) or cell type(s). For a number of disorders of the above tissues or cells, particularly of the bone, and the stomach, expression of this gene at significantly higher or lower levels may be routinely detected in certain tissues (e.g., bone, and stomach, skeletal, gastrointestinal, and cancerous and wounded tissues) or bodily fluids (e.g.lymph, chyme, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in skeletal tissue indicates that polynucleotides and polypeptides corresponding to this gene are useful for diagnosis and treatment of skeletal or gastrointestinal disorders, particularly cancer. Similarly, the expression of this gene product in skeletal tissue would suggest a role in the detection and treatment of disorders and conditions affecting the skeletal system, in particular osteoporosis, bone cancer, as well as, disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 697 of SEQ ID NO:70, b is an integer of 15 to 711, where both a and b correspond to the positions of nucleotide residues shown in SEQ ID NO:70, and where the b is greater than or equal to a +14.

Features of Protein Encoded by Gene No: 61

The gene encoding the disclosed cDNA is believed to reside on the X chromosome. Accordingly, polynucleotides related to this invention are useful as a marker in linkage analysis for the X chromosome.

This gene is expressed primarily in epididymus, and lymph node of breast cancer, and to a lesser extent in many other tissues.

Therefore, polynucleotides and polypeptides of the invention are useful as reagents for differential identification of the tissue(s) or cell type(s) present in a biological sample and for diagnosis of diseases and conditions, which include, but are not limited to, abnormalities of the epididymus, and breast cancer or other reproductive conditions. Similarly, polypeptides and antibodies directed to these polypeptides are useful in providing immunological probes for differential identification of the tissue(s) or cell type(s). For a number of disorders of the above tissues or cells, particularly of the epididymus and breast, expression of this gene at significantly higher or lower levels may be routinely detected in certain tissues and cell types (e.g., epididymus and other reproductive tissue, lymphoid tissue, and mammary tissue, and cancerous and wounded tissues) or bodily fluids (e.g. lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 181 as residues: Arg-57 to Ser-65.

The tissue distribution in reproductive tissues indicates that polynucleotides and polypeptides corresponding to this gene are useful for diagnosis and treatment of abnormalities of the epididymus, breast cancer, or other reproductive disorders. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 921 of SEQ ID NO:71, b is an integer of 15 to 935, where both a and b correspond to the positions of nucleotide residues shown in SEQ ID NO:71, and where the b is greater than or equal to a +14.

Features of Protein Encoded by Gene No: 62

The translation product of this gene appears to be the human homolog of bovine NADH dehydrogenase which is thought to be important in cellular metabolism. In specific embodiments, the polypeptides of the invention comprise the amino acid sequence: SMSALTRLASFARVGGRLFRS-GCARTAGDGGVRHAGGGVHIEPRY RQFPQLTR-SQVFQSEFFSGLMWFWILWRFWHDSEEV-LGHFPYPDPSQWTDEEL GIPPDDED (SEQ ID NO:321), or fragments thereof. Polynucleotides encoding this polypeptide are also encompassed by the invention.

This gene is expressed in larynx tumor, lymph node, brain amygdala, human cardiomyopathy, and retina.

Therefore, polynucleotides and polypeptides of the invention are useful as reagents for differential identification of the tissue(s) or cell type(s) present in a biological sample and for diagnosis of diseases and conditions, which include, but are not limited to, diseases affecting cellular metabolism. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues and cell types (e.g., larynx, lymphoid tissue, endothelial, brain and other tissue of the nervous system, heart and cardiovascular tissue, and retina, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 182 as residues: Pro-42 to Thr-51, Pro-85 to Glu-95.

The tissue distribution and homology to NADH dehydrogenase indicates that polynucleotides and polypeptides corresponding to this gene are useful for the treatment and diagnosis of diseases involving cellular metabolism. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 490 of SEQ ID NO:72, b is an integer of 15 to 504, where both a and b correspond to the positions of nucleotide residues shown in SEQ ID NO:72, and where the b is greater than or equal to a +14.

Features of Protein Encoded by Gene No: 63

This gene is expressed primarily in amygdala, and to a lesser extent in many other tissues.

Therefore, polynucleotides and polypeptides of the invention are useful as reagents for differential identification of the tissue(s) or cell type(s) present in a biological sample and for diagnosis of diseases and conditions, which include, but are not limited to, neural disorders, particularly neurodegenerative disorders or abnormalities of the amygdala. Similarly, polypeptides and antibodies directed to these polypeptides are useful in providing immunological probes for differential identification of the tissue(s) or cell type(s). For a number of disorders of the above tissues or cells, particularly of the amygdala, expression of this gene at significantly higher or lower levels may be routinely detected in certain tissues and cell types (e.g.neural, amygdala, and lymphoid tissue, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 183 as residues: Gln-17 to Glu-29, Pro-41 to Phe-46, Ser-59 to Ile-70, Thr-97 to Leu-105.

The tissue distribution in neural tissue indicates that polynucleotides and polypeptides corresponding to this gene are useful for diagnosis and treatment of abnormalities of amygdala. Similarly, expression within neural tissues suggests that the protein product of this clone would be useful for the detection/treatment of neurodegenerative disease states, behavioural disorders, or inflamatory conditions such as Alzheimers Disease, Parkinsons Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 606 of SEQ ID NO:73, b is an integer of 15 to 620, where both a and b correspond to the positions of nucleotide residues shown in SEQ ID NO:73, and where the b is greater than or equal to a +14.

Features of Protein Encoded by Gene No: 64

This gene is expressed primarily in female bladder, and to a lesser extent in chronic synovitis and hemangiopericytoma.

Therefore, polynucleotides and polypeptides of the invention are useful as reagents for differential identification of the tissue(s) or cell type(s) present in a biological sample and for diagnosis of diseases and conditions, which include, but are not limited to, urogenital or skeletal disorders, particularly bladder cancer. Similarly, polypeptides and antibodies directed to these polypeptides are useful in providing immunological probes for differential identification of the tissue(s) or cell type(s). For a number of disorders of the above tissues or cells, particularly of the urinary tract, expression of this gene at significantly higher or lower levels may be routinely detected in certain tissues or cell types (e.g., bladder, synovial tissue, and vascular tissue, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 184 as residues: Pro-2 to Gln-7, Pro-27 to Phe-34.

The tissue distribution in urogenital tissue indicates that polynucleotides and polypeptides corresponding to this gene are useful for treatments of defects of the urinary tract, especially bladder cancer. Alternatively, expression within synovitis tissue suggests a role in the detection and treatment of disorders and conditions affecting the skeletal system, in particular osteoporosis, bone cancer, as well as, disorders afflicting connective tissues such as arthritis, trauma, tendonitis, chrondomalacia, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 567 of SEQ ID NO:74, b is an integer of 15 to 581, where both a and b correspond to the positions of nucleotide residues shown in SEQ ID NO:74, and where the b is greater than or equal to a +14.

Features of Protein Encoded by Gene No: 65

This gene is expressed primarily in fetal spleen, and to a lesser extent in hemangiopericytoma, thymus, and synovial sarcoma.

Therefore, polynucleotides and polypeptides of the invention are useful as reagents for differential identification of the tissue(s) or cell type(s) present in a biological sample and for diagnosis of diseases and conditions, which include, but are not limited to, defects of immune of hematopoietic systems. Similarly, polypeptides and antibodies directed to these polypeptides are useful in providing immunological probes for differential identification of the tissue(s) or cell type(s). For a number of disorders of the above tissues or cells, particularly of the immune of hematopoietic systems, expression of this gene at significantly higher or lower levels may be routinely detected in certain tissues or cell types (e.g.immune, hematopoietic, spleen, vascular tissue, thymus, blood cells, and synovial tissue, and cancerous and wounded tissues) or bodily fluids (e.g.lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The protein product of this gene is useful for treatment of defects of the immune or hematopoietic systems, because of the gene's expression in thymus and spleen. Similarly, the secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g.for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility);

chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1829 of SEQ ID NO:75, b is an integer of 15 to 1843, where both a and b correspond to the positions of nucleotide residues shown in SEQ ID NO:75, and where the b is greater than or equal to a +14.

Features of Protein Encoded by Gene No: 66

This gene is expressed primarily in human pituitary and to a lesser extent in placenta and fetal lung.

Therefore, polynucleotides and polypeptides of the invention are useful as reagents for differential identification of the tissue(s) or cell type(s) present in a biological sample and for diagnosis of diseases and conditions, which include, but are not limited to, endocrine growth disorders. Similarly, polypeptides and antibodies directed to these polypeptides are useful in providing immunological probes for differential identification of the tissue(s) or cell type(s). For a number of disorders of the above tissues or cells, particularly of the endocrine system, expression of this gene at significantly higher or lower levels may be routinely detected in certain tissues or cell types (e.g., pituitary and other endocrine tissue, placenta, developmental and pulmonary tissue, and cancerous and wounded tissues) or bodily fluids (e.g.lymph, amniotic fluid, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 186 as residues: Val-38 to Asn-44, Gly-53 to Ser-65.

The tissue distribution in fetal tissue indicates that polynucleotides and polypeptides corresponding to this gene are useful for treatment of disorders related to endocrine or pituitary dysfunction, particularly growth disorders. Similarly, expression within fetal tissue and other cellular sources marked by proliferating cells suggests that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1427 of SEQ ID NO:76, b is an integer of 15 to 1441, where both a and b correspond to the positions of nucleotide residues shown in SEQ ID NO:76, and where the b is greater than or equal to a +14.

Features of Protein Encoded by Gene No: 67

The translation product of this gene shares sequence homology with a *Caenorhabditis elegans* gene. In specific embodiments, the polypeptides of the invention comprise the sequence: DPRRPNKVLRYKPPPSE CNPALDDPTP (SEQ ID NO:323); DYMNLLGMIFSMCGLMLKLKW-CAWVA VYCS (SEQ ID NO:324); FISFANSRSSEDT-KQMMSSF (SEQ ID NO:322); and/or MLSISAVVM-SYLQN PQPMTPPW (SEQ ID NO:325). Polynucleotides encoding these polypeptides are also encompassed by the invention. The gene encoding the disclosed cDNA is believed to reside on chromosome 19. Accordingly, polynucleotides related to this invention are useful as a marker in linkage analysis for chromosome 19.

This gene is expressed primarily in primary breast cancer and lymph node breast cancer and to a lesser extent in adult brain, lung cancer, colon cancer, epithelioid sarcoma, and Caco-2 cell line.

Therefore, polynucleotides and polypeptides of the invention are useful as reagents for differential identification of the tissue(s) or cell type(s) present(in a biological sample and for diagnosis of diseases and conditions, which include, but are not limited to, reproductive, neural, or endothelial disorders, particularly cancer. Similarly, polypeptides and antibodies directed to these polypeptides are useful in providing immunological probes for differential identification of the tissue(s) or cell type(s). For a number of disorders of the above tissues or cells, particularly of the cancer and tumor tissues, expression of this gene at significantly higher or lower levels may be routinely detected in certain tissues or cell types (e.g., mammary tissue, lymphoid tissue, brain and other tissue of the nervous system, lung, colon, and epithelium, and cancerous and wounded tissues) or bodily fluids (e.g.lymph, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 187 as residues: Asn-34 to Lys-42.

The tissue distribution in a variety of cancer tissues indicates that polynucleotides and polypeptides corresponding to this gene are useful for treatment and diagnosis of a variety of cancer and tumor types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 896 of SEQ ID NO:77, b is an integer of 15 to 910, where both a and b correspond to the positions of nucleotide residues shown in SEQ ID NO:77, and where the b is greater than or equal to a +14.

Features of Protein Encoded by Gene No: 68

The translation product of this gene shares sequence homology with steroid membrane binding protein. The translation product of this gene has recently been published as progesterone binding protein. See Genbank AJ002030. Preferred polypeptides encoded by this gene comprise the following amino acid sequence: AAGDGDVKLGTLGSG-SESSNDGGSESPGDAGAAAXGGGWAAAALALLTG GGE (SEQ ID NO:326), or STHASGRAVMAAGDGD-VKLGTLGSGSESSNDGG SESPGDAGAAAXGGG-WAAAALALLTGGGE (SEQ ID NO:327). The gene encoding the disclosed cDNA is believed to reside on chromosome 4. Accordingly, polynucleotides related to this invention are useful as a marker in linkage analysis for chromosome 4.

This gene is expressed primarily in breast, and to a lesser extent in placenta and fetal tissue.

Therefore, polynucleotides and polypeptides of the invention are useful as reagents for differential identification of the tissue(s) or cell type(s) present in a biological sample and for diagnosis of diseases and conditions, which include, but are not limited to, breast cancer or developmental disorders. Similarly, polypeptides and antibodies directed to these polypeptides are useful in providing immunological probes for differential identification of the tissue(s) or cell type(s). For a number of disorders of the above tissues or cells, particularly of breast or fetal tissues, expression of this gene at significantly higher or lower levels may be routinely detected in certain tissues or cell types (e.g.reproductive, mammary tissue, placenta, and fetal tissue, and cancerous and wounded tissues) or bodily fluids (e.g.lymph, amniotic fluid- breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 188 as residues: Pro-43 to Asp-49, Gln-54 to Pro-64, Asp-110 to Asp-118, Lys-138 to Tyr-143, Pro-150 to Asp-170.

The tissue distribution in reproductive tissues combined with the homology to a steroid membrane binding protein and to progesterone binding protein indicates that the protein products of this gene are useful for treatment of breast cancers, especially those caused by estrogen and progesterone binding. Similarly, expression within fetal tissues and other cellular sources marked by proliferating cells suggests that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2762 of SEQ ID NO:78, b is an integer of 15 to 2776, where both a and b correspond to the positions of nucleotide residues shown in SEQ ID NO:78, and where the b is greater than or equal to a +14.

Features of Protein Encoded by Gene No: 69

It is likely that the open reading frame containing the predicted signal peptide continues in the 5' direction. Therefore, preferred polypeptides encoded by this gene comprise the following amino acid sequence:

AADNYGIPRACRNSARSYGAAWLLLXPAGSSRVE (SEQ ID NO:328)

PTQDISISDQLGGQDVPVFRNLSLLVVGVGAVFS

LLFHLGTRERRRPHAXEPGEHTPLLAPATAQPLL

LWKHWLREXAFYQVGILYMTTRLIVNLSQTYMAM

YLTYSLHLPKKFIATIPLVMYLSGFLSSFLMKPI

NKCIGRN.

This gene is expressed primarily in macrophage (GM-CSF treated), and to a lesser extent in monocytes and dendritic cells.

Therefore, polynucleotides and polypeptides of the invention are useful as reagents for differential identification of the tissue(s) or cell type(s) present in a biological sample and for diagnosis of diseases and conditions, which include, but are not limited to, immune or hematopoietic disorders, particularly inflammation and infection. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g.immune, macrophages and other blood cells, and dendritic cells, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in immune tissue indicates that the protein products of this gene are useful for treatment of infection or inflammation or other events or defects involving the immune system. Similarly, the tissue distribution suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1473 of SEQ ID NO:79, b is an integer of 15 to 1487, where both a and b correspond to the positions of nucleotide residues shown in SEQ ID NO:79, and where the b is greater than or equal to a +14.

Features of Protein Encoded by Gene No: 70

This gene was found to have homology to a conserved human 15 kDa selenoprotein (See Genbank Accession No. gil3095111 (AF051894)) which may be involved in the regulation of important cellular functions such as metabolism or cell cycle regulation.

This gene is expressed primarily in adult brain and to a lesser extent in thyroid, 12 week old early stage human, and stromal cell TF274.

Therefore, polynucleotides and polypeptides of the invention are useful as reagents for differential identification of the tissue(s) or cell type(s) present in a biological sample and for diagnosis of diseases and conditions, which include, but are not limited to, neurological or neuro-endocrine diseases. Similarly, polypeptides and antibodies directed to these polypeptides are useful in providing immunological probes for differential identification of the tissue(s) or cell type(s). For a number of disorders of the above tissues or cells, particularly of the central nervous or endocrine systems, expression of this gene at significantly higher or lower levels may be routinely detected in certain tissues and cell types (e.g., brain and other tissue of the nervous system, developmental, immune, thyroid, endocrine, and stromal cells, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 190 as residues: Pro-65 to Cys-71.

The tissue distribution in neural tissue indicates that the protein products of this gene are useful for treatment and diagnosis of neurological diseases or metabolic conditions involving the neuro-endocrine system. Similarly, the protein product of this clone would be useful for the detection/treatment of neurodegenerative disease states, behavioural disorders, or inflamatory conditions such as Alzheimers Disease, Parkinsons Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:80 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1549 of SEQ ID NO:80, b is an integer of 15 to 1563, where both a and b correspond to the positions of nucleotide residues shown in SEQ ID NO:80, and where the b is greater than or equal to a +14.

Features of Protein Encoded by Gene No: 71

In specific embodiments, polypeptides of the invention comprise the following amino acid sequence: CTLAMWX-LGHCDPRRCTGRKLARLGLVRCL RLGHRFGGLVL-SPVGKQYASPADRQLVAQSGVAVBDC-SWARLDETPFGK (SEQ ID NO:329). Polynucleotides encoding these polypeptides are also encompassed by the invention.

This gene is expressed in helper T-cells and, to a lesser extent, in adult brain and adult testes.

Therefore, polynucleotides and polypeptides of the invention are useful as reagents for differential identification of the tissue(s) or cell type(s) present in a biological sample and for diagnosis of diseases and conditions, which include, but are not limited to, immune disorders, meningitis or reproductive problems. Similarly, polypeptides and antibodies directed to these polypeptides are useful in providing immunological probes for differential identification of the tissue(s) or cell type(s). For a number of disorders of the above tissues or cells, particularly of the immune, neural and reproductive systems, expression of this gene at significantly higher or lower levels may be routinely detected in certain tissues and cell types (e.g., T-cells and other blood cells, brain and other tissue of the nervous system, testes and other reproductive tissue, and cancerous and wounded tissues) or bodily fluids (e.g.seminal fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 191 as residues: Val-18 to Tyr-24, Ala-89 to Asp-99, Asp-104 to Ala-1 17, Leu-121 to Pro-136.

The tissue distribution in immune cells indicates that polynucleotides and polypeptides corresponding to this gene are useful for the treatment and diagnosis of immune and reproductive disorders. Similarly, the secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g.for treating human immunodeficiency virus infection, cancer, autoimmune diseases and allergy); regulation of hematopoiesis (e.g. for treating anaemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating haemophilia, cardiac infarction etc.); anti-inflammatory activity (e.g. for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:81 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1006 of SEQ ID NO:81, b is an integer of 15 to 1020, where both a and b correspond to the positions of nucleotide residues shown in SEQ ID NO:81, and where the b is greater than or equal to a +14.

Features of Protein Encoded by Gene No: 72

The translated polypeptide of this contig has a high degree of identity with the Ob Receptor-Associated Protein deposited as GenBank Accession No. 2266638. No function has been determined for the Ob Receptor-Associated Protein, however it is expressed upon stimulation of the Ob Receptor by Leptin. In specific embodiments, polypeptides of the invention comprise the following amino acid sequence: SGRGARSDVTAMAGIKALISLSFG-GAIGLMFLMLGCALPIYNKYWPLFVLFFYI LSPIPY-CIARRLVDDTDA (SEQ ID NO:330). Polynucleotides encoding these polypeptides are also encompassed by the invention.

This gene is expressed in T-cells and to a lesser extent in endothelial and bone marrow cells.

Therefore, polynucleotides and polypeptides of the invention are useful as reagents for differential identification of the tissue(s) or cell type(s) present in a biological sample and for diagnosis of diseases and conditions, which include, but are not limited to, acute lymphoblastic leukemia, hematapoetic disorders. Similarly, polypeptides and antibodies directed to these polypeptides are useful in providing immunological probes for differential identification of the tissue(s) or cell type(s). For a number of disorders of the above tissues or cells, particularly of the immune and hematapoetic systems, expression of this gene at significantly higher or lower levels may be routinely detected in certain tissues and cell types (e.g.immune, T-cells and other blood cells, endothelial cells, and bone marrow, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder Preferred epitopes include those comprising a sequence shown in SEQ ID NO. 192 as residues: Ser-61 to Trp-70.

The tissue distribution in T-cells indicates that polynucleotides and polypeptides corresponding to this gene are useful for treatment and diagnosis of leukemia and other disorders of the primary immune system. In addition, since this gene appears to be related to the Ob Receptor-Related Protein, it is likely that this polypeptide is also involved in the Ob/Leptin signal transduction cascade. As a result, this protein may be of use in the molecular diagnosis and therapeutic intervention of obesity and related disorders. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:82 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 756 of SEQ ID NO:82, b is an integer of 15 to 770, where both a and b correspond to the positions of nucleotide residues shown in SEQ ID NO:82, and where the b is greater than or equal to a +14.

Features of Protein Encoded by Gene No: 73

The translation product of this contig has homology with furin, a protein thought to be a key endopeptidase in the constitutive secretory pathway. The identification and initial characterization of Furin was reported by Takahasi and colleagues (Biochem Biophys Res Commun 1993 Sep. 15;195(2):1019–1026).

This gene is expressed primarily in neutrophils.

Therefore, polynucleotides and polypeptides of the invention are useful as reagents for differential identification of the tissue(s) or cell type(s) present in a biological sample and for diagnosis of diseases and conditions, which include, but are not limited to, diseases of the immune system such as allergies, wound healing and antigen recognition. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g.immune tissues, neutrophils and other blood cells, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for treatment of allergies or other immune disorders since neutrophils are an important part of an allergic response. Further, since this protein appears to be related to furin, it can be used diagnostically and therapeutically to treat secretory protein processing disorders. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:83 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 467 of SEQ ID NO:83, b is an integer of 15 to 481, where both a and b correspond to the positions of nucleotide residues shown in SEQ ID NO:83, and where the b is greater than or equal to a +14.

Features of Protein Encoded by Gene No: 74

This gene is expressed in the frontal cortex.

Therefore, polynucleotides and polypeptides of the invention are useful as reagents for differential identification of the tissue(s) or cell type(s) present in a biological sample and for diagnosis of-diseases and conditions, which include, but are not limited to, of the motor activity and sensory functions that involve the central nervous system. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain and other tissue of the nervous system, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in neural tissue indicates that polynucleotides and polypeptides corresponding to this gene are useful for the detection and treatment of neural disorders that affect cognitive functions. Similarly, the protein product of this clone would be useful for the detection/treatment of neurodegenerative disease states, behavioural disorders, or inflamatory conditions such as Alzheimers Disease, Parkinsons Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:84 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 630 of SEQ ID NO:84, b is an integer of 15 to 644, where both a and b correspond to the positions of nucleotide residues shown in SEQ ID NO:84, and where the b is greater than or equal to a +14.

Features of Protein Encoded by Gene No: 75

The translation product of this gene shares sequence homology with inorganic pyrophophatase which is thought to be important in the catalysis the hydrolysis of diphosphate bonds, chiefly in nucleoside di- and triphosphates and essential enzymes that are important for controlling the cellular levels of inorganic pyrophosphate (PPi). The bovine homolog of this gene has been identified by Yang and Wensel (J. Biol. Chem. 267:24641–24647 (1992)). In specific embodiments, polypeptides of the invention comprise the following amino acid sequence:

ARVRXRGALSLSVGAACGLVALWQRRRQDSGT. (SEQ ID NO:331)

Polynucleotides encoding these polypeptides are also encompassed by the invention.

This gene is expressed in osteoclastoma cells and to a lesser extent in- epithelial cells.

Therefore, polynucleotides and polypeptides of the invention are useful as reagents for differential identification of the tissue(s) or cell type(s) present in a biological sample and for diagnosis of diseases and conditions, which include, but are not limited to, osteoporosis and other skeletal disorders. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels may be routinely detected in certain tissues and cell types (e.g., bone, and epithelial cells, and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 195 as residues: Lys-22 to Tyr-28, Asp-64 to Lys-77, Pro-86 to Ile-91, Gln-99 to Pro-1 19, Tyr-169 to Asp-174, Lys-176 to Gly-181, Trp-189 to Asn-202, Lys-233 to Gly-239, Ser-250 to Asp-257.

The tissue distribution in osteoclastoma cells and homology to inorganic pyrophophatase indicates that polynucleotides and polypeptides corresponding to this gene are useful for treatment and diagnosis of osteoporosis through the removal of bone by demineralization. Similarly, the expression of this gene product in osteoclastoma cells would suggest a role in the detection and treatment of disorders and conditions affecting the skeletal system, in particular osteoporosis, bone cancer, as well as, disorders afflicting connective tissues such as arthritis, trauma, tendonitis, chrondomalacia, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO: 85 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1337 of SEQ ID NO:85, b is an integer of 15 to 1351, where both a and b correspond to the positions of nucleotide residues shown in SEQ ID NO:85, and where the b is greater than or equal to a +14.

Features of Protein Encoded by Gene No: 76

The translation product of this gene shares exact sequence homology with ATP sulfurylase/APS kinase (GenBank Accession No. 2673862) which is thought to be important in biosynthesis of the activated sulfate donor, adenosine 3'-phosphate 5'-phosphosulfate, involves the sequential action of two enzyme activities: ATP sulfurylase, which catalyzes the formation of adenosine 5'-phosphosulfate (APS) from ATP and free sulfate, and APS kinase, which subsequently phosphorylates APS to produce adenosine 3'-phosphate 5'-phosphosulfate. In specific embodiments, polypeptides of the invention comprise the following amino acid sequence:

LSNNAQNWGMQRATNVTYQAHHVSRNKRGQVVGTRGGFRGCTVWL (SEQ ID NO:332), VSMALEEYLVCHGIPCYTLDGDNIRQGLNKNLGFSPED (SEQ ID NO:333), TQDRNNARQIHEGASLPFFVFVDAPLHVCEQRDVKGLY (SEQ ID NO:334), FTGIDSEYEKPEAPELVLKTDSCDVNDCVQQVVELLQERD (SEQ ID NO:335), AETLPALKINKVDMQWVQVLAEGWATPLNGFMREREYLQCL (SEQ ID NO:336), VPIVLTATHEDKERLDGCTAFALMYEGRRV (SEQ ID NO:337), IGGDLQVLDRVYWNDGLDQYRLTPTELKQKFKDMNADAV (SEQ ID NO:338), GHALLMQDTHKQLLERGYRRPVLLLHPLGGWTKDDDV (SEQ ID NO:339), MYAGPTEVQWHCRARMVAGANFYIVGRDPAGMPHPETGKDL (SEQ ID NO:340), LTMAPGLITLEIVPFRVAAYNKKKKRMDYYDSEH (SEQ ID NO:341) or, GFMAPKAWTVLTEYYKSLE (SEQ ID NO:342). Polynucleotides encoding these polypeptides are also encompassed by the invention.

This gene is expressed in osteoclastoma cells and to a lesser extent in developmental tissues.

Therefore, polynucleotides and polypeptides of the invention are useful as reagents for differential identification of the tissue(s) or cell type(s) present in a biological sample and for diagnosis of diseases and conditions, which include, but are not limited to, antibiotic resistant bacterial infections, osteoarthritis and other auto immune diseases, or skeletal disorders. Similarly, polypeptides and antibodies directed to these polypeptides are useful in providing immunological probes for differential identification of the tissue(s) or cell type(s). For a number of disorders of the above tissues or cells, particularly of the immune or skeletal structure expression of this gene at significantly higher or lower levels may be routinely detected in certain tissues or cell types (e.g., bone, and developmental tissues, and -cancerous and wounded tissues) or bodily fluids (e.g.lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 196 as residues: Asn-15 to Trp-20, Ser-36 to Gly-41, Pro-103 to Val-110, Pro-134 to Arg-143, Leu-173 to Arg-178, Ser-190 to Ala-197, His-314 to Arg-319, Arg-354 to Asn-362, Asp-391 to Arg-397, Glu-402 to Asp-409, Asp-434 to Leu-439, Glu-441 to Arg-446, Gly-455 to Asp-462, Pro-528 to His-541, Asn-566 to Arg-571, Tyr-574 to Glu-581, Thr-589 to Glu-603.

The tissue distribution and homology to ATP sulfurylase/ APS kinase indicates that polynucleotides and polypeptides corresponding to this gene are useful for the treatment or detection of autoimmune diseases. Similarly,- the expression of this gene product in synovium would suggest a role in the detection and treatment of disorders and conditions affecting the skeletal system, in particular osteoporosis, bone cancer, as well as, disorders afflicting connective tissues such as arthritis, trauma, tendonitis, chrondomalacia, autoimmune disorders such as rheumatoid arthritis, lupus, scleroderma, and dermatomyositis as well as dwarfism, spinal deformation, and specific joint abnormalities as well as chondrodysplasias (i.e. spondyloepiphyseal dysplasia congenita, familial osteoarthritis, Atelosteogenesis type II, metaphyseal chondrodysplasia type Schmid). Protein, as well as, antibodies directed against the protein may show utility as a tumor marker and/or immunotherapy targets for the above listed tissues. Many polynucleotide sequences, such as EST sequences, are publicly available and accessible through sequence databases. Some of these sequences are related to SEQ ID NO:86 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2513 of SEQ ID NO:86, b is an integer of 15 to 2527, where both a and b correspond to the positions of nucleotide residues shown in SEQ ID NO:86, and where the b is greater than or equal to a +14.

Features of Protein Encoded by Gene No: 77

This polypeptide is identical to the SLP-76-associated protein reported by Musci and colleagues (J. Biol. Chem. 272 (18), 11674–11677 (1997)) and to the FYB protein reported by da Silva and coworkers (Proc. Natl. Acad. Sci. U.S.A. (1997) In press). These proteins have been reported to be novel T-cell Proteins which bind FYN and SLP-76 and regulate IL-2 production. Preferred polypeptides encoded by this gene comprise the following amino acid sequence:

RITDNPEGKWLGRTARGSYGYIK TTAVEIXYD-
SLKLKKDSLGAPSRPIEDDQEVYDD-
VAEQDDISSHSQSGSGGIFPP PPDDDIYDG-
IEEEDADDGFPAPPKQLDMGDEVYDDVDTSDFPVSS-
AEMSQGTNV GKAKTEEKDLKKLKKQXKEXKD-
FRKKFKYDGEIRVLYSTKVTTSITSKKWGT RDLQVK-
PGESLEVIQTIDDTKVLCRNEEGKYGYV-
LRSYLADNDGEIYDDIADGC IYDND (SEQ ID NO:343).

This gene is expressed in CD34 positive cells (hematopoietic progenitor cells) and to a lesser extent in adult spleen derived from a chronic lymphocytic leukemia patient.

Therefore, polynucleotides and polypeptides of the invention are useful as reagents for differential identification of the tissue(s) or cell type(s) present in a biological sample and for diagnosis of diseases and conditions, which include, but are not limited to, chronic lymphocytic leukemia; hematopoietic disorders. Similarly, polypeptides and antibodies directed to these polypeptides are useful in providing immunological probes for differential identification of the tissue(s) or cell type(s). For a number of disorders of the above tissues or cells, particularly of the immune and hematopoietdc systems, expression of this gene at significantly higher or lower levels may be routinely detected in certain tissues or cell types (e.g., T-cells and other blood cells, bone marrow, hematopoietic cells, and spleen, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Further, nucleic acids and polypeptides of the present invention are useful both diagnostically and therapeutically in the intervention of immune and other disorders in which the ability to alter IL-2 expression is desired. Preferred epitopes include those comprising a sequence shown in SEQ ID NO. 197 as residues: Ala-17 to Lys-37, Val-39 to Ser-45, Lys-59 to His-70, Arg-90 to Leu-95, Lys-97 to Lys-107, Ser-1 17 to Leu-124, Phe-133 to Ser-138, Trp-146 to Leu-167, Pro-175 to Asn-185, Lys-190 to Ser-211, Pro-213 to Ser-222, His-230 to Pro-235, Pro-240 to Pro-246, Pro-253 to Gly-261, Leu-271 to Leu-303, Leu-305 to Leu-326, Lys-343 to Leu-349, Thr-363 to Leu-371, Arg-373 to Tyr-381, Tyr-391 to Leu-401, Pro-404 to Val-414, Ser-426 to Ser-432, Ile-448 to Ser-457, Gln-462 to Trp-468, Lys-477 to Ser-501, Asp-518 to Ser-523, Ala-541 to Gln-554.

The tissue distribution in immune cells indicates that polynucleotides and polypeptides corresponding to this gene are useful for the treatment of a variety of hematopoietic disorders. The noted expression of this gene in hematopoietic progenitor cell—as determined by its expression on CD34 positive hematopoietic stem and progenitor cells—indicates that it plays a critical role in the expansion or proliferation of hematopoietic stem/progenitor cells, as well as in the differentiation of the various blood cell lineages. Thus it could be useful in the reconstitution of the hematopoietic system of patients with leukemias and other hematopoietic diseases. Protein, as well as, antibodies directed against the protein may show utility as a tissue-specific marker and/or immuntherapy target for the above-listed tissues. Many polynucleotide sequences, such as EST sequences, are publicly available and accessible through sequence databases. Some of these sequences are related to SEQ ID NO:87 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2552 of SEQ ID NO:87, b is an integer of 15 to 2566, where both a and b correspond to the positions of nucleotide residues shown in SEQ ID NO:87, and where the b is greater than or equal to a +14.

Features of Protein Encoded by Gene No: 78

This gene is homologous to heparin cofactor II (HCII) which is a 66-kDa plasma glycoprotein that inhibits thrombin rapidly in the presence of dermatan sulfate or heparin.

This gene is expressed in apoptotic and anergic T-cells.

Therefore, polynucleotides and polypeptides of the invention are useful as reagents for differential identification of the tissue(s) or cell type(s) present in a biological sample and for diagnosis of diseases and conditions, which include, but are not limited to, thrombopienia T-cell lymphomas; Hodgkin's lymphoma. Similarly, polypeptides and antibodies directed to these polypeptides are useful in providing immunological probes for differential identification of the tissue(s) or cell type(s). For a number of disorders of the above tissues or cells, particularly of the immune system—most notably the T-cell compartment, expression of this gene at significantly higher or lower levels may be routinely detected in certain tissues and cell types (e.g., T-cells and other blood cells, and lymphoid tissue, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The homology to heparin cofactor II (HCII) and the tissue distribution indicates that polynucleotides and polypeptides corresponding to this gene are useful for the treatment and diagnosis of hematopoietic disorders particularly in thrombopoesis, most notably of the T-cell compartment. This could include immune modulation, inflammation, immune surveillance, graft rejection, and autoimmunity. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:88 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 526 of SEQ ID NO:88, b is an integer of 15 to 540, where both a and b correspond to the positions of nucleotide residues shown in SEQ ID NO:88, and where the b is greater than or equal to a +14.

Features of Protein Encoded by Gene No: 79

The translation product of this gene shares sequence homology with a mouse protein believed to represent an integral membrane protein.

This gene is expressed in fetal cochlea and epididymus and to a lesser extent in adult spleen and osteoclastoma.

Therefore, polynucleotides and polypeptides of the invention are useful as reagents for differential identification of the tissue(s) or cell type(s) present in a biological sample and for diagnosis of diseases and conditions, which include, but are not limited to, osteoclastoma; disorders of the inner ear; male fertility disorders. Similarly, polypeptides and antibodies directed to these polypeptides are useful in providing immunological probes for differential identification of the tissue(s) or cell type(s). For a number of disorders of the above tissues or cells, particularly of the inner ear; male reproductive tract; bone; and immune systems, expression of this gene at significantly higher or lower levels may be routinely detected in certain tissues or cell types (e.g., cochlea, epididymus and other reproductive tissue, spleen, immune tissue, and bone, and cancerous and wounded tissues) or bodily fluids (e.g., lymph, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 199 as residues: Lys-13 to Gly-23, Cys-38 to Asp-43, Gly-48 to Trp-53, Cys-223 to Ile-237, Ile-240 to Ser-246.

The tissue distribution in reproductive tissue indicates that polynucleotides and polypeptides corresponding to this gene are useful for the treatment of hearing and fertility disorders. Likewise, it may have a role in the modulation of immune function and in the treatment of osteoporosis. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:89 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1849 of SEQ ID NO:89, b is an integer of 15 to 1863, where both a and b correspond to the positions of nucleotide residues shown in SEQ ID NO:89, and where the b is greater than or equal to a +14.

Features of Protein Encoded by Gene No: 80

The translation product of this gene shares sequence homology with reticulocalbin which is thought to be important in the binding of calcium, particularly within the endoplasmic reticulum.

This gene is expressed in endothelial cells and stromal cells and to a lesser extent in osteoblasts, osteoclasts, and T-cells.

Therefore, polynucleotides and polypeptides of the invention are useful as reagents for differential identification of the tissue(s) or cell type(s) present in a biological sample and for diagnosis of diseases and conditions, which include, but are not limited to, osteoperosis; osteoclastomas; T-cell lymphomas; Hodgkin's disease. Similarly, polypeptides and antibodies directed to these polypeptides are useful in providing immunological probes for differential identification of the tissue(s) or cell type(s). For a number of disorders of the above tissues or cells, particularly of the vasculature, bone, and immune systems - particularly the T-cell compartments, expression of this gene at significantly higher or lower levels may be routinely detected in certain tissues and cell types (e.g., endothelial cells, stromal cells, bone, T-cells and other blood cells, and lymphoid tissue, and cancerous and wounded tissues) or bodily fluids.(e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 200 as residues: Lys-20 to Arg-27, Pro-32 to Asp-48, Leu-64 to Arg-72, Asp-108 to Lys-114, Glu-128 to Thr-133, Asp-139 to Phe-147, Thr-196 to Ala-204, Tyr-218 to Glu-228, Val-230 to Gln-236, Arg-241 to Lys-255, Glu-276 to Lys-287.

The tissue distribution and homology to reticulocalbin indicates that polynucleotides and polypeptides corresponding to this gene are useful for the diagnosis and treatment of bone disorders such as osteoporosis; the diagnosis and treatment of T-cell lymphomas and Hodgkin's lymphoma; and the treatment of diseases and defects of the vasculature, such as vascular leak syndrome and aberrant angiogenesis that accompanies tumor growth. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:90 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2464 of SEQ ID NO:90, b is an integer of 15 to 2478, where both a and b correspond to the positions of nucleotide residues shown in SEQ ID NO:90, and where the b is greater than or equal to a +14.

Features of Protein Encoded by Gene No: 81

The translation product of this gene shares sequence homology with a family of peptide transport genes—particularly the AtPTR2-B gene from *Arabidopsis*—which are thought to be important in the uptake of small peptides.

This gene is expressed in a number of fetal tissues, most notably lung, brain,. cochlea, and liver/spleen, and to a lesser extent in osteoclastoma and endometrial tumors.

Therefore, polynucleotides and polypeptides of the invention are useful as reagents for differential identification of the tissue(s) or cell type(s) present in a biological sample and for diagnosis of diseases and conditions, which include, but are not limited to, osteoclastoma; endometrial tumors; cancer; leukemias. Similarly, polypeptides and antibodies directed to these polypeptides are useful in providing immunological probes for differential identification of the tissue(s) or cell type(s). For a number of disorders of the above tissues or cells, particularly of the bone and endometrium, expression of this gene at significantly higher or lower levels may be routinely detected in certain tissues or cell types (e.g., fetal tissue, pulmonary tissue, bone, brain and other tissue of the nervous system, cochlea, liver, and spleen, and cancerous and wounded tissues) or bodily fluids (e.g., lymph, pulmonary surfactant or sputum, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 201 as residues: Lys-186 to Asn-199, Pro-202 to Ala-207.

The tissue distribution in fetal tissues combined with the homology to peptide transport proteins indicates that polynucleotides and polypeptides corresponding to this gene are useful for the control of cell proliferation, owing to its strong expression in fetal tissues undergoing active cell division, as well as its expression in a variety of tumors or cancers of adult tissues. Potentially, it may regulate the uptake of peptides that stimulate cell proliferation. This gene product may also be useful in stimulating the uptake of a variety of peptide-based drug compounds. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:91 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2044 of SEQ ID NO:91, b is an integer of 15 to 2058, where both a and b correspond to the positions of nucleotide residues shown in SEQ ID NO:91, and where the b is greater than or equal to a +14.

Features of Protein Encoded by Gene No: 82

This gene is expressed in fetal liver and spleen and to a lesser extent in endothelial cells.

Therefore, polynucleotides and polypeptides of the invention are useful as reagents for differential identification of the tissue(s) or cell type(s) present in a biological sample and for diagnosis of diseases and conditions, which include, but are not limited to, cancer and tumors of a hematopoietic and/or endothelial cell origin; leukemias. Similarly, polypeptides and antibodies directed to these polypeptides are useful in providing immunological probes for differential identification of the tissue(s) or cell type(s). For a number of disorders of the above tissues or cells, particularly of the immune system and/or vasculature, expression of this gene at significantly higher or lower levels may be routinely detected in certain tissues and cell types (e.g., liver, spleen, endothelial cells, vascular tissue, and tissue and cells of the immune system, and cancerous and wounded tissues) or bodily fluids (e.g., lymph, amniotic fluid, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder Preferred epitopes include those comprising a sequence shown in SEQ ID NO. 202 as residues: Met-1 to Asp-9, Arg-66 to Gly-76, Asp-164 to Arg-171.

The tissue distribution in immune tissue indicates that polynucleotides and polypeptides corresponding to this gene are useful for the treatment of disorders of the immune system. Expression of this gene product in both fetal liver/spleen and endothelial cells indicates that it may be expressed in the hemangioblast, the progenitor cell for both the immune system and the vasculature. Thus, it is most likely expressed in hematopoietic stem cells, and may be useful for the expansion of hematopoietic stem and progenitor cells in conjunction with cancer treatment for a variety of leukemias. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:92 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1397 of SEQ ID NO:92, b is an integer of 15 to 1411, where both a and b correspond to the positions of nucleotide residues shown in SEQ ID NO:92, and where the b is greater than or equal to a +14.

Features of Protein Encoded by Gene No: 84

The translation product of this gene shares sequence homology with NADH dehydrogenase which is thought to be important in cellular metabolism.

This gene is expressed in fetal dura mater and to a lesser extent in T-cells and hypothalamus.

Therefore, polynucleotides and polypeptides of the invention are useful as reagents for differential identification of the tissue(s) or cell type(s) present in a biological sample and for diagnosis of diseases and conditions, which include, but are not limited to, diseases affecting cellular metabolism. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues and cell types (e.g., fetal tissue, T-cells and other blood cells, and brain and other tissue of the nervous system, and cancerous and wounded tissues) or bodily fluids (e.g., amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 204 as residues: Pro-27 to Gln-32, Arg-42 to Glu-51.

The tissue distribution and homology to NADH dehydrogenase indicates that polynucleotides and polypeptides corresponding to this gene are useful for treatment and diagnosis of diseases involving cellular metabolism. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ D NO:94 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 743 of SEQ ID NO:94, b is an integer of 15 to 757, where both a and b correspond to the positions of nucleotide residues shown in SEQ ID NO:94, and where the b is greater than or equal to a +14.

Features of Protein Encoded by Gene No: 85

The translation product of this gene shares sequence homology with I-TRAF, a novel TNF receptor associated factor (TRAF)-interacting protein that regulates TNF receptor-mediated signal transduction. This protein is thought to be important in regulating the cellular response to tumor necrosis factor (TNF), which is an important mediator of inflammation.

This gene is expressed in endothelial cells and to a lesser extent in glioblastoma and osteoblastoma.

Therefore, polynucleotides and polypeptides of the invention are useful as reagents for differential identification of the tissue(s) or cell type(s) present in a biological sample and for diagnosis of diseases and conditions, which include, but are not limited to, inflammation; glioblastoma and osteoblastoma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g., endothelial cells, bone, and glial cells and tissue of the nervous system, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO. 205 as residues: Glu-15 to Thr-22, Glu-46 to Leu-62, Arg-103 to Glu-119, Gln-127 to Glu-132, Asn-152 to Trp-158, Gln-191 to Gln-210, Glu-264 to Thr-271, Tyr-282 to Leu-288, Trp-319 to Thr-331, Glu-335 to Ser-348, Ser-353 to Ser-358, Asp-382 to Asn-392.

The tissue distribution in endothelial cells combined with the homology to the I-TRAF protein indicates that polynucleotides and polypeptides corresponding to this gene are useful for treatment and diagnosis of inflammatory diseases, including rheumatoid arthritis, sepsis, inflammatory bowel disease, and psoriasis, particularly where tumor necrosis factor is known to be involved. Protein, as well as, antibodies directed against the protain may show utility as a tissue-specific marker and/or immunthrapy target for the above-listed tissues. Many polynucleotide sequences, such as EST sequences, are publicly available and accessible through sequence databases. Some of these sequences are related to SEQ ID NO:95 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2380 of SEQ ID NO:95, b is an integer of 15 to 2394, where both a and b correspond to the positions of nucleotide residues shown in SEQ ID NO:95, and where the b is greater than or equal to a +14.

Features of Protein Encoded by Gene No: 86

This gene has homology with a candidate gene involved in X-linked Retinopathy reported by Wong and colleagues (Genomics 15:467–471 (1993)).

This gene is expressed in a T-cell line.

Therefore, polynucleotides and polypeptides of the invention are useful as reagents for differential identification of the tissue(s) or cell type(s) present in a biological sample and for diagnosis of diseases and conditions, which include, but are not limited to, inflammation and autoimmune diseases; T-cell lymphoma. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues and cell types (e.g., T-cells and other blood cells, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for treatment and diagnosis of inflammatory disorders such as sepsis, inflammatory bowel disease, psoriasis, and rheumatoid arthritis as well as autoimmune disease such as lupus. It could also be useful in immune modulation and in the process of immune surveillance. The present invention can be used diagnostically and therapeutically to treat X-linked Retinopathy. Protein, as well as, antibodies directed against the protain may show utility as a tissue-specific marker and/or immunthrapy target for the above-listed tissues. Many polynucleotide sequences, such as EST sequences, are publicly available and accessible through sequence databases. Some of these sequences are related to SEQ ID NO:96 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 658 of SEQ ID NO:96, b is an integer of 15 to 672, where both a and b correspond to the positions of nucleotide residues shown in SEQ ID NO:96, and where the b is greater than or equal to a +14.

Features of Protein Encoded by Gene No: 87

This gene is expressed in human brain tissue. Therefore, polynucleotides and polypeptides of the invention are useful as reagents for differential identification of the tissue(s) or cell type(s) present in a biological sample and for diagnosis of diseases and conditions, which include, but are not limited to, brain disorders; neurodegenerative disorders; tumors of a brain origin. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues (e.g., brain and other tissue of the nervous system, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred epitopes include those comprising a sequence shown in SEQ ID NO:211 as residues: Cys-32 to Tyr-38. Preferred epitopes include those comprising a sequence shown in SEQ ID NO.207 as residues: Cys-32 to Tyr-38.

The tissue distribution in neural tissue indicates that polynucleotides and polypeptides corresponding to this gene are useful for treatment and diagnosis of CNS disorders such as epilepsy, paranoia, depression, Alzheimer's disease, and schizophrenia. It could be useful in the survival and/or proliferation of neurons and could effect neuronal regeneration. Protein, as well as, antibodies directed against the protain may show utility as a tissue-specific marker and/or immuntherapy target for the above-listed tissues. Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1665 of SEQ ID NO:11, b is an integer of 15 to 1679, where both a and b correspond to the-positions of nucleotide residues shown in SEQ ID NO:11, and where the b is greater than or equal to a +14.

Many polynucleotide sequences, such as EST sequences, are publicly available and accessible through sequence databases. Some of these sequences are related to SEQ ID NO:97 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1405 of SEQ ID NO:97, b is an integer of 15 to 1419, where both a and b correspond to the positions of nucleotide residues shown in SEQ ID NO:97, and where the b is greater than or equal to a +14.

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HAGEW82 | 97923 Mar. 07, 1997 209071 May 22, 1997 | Uni-ZAP XR | 11 | 1679 | 247 | 1607 | 353 | 353 | 121 | 1 | | | 31 |
| 2 | HAGFY16 | 97923 Mar. 07, 1997 209071 May 22, 1997 | Uni-ZAP XR | 12 | 1963 | 209 | 1922 | 251 | 251 | 122 | 1 | 28 | 29 | 198 |
| 2 | HAGFY16 | 97923 Mar. 07, 1997 209071 May 22, 1997 | Uni-ZAP XR | 98 | 1830 | 87 | 1786 | 128 | 128 | 208 | 1 | 26 | 27 | 45 |
| 3 | HALAA60 | 97923 Mar. 07, 1997 209071 May 22, 1997 | Uni-ZAP XR | 13 | 1212 | 1 | 1212 | 99 | 99 | 123 | 1 | 24 | 25 | 39 |
| 4 | HAPBL78 | 97923 Mar. 07, 1997 209071 May 22, 1997 | Uni-ZAP XR | 14 | 2061 | 882 | 2061 | 900 | 900 | 124 | 1 | 22 | 23 | 23 |
| 5 | HASAV70 | 97923 Mar. 07, 1997 209071 May 22, 1997 | Uni-ZAP XR | 15 | 1412 | 10 | 733 | 103 | 103 | 125 | 1 | 20 | 21 | 110 |
| 6 | HBNAF22 | 97923 Mar. 07, 1997 209071 May 22, 1997 | Uni-ZAP XR | 16 | 1052 | 276 | 880 | 538 | 538 | 126 | 1 | 23 | 24 | 63 |
| 7 | HBNBL77 | 97923 Mar. 07, 1997 209071 May 22, 1997 | Uni-ZAP XR | 17 | 683 | 1 | 683 | 181 | 181 | 127 | 1 | | | 30 |
| 8 | HCDDR90 | 97923 Mar. 07, 1997 209071 May 22, 1997 | Uni-ZAP XR | 18 | 1054 | 86 | 1007 | 86 | 86 | 128 | 1 | 23 | 24 | 53 |
| 9 | HCEEF50 | 97923 Mar. 07, 1997 209071 May 22, 1997 | Uni-ZAP XR | 19 | 1393 | 132 | 1393 | 192 | 192 | 129 | 1 | 17 | 18 | 57 |
| 10 | HCEMU42 | 97923 Mar. 07, 1997 209071 | Uni-ZAP XR | 20 | 1215 | 277 | 1070 | 401 | 401 | 130 | 1 | 18 | 19 | 216 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 11 | HCENE16 | 97923 May 22, 1997 | Uni-ZAP XR | 21 | 2042 | 614 | 2011 | 793 | 793 | 131 | 1 | 26 | 27 | 49 |
| 12 | HMSJJ74 | 97923 May 22, 1997 209071 Mar. 07, 1997 | Uni-ZAP XR | 22 | 1872 | 21 | 1872 | 69 | 69 | 132 | 1 | 23 | 24 | 68 |
| 13 | HCUBF15 | 97923 May 22, 1997 209071 Mar. 07, 1997 | ZAP Express | 23 | 289 | 1 | 289 | 89 | 89 | 133 | 1 | 29 | 30 | 52 |
| 14 | HE2DE47 | 97923 May 22, 1997 209071 Mar. 07, 1997 | Uni-ZAP XR | 24 | 3533 | 2821 | 3532 | 808 | 808 | 134 | 1 | 30 | 31 | 540 |
| 14 | HE2DE47 | 97923 May 22, 1997 209071 Mar. 07, 1997 | Uni-ZAP XR | 99 | 1145 | 435 | 1115 | 515 | 515 | 209 | 1 | 22 | 23 | 81 |
| 15 | HKMLH01 | 97923 May 22, 1997 Mar. 07, 1997 | pBluescript | 25 | 1148 | 171 | 907 | 196 | 196 | 135 | 1 | 26 | 27 | 57 |
| 15 | HE6DG34 | 97923 Mar. 07, 1997 209071 May 22, 1997 | Uni-ZAP XR | 100 | 734 | 25 | 734 | 295 | 295 | 210 | 1 | 36 | 37 | 49 |
| 16 | HE9DG49 | 97923 Mar. 07, 1997 209071 May 22, 1997 | Uni-ZAP XR | 26 | 717 | 1 | 717 | 70 | 70 | 136 | 1 | 27 | 28 | 201 |
| 16 | HE9DG49 | 97923 Mar. 07, 1997 209071 May 22, 1997 | Uni-ZAP XR | 101 | 713 | 17 | 713 | 78 | 78 | 211 | 1 | 28 | 29 | 203 |
| 17 | HELBA06 | 97923 Mar. 07, 1997 209071 May 22, 1997 | Uni-ZAP XR | 27 | 1099 | 1 | 1099 | 38 | 38 | 137 | 1 | 22 | 23 | 216 |
| 17 | HELBA06 | 97923 Mar. 07, 1997 209071 May 22, 1997 | Uni-ZAP XR | 102 | 1080 | 1 | 1080 | 149 | 149 | 212 | 1 | 25 | 26 | 186 |
| 18 | HSLFM29 | 97923 Mar. 07, 1997 209071 May 22, 1997 | Uni-ZAP XR | 28 | 941 | 171 | 941 | 128 | 128 | 138 | 1 | 42 | 43 | 102 |
| 19 | HELBW38 | 97923 Mar. 07, 1997 209071 May 22, 1997 | Uni-ZAP XR | 29 | 756 | 62 | 756 | 294 | 294 | 139 | 1 | 30 | 31 | 112 |
| 20 | HETHN28 | 97923 Mar. 07, 1997 209071 May 22, 1997 | Uni-ZAP XR | 30 | 2100 | 408 | 2093 | 496 | 496 | 140 | 1 | | | 20 |
| 21 | HFCDK17 | 97923 Mar. 07, 1997 209071 May 22, 1997 | Uni-ZAP XR | 31 | 1448 | 475 | 1392 | 567 | 567 | 141 | 1 | | | 30 |
| 22 | HFEAF41 | 97923 Mar. 07, 1997 209071 May 22, 1997 | Uni-ZAP XR | 32 | 456 | 1 | 409 | 21 | 21 | 142 | 1 | 28 | 29 | 99 |
| 23 | HFKFL13 | 97923 Mar. 07, 1997 209071 May 22, 1997 | Uni-ZAP XR | 33 | 1326 | 1 | 1322 | 210 | 210 | 143 | 1 | | | 8 |
| 24 | HFSBG13 | 97923 Mar. 07, 1997 209071 May 22, 1997 | Uni-ZAP XR | 34 | 710 | 1 | 710 | 242 | 242 | 144 | 1 | 16 | 17 | 39 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 25 | HFTBE43 | 97923 Mar. 07, 1997 209071 May 22, 1997 | Uni-ZAP XR | 35 | 1188 | 110 | 1161 | 178 | 178 | 145 | 1 | 26 | 27 | 131 |
| 26 | HFTDJ36 | 97923 Mar. 07, 1997 209071 May 22, 1997 | Uni-ZAP XR | 36 | 956 | 1 | 938 | 144 | 144 | 146 | 1 | 21 | 22 | 32 |
| 27 | HKTAC77 | 97924 Mar. 07, 1997 | Uni-ZAP XR | 37 | 1603 | 974 | 1581 | 1104 | 1104 | 147 | 1 | | | 14 |
| 28 | HLHSH36 | 97924 Mar. 07, 1997 | pBluescript | 38 | 1089 | 55 | 1067 | | 209 | 148 | 1 | | | 8 |
| 29 | HLHSV96 | 97924 Mar. 07, 1997 | pBluescript | 39 | 629 | 1 | 629 | 119 | 119 | 149 | 1 | 32 | 33 | 68 |
| 30 | HLQBQ86 | 97924 Mar. 07, 1997 | Lambda ZAP II | 40 | 1964 | 408 | 1793 | 581 | 581 | 150 | 1 | | | 26 |
| 31 | HLTBX31 | 97924 Mar. 07, 1997 | Uni-ZAP XR | 41 | 1522 | 13 | 1123 | 126 | 126 | 151 | 1 | 32 | 33 | 195 |
| 32 | HLTCJ63 | 97924 Mar. 07, 1997 | Uni-ZAP XR | 42 | 875 | 1 | 875 | 43 | 43 | 152 | 1 | 18 | 19 | 91 |
| 33 | HMKAH44 | 97924 Mar. 07, 1997 | pSport1 | 43 | 843 | 1 | 843 | 171 | 171 | 153 | 1 | 30 | 31 | 31 |
| 34 | HMQAJ64 | 97924 Mar. 07, 1997 | Uni-ZAP XR | 44 | 489 | 3 | 489 | 55 | 55 | 154 | 1 | 19 | 20 | 90 |
| 34 | HMQAJ64 | 97924 Mar. 07, 1997 | Uni-ZAP XR | 103 | 489 | 6 | 489 | 58 | 58 | 213 | 1 | 22 | 23 | 90 |
| 35 | HOABG65 | 97924 Mar. 07, 1997 | Uni-ZAP XR | 45 | 534 | 1 | 534 | 17 | 17 | 155 | 1 | 18 | 19 | 89 |
| 36 | HODCL36 | 97924 Mar. 07, 1997 | Uni-ZAP XR | 46 | 1374 | 1 | 1374 | 15 | 15 | 156 | 1 | 20 | 21 | 174 |
| 36 | HODCL36 | 97924 Mar. 07, 1997 | Uni-ZAP XR | 104 | 1529 | 40 | 1399 | 54 | 54 | 214 | 1 | 27 | 28 | 48 |
| 37 | HODCL50 | 97924 Mar. 07, 1997 | Uni-ZAP XR | 47 | 596 | 1 | 596 | 269 | 269 | 157 | 1 | 27 | 28 | 45 |
| 38 | HODCV74 | 97924 Mar. 07, 1997 | Uni-ZAP XR | 48 | 851 | 99 | 822 | 170 | 170 | 158 | 1 | | | 23 |
| 39 | HODCZ16 | 97924 Mar. 07, 1997 | Uni-ZAP XR | 49 | 2020 | 569 | 2020 | 638 | 638 | 159 | 1 | 17 | 18 | 70 |
| 40 | HTOEU03 | 97924 Mar. 07, 1997 | Uni-ZAP XR | 50 | 2432 | 848 | 2432 | 99 | 99 | 160 | 1 | 19 | 20 | 323 |
| 40 | HTOEU03 | 97924 Mar. 07, 1997 | Uni-ZAP XR | 105 | 2435 | 849 | 2435 | 928 | 928 | 215 | 1 | 31 | 32 | 70 |
| 41 | HPBCJ74 | 97924 Mar. 07, 1997 | pBluescript SK- | 51 | 2340 | 1627 | 2340 | 150 | 150 | 161 | 1 | 60 | 61 | 320 |
| 41 | HPBCJ74 | 97924 Mar. 07, 1997 | pBluescript SK- | 106 | 805 | 92 | 791 | 239 | 239 | 216 | 1 | 21 | 22 | 83 |
| 42 | HPMBU33 | 97924 Mar. 07, 1997 | Uni-ZAP XR | 52 | 601 | 188 | 601 | 432 | 432 | 162 | 1 | | | 31 |
| 43 | HSAUL66 | 97924 Mar. 07, 1997 | Uni-ZAP XR | 53 | 359 | 1 | 337 | 142 | 142 | 163 | 1 | 18 | 19 | 72 |
| 44 | HSIDQ18 | 97924 Mar. 07, 1997 | Uni-ZAP XR | 54 | 1141 | 1 | 1141 | 25 | 25 | 164 | 1 | 30 | 31 | 281 |
| 44 | HSIDQ18 | 97924 Mar. 07, 1997 | Uni-ZAP XR | 107 | 1166 | 21 | 1166 | 433 | 433 | 217 | 1 | 30 | 31 | 43 |
| 45 | HSJBB37 | 97924 Mar. 07, 1997 | Uni-ZAP XR | 55 | 1560 | 413 | 1498 | 714 | 714 | 165 | 1 | 31 | 32 | 81 |
| 46 | HSJBQ79 | 97924 Mar. 07, 1997 | Uni-ZAP XR | 56 | 1507 | 164 | 608 | 57 | 57 | 166 | 1 | 19 | 20 | 327 |
| 46 | HSJBQ79 | 97924 Mar. 07, 1997 | Uni-ZAP XR | 108 | 586 | 4 | 586 | 35 | 35 | 218 | 1 | 23 | 24 | 184 |
| 47 | HTEGA76 | 97958 Mar. 13, 1997 209072 May 22, 1997 | Uni-ZAP XR | 57 | 450 | 1 | 450 | 90 | 90 | 167 | 1 | 43 | 44 | 65 |
| 48 | HTEJN13 | 97958 Mar. 13, 1997 209072 May 22, 1997 | Uni-ZAP XR | 58 | 1147 | 1 | 1147 | 163 | 163 | 168 | 1 | 15 | 16 | 159 |
| 48 | HTEJN13 | 97958 Mar. 13, 1997 209072 May 22, 1997 | Uni-ZAP XR | 109 | 1134 | 1 | 1134 | 155 | 155 | 219 | 1 | 19 | 20 | 71 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 49 | HTHBL86 | 97958 Mar. 13, 1997 209072 May 22, 1997 | Uni-ZAP XR | 59 | 777 | 1 | 777 | 115 | 115 | 169 | 1 | 18 | 19 | 123 |
| 50 | HTSFO71 | 97958 Mar. 13, 1997 209072 May 22, 1997 | pBluescript | 60 | 1191 | 48 | 598 | 52 | 52 | 170 | 1 | 30 | 31 | 129 |
| 50 | HTSFO71 | 97958 Mar. 13, 1997 209072 May 22, 1997 | pBluescript | 110 | 1333 | 594 | 1333 | 829 | 829 | 220 | 1 | | | 10 |
| 51 | HAPNO80 | 209235 Sep. 04, 1997 | Uni-ZAP XR | 61 | 1580 | 443 | 1554 | 114 | 114 | 171 | 1 | 1 | 2 | 372 |
| 51 | HAUCC47 | 97958 Mar. 13, 1997 | Uni-ZAP XR | 111 | 1015 | 249 | 708 | 244 | 244 | 221 | 1 | 28 | 29 | 138 |
| 52 | HBMCL41 | 97958 Mar. 13, 1997 209072 May 22, 1997 | pBluescript | 62 | 1117 | 105 | 1034 | 182 | 182 | 172 | 1 | 28 | 29 | 216 |
| 53 | HCFLD84 | 97958 Mar. 13, 1997 209072 May 22, 1997 | pSport1 | 63 | 361 | 1 | 361 | 97 | 97 | 173 | 1 | 32 | 33 | 55 |
| 54 | HE8EM69 | 97958 Mar. 13, 1997 209072 May 22, 1997 | Uni-ZAP XR | 64 | 1668 | 1 | 1638 | 150 | 150 | 174 | 1 | 20 | 21 | 23 |
| 55 | HE8EZ48 | 97958 Mar. 13, 1997 209072 May 22, 1997 | Uni-ZAP XR | 65 | 1353 | 35 | 1303 | 231 | 231 | 175 | 1 | 33 | 34 | 103 |
| 56 | HEBGF73 | 97958 Mar. 13, 1997 209072 May 22, 1997 | Uni-ZAP XR | 66 | 1011 | 655 | 1011 | 703 | 703 | 176 | 1 | 38 | 39 | 48 |
| 57 | HFEBF41 | 97958 Mar. 13, 1997 209072 May 22, 1997 | Uni-ZAP XR | 67 | 1193 | 267 | 1090 | 459 | 459 | 177 | 1 | 35 | 36 | 96 |
| 58 | HFRBU14 | 97958 Mar. 13, 1997 209072 May 22, 1997 | Uni-ZAP XR | 68 | 560 | 1 | 560 | 63 | 63 | 178 | 1 | 29 | 30 | 95 |
| 59 | HFVGZ79 | 97958 Mar. 13, 1997 209072 May 22, 1997 | pBluescript | 69 | 1657 | 765 | 1581 | 839 | 839 | 179 | 1 | 21 | 22 | 27 |
| 60 | HHGCM76 | 97958 Mar. 13, 1997 209072 May 22, 1997 | Lambda ZAP II | 70 | 711 | 8 | 711 | 270 | 270 | 180 | 1 | 22 | 23 | 89 |
| 60 | HHGCM76 | 97958 Mar. 13, 1997 209072 May 22, 1997 | Lambda ZAP II | 112 | 711 | 8 | 711 | 270 | 270 | 222 | 1 | | | 11 |
| 61 | HHGCO88 | 97958 Mar. 13, 1997 209072 May 22, 1997 | Lambda ZAP II | 71 | 935 | 111 | 935 | 272 | 272 | 181 | 1 | 19 | 20 | 65 |
| 62 | HHGCP52 | 97958 Mar. 13, 1997 209072 May 22, 1997 | Lambda ZAP II | 72 | 504 | 113 | 484 | 45 | 45 | 182 | 1 | 15 | 16 | 105 |
| 63 | HHGDB72 | 97958 Mar. 13, 1997 209072 May 22, 1997 | Lambda ZAP II | 73 | 620 | 1 | 620 | 96 | 96 | 183 | 1 | 18 | 19 | 132 |
| 64 | HHGDI71 | 97958 Mar. 13, 1997 209072 May 22, 1997 | Lambda ZAP II | 74 | 581 | 156 | 581 | 248 | 248 | 184 | 1 | 32 | 33 | 69 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 65 | HHSDI45 | 97958 Mar. 13, 1997 209072 May 22, 1997 | Uni-ZAP XR | 75 | 1843 | 537 | 1786 | 630 | 630 | 185 | 1 | 27 | 28 | 45 |
| 66 | HHSEB66 | 97958 Mar. 13, 1997 209072 May 22, 1997 | Uni-ZAP XR | 76 | 1441 | 116 | 800 | 167 | 167 | 186 | 1 | 36 | 37 | 65 |
| 67 | HAUAI83 | 97958 Mar. 13, 1997 209072 May 22, 1997 | Uni-ZAP XR | 77 | 910 | 1 | 886 | 253 | 253 | 187 | 1 | 37 | 38 | 49 |
| 67 | HJPAZ83 | 97958 Mar. 13, 1997 209072 May 22, 1997 | Uni-ZAP XR | 113 | 1076 | 398 | 1076 |  | 575 | 223 | 1 | 11 | 12 | 23 |
| 68 | HLDBO49 | 97958 Mar. 13, 1997 209072 May 22, 1997 | pCMVSport 3.0 | 78 | 2776 | 18 | 1888 | 187 | 187 | 188 | 1 | 14 | 15 | 170 |
| 69 | HLDBQ19 | 209226 Aug. 28, 1997 | pCMVSport 3.0 | 79 | 1487 | 401 | 1487 | 534 | 534 | 189 | 1 | 22 | 23 | 132 |
| 69 | HLDBQ19 | 97958 Mar. 13, 1997 209072 May 22, 1997 | pCMVSport 3.0 | 114 | 1525 | 401 | 1480 | 534 | 534 | 224 | 1 | 22 | 23 | 66 |
| 70 | HMSGT42 | 97958 Mar. 13, 1997 209072 May 22, 1997 | Uni-ZAP XR | 80 | 1563 | 33 | 1077 | 40 | 40 | 190 | 1 | 32 | 33 | 92 |
| 71 | HMWIC78 | 97957 Mar. 13, 1997 209073 May 22, 1997 | Uni-Zap XR | 81 | 1020 | 18 | 780 | 238 | 238 | 191 | 1 | 23 | 24 | 176 |
| 72 | HTTCT79 | 97957 Mar. 13, 1997 209073 May 22, 1997 | Uni-ZAP XR | 82 | 770 | 101 | 770 | 286 | 286 | 192 | 1 | 26 | 27 | 70 |
| 73 | HNGJU84 | 97957 Mar. 13, 1997 209073 May 22, 1997 | Uni-ZAP XR | 83 | 481 | 1 | 481 | 58 | 58 | 193 | 1 | 20 | 21 | 25 |
| 74 | HNTAC73 | 97957 Mar. 13, 1997 209073 May 22, 1997 | pCMVSport 3.0 | 84 | 644 | 1 | 623 | 14 | 14 | 194 | 1 | 25 | 26 | 73 |
| 75 | HOSEI45 | 97957 Mar. 13, 1997 209073 May 22, 1997 | Uni-ZAP XR | 85 | 1351 | 435 | 1284 | 98 | 98 | 195 | 1 | 12 | 13 | 289 |
| 75 | HOSEI45 | 97957 Mar. 13, 1997 209073 May 22, 1997 | Uni-ZAP XR | 115 | 1350 | 428 | 1283 |  | 545 | 225 | 1 |  |  | 28 |
| 76 | HOSFD58 | 97957 Mar. 13, 1997 209073 May 22, 1997 | Uni-ZAP XR | 86 | 2527 | 290 | 1747 | 56 | 56 | 196 | 1 | 30 | 31 | 624 |
| 76 | HOSFD58 | 97957 Mar. 13, 1997 209073 May 22, 1997 | Uni-ZAP XR | 116 | 2527 | 288 | 1747 | 477 | 477 | 226 | 1 | 32 | 33 | 61 |
| 77 | HSAUM95 | 97957 Mar. 13, 1997 209073 May 22, 1997 | Uni-ZAP XR | 87 | 2566 | 1843 | 2566 | 251 | 251 | 197 | 1 | 30 | 31 | 649 |
| 77 | HSAUM95 | 97957 Mar. 13, 1997 209073 May 22, 1997 | Uni-ZAP XR | 117 | 1098 | 375 | 1098 | 677 | 677 | 227 | 1 | 21 | 22 | 29 |

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 78 | HSAUR67 | 97957 Mar. 13, 1997 209073 May 22, 1997 | Uni-ZAP XR | 88 | 540 | 1 | 540 | 83 | 83 | 198 | 1 | 32 | 33 | 55 |
| 79 | HSKDI81 | 97957 Mar. 13, 1997 209073 May 22, 1997 | Uni-ZAP XR | 89 | 1863 | 152 | 1165 | 188 | 188 | 199 | 1 | 11 | 12 | 266 |
| 79 | HSKDI81 | 97957 Mar. 13, 1997 209073 May 22, 1997 | Uni-ZAP XR | 118 | 1679 | 152 | 1166 | 315 | 315 | 228 | 1 | | | 18 |
| 80 | HSKDW91 | 97957 Mar. 13, 1997 209073 May 22, 1997 | Uni-ZAP XR | 90 | 2478 | 1149 | 2449 | 92 | 92 | 200 | 1 | 19 | 20 | 315 |
| 81 | HTLEX50 | 97957 Mar. 13, 1997 209073 May 22, 1997 | Uni-ZAP XR | 91 | 2058 | 476 | 2058 | 414 | 414 | 201 | 1 | 20 | 21 | 207 |
| 82 | HSKHL65 | 97957 Mar. 13, 1997 209073 May 22, 1997 | pBluescript | 92 | 1411 | 345 | 1411 | 157 | 157 | 202 | 1 | 69 | 70 | 195 |
| 82 | HSKHL65 | 97957 Mar. 13, 1997 209073 May 22, 1997 | pBluescript | 119 | 1411 | 345 | 1411 | 526 | 526 | 229 | 1 | 37 | 38 | 72 |
| 83 | HHFGA11 | 97957 Mar. 13, 1997 209073 May 22, 1997 | Uni-ZAP XR | 93 | 2187 | 147 | 2184 | 397 | 397 | 203 | 1 | 30 | 31 | 330 |
| 83 | HOEBX83 | 97957 Mar. 13, 1997 209073 May 22, 1997 | Uni-ZAP XR | 120 | 2223 | 144 | 2136 | 198 | 198 | 230 | 1 | 20 | 21 | 142 |
| 84 | HWTBL40 | 97957 Mar. 13, 1997 209073 May 22, 1997 | Uni-ZAP XR | 94 | 757 | 524 | 608 | 445 | 445 | 204 | 1 | 20 | 21 | 58 |
| 85 | HBXFG80 | 97957 Mar. 13, 1997 209073 May 22, 1997 | ZAP Express | 95 | 2394 | 481 | 2394 | 523 | 523 | 205 | 1 | 1 | 2 | 392 |
| 86 | HCACY32 | 97957 Mar. 13, 1997 209073 May 22, 1997 | Uni-ZAP XR | 96 | 672 | 1 | 672 | 117 | 117 | 206 | 1 | 21 | 22 | 26 |
| 87 | HCEDO21 | 97957 Mar. 13, 1997 209073 May 22, 1997 | Uni-ZAP XR | 97 | 1419 | 1 | 1419 | 207 | 207 | 207 | 1 | 20 | 21 | 38 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is-useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., +2 or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brudag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/ alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05,. Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini; relative to the the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human MRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and i.e.; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219: 660–666 (1983).)

Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

As used herein, the term, "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).) Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ D NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a-single chromosome-or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix - see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from-DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA imrunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemnical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g., afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalrmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles- ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTL V-I, HTL V-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's , warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: *Actinomycetales* (e.g., *Corynebacterium, Mycobacterium, Norcardia*), *Aspergillosis, Bacillaceae* (e.g., *Anthrax, Clostridium*), *Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae* (*Klebsiella, Salmonella, Serratia, Yersinia*), *Erysipelothrix, Helicobacter, Legionellosis, Leptospirosis, Listeria, Mycoplasmatales, Neisseriaceae* (e.g., *Acinetobacter, Gonorrhea, Menigococcal*), *Pasteurellacea Infections* (e.g., *Actinobacillus, Heamophilus, Pasteurella*), *Pseudomonas, Rickettsiaceae, Chlamydiaceae, Syphilis*, and *Staphylococcal*. These bacterial or fungal families can cause the following diseases or symptoms, including, but not limited to: bacteria, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: *Amebiasis, Babesiosis, Coccidiosis, Cryptosporidiosis, Dientamoebiasis, Dourine, Ectoparasitic, Giardiasis, Helrrinthiasis, Leishmaniasis, Theileriasis, Toxoplasmosis, Trypanosoniasis*, and *Trichomonas*. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276: 59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g., monocytes, fibroblasts, neutrophils, T-cells, mast cells, eosinophils; epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate sells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair-color, eye color, skin, percentage of adipose tissue, pigmentation, size, and shape (e.g., cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders); tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

OTHER PREFERRED EMBODIMENTS

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment-is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence t least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any-integer-as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the. ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286, 636), Uni-Zap XR (U.S. Pat. Nos. 5,128, 256 and 5,286, 636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9 : (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a-deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosysterns DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning:

A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 µl of reaction mixture with 0.5 ug of the above cDNA template. A convenient reaction mixture is 1.5–5 mM $MgCl_2$, 0.01% (w/v) gelatin, 20 µM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 720C for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7): 1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for MRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BarnHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BarnHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6M guanidine-HCl, pH 8, the column is first washed with 10 volumes of 6M guanidine-HCl, pH 8, then washed with 10 volumes of 6M guanidine-HCl pH 6, and finally the polypeptide is eluted with 6M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 niM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E. coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is' confirmed by DNA sequencing.

Five μg of a plasmid containing the polynucleotide is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One μg of BaculoGold™ virus DNA and 5 μg of the plasmid are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 μCi of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of MRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharrmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB 101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

```
Human IgG Fc region:
GGGATCCGGAGCCCAAATCTTCTGACAAAACTCACAC  (SEQ ID NO:1)

ATGCCCACCGTGCCCAGCACCTGAATTCGAGGGTGCA

CCGTCAGTCTTCCTCTTCCCCCCAAAACCCAAGGACA

CCCTCATGATCTCCCGGACTCCTGAGGTCACATGCGT

GGTGGTGGACGTAAGCCACGAAGACCCTGAGGTCAAG

TTCAACTGGTACGTGGACGGCGTGGAGGTGCATAATG

CCAAGACAAAGCCGCGGGAGGAGCAGTACAACAGCAC

GTACCGTGTGGTCAGCGTCCTCACCGTCCTGCACCAG

GACTGGCTGAATGGCAAGGAGTACAAGTGCAAGGTCT

CCAACAAAGCCCTCCCAACCCCCATCGAGAAAACCAT

CTCCAAAGCCAAAGGGCAGCCCCGAGAACCACAGGTG

TACACCCTGCCCCCATCCCGGGATGAGCTGACCAAGA

ACCAGGTCAGCCTGACCTGCCTGGTCAAAGGCTTCTA

TCCAAGCGACATCGCCGTGGAGTGGGAGAGCAATGGG

CAGCCGGAGAACAACTACAAGACCACGCCTCCCGTGC

TGGACTCCGACGGCTCCTTCTTCCTCTACAGCAAGCT

CACCGTGGACAAGAGCAGGTGGCAGCAGGGGAACGTC

TTCTCATGCTCCGTGATGCATGAGGCTCTGCACAACC

ACTACACGCAAGAGAGCCTCTCCCTGTCTCCGGGTAA

ATGAGTGCGACGGCCGCGACTCTAGAGGAT
```

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/mi of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/mn. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17-602E Biowhittaker). Let the cells grow overnight.

The next day, mix together in a sterile solution basin: 300 ul Lipofectamine (18324-012 Gibco/BRL) and 5 ml Opti-mem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a12-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1% BSA in DMEM with 1× penstrep, or CHO-5 media (116.6 mg/L of $CaCl2$ (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/LD of Stearic Acid; 2.20 mg/L of Tween 80; 4551 mg/L of D-Glucose; 130.85 mg/ml of L- Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/mi of L-Cystine-2HCL; 7.35 mg/ml of L-Glutamic Acid; 365.0 mg/ml of L-Glutamine; 18.75 mg/mil of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/mil of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1× penstrep. (BSA (81-068-3 Bayer) 100 gm dissolved in 1 L DAEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37° C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supematant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as-a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, L-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is: 5' :GCGCCTC-GAGATTTCCCCGAAATCTAGATTTC-CCCGAAATGATTTCCCCG AAATGATTTC-CCCGAAATATCTGCCATCTCAATTAG:3' (SEQ ID NO:3)

The downstream primer is complementary to the SV40 promoter and is flanked with a Hind III site: 5':GCGGCAAGCIT=GCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

| | | JAKs | | | | |
|---|---|---|---|---|---|---|
| Ligand | tyk2 | Jak1 | Jak2 | Jak3 | STATS | GAS (elements) or ISRE |
| IFN family | | | | | | |
| IFN-a/B | + | + | – | – | 1, 2, 3 | ISRE |
| IFN-g | | + | + | – | 1 | GAS (IRF1 > Lys6 > IFP) |
| Il-10 | + | ? | ? | – | 1, 3 | |
| gp130 family | | | | | | |
| IL-6 (Pleiotrohic) | + | + | + | ? | 1, 3 | GAS (IRF1 > Lys6 > IFP) |
| Il-11(Pleiotrohic) | ? | + | ? | ? | 1, 3 | |
| OnM(Pleiotrohic) | ? | + | + | ? | 1, 3 | |
| LIF(Pleiotrohic) | ? | + | + | ? | 1, 3 | |
| CNTF(Pleiotrohic) | –/+ | + | + | ? | 1, 3 | |
| G-CSF(Pleiotrohic) | ? | + | ? | ? | 1, 3 | |
| IL-12(Pleiotrohic) | + | – | + | + | 1, 3 | |
| g-C family | | | | | | |
| IL-2 (lymphocytes) | – | + | – | + | 1, 3, 5 | GAS |
| IL-4 (lymph/myeloid) | – | + | – | + | 6 | GAS (IRF1 = IFP >> Ly6)(IgH) |
| IL-7 (lymphocytes) | – | + | – | + | 5 | GAS |
| IL-9 (lymphocytes) | – | + | – | + | 5 | GAS |
| IL-13 (lymphocyte) | – | + | ? | ? | 6 | GAS |
| IL-15 | ? | + | ? | + | 5 | GAS |
| gp140 family | | | | | | |
| IL-3 (myeloid) | – | – | + | – | 5 | GAS (IRF1 > IFP >> Ly6) |
| IL-5 (myeloid) | – | – | + | – | 5 | GAS |
| GM-CSF (myeloid) | – | – | + | – | 5 | GAS |
| Growth hormone family | | | | | | |
| GH | ? | – | + | – | 5 | |
| PRL | ? | +/– | + | – | 1, 3, 5 | |
| EPO | ? | – | + | – | 5 | GAS (B-CAS > IRF1 = IFP >> Ly6) |
| Receptor Tyrosine Kinases | | | | | | |
| EGF | ? | + | + | – | 1, 3 | GAS (IRF1) |
| PDGF | ? | + | + | – | 1, 3 | |
| CSF-1 | ? | + | + | – | 1, 3 | GAS (not IRF1) |

5':<u>CTCGAG</u>ATTTCCCCGAAATCTAGATTTCCCCGAA (SEQ ID NO:5)

ATGATTTCCCCGAAATGATTTCCCCGAAATATCTGCC

ATCTCAATTAGTCAGCAACCATAGTCCCGCCCCTAAC

TCCGCCCATCCCGCCCCTAACTCCGCCCAGTTCCGCC

CATTCTCCGCCCCATGGCTGACTAATTTTTTTTATTT

ATGCAGAGGCCGAGGCCGCCTCGGCCTCTGAGCTATT

CCAGAAGTAGTGAGGAGGCTTTTTTGGAGGCCTAGGC

TTTTGCAAA<u>AAGCTT</u>:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, II-2/NFAT, or NF-KB/GAS). Similarly, other cell lines can be used to test reporter construct activity, such as HELA (epithelial), HUVEC (endotielial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI +10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/mi. Then add 1 ml of $1\times10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 4° C. and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 14

High-Throughput Screening Assay Identifying Myeloid Activity

The following protocol is used to assess myeloid activity by identifying factors, such as growth factors and cytokines, that may proliferate or differentiate myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11. Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
5' GCGCTCGAGGGATGACAGCGATAGAACCCCGG-   (SEQ ID NO:6)
3'

5' GCGAAGCTTCGCGACTCCCCGGATCCGCCTC-3' (SEQ ID NO:7)
```

Using the GAS:SEAP/Neo vector produced in Example 12, EGRI amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #212449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor κB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-κB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:

5':GCGGCCTCGAGGGGACTTTCCCGGGGACTTTCCG (SEQ ID NO:9)

GGGACTTTCCGGGACTTTCCATCCTGCCATCTCAATT
AG:3'

The downstream primer is complementary to the 3' end of the SV40 promoter and is flanked with a Hind III site:

5':GCGGCAAGCTTTTTGCAAAGCCTAGGC:3'    (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5':CTCGAGGGGACTTTCCCGGGGACTTTC-    (SEQ ID NO:10)
CGGGGGA

CTTTCCGGGACTTTCCATCTGCCATCTCAATTAGTC

AGCAACCATAGTCCCGCCCGCCCCTAACTCCGCCCA

TCCCGCCCCTAACTCCGCCCAGTTCCGCCCATTCTC

CGCCCCATGGCTGACTAATTTTTTTTATTTATGCAG

AGGCCGAGGCCGCCTCGGCCTCTGAGCTATTCCAGA

AGTAGTGAGGAGGCTTTTTTGGAGGCCTAGGCTTTT

GCAAAAAGCTT:3'

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-κB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1, 10 ng) is added to wells H9, H10, and H11, with a 5-10 fold activation typically observed.

Example 17

Assay for SEAP Activity

As a reporter molecule for the assays described in Examples 13–16, SEAP activity is assayed using the Tropix Phospho-light Kit (Cat. BP400) according to the following general procedure. The Tropix Phospho-light Kit supplies the Dilution, Assay, and Reaction Buffers used below.

Prime a dispenser with the 2.5×Dilution Buffer and dispense 15 µl of 2.5×2 dilution buffer into Optiplates containing 35 µl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 µl Assay Buffer and incubate at room temperature 5 min. Empty the dispenser and prime with the Reaction Buffer (see the table below). Add 50 µl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the lurminometer. Set H12 as blank, and print the results. An increase in chemilurninescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |

-continued

Reaction Buffer Formulation:

| # of plates | Rxn buffer diluent (ml) | CSPD (ml) |
|---|---|---|
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-3 solution in 10% pluronic acid DMSO is added to each ml of cell suspension. The tube is then placed in a 37° C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change- in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase. RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg,/ml), all of which can be purchased from Sigma Chemicals (St. Louis, Mo.) or 10% Matrigel purchased from Becton Dickinson (Bedford,Mass.), or calf serum, rinsed with PBS and stored at 4° C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford,Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15M NaCl, 1% Triton X-100, 0.1% SDS, 2 mM Na3VO4, 2 mM Na4P207 and a cocktail of protease inhibitors (#1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$(5 mM ATP/50 mM MgCl$_2$), then 10 ul of 5×Assay Buffer (40 mM imidazole hydrochloride, pH7.3, 40 mM beta-glycerophosphate, 1 mM EGTA, 100 mM MgCl$_2$, 5 mM MnCl$_2$, 0.5 mg/mil BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The secreted polypeptide is also suitably administered by sustained-release systems. Suitable examples of sustained-release compositions include semi-permeable polymer matrices in the form of shaped articles, e.g., films, or ntirocapsules. Sustained-release matrices include polylactides (U.S. Pat. No. 3,773,919, EP 58,481), copolymers of L-glutamic acid and camma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83-118008; U.S.

Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamnic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/mi to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules pr vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated antibody or fragment thereof that specifically binds to a polypeptide selected from the group consisting of:
   (a) a polypeptide encoded by SEQ ID NO:15, wherein said polypeptide comprises the amino acid sequence of SEQ ID NO:243;
   (b) a polypeptide whose amino acid sequence consists of at least 30 contiguous amino acid residues of the polypeptide in (a);
   (c) a polypeptide whose amino acid sequence consists of at least 50 contiguous amino acid residues of the polypeptide in (a); and
   (d) a polypeptide whose amino acid sequence consists of amino acid residues 1 to 28 of SEQ ID NO:243.

2. The antibody or fragment thereof of claim 1 that specifically binds polypeptide (a).

3. The antibody or fragment thereof of claim 1 that specifically binds polypeptide (b).

4. The antibody or fragment thereof of claim 3 that specifically binds a polypeptide encoded by SEQ ID NO:15, wherein said polypeptide comprises the amino acid sequence of SEQ ID NO:243.

5. The antibody or fragment thereof of claim 1 that specifically binds polypeptide (c).

6. The antibody or fragment thereof of claim 1 which is a polyclonal antibody.

7. The antibody or fragment thereof of claim 1 which is a monoclonal antibody.

8. The antibody or fragment thereof of claim 1 which is selected from the group consisting of:
   (a) a chimeric antibody;
   (b) a humanized antibody;
   (c) a single chain antibody; and
   (d) a Fab fragment.

9. The antibody or fragment thereof of claim 1 which is labeled.

10. The antibody or fragment thereof of claim 1 wherein said polypeptide bound by said antibody or fragment thereof is glycosylated.

11. The antibody or fragment thereof of claim 1 wherein said antibody or fragment thereof specifically binds to said polypeptide in a Western blot.

12. The antibody or fragment thereof of claim 1 wherein said antibody or fragment thereof specifically binds to said polypeptide in an ELISA.

13. An isolated cell that produces the antibody or fragment thereof of claim 1.

14. A hybridoma that produces the antibody or fragment thereof of claim 1.

15. A method of detecting the polypeptide of claim 1 in a biological sample comprising:
   (a) contacting the biological sample with the antibody or fragment thereof of claim 1;
   (b) allowing a complex to form between said polypeptide and said antibody of claim 1; and
   (c) detecting said complex.

16. The antibody or fragment thereof of claim 1 that specifically binds polypeptide (d).

17. The antibody or fragment thereof of claim 16 which is a polyclonal antibody.

18. The antibody or fragment thereof of claim 16 which is a monoclonal antibody.

19. The antibody or fragment thereof of claim 16 which is selected from the group consisting of:
   (a) a chimeric antibody;
   (b) a humanized antibody;
   (c) a single chain antibody; and
   (d) a Fab fragment.

20. The antibody or fragment thereof of claim 16 which is labeled.

21. The antibody or fragment thereof of claim 16 wherein said polypeptide bound by said antibody or fragment thereof is glycosylated.

22. The antibody or fragment thereof of claim 16 wherein said antibody or fragment thereof specifically binds to said polypeptide in a Western blot.

23. The antibody or fragment thereof of claim 16 wherein said antibody or fragment thereof specifically binds to said polyp eptide in an ELISA.

24. An isolated cell that produces the antibody or fragment thereof of claim 16.

25. A hybridoma that produces the antibody or fragment thereof of claim 16.

* * * * *

UNITED STATES PATENT AND TRADEMARK OFFICE
CERTIFICATE OF CORRECTION

PATENT NO. : 7,169,565 B2  Page 1 of 1
APPLICATION NO. : 10/960251
DATED : January 30, 2007
INVENTOR(S) : Ruben et al.

It is certified that error appears in the above-identified patent and that said Letters Patent is hereby corrected as shown below:

In the Specification:

At column 142, in the second full paragraph, line 3 (SEQ ID NO:4), delete "5':

GCGGCAAGC1T=GCAAAGCCTAGGC: 3'" and insert --5':

GCGGCAAGCTTTTGCAAAGCCTAGGC: 3'--

At column 147, in the fifth full paragraph, line 8 (SEQ. ID NO:10), delete "5´:
CTCGAGGGGACTTTCCCGGGGACTTTCCGGGGGACTTTCCGGGACTTTCCATCTGCCATCTCAATT
AGTCAGCAACCATAGTCCCGCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCTCGGC
CTCTGAGCTATTCCAGAAGTAGTGAGGAGGCTTTTTTGGAGGCCTAGGCTTTTGCAAAAAGCTT: 3'"
and insert -- 5´:
CTCGAGGGGACTTTCCCGGGGACTTTCCGGGGACTTTCCGGGACTTTCCATCTGCCATCTCAATTA
GTCAGCAACCATAGTCCCGCCCGCCCCTAACTCCGCCCATCCCGCCCCTAACTCCGCCCAGTTCC
GCCCATTCTCCGCCCCATGGCTGACTAATTTTTTTTATTTATGCAGAGGCCGAGGCCGCCTCGGCC
TCTGAGCTATTCCAGAAGTAGTGAGGAGGCTTTTTTGGAGGCCTAGGCTTTTGCAAAAAGCTT:3´ --

Signed and Sealed this

Tenth Day of April, 2007

JON W. DUDAS
*Director of the United States Patent and Trademark Office*

SEQUENCE LISTING

<160> NUMBER OF SEQ ID NOS: 343

<210> SEQ ID NO 1
<211> LENGTH: 733
<212> TYPE: DNA
<213> ORGANISM: Homo sapiens

<400> SEQUENCE: 1

```
gggatccgga gcccaaatct tctgacaaaa ctcacacatg cccaccgtgc ccagcacctg      60
aattcgaggg tgcaccgtca gtcttcctct tcccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agcccctccca acccccatcg     360 agaaaaccat ctccaaagcc aaagggcagc cccgagaacc acaggtgtac accctgcccc     420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
acaaccacta cacgcagaag agcctctccc tgtctccggg taaatgagtg cgacggccgc     720
gactctagag gat                                                       733
```

```
<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally
      ocurring L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc    60
cccgaaatat ctgccatctc aattag                                        86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc                                       27

<210> SEQ ID NO 5
<211> LENGTH: 271
<212> TYPE: DNA
<213> ORGANISM: Homo sapiens

<400> SEQUENCE: 5
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgcccccat ggctgactaa ttttttttat  180
ttatgcagag gccgaggccg cctcggcctc tgagctattc cagaagtagt gaggaggctt   240
ttttggaggc ctaggctttt gcaaaaagct t                                  271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaaccccc gg                                32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                  31

<210> SEQ ID NO 8
<211> LENGTH: 12
```

```
<212> TYPE: DNA
<213> ORGANISM: Homo sapiens

<400> SEQUENCE: 8
ggggactttc cc                                                           12

<210> SEQ ID NO 9
<211> LENGTH: 73
<212> TYPE: DNA
<213> ORGANISM: Homo sapiens

<400> SEQUENCE: 9
gcggcctcga ggggactttc cggggactt tccggggact ttccatcctg                   60
ccatctcaat tag                                                          73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct       60
caattagtca gcaaccatag tcccgcccct aactccgccc atcccgcccc taactccgcc      120
cagttccgcc cattctccgc cccatggctg actaattttt tttatttatg cagaggccga      180
ggccgcctcg gcctctgagc tattccagaa gtagtgagga ggcttttttg gaggcctagg      240
cttttgcaaa aagctt                                                      256

<210> SEQ ID NO 11
<211> LENGTH: 1679
<212> TYPE: DNA
<213> ORGANISM: Homo sapiens
<220> FEATURE:
<221> NAME/KEY: SITE
<222> LOCATION: (1656)
<223> OTHER INFORMATION: n equals a,t,g, or c
<220> FEATURE:
<221> NAME/KEY: SITE
<222> LOCATION: (1664)
<223> OTHER INFORMATION: n equals a,t,g, or c

<400> SEQUENCE: 11
gcagcgcacc cgggcgatcg cttcacggat gcggacgacg tagccatcct tacctacgtg       60
aaggaaaatg cccgctcgcc cagctccgtc accggtaacg ccttgtggaa agcgatggag      120
aagagctcgc tcacgcagca ctcgtggcag tccctgaagg accgctacct caagcacctg      180
cggggccagg agcataagta cctgctgggg gacgcgccgg tgagccctc ctcccagaag       240 ctcaagcgga aggcggagga ggacccggag gccgcggata gcgggaacc acagaataag       300 agaactccag atttgcctga agaagagtat gtgaaggaag aaatccagga gaatgaagaa      360
gcagtcaaaa agatgcttgt ggaagccacc cgggagtttg aggaggttgt ggtggatgag      420
agccctcctg attttgaaat acatataact atgtgtgatg atgatccacc cacacctgag      480
gaagactcag aaacacagcc tgatgaggag gaagaagaag aagaagaaaa agtttctcaa      540
ccagaggtgg gagctgccat taagatcatt cggcagttaa tggagaagtt taacttggat      600
ctatcaacag ttacacaggc cttcctaaaa aatagtggtg agctggaggc tacttccgcc      660
ttcttagcgt ctggtcagag agctgatgga tatcccattt ggtcccgaca agatgacata      720
gatttgcaaa aagatgatga ggataccaga gaggcattgg tcaaaaaatt tggtgctcag      780
```

| | |
|---|---|
| aatgtagctc ggaggattga atttcgaaag aaataattgg caagataatg agaaaagaaa | 840 |
| aaagtcatgg taggtgaggt ggttaaaaaa aattgtgacc aatgaacttt agagagttct | 900 |
| tgcattggaa ctggcactta tttttctgacc atcgctgctg ttgctctgtg agtcctagat | 960 |
| ttttgtagcc aagcagagtt gtagagggg ataaaaagaa aagaaattgg atgtatttac | 1020 |
| agctgtcctt gaacaagtat caatgtgttt atgaaaggaa gatctaaatc agacaggagt | 1080 |
| tggtctacat agtagtaatc cattgttgga atggaaccct tgctatagta gtgacaaagt | 1140 |
| gaaaggaaat ttaggaggca taggccattt caggcagcat aagtaatctc ctgtcctttg | 1200 |
| gcagaagctc ctttagattg ggatagattc caaataaaga atctagaaat aggagaagat | 1260 |
| ttaattatga ggccttgaac acggattatc cccaaaccct tgtcatttcc cccagtgagc | 1320 |
| tctgatttct agactgcttt gaaaatgctg tattcatttt gctaacttag tatttgggta | 1380 |
| ccctgctctt tggctgttct tttttggag cccttctcag tcaagtctgc cggatgtctt | 1440 |
| tctttaccta cccctcagtt ttccttaaaa cgcgcacaca actctagaga gtgttaagaa | 1500 |
| taatgttact tggttaatgt gttatttatt gagtattgtt tgtgctaagc attgtgttag | 1560 |
| atttaaaaaa ttagtggatt gactccactt tgttgtgttg ttttcattgt tgaaaataaa | 1620 |
| tataactttg tattcgaaaa aaaaaaaaaa aaaatnrctg cggnccgaca agggaattc | 1679 |

<210> SEQ ID NO 12
<211> LENGTH: 1963
<212> TYPE: DNA
<213> ORGANISM: Homo sapiens
<220> FEATURE:
<221> NAME/KEY: SITE
<222> LOCATION: (335)
<223> OTHER INFORMATION: n equals a,t,g, or c
<220> FEATURE:
<221> NAME/KEY: SITE
<222> LOCATION: (1959)
<223> OTHER INFORMATION: n equals a,t,g, or c

<400> SEQUENCE: 12

| | |
|---|---|
| ggatcctcgc ggcggcggcg gtgcttacag cctgagaaga gcgtctcgcc cgggagcggc | 60 |
| ggcggccatc gagacccacc caaggcgcgt ccccctcggc ctcccagcgc tcccaagccg | 120 |
| cagcggccgc gccccttcag ctagctcgct cgctcgctct gcttccctgc tgccggctgc | 180 |
| gcatggcktt ggcgttggcg gcgctggcgg cggtcgagcc gcctgcgcag ccggtaccag | 240 |
| cagttgcaga atgaagaaga gtctggagaa cctgaacagg ctgcaggtga tgctcctcca | 300 |
| ccttacagca gcatttctgc agagagcgca gcatnatttt gactacaagg atgagtctgg | 360 |
| gtttccaaag cccccatctt acaatgtagc tacaacactg cccagttatg atgaagcgga | 420 |
| gaggaccaag gctgaagcta ctatcccttt ggttcctggg agagatgagg attttgtggg | 480 |
| tcgggatgat tttgatgatg ctgaccagct gaggatagga aatgatggga ttttcatgtt | 540 |
| aactttttc atggcattcc tctttaactg gattgggttt ttcctgtctt tttgcctgac | 600 |
| cacttcagct gcaggaaggt atggggccat ttcaggattt ggtctctctc taattaaatg | 660 |
| gatcctgatt gtcaggtttt ccacctattt ccctggatat tttgatggtc agtactggct | 720 |
| ctggtgggtg ttccttgttt taggctttct cctgtttctc agaggattta tcaattatgc | 780 |
| aaaagttcgg aagatgccag aaactttctc aaatctcccc aggaccagag ttctctttat | 840 |
| ttattaaaga tgttttctgg caaaggcctt cctgcattta tgaattctct ctcaagaagc | 900 |
| aagagaacac ctgcaggaag tgaatcaaga tgcagaacac agaggaataa tcacctgctt | 960 |
| taaaaaaata aagtactgtt gaaaagatca tttctctcta tttgttccta ggtgtaaaat | 1020 |

-continued

```
tttaatagtt aatgcagaat tctgtaatca ttgaatcatt agtggttaat gtttgaaaaa      1080
gctcttgcaa tcaagtctgt gatgtattaa taatgcctta tatattgttt gtagtcattt      1140
taagtagcat gagccatgtc cctgtagtcg gtagggggca gtcttgcttt attcatcctc      1200
catctcaaaa tgaacttgga attaaatatt gtaagatatg tataatgctg gccattttaa      1260
aggggttttc tcaaaagtta aacttttgtt atgactgtgt ttttgcacat aatccatatt      1320
tgctgttcaa gttaatctag aaatttattc aattctgtat gaacacctgg aagcaaaatc      1380
atagtgcaaa aatacattta aggtgtggtc aaaaataagt ctttaattgg taaataataa      1440
gcattaattt tttatagcct gtattcacaa ttctgcggta ccttattgta cctaagggat      1500
tctaaaggtg ttgtcactgt ataaaacaga agcactagg atacaaatga agcttaatta       1560
ctaaaatgta attcttgaca ctctttctat aattagcgtt cttcacccccc accccaccc     1620 ccaccccccct tattttcctt ttgtctcctg gtgattaggc caaagtctgg gagtaaggag    1680
aggattaggt acttaggagc aaagaaagaa gtagcttgga acttttgaga tgatccctaa      1740
catactgtac tacttgcttt tacaatgtgt tagcagaaac cagtgggtta taatgtagaa      1800
tgatgtgctt tctgcccaag tggtaattca tcttggtttg ctatgttaaa actgtaaata     1860
caacagaaca ttaataaata tctcttgtgt agcacccttta aaaaaaaaaa aaaaaaaaa     1920 aaaaaaaaaa aaaaaaaaa aaaaaaaaaa aaaaaaana aaa                          1963
```

<210> SEQ ID NO 13
<211> LENGTH: 1212
<212> TYPE: DNA
<213> ORGANISM: Homo sapiens

<400> SEQUENCE: 13

```
tgtttgaagt tgttactttt gtttacagca aagtttgatg tagtgtgcag tagtgagctc        60
tagactgatc ttttctaaa tcagaaagtg attaaagtat gcacaaccaa aggcaggttt        120 ttcttttca tttattcagc aactatttat taagcatcaa ctctgtgcca ggcacgttac       180
tagctgctac atactgtctg aacatgacat acggttaagt aactttacaa ttattatcaa      240
atacttcaat gtagatattt cttaagttga aatagcatta actaggataa tgctttcatg      300
ttattttatt tgtcttgtga tagaaattca actttgtacc atcttaaaac taggttgcta      360
taaaaatagg aggatgaagt caataaagtt tatgccagtt taaaaactgg aaggaaaagg     420
taagagctct ccattataaa atagttgcat tcggttaatt tttacacatt agtgcattgc      480
gtatatcaac tggccctcaa tgaagcattt aagtgcttgg aattttacta aactgacttt     540
tttgcaactt tgggagattt tgaggggag tgttgaaaat tgccaaacac tcacctctta      600
ctcaaaactt caaataaaat acacattttc aagagggagc acctttata tttgataagt       660 tttcattata aaccttataa taccagtcac aaagaggttg tctgtctatg gtttagcaaa      720
catttgcttt tcttttttgga agtgtgattg caattgcaga acagaaagtg agaaaacact     780
gccagcggtg attgctactt gaggtagttt tttacaacta ccatttcccc tccatgaaat      840
tatgtgaaat ttattttatc tttgggaaaa gttgagaaga tagtaaaaga attaggaatt     900
taaaattaca gggaaaaata tgtaagtgaa agcaataaa tattttgttc actttgctat      960
caagatgttc actatcagat atttattata tggcagcaat ttatattttt aatcattgcc     1020
cattaataga cgcagtaaaa tattttttgaa tcagacattt gggggtttgta tgtgcattaa    1080 aattgtctttt tgtactgtaa gttactgtta atttgaatat tttattgaac tgtctccctg   1140
```

| | |
|---|---:|
| tgcctttata atataaagtt gtttctacaa cttttaatga tcttaataaa gaatacttta | 1200 |
| agaaaaaaaa aa | 1212 |

<210> SEQ ID NO 14
<211> LENGTH: 2061
<212> TYPE: DNA
<213> ORGANISM: Homo sapiens
<220> FEATURE:
<221> NAME/KEY: SITE
<222> LOCATION: (1703)
<223> OTHER INFORMATION: n equals a,t,g, or c
<220> FEATURE:
<221> NAME/KEY: SITE
<222> LOCATION: (1796)
<223> OTHER INFORMATION: n equals a,t,g, or c

<400> SEQUENCE: 14

| | |
|---|---:|
| ggttttcctc cgacttccgg acatctccct gggagtcgcg cagagtggag tcaaaggcaa | 60 |
| ccagtgctcg ctgcggtctc tggggatcgg gaccgcggcg gcggcccgcg agcgggatgt | 120 |
| tccgggcctt gagcagttgg ttgggcttgc agcagccggt ggcaggcggt gggcagccca | 180 |
| atggagatgc tccacccgag cagccgtccg agacggtggc tgagtctgcg gaggaggagc | 240 |
| tgcagcaagc gggagaccag gagctcctcc accaggccaa agacttcggc aactatttat | 300 |
| ttaactttgc atctgctgcc acaaaaaaga taactgaatc agttgctgaa acagcacaaa | 360 |
| caataaagaa atccgtagaa gaggaaaaaa tagatggcat cattgacaag acaattatag | 420 |
| gagattttca gaaggaacag aaaaaattg ttgaagagca acatacaaag aagtcagaag | 480 |
| cagctgtgcc cccatgggtt gacactaacg atgaagaaac aattcaacaa caaattttgg | 540 |
| ccttatcagc tgacaagagg aatttccttc gtgaccctcc ggctggcgtg caatttaatt | 600 |
| tcgactttga tcagatgtac cccgtggccc tggtcatgct ccaggaggat gagctgctar | 660 |
| caagatgaga tttgccctcg ttcctaaact tgtgaaggaa gaagtgttct ggaggaacta | 720 |
| cttttaccgc gtctccctga ttaagcagtc agcccagctc acggccctgg ctgcccaaca | 780 |
| gcaggccgca gggaagggag gagaagagca atggcagaga caagatttg ccgctggaga | 840 |
| ggcagtacgg cccaaaacgc cacccgttgt aatcaaatct cagcttaaaa ctcaagagga | 900 |
| tgaggaagaa atttctacta gcccaggtgt ttctgagttt gtcagtgatg ccttcgatgc | 960 |
| ctgtaaccta aatcaggaag atctaaggaa agaaatggag caactagtgc ttgacaaaaa | 1020 |
| gcaagaggag acagccgtac tggaagagga ttctgcagat tgggaaaaag aactgcagca | 1080 |
| ggaacttcaa gaatatgaag tggtgacaga atctgaaaaa cgagatgaaa actgggataa | 1140 |
| ggaaatagag aaaatgcttc aagaggaaaa ttagctgttc ctgaaataga gaataatcc | 1200 |
| ttaacagtct gcaaactgac attaaattct agatgttgac aattactgaa tcagaaggca | 1260 |
| tgaaagagta aattttatg aaattcaaaa ttattctttt ttcaagttga aacttgcctc | 1320 |
| ttctacttta aaaagtata tagaacagtt acttctaata atcagaaaga gatgttttat | 1380 |
| agaacatttc tttaatataa agttagagat gtcttcatag gcagtatggc tatctttgcc | 1440 |
| acagaaacat aagtaaaatt ttagagttct gttttccatg aggtcaaaaa tataatttat | 1500 |
| tcctcagtca tggttttcta aatatctgta ctccacattc cattttaatt gatatgaggg | 1560 |
| tgttaaagta cctacttaat gggttgatta ctatcaaaat gaccaaatta taccaaagaa | 1620 |
| cttaagagga agcactttca gaactattca cttgccaggt attttctaaa attccacctg | 1680 |
| aaagccaaaa gataaaatac atnagttgga ttttaatgat ataagcatca cacaatttta | 1740 |
| cattaagaaa tactgtgcag cccatgcgtg gtggctcagg cctgtaatcc cagcantttg | 1800 |

| | | |
|---|---|---|
| ggaggccgag gtgggcagat caccggaggt caggagttcg agaccagcct tgccaacata | 1860 |
| gtgaaaccct gtctttacta aaaatacaaa aattagccgg gcatggtggc aggcacctgt | 1920 |
| aatcccagct actagggagg cttttgaacc caggaggcag aggttgcagc gagctgagat | 1980 |
| cgcgccactg cactccagcc tgggtgatag agtgagattc agtctcaaaa aaaaaaaaa | 2040 |
| aaaaaaaaaa aatgacctcg a | 2061 |

```
<210> SEQ ID NO 15
<211> LENGTH: 1412
<212> TYPE: DNA
<213> ORGANISM: Homo sapiens
<220> FEATURE:
<221> NAME/KEY: SITE
<222> LOCATION: (1362)
<223> OTHER INFORMATION: n equals a,t,g, or c
<220> FEATURE:
<221> NAME/KEY: SITE
<222> LOCATION: (1369)
<223> OTHER INFORMATION: n equals a,t,g, or c
<220> FEATURE:
<221> NAME/KEY: SITE
<222> LOCATION: (1397)
<223> OTHER INFORMATION: n equals a,t,g, or c
```

<400> SEQUENCE: 15

| | | |
|---|---|---|
| cccttcatct gcgttgccag gaaccctgtc agcagaaact tctcaagccc catccttgcc | 60 |
| aggaagctct gtgaaggtgc tgctgatgac ccagattcct ccatggtcct cctgtgtctc | 120 |
| ctgttggtgc ccctcctgct cagtctcttt gtactgggc tatttctttg gtttctgaag | 180 |
| agagagagac aagaagagta cattgaagag aagaagagag tggacatttg tcgggaaact | 240 |
| cctaacatat gccccattc tggagagaac acagagtacg acacaatccc tcacactaat | 300 |
| agaacaatcc taaggaaga tccagcaaat acggtttact ccactgtgga ataccgaaa | 360 |
| aagatggaaa atccccactc actgctcacg atgccagaca caccaaggct atttgcctat | 420 |
| gagaatgtta tctagacagc agtgcactcc cctaagtctc tgctcaaaaa aaaaacaatt | 480 |
| ctcggcccaa agaaaacaat cagaagaatt cactgatttg actagaaaca tcaaggaaga | 540 |
| atgaagaacg ttgacttttt tccaggataa attatctctg atgcttcttt agatttaaga | 600 |
| gttcataatt ccatccactg ctgagaaatc tcctcaaacc cagaaggttt aatcacttca | 660 |
| tcccaaaaat gggattgtga atgtcagcaa accataaaaa aagtgcttag aagtattcct | 720 |
| ataaaaatgt aaatgcaagg tcacacatat taatgacagc ctgttgtatt aatgatggct | 780 |
| ccaggtcagt gtctggagtt tcattccatc ccagggcttg gatgtcagga ttataccaag | 840 |
| agtcttgcta ccaggagggc aagaagacca aaacagacag acaagtccag cagaagcaga | 900 |
| tgcacctgac aaaaatggat gtattaattg gctctataaa ctatgtgccc agcaytatgc | 960 |
| tgagcttaca ctaattggtc agacatgctg tctgccctca tgaaattggc tccaaatgaw | 1020 |
| tgaactactt tcatgagcag ttgtagcagg cctgaccaca gattcccaga gggccaggtg | 1080 |
| tggatccaca ggacttgaag gtcaaagttc acaaagatga agaatcaggg tagctgacca | 1140 |
| tgtttggcag atactataat ggagacacag aagtgtgcat ggcccaagga caaggacctc | 1200 |
| cagccaggct tcatttatgc acttgtctgc aaaagaaaag tctaggtttt aaggctgtgc | 1260 |
| cagaacccat cccaataaag agaccgagtc tgaagtcaca ttgtaaatct agtgtaggag | 1320 |
| acttggagtc aggcagtgag actggtgggg cacgggggc antgggtant gtaaacctt | 1380 |
| taaagatggt taattcntca ttagtgtttt tt | 1412 |

<210> SEQ ID NO 16
<211> LENGTH: 1052
<212> TYPE: DNA
<213> ORGANISM: Homo sapiens

<400> SEQUENCE: 16

```
ttcctctcct ctctctaccc ctcctgtctc tcctcccctc ctctctcttc ctctcctctc      60
tctcttcctc tcctctctct tcccttcctg tctctcttcc cctcctctct ctcttcctgt     120
cctctatctc ttccccctcct ctatctcttc ctctcctctc tctcttcctc tcctctctct    180
ctcttscttt cttctctctc tcctgtctcg gctgttgtgg gttgcaggtt gggtgctgct     240
gttgtggtcc ttcccagaaa ctgccagtag agggcagcct gggcatccta atgcttactc     300
tggttgttac acaaagaaaa tattggggtc actggcgagc ccacccacac tcaccagaat     360
ctccactgta gtcccctaa caaacagccc ttcacttcct ctcccacttc agcaatttgt      420
attttgatgc cattggcctc agatcagagt gttttaaatc atcacgccct ggcttatccc     480
tggtcgagcc aggacacggg gtgcttcagt gggtctgtca ccctctctcc ttgaagcatg     540
ttgcttttat ttatttactt ttactctcac cctgctcctg taccagcagg ggccacttca     600
aagccaaggt acagggtgat aacttgtggt ccagcatcag ttttctccac ttctttctcc     660
cactcacccc cagcaaggtg cctggggaga cttgagcaga tgtttcattt tggcctggcc     720
agtggctgaa agcaggcctc caatgcactg tgacctctgg cttccccagc agctttccca     780
gagaggcaga ggggccttcc acagcccggg ttctcctgct gcctcctgcc tgctgcagct     840
gcaggcattc tgaggggcaa cgtggaggaa gggccaggga tgcatgggat tttaattgtt     900
tcatcacacc ttccccgtgg caaagaaaca gtcagtcctc ttcaggtgtc ttctggattt     960
ctggtgatgg acagagaaat ctttttacag tttcaaatta tgttcaacaa ataaaaattg    1020
cattttttat tttggaaaaa aaaaaaaaaa aa                                  1052
```

<210> SEQ ID NO 17
<211> LENGTH: 683
<212> TYPE: DNA
<213> ORGANISM: Homo sapiens

<400> SEQUENCE: 17

```
aattcggcag aggcacttat catgtacata tagcctgttt tttagcattg ttagacaaag      60
taggcatatt cctttccatc caagaactca taacctagta attgtagttg gctgatagct     120
cattgcccat acacaaggat ctaacacaac ctcttgaata acatccccc ttattcagaa      180
atgccttttc ctatttccat attgcaactt tgcttacaaa tttccaatct gtctttctgt     240
ttacagaaga tatacaaaat tcctttttgta tgatctcttt atatctcttg attttctttt     300
gtgtttgcta ccaaagggcc tgcacatagt gagaagattg tgcatgatct gtgagctcta     360
ccacacctgg aattagggat caccaatatg agaaaaaaaa ttggaggtac aaataacatt     420
atcatatgtw attggcatat aaattacaga tgtwtctatg actaaaaacc ctgtggatat     480
waaccmaatg cagataawtw taataaaatw twtaaaaatw twatcmaata atgatagtgc     540
tattcaaata cttcaaattt gcacagtgat ttatttctta aaatatgtta acacatgtga     600
gccaatacac tgaggtcact ggataaataa acagattctt gcaaaaaaaa aaaaaaaaa      660
actcgagggg ggcccgtacc ctt                                             683
```

<210> SEQ ID NO 18
<211> LENGTH: 1054

```
<212> TYPE: DNA
<213> ORGANISM: Homo sapiens
<220> FEATURE:
<221> NAME/KEY: SITE
<222> LOCATION: (74)
<223> OTHER INFORMATION: n equals a,t,g, or c
<220> FEATURE:
<221> NAME/KEY: SITE
<222> LOCATION: (1014)
<223> OTHER INFORMATION: n equals a,t,g, or c

<400> SEQUENCE: 18
```

| | | | | | |
|---|---|---|---|---|---|
| aaactcattt | aggtgacact | atagaaggta | cgcctgcagg | taccggtccg | gaattcccgg | 60 |
| gtcgacccac | gmgnccggcg | acaagatggc | agcagcgtgt | cggagcgtga | agggcctggt | 120 |
| ggcggtaata | accggaggag | cctcgggcct | gggcctggcc | acggcggacg | acttgtgggg | 180 |
| cagggagcct | ctgctgtgct | tctggacctg | cccaactcgg | gtggggaggc | ccaagccaag | 240 |
| aagttaggaa | acaactgcgt | tttcgcccca | gccgacgtga | cctctgagaa | ggatgtgcaa | 300 |
| acagctctgg | ctctagcaaa | aggaaagttt | ggccgtgtgg | atgtagctgt | caactgtgca | 360 |
| ggcatcgcgg | tggctagcaa | gacgtacaac | ttaaagaagg | gccagaccca | taccttggaa | 420 |
| gacttccagc | gagttcttga | tgtgaatctc | atgggcacct | tcaatgtgat | ccgcctggtg | 480 |
| gctggtgaga | tgggccagaa | tgaaccagac | cagggaggcc | aacgtggggt | catcatcaac | 540 |
| actgccagtg | tggctgcctt | cgagggtcag | gttggacaag | ctgcatactc | tgcttccaag | 600 |
| ggggaatag | tgggcatgac | actgcccatt | gctcgggatc | tggctcccat | aggtatccgg | 660 |
| gtgatgacca | ttgccccagg | tctgtttggc | accccactgc | tgaccagcct | cccagagaaa | 720 |
| gtgtgcaact | tcttggccag | ccaagtgccc | ttccctagcc | gactgggtga | ccctgctgag | 780 |
| tatgctcacc | tcgtacaggc | catcatcgag | aacccattcc | tcaatggaga | ggtcatccgg | 840 |
| ctggatgggg | ccattcgtat | gcagccttga | agggagaagg | cagagaaaac | acacgctcct | 900 |
| ctgcccttcc | tttccctggg | gtactactct | ccagcttggg | aggaagccca | gtagccattt | 960 |
| tgtaactgcc | taccagtcgc | cctctgtgcc | taataaagtc | tcttttctc | acanaaaaaa | 1020 |
| aaaaaaaaaa | aaaaaaaaaa | aaaaaaaaaa | aaaa | | | 1054 |

```
<210> SEQ ID NO 19
<211> LENGTH: 1393
<212> TYPE: DNA
<213> ORGANISM: Homo sapiens
<220> FEATURE:
<221> NAME/KEY: SITE
<222> LOCATION: (127)
<223> OTHER INFORMATION: n equals a,t,g, or c
<220> FEATURE:
<221> NAME/KEY: SITE
<222> LOCATION: (376)
<223> OTHER INFORMATION: n equals a,t,g, or c
<220> FEATURE:
<221> NAME/KEY: SITE
<222> LOCATION: (447)
<223> OTHER INFORMATION: n equals a,t,g, or c
<220> FEATURE:
<221> NAME/KEY: SITE
<222> LOCATION: (782)
<223> OTHER INFORMATION: n equals a,t,g, or c
<220> FEATURE:
<221> NAME/KEY: SITE
<222> LOCATION: (1379)
<223> OTHER INFORMATION: n equals a,t,g, or c
<220> FEATURE:
<221> NAME/KEY: SITE
<222> LOCATION: (1382)
<223> OTHER INFORMATION: n equals a,t,g, or c
<220> FEATURE:
```

```
<221> NAME/KEY: SITE
<222> LOCATION: (1383)
<223> OTHER INFORMATION: n equals a,t,g, or c

<400> SEQUENCE: 19
ggaacaagct gggatatgtg agcgttaagc tactcacatc cttcaaaaag gtgaaacatc      60
ttacacggga ctggagaacc acagcacatg ctttgaagta ttcagtggtc cttgagttga     120
atgaggncca ccggaaggtg aggaggacca cccccgtccc actgttcccc aacgagaacc     180
tccccagcaa gatgctcctg gtctatgatc tctacttgty cctaagctg tgggctctgg      240 ccacccccca gaagaatggg aagggtgcaa garaaggtga tggaacacct gctcaagctt     300
tttgggactt ttggagtcat ctcatcagtg cggatcctca aacctgggag agagctgccc     360
cctgacatcc ggaggntcca gcagccgcta cagctcctct gaccccgaga gcaaccccac     420
atcccctatg gcgggccgac ggcacgngkc caccaacaag ctcagcccgt ctggccacca     480
gaatctcttt ctgagtccaa atgcctcccc gtgcacaagt ccttggagca gccccttggc     540
ccaacgcaaa ggcgtttcca gaaagtcccc actggcggag gaaggtagac tgaactgcag     600
caccagccct gagatcttcc gcaagtgtat ggattattcc tctgacagca gcgtcactcc     660
ctctggcagc ccctgggtcc ggaggcgtcg ccaagccgag atggggaccc aggagaaaag     720
ccccggtacg agtcccctgc tctcccggaa gatgcagact gcagatgggs tacccgtagg     780
tngcttgagg ttgcccaggg gtcctgacaa caccagagga tttcatggcc atgagaggag     840
cagggcctgt gtataaatac cttctatttt taatacaagc tccactgaaa accaccttcg     900
ttttcaaggt tctgacaaac acctggcatg acagaatgga attcgttccc ctttgagaga     960
ttttttattc atgtagacct cttaatttat ctatctgtaa tatacataaa tcggtacgcc    1020
atggtttgaa gaccaccttc tagttcagga ctcctgttct tcccagcatg gccactattt    1080
tgatgatggc tgatgtgtgt gagtgtgatg gccctgaagg gctgtaggac ggaggttccc    1140
tgggggaagt ctgttctttg gtatggaatt tttctctctt ctttggtatg gaattttttcc   1200 cttcagtgac tgagctgtcc tcgataggcc atgcaagggc ttcctgagag ttcaggaaag    1260
ttctcttgtg caacagcaag tagctaagcc tatagcatgg tgtcttgtag gaccaaatcg    1320
atgttacctg tcaagtaaat aaataataaa acacccaact gggagtgctg aaaaaaaana    1380
annaaaaaac tcg                                                       1393

<210> SEQ ID NO 20
<211> LENGTH: 1215
<212> TYPE: DNA
<213> ORGANISM: Homo sapiens
<220> FEATURE:
<221> NAME/KEY: SITE
<222> LOCATION: (15)
<223> OTHER INFORMATION: n equals a,t,g, or c
<220> FEATURE:
<221> NAME/KEY: SITE
<222> LOCATION: (61)
<223> OTHER INFORMATION: n equals a,t,g, or c
<220> FEATURE:
<221> NAME/KEY: SITE
<222> LOCATION: (65)
<223> OTHER INFORMATION: n equals a,t,g, or c
<220> FEATURE:
<221> NAME/KEY: SITE
<222> LOCATION: (104)
<223> OTHER INFORMATION: n equals a,t,g, or c
<220> FEATURE:
<221> NAME/KEY: SITE
<222> LOCATION: (180)
<223> OTHER INFORMATION: n equals a,t,g, or c
```

<400> SEQUENCE: 20

| | | | | | |
|---|---|---|---|---|---|
| aggaaaagtt | ttccnaattg | gaaagcgggc | agtgagcgca | acgcaattaa | tgtgagttag | 60 |
| ntcantcatt | aggcacccca | ggctttacac | tttatgcttc | cggntcgtat | gttgtgtgga | 120 |
| attgtgagcg | gataacaatt | tcacacagga | aacagctatg | accatgatta | cgccaagctn | 180 |
| taatacgact | cactataggg | aaagctggta | cgcctgcagg | taccggtccg | gaattcccgg | 240 |
| gtcgacccac | gcgtccgccc | acgcgtccgt | gaaaatccga | agtgccgcgg | aaagtggagg | 300 |
| tgagggccgc | ccgccctaga | ggtgcccgtc | cgagaggcag | agctgacaag | gaaggtttcg | 360 |
| agcgttttgc | tggcaaaggg | atttcttaca | acctccaggc | atgcgtcttt | ctgccctgct | 420 |
| ggccttggca | tccaaggtca | ctctgccccc | ccattaccgc | tatgggatga | gccccccagg | 480 |
| ctctgttgca | gacaagagga | agaaccccccc | atggatcagg | cggcgcccag | tggttgtgga | 540 |
| acccatctct | gatgaagact | ggtatctgtt | ctgtggggac | acggtggaga | tcctagaagg | 600 |
| caaggatgcc | gggaagcagg | gcaaagtggt | tcaagttatc | cggcagcgaa | actgggtggt | 660 |
| cgtgggaggg | ctgaacacac | attaccgcta | cattggcaag | accatggatt | accgggggaac | 720 |
| catgatccct | agtgaagccc | ccttgctcca | ccgccaggtc | aaacttgtgg | atcctatgga | 780 |
| caggaaaccc | actgagatcg | agtggagatt | tactgaagca | ggagagcggg | tacgagtctc | 840 |
| cacacgatca | gggagaatta | tccctaaacc | cgaatttccc | agagctgatg | gcatcgtccc | 900 |
| tgaaacgtgg | attgatgcc | ccaaagacac | atcagtggaa | gatgctttag | aaagaaccta | 960 |
| tgtgccctgt | ctaaagacac | tgcaggagga | ggtgatggag | gccatgggga | tcaaggagac | 1020 |
| ccggaaatac | aagaaggtct | attggtattg | agcctggggc | agagcagctc | ctccccaact | 1080 |
| tctgtcccag | ccttgaaggc | tgaggcactt | cttttcaga | tgccaataaa | gagcacttta | 1140 |
| tgagtcctcc | aaaaaaaaa | aaaaaaaaa | aaaaaaaaa | aaaaaaaaa | aaaaaaaaa | 1200 |
| aaaagggggcg | gccgc | | | | | 1215 |

<210> SEQ ID NO 21
<211> LENGTH: 2042
<212> TYPE: DNA
<213> ORGANISM: Homo sapiens

<400> SEQUENCE: 21

| | | | | | |
|---|---|---|---|---|---|
| ctgcatccag | gcgcagaata | acctgggtat | cttgtggtct | gaaagagaga | aattgaaact | 60 |
| gcacaggctt | acctagagtc | atcagaagca | ctatataatc | agtatatgaa | agaggttggg | 120 |
| agtcctcctc | ttgatcctac | tgagcgtttt | cttctgaaga | agagaaactt | actgaacaag | 180 |
| agagatcaaa | aagatttgaa | aaggtttata | ctcataacct | atattcccta | gctcaagtct | 240 |
| accagcatct | ggaaatgttt | gagaaggctg | ctcactattg | ccatagtaca | ctaaaacgcc | 300 |
| agcttgagca | caatgcctac | catcctatag | agtgggctat | caatgctgct | accttgtcac | 360 |
| agttttacat | caataagcta | tgctttatgg | aggccaggca | ctgtttatca | gctgctaatg | 420 |
| tcattttttgg | tcaaactgga | agatctcag | ccacagaaga | cactcctgaa | gctgaaggag | 480 |
| aagtgccaga | gctttatcat | caaagaaagg | gggaaatagc | aaggtgctgg | atcaaatact | 540 |
| gtttgactct | catgcagaat | gcccaactct | ccatgcagga | caacatagga | gagcttgatc | 600 |
| ttgataaaca | gtctgaactt | agagctttaa | ggaaaaaaga | actagatgag | gaggaaagca | 660 |
| ttcggaaaaa | agctgtgcag | tttgaaccgt | gtgaactgtg | tgatgccatc | tctgcagtag | 720 |
| aagagaaagt | gagctacttg | agacctttag | attttgaaga | agccagagaa | cttttcttat | 780 |

```
tgggtcagca ctatgtcttt gaggcaaaag agttctttca gattgatggt tatgtcactg      840
accatattga agttgtccaa gaccacagtg ctctgtttaa ggtgcttgca ttctttgaaa      900
ctgacatgga gagacggtgc aagatgcata acgcrgaat  agccatgcta gagcccctaa      960
ctgtagacct gaatccacag tattatctgt tggtcaacag acagatccag tttgaaattg     1020
cacatgctta ctatgatatg atggatttga aggttgccat tgctgacagg ctaagggatc     1080
ctgattcaca cattgtaaaa aaataaata  atcttaataa gtcagcactg aagtactacc     1140
agctcttctt agactccctg agagaccaa  ataaagtatt ccctgagcat ataggggaag     1200
atgttcttcg ccctgccatg ttagctaagt ttcgagttgc ccgtctctat ggcaaaatca     1260
ttactgcaga tcccaagaaa gagctggaaa atttggcaac atcattggga acattacaaa     1320
tttattgttg attactgtga aaagcatcct gaggccgccc aggaaataga agttgagcta     1380
gaacttagta aagagatggt tagtcttctc ccaacaaaaa tggagagatt cagaaccaag     1440
atggccctga cttaatcctt gtttttaaag aaggaaatg  tgcaatattg aagtgatctt     1500
tttccctagt cagacaggcc caattccatt gtgatgttta cctttatagc caggtgagtg     1560
cagtttgaac ttgagataca gtcaactgag tgtttgctag gatcctaagg aacataaagt     1620
taattaaaaa cttacaccta attatgtaaa ttgccttgtt aaagacatgt gatttgtatt     1680
ttagatgctt gttcctatt  aaaatacaga catttctacc ctcagtttct aaatgtagac     1740
tatttgttgg ctagtacttg atagattcct tgtaagaaaa aatgctgggt aatgtacctg     1800
gtaacaagcc tgttaatata ttaagattga aaaagtaact tctatagtta ctccttctaa     1860
aatatttgac ttcctacatt cccccaccc  aaaatctttc ccttttgaaa atactaaaaa     1920
ctaagttatg ttattataaa gtgtaaaatg gtttgtctta attataggag aaaaaggcct     1980
tgttagaaat aaaataaact gacttatttc actaatgaaa aaaaaaaaa  aaaaaaaaa      2040 tt                                                                    2042

<210> SEQ ID NO 22
<211> LENGTH: 1872
<212> TYPE: DNA
<213> ORGANISM: Homo sapiens
<220> FEATURE:
<221> NAME/KEY: SITE
<222> LOCATION: (1871)
<223> OTHER INFORMATION: n equals a,t,g, or c

<400> SEQUENCE: 22
gggtcgaccc acgcgtccga ttggcctaga gctcctgtga ccgagagcgc cacggaagcc       60
tggggatgat gtcgggcagc tttattcttt gcttggcttt ggtaactagg tggtcccctc      120
aagcatcctc agttcctctt gctgtttatg aatctaagac aaggaagtcc tatagaagcc      180
aaagggacag ggacggaaag gacaggtccc aagggatggg gctgtcttta cttgtggaaa      240
ccaggaaatt gctcctctca gccaaccaag gttgaccaca caccacccctt ccggagcagc      300 tcagtcagcc ctcggggacg rgaaaccaca agcgcagaga cgctgaggcc caggcaggtg      360
aagaggaagt ggctttgggt ttttaaagta ggtgagcgtg acctctctga ctgcttcttc      420
cccggggggg actgcaaacc gctcagggtt gcggcagagc catggacttc cggtccctgc      480
aacgggtgac ctaagcgtgg tgcacccatc agtcacgcag gaggactgac ttgacagacg      540
aaagacaagc ccggatgaca cagggtgaga agagtcaggg ccgcacctct gtccctgcaa      600
accaacaggt gcatggtgag tgtggcagtc cccacagctc cacaatgggc tccccgcca       660 acggggacga cagggatctt caggaacttc tgacctcacc aagtcaagtg gaccactctc      720
```

```
cactccacga ggatgtgaaa cggttctttta aaatgggatt ttagagcctc gggaatgcat      780
gtgcgtcgca tctttcatat tatgggtcag gatagattca tttcttgcaa catagtggaa      840
aagatataag ctgcagtaat ttgctctttg aatgaccgtc accccccagta taggatatgc     900
ttgtatcccc ccgtcactcc tccgcctgtt ttttaaactt ttccaccacc tgcgtccaaa      960
aagaatgtta tagcgagtgc tcttaaatgt tgaacctggg tgttgcttcc gggccagtct     1020
gcgtggctcc atgaaaagct cactgctgcc ccagccgggc ttcttagagg aggtcagttg     1080
tcctatgtat catcatttac tctgggaatc ctactgtgaa atcatgtctg tattttctg      1140
gagcagttca catagagtag aatgtggaat ttcccgtgaa cgtctccttc ctcccccgta     1200
tctgccgcct gtcacttcgc caccgtgcta gaatactgtt gtgttgtaag atgactaatt     1260
ttaaaagaac ctgccctgaa aagttcttag aaacgcaatg aaagggagga acttgtcctt     1320
tacccagttt ttcctttgta ggatgggaaa gtataaaaag gcacagaagg ttgtcatggg     1380
ctgttccttg ggggttttta tcctgctcac cgtggagata agcctgcggc ttgtctaacc     1440
agcgcagcgm aaaggtctca atgccttttg gtaacatccg tcattgcaga agaaagttta     1500
cacgacgtca aaaagtgacg ttcatgctaa gtgttttttcc agaaatattg gtttcatgtt     1560
tcttattkgc tctgcctcct gtgcttatat catccaaaaa cttttttaaaa aggtccagaa     1620
ttctatttta acctgatgtt gagcaccttt aaaacgttcg tatgtgtgtt gcactaattc     1680
taaactttgg aggcattttg ctgtgtgagg ccgatcgcca ctgtaaaggt cctagagttg     1740
cctgtttgtc tctggagatg gaattaaacc aaataaagag cttccactgg aggcttgtat     1800
tgaccttgta actatatgtt aatctcgtgt taaaataaaa ataacttgt gaaaaaaaaa      1860
aaaaaaaaac nt                                                         1872

<210> SEQ ID NO 23
<211> LENGTH: 289
<212> TYPE: DNA
<213> ORGANISM: Homo sapiens
<220> FEATURE:
<221> NAME/KEY: SITE
<222> LOCATION: (284)
<223> OTHER INFORMATION: n equals a,t,g, or c

<400> SEQUENCE: 23
catttaccca cctatcaaca tgtttgcttt ctcttttgtt ggtgagaatg agtggcttct       60
tgctcctagc tagagccagt ccttccatat gtgcttaga ttcttcctgt tttgttcaag       120
aatattgctc aagctattct tcctcctgtt tcctgcatca gcatttcccc tctctactag      180
atcatctctg tcagtaaatg aacatgttgt tgtttctcct agaagtactg tttctatatc      240
tagatagtac tctagctaga gttaaaaaaa aaaaaaaaa cctngggg                   289

<210> SEQ ID NO 24
<211> LENGTH: 3533
<212> TYPE: DNA
<213> ORGANISM: Homo sapiens
<220> FEATURE:
<221> NAME/KEY: SITE
<222> LOCATION: (44)
<223> OTHER INFORMATION: n equals a,t,g, or c

<400> SEQUENCE: 24
ttttatttac ttcaaattaa ctgtacttta ctcaaataga aangaataa ttttcacatt        60
atgaagctac acaattccaa aatacacatg ctgaggctct tttttaagtcc gaattgtcta    120
```

-continued

```
gtaattacaa aaaagtgaag agtttacaga tatacaagga aataaaggcg aattattgca   180
aagaaaacaa gtttaatttc actttgaatg acaacgattt ttctggaaag cagatacttc   240
actcctttaa gtttccaccc aagccacaat aatttcaaac ggtcttgcgg atgacccagc   300
tggtcactct tgtttatgtg gggactggag gtaatgagag ccaaaaaaag tgctataaac   360
ctaatttggc tagagcaagt tcacacgaca cgaccgtgct ttaaaaactt gctctccatt   420
atgtacttcc ttccatcagg ttggggaaaa aaaatggtg gggatggtga gtaaacacac   480
cagtggtttc atcagagggg aactcactac tcaggaggtg acggtgacgt ggtgccggtc   540
cctgaagtac gcgcacaagc tccggaggtt gcgggagctt ccgctgccgc ctggagggaa   600
gccggagcga cgggggtcac ggcggcggtc agagggtaaa ggtcttgctc ccagcagcct   660
ccgcggtgga tacgtcgcca tcttggatcc gcgggacaag aaaattcatg cgagggagac   720
gtggtgggcg gtccttcctg tgacacgacc cttgagtgac agttctattt gattgcctcc   780
ggtactgtga ggaaaggaca cgactctatg gtgaggactg atggcatac attatctgag   840
aaaagaaact accaggtgac aaacagcatg tttggtgctt caagaaagaa gtttgtagag   900
ggggtcgaca gtgactacca tgacgaaaac atgtactaca gccagtcttc tatgtttcca   960
catcggtcag aaaaagatat gctggcatca ccatctacat caggtcagct gtctcagttt  1020
ggggcaagtt tatacgggca acaaagtgca ctaggccttc caatgagggg gatgagcaac  1080
aatacccctc agttaaatcg cagcttatca caaggcactc agttaccgag ccacgtcacg  1140
ccaacaacag gggtaccaac aatgtcactt cacacgcctc catctccaag cagggtatt  1200
ttgcctatga atcctargaa tatgatgaac cactcccagg ttggtcaggg cattggaatt  1260
cctagcagga caaatagcat gagcagttca gggttaggta gccccaacag aagctcgcca  1320
agcataatat gtatgccaaa gcagcagcct tctcgacagc cttttactgt gaacagtatg  1380
tctggatttg gaatgaacag gaatcaggca tttggaatga ataactcctt atcaagtaac  1440
attttaatg gaacagacgg aagtgaaaat gtgacaggat tggaccttc agatttccca  1500
gcattagcag accgaaacag gagggaagga agtggtaacc caactccatt aataaacccc  1560
ttggctggaa gagctcctta tgttggaatg gtaacaaaac cagcaaatga acaatcccag  1620
gacttctcaa tacacaatga agattttcca gcattaccag gctccagcta taaagatcca  1680
acatcaagta atgatgacag taaatctaat ttgaatacat ctggcaagac aacttcaagt  1740
acagatggac ccaaattccc tggagataaa agttcaacaa cacaaaataa taaccagcag  1800
aaaaaaggga tccaggtgtt acctgatggt cgggttacta acattcctca agggatggtg  1860
acggaccaat ttggaatgat tggcctgtta acatttatca gggcagcaga acagacccca  1920
ggaatggtac atcttgcatt aggaagtgac ttaacaacat taggcctcaa tctgaactct  1980
cctgaaaatc tctaccccaa atttgcgtca ccctgggcat cttcaccttg tcgacctcaa  2040
gacatagact tccatgttcc atctgagtac ttaacgaaca ttcacattag ggataagctg  2100
gctgcaataa aacttggccg atatggtgaa gaccttctct tctatctcta ttacatgaat  2160
ggaggagacg tattacaact tttagctgca gtggagcttt ttaaccgtga ttggagatac  2220
cacaaagaag aacgagtatg gattaccagg gcaccaggca tggagccaac aatgaaaacc  2280
aatacctatg agagggaac atattacttc tttgactgtc ttaactggag gaaagtagct  2340
aaggagttcc atctggaata tgacaaatta gaagaacggc ctcacctgcc atccaccttc  2400
aactacaacc ctgctcagca agccttctaa aaaaaaaaa aaaaaaaaa aaaaagactt  2460
ccctttttctt gggggtatggc tgtctcagca caatactcaa cataactgca gaactgatgt  2520
```

```
ggctcaggca ccctggtttt aattccttga ggatctggca attggcttac gcaaaaggtc   2580
accatttgag gtcctgcctt actaattatg tgctgcccaa caactaaatt tgtaatttgt   2640
ttttctctag tttgagcagg gtctgaattt tttcatttat ttccttttt gccagcagac    2700 agacttgagt ctgtaaagac aagcaaatac actgacagaa gtttaccata gtttctaaaa   2760
tgtaaaaaag aaaacccca aaagactcaa gaaaattaga ccacaaattt tgcattgttc    2820
attgtagcac tattggtaat aaaataacaa atgtttgtgc attttatgt gaagatcctt    2880 ctcgtatttc atttggaaag atgagcaaga ggtctgcttc cttcatttta cttcccttc    2940 tgtttttgaa aggcagtttc gccaagctta atgcaagaat atctgactgt ttagaagaaa   3000
gatattgcca caatctctgg atggttttcc agggttgtgt tattactgag cttcatcttt   3060
ccagaatgag caaaacactg tccagtcttt gttacgattt tgtaataaat gtgtacattt   3120
tttttaaatt tttggacatc acatgaataa aggtatgtat gtacgaatgt gtatatatta   3180
tatatatgac atctattttg gaaaatgttt gccctgctgt acctcatttt taggaggtgt   3240
gcatggatgc aatatatgaa aatgggacat tctggaactg ctggtcaggg gactttgtcg   3300
ccctgtgcac taaaagggcc agattttcag cagccaagga catccatacc caagtgaatg   3360
tgatgggact taaaagaagt gaactgagac aattcactct ggctgtttga acagcagcgt   3420
ttcataggaa gagaaaaaaa gatcaatctt gtatttctg accacataaa ggcttcttct    3480
ctttgtaata aagtagaaaa gctctcctca aaaaaaaaaa aaaaaaactc gag           3533
```

<210> SEQ ID NO 25
<211> LENGTH: 1148
<212> TYPE: DNA
<213> ORGANISM: Homo sapiens

<400> SEQUENCE: 25

```
acccacgcgt ccgcaaatta tacttcctca ttcatattat gttgatacaa aagaccttgg     60
cagccatttc tcccagcagt tttaaaggat gaacattgga tttcatgcca tcccatagaa    120
aacctgtttt aaaattttag ggatctttac ttggtcatac atgaaaagta cactgcttag    180
aaattataga ctattatgat ctgtccacag tgcccattgt cacttctttg tctcatttct    240 tcccttttgtt ccttagtcat ccaaataagc ctgaaaacca taagagatat tactttattg    300
aatatggttg gcattaaatt tagcatttca ttatctaaca aaattaatat aaattccagg    360
acatggtaaa atgtgtttta ataaccccca gacccaaatg aaaatttcaa agtcaatacc    420
agcagattca tgaaagtaaa tttagtccta taattttcag cttaattata aacaaaggaa    480
caaataagtg gaagggcagc tattaccatt cgcttagtca aaacattcgg ttactgccct    540
ttaatacact cctatcatca gcacttccac catgtattac aagtcttgac ccatccctgt    600
cgtaactcca gtaaaagtta ctgttactag aaaatttta tcaattaact gacaaatagt    660
ttctttttaa agtagtttct tccatcttta ttctgactag cttccaaaat gtgttccctt    720
tttgaatcga ggtttttttg ttttgttttg tttttctgaaa aaatcataca actttgtgct    780
tctattgctt ttttgtgttt tgttaagcat gtcccttggc ccaaatggaa gaggaaatgt    840
ttaattaatg cttttttagtt taaataaatt gaatcattta taataatcag tgttaacaat    900
ttagtgaccc ttggtaggtt aaaggttgca ttatttatac ttgagatttt ttttccctaa    960
ctattctgtt ttttgtactt taaaactatg ggggaaatat cactggtctg tcaagaaaca   1020
gcagtaatta ttactgagtt aaattgaaaa gtccagtgga ccaggcattt cttatataaa   1080
```

-continued

```
taaaattggt ggtactaatg tgaaaaaaaa aaaaaaaaaa aactcgaggg gggcccggta    1140
ccctatta                                                             1148

<210> SEQ ID NO 26
<211> LENGTH: 717
<212> TYPE: DNA
<213> ORGANISM: Homo sapiens

<400> SEQUENCE: 26
ggcacgagct agctgccgcc acccgaacag cctgtcctgg tgccccggct ccctgccccg      60
cgcccagtca tgaccctgcg cccctcactc ctcccgctcc atctgctgct gctgctgctg     120
ctcagtgcgg cggtgtgccg ggctgaggct gggctcgaaa ccgaaagtcc cgtccggacc     180
ctccaagtgg agaccctggt ggagccccca gaaccatgtg ccgagcccgc tgcttttgga     240
gacacgcttc acatacacta cacgggaagc ttggtagatg gacgtattat tgacacctcc     300
ctgaccagag accctctggt tatagaactt ggccaaaagc aggtgattcc aggtctggag     360
cagagtcttc tcgacatgtg tgtgggagag aagcgaaggg caatcattcc ttctcacttg     420
gcctatggaa aacggggatt tccaccatct gtcccagcgg atgcagtggt gcagtatgac     480
gtggagctga ttgcactaat ccgagccaac tactggctaa agctggtgaa gggcattttg     540
cctctggtag ggatgccat ggtgccagcc tccctgggcc tcattgggta tcacctatac      600
agaaaggcca atagacccaa agtctccaaa agaagctca aggaagagaa acgaaacaag       660
agcaaaaaga aataataaat aataaatttt aaaaaaaaaa aaaaaaaaaa aaaaaaa        717

<210> SEQ ID NO 27
<211> LENGTH: 1099
<212> TYPE: DNA
<213> ORGANISM: Homo sapiens
<220> FEATURE:
<221> NAME/KEY: SITE
<222> LOCATION: (1030)
<223> OTHER INFORMATION: n equals a,t,g, or c

<400> SEQUENCE: 27
ggcacgagcc gatgtggaca tcatcctgtc tatccccatg ttcctgcgcc tgtacctgat      60
cgcccgagtc atgctgctgc acagcaagct cttcaccgat gcctcgtccc gcagcatcgg     120
ggccctcaac aagatcaact tcaacacccg ctttgtcatg aagacgctca tgaccatctg     180
ccctggcact gtgctgctcg tgttcagcat ctctctgtgg atcattgctg cctggaccgt     240
ccgtgtctgt gaaagtcctg aatcaccagc ccagccttct ggctcatcac ttcctgcttg     300
gtaccatgac cagcaggacg taactagtaa ctttctgggt gccatgtggc tcatctccat     360
cacattcctt tccattggtt atgggacat ggtgccccac acatactgtg ggaaaggtgt      420
ctgtctcctc actggcatca tgggtgcagg ctgcactgcc cttgtggtgg ccgtggtggc     480
ccgaaagctg gaactcacca agcggagaa gcacgttcat aacttcatga tggacactca      540
gctcaccaag cggatcaaga atgctgcagc caatgtcctt cgggaaacat ggttaatcta     600
taaacacaca aagctgctaa agaagattga ccatgccaaa gtgaggaaac accagaggaa     660
gttcctccca agctatccac cagtttgagg agcgtcccag atggaacaga ggaaagctga     720
gtgaccaagc caacactctg gtggaccttt ccaagatgca gaatgtcatg tatgacttaa     780
tcacagaact caatgaccgg agcgaagacc tggagaagca gattggcagc ctggagtcga     840
agctggagca tctcaccgcc agcttcaact ccctgccgct gctcatcgcc gacaccctgc     900
gccagcagca gcagcagctc ctgtctgcca tcatcgaggc ccggggtgtc agcgtggcag     960
```

| | |
|---|---|
| tgggcaccac ccacacccca atctccgata gccccattgg ggtcagctcc acctccttcc | 1020 |
| cgaccccgtn cacaagttca agcagttgct aaataaatct ccccactcca gaagcattaa | 1080 |
| aaaaaaaaaa aaaaaaaa | 1099 |

<210> SEQ ID NO 28
<211> LENGTH: 941
<212> TYPE: DNA
<213> ORGANISM: Homo sapiens
<220> FEATURE:
<221> NAME/KEY: SITE
<222> LOCATION: (864)
<223> OTHER INFORMATION: n equals a,t,g, or c
<220> FEATURE:
<221> NAME/KEY: SITE
<222> LOCATION: (897)
<223> OTHER INFORMATION: n equals a,t,g, or c
<220> FEATURE:
<221> NAME/KEY: SITE
<222> LOCATION: (938)
<223> OTHER INFORMATION: n equals a,t,g, or c

<400> SEQUENCE: 28

| | |
|---|---|
| aattcggcag agagccaacc gagggcgttc ctgtcggggc tgcagcggcg ggagggagcc | 60 |
| cagtggaggc gccctcccga agcgccactg cccatgctga ccacccagcc ctccggctgc | 120 |
| tgatgtcatg agtaacacca ctgtgcccaa tgcccccag gccaacagcg actccatggt | 180 |
| gggctatgtg ttggggccct tcttcctcat caccctggtc ggggtggtgg tggctgtggt | 240 |
| aatgtatgta cagaagaaaa agcgggtgga ccggctgcgc catcacctgc tccccatgta | 300 |
| cagctatgac ccagctgagg aactgcatga ggctgagcag gagctgctct ctgacatggg | 360 |
| agaccccaag gtggtacatg gctggagag tggctaccag cacaagcgga tgccactgct | 420 |
| ggatgtcaag acgtgacctg acccccttgc cccacccttc agagcctggg gtyctggact | 480 |
| gcctggggcc ctgccatctg cttcccctgc tgtcacctgg stcccctgc tgggtgctgg | 540 |
| gtctccattt ctccctccac ccaccctcag cagcatctgc ttcccatgcc ctcaccatca | 600 |
| cctcactgcc cccaggcctt ctgccctttg tgggtgttga gctcaccgcc cacccacagg | 660 |
| cactcatggg aagaggcttt ccttctggga tggcggcggc tggtagacac ctttgctttc | 720 |
| tctagccctc ctgggctggg cttgggcaca aatcccagg caggctttgg agttgtttcc | 780 |
| atggtgatgg ggccagatgt atagtattca gtatatattt tgtaaataaa aтgтттгтgт | 840 |
| gctaaaaaaa aaaaaaaaaa atcnaagggg gggccggtac ccaaatccc cctatantga | 900 |
| attcgtatta acaattcact tggggccgtc cttttaanaa c | 941 |

<210> SEQ ID NO 29
<211> LENGTH: 756
<212> TYPE: DNA
<213> ORGANISM: Homo sapiens

<400> SEQUENCE: 29

| | |
|---|---|
| ggcacgagga agctggagcg ggccggcggt gcagtcacgg gggagcgagg cctgctgggc | 60 |
| ttggcaacga gggactcggc ctcggaggcg acccagacca cacagacact gggtcaagga | 120 |
| gtaagcagag gataaacaac tggaaggaga gcaagcacaa agtcatcatg gcttcagcgt | 180 |
| ctgctcgtgg aaaccaagat aaagatgccc attttccacc accaagcaag cagagcctgt | 240 |
| tgттттгтgтcc aaaatcaaaa ctgcacatcc acagagcaga gatctcaaag attatgcgag | 300 |
| aatgtcagga agaaagtttc tggaagagag ctctgccttt ttctcttgta agcatgcttg | 360 |

```
tcacccaggg actagtctac caaggttatt tggcagctaa ttctagattt ggatcattgc    420
ccaaagttgc acttgctggt ctcttgggat ttggccttgg aaaggtatca tacataggag    480
tatgccagag taaattccat ttttttgaag atcagctccg tggggctggt tttggtccac    540
agcataacag gcactgcctc cttacctgtg aggaatgcaa aataaagcat ggattaagtg    600
agaagggaga ctctcagcct tcagcttcct aaattctgtg tctgtgactt tcgaagtttt    660
ttaaacctct gaatttgtac acatttaaaa tttcaagtgt actttaaaat aaaatacttc    720
taatggaaaa aaaaaaaaaa aaaaaaaaaa actcga                              756
```

<210> SEQ ID NO 30
<211> LENGTH: 2100
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c

<400> SEQUENCE: 30

```
nccagaggca gaaagtcctg cttctggggc gtaacctaca ggatatcctt ggaacagaag     60
atcttattgt ggaagtract tccaatgatg ctgtgagatt ttatccctgg accattgata    120
ataaatacta ttcagcagac atcaatctat gtgtggtgcc aaacaaattt cttgttactg    180
cagagattgc agaatctgtc caagcatttg tggtttactt tgacagcaca caaaaatcgg    240
gccttgatag tgtctcctca tggcttccac tggcaaaagc atggttaccy gaggtgatga    300
tcttggtctg cgatagagtg tctgaagatg gtataaaccg acaaaaagct caagaatggt    360
gcatccaaac atggctttga attggtagaa cttagtccag aggagttgcc tgaggaggat    420
gatgacttcc cagaatctac aggagtaaag cgaattgtcc aagccctgaa tgccaatgtg    480
tggtccaatg tagtgatgaa gaatgatagg aaccaaggct ttagcttgct gcaactcatt    540
gactggaaca aaccatagca ttgggtcagc agatccctgt cacccagagc aaccccattt    600
gccagcagca gatagtactg aatccctctc tgatcatcgg ggtggtgcat ctaacacaac    660
agatgcccag gttgatagca ttgtggatcc catgttagat ctggatattc aagaattagc    720
cagtcttacc actggaggag gagatgtgga gaattttgaa agactctttt caaagttaaa    780
ggaaatgaaa gacaaggctg cgacgcttcc tcatgagcaa agaaaagtgc atgcagaaaa    840
ggtggccaaa gcattctgga tggcaatcgg gggagacaga gatgaaattg aaggcctttc    900
atctgatgaa gagcactgaa ttattcatac tagggtttga ccaacaaaga tgctagctgt    960
ctctgagata cctctctact cagcccagtc atattttgcc aaaattgccc ttatcatgtt   1020
ggctgcctga cttgttttata gggtcccctt aattttagtt tttagtagga ggttaaggag   1080
aaatcttttt tttcctcagt atattgtaag agagtgagga atacagtgat agtaatgagt   1140
gaggatttct taaatrtact tttttttgt tctaggaatg agggtaggat aaatctcaga   1200
ggtctgtgtg atttactcaa gttgaagaca acctccaggc cattcctggt caaccttta    1260 agtagcattt ccagcattca cacttgatac tgcacatcag gagttgtgtc acctttcctg   1320
ggtgatttgg gttttctcca ttcaaggagc ttgtagctct gaagctatga tgcttttatt   1380
gggaggaaag gaggcagctg cagaattgat gtgagctatg tggggccgaa gtctcagccc   1440
gcagctaagt ctctacctaa gaaaatgcct ctgggcattc ttttgaagta tagtgtctga   1500
gctcatgcta gaaagaatca aaaagccagt gtggattttt agactgtaat aaatgaggca   1560
aaggatttct attccagtgg gaagraaacc tctctactga gttgtggggg atatgttgta   1620
```

-continued

| | |
|---|---|
| tgttagagag aaccttaagg agtccttgta tgggccatgg agacagtatg tgataacata | 1680 |
| ccgtgatttt catgaagaaa ttcttctgtc ttagagttct cccctgctgc ttgagatgcc | 1740 |
| agagctgtgt tgttgcacac ctgcaaaaca aggcacattt cccccttct ctttaaagcc | 1800 |
| aaagagagat cactgccaaa gtgggagcac taaggggtgg gtggggaagt gaaatgttag | 1860 |
| gcgatgaatt cctgagcacc ttgttttct tccaaggttc gtagctcctc tctgcccttc | 1920 |
| caagcctgta acctcggagg actatctttt gttctttatc ctttgtcttg tttgagtggg | 1980 |
| tcagccccag aggaactgat aagcaaatgg caagttttta aaggaagagt ggaaagtact | 2040 |
| gcaaataaaa atccttattt gttttgtag aaaaaaaaaa aaaaaaaaa aaaaaaaag | 2100 |

<210> SEQ ID NO 31
<211> LENGTH: 1448
<212> TYPE: DNA
<213> ORGANISM: Homo sapiens

<400> SEQUENCE: 31

| | |
|---|---|
| aaaaaaaaaa aaagcccacc tgaaagcctg tctctttcca ctttgttggc ccttccagtg | 60 |
| ggattatcga gcatgttgtt ttttcatagt gccttttcc ttatttcaag ggttgcttct | 120 |
| gagtggtgtt ttttttttt ttaatttgtt ttgttttaaa ataagttaaa gacagtccag | 180 |
| agcttttcag ccaatttgtc tcctactctg tgtaaatatt tttccctccg ggcaggggag | 240 |
| ccagggtaga gcaaaggaga caagcaggag tggaaggtga ggcgttctcc tgcttgtact | 300 |
| aagccaggag stttaagctc cagctttaag ggttgtgagc cccttgggt tcagggaact | 360 |
| gcttgcccag ggtgcagtgt gagtgtgatg ggccaccggg gcaagaggga aggtgaccgc | 420 |
| ccagctctcc cacatcccac tggatctggc ttacaggggg gtcggaagcc tgtcctcacc | 480 |
| gtctcggggg ttgtggcccc cgcccctcc ctatatgcac ccctggaacc agcaagtccc | 540 |
| agacaaggag agcggaggag gaagtcatgg gaacgcagcc tccagttgta gcaggtttca | 600 |
| ctattcctat gctggggtac acagtgagag tactcacttt tcacttgtct tgctcttaga | 660 |
| ttgggccatg gctttcatcc tgtgtcccct gacctgtcca ggtgagtgtg agggcagcac | 720 |
| tgggaagctg gagtgctgct tgtgcctccc ttcccagtgg gctgtgttga ctgctgctcc | 780 |
| ccaccctac cgatggtccc aggaagcagg gagagttggg gaaggcaaga ttggaaagac | 840 |
| aggaagacca aggcctcggc agaactctct gtcttctctc cacttctggt ccctgtggt | 900 |
| gatgtgcctg taatctttt ctccacccaa accccttccc acgacaaaaa caagactgcc | 960 |
| tccctctctt ccgggagctg gtgacagcct tgggcctttc agtcccaaag cggccgatgg | 1020 |
| gagtctccct ccgactccag atatgaacag ggcccaggcc tggagcgttt gctgtgccag | 1080 |
| gaggcggcag ctcttctggg cagagcctgt ccccgccttc cctcactctt cctcatcctg | 1140 |
| cttctctttt cctcgcagat gataaaagga atctggcatt ctacacctgg accatttgat | 1200 |
| tgttttattt tggaattggt gtatatcatg aagccttgct gaactaagtt ttgtgtgtat | 1260 |
| atatttaaaa aaaaaatcag tgtttaaata aagacctatg tacttaatcc tttaactctg | 1320 |
| cggatagcat ttggtaggta gtgattaact gtgaataata aatacacaat gaattcttma | 1380 |
| aaaaaaaaaa aaaaaaaaaa aaaaaaaaaa aaacccgggg gggcccg ggccccaatt | 1440 |
| cccccccaa | 1448 |

<210> SEQ ID NO 32
<211> LENGTH: 456
<212> TYPE: DNA

```
<213> ORGANISM: Homo sapiens
<220> FEATURE:
<221> NAME/KEY: SITE
<222> LOCATION: (444)
<223> OTHER INFORMATION: n equals a,t,g, or c

<400> SEQUENCE: 32
ggcacagcaa acttgacgcc atgaagatcc cggtccttcc tgccgtggtg ctcctctccc     60
tcctggtgct ccactctgcc cagggagcca ccctgggtgg tcctgaggaa gaaagcacca    120
ttgagaatta tgcgtcacga cccgaggcct ttaacacccc gttcctgaac atcgacaaat    180
tgcgatctgc gtttaaggct gatgagttcc tgaactggca cgccctcttt gagtctatca    240
aaaggaaact tcctttcctc aactgggatg cctttcctaa gctgaaagga ctgaggagcg    300
caactcctga tgcccagtga ccatgacctc cactggaaga gggggctagc gtgagcgctg    360
attctcaacc taccataact ctttcctgcc tcaggaactc aataaaaaca ttttccatcc    420
aaaaaaaaaa aaaaaaaaac cccnggggg gcccgg                               456

<210> SEQ ID NO 33
<211> LENGTH: 1326
<212> TYPE: DNA
<213> ORGANISM: Homo sapiens
<220> FEATURE:
<221> NAME/KEY: SITE
<222> LOCATION: (352)
<223> OTHER INFORMATION: n equals a,t,g, or c
<220> FEATURE:
<221> NAME/KEY: SITE
<222> LOCATION: (1324)
<223> OTHER INFORMATION: n equals a,t,g, or c

<400> SEQUENCE: 33
ggcacgagtg caggcccaga gaggactcat tgaaaggact gaaagggag gtggcgtttt      60
cttcctaccc aaacttaccc ctgtgagctg acagcttgg tagcacctgc ctggacttag    120
atggtggtag ccaagaagac tgacatttta gggaacagga cggggaggag aaggctctgg    180
cacacacaca tgtgtccata tgtcctgcaa tggtctgggg actattgcta ggctaggagc    240
cctaagtgtc ttcttcctca tgtctmttct cccctgtstc atgggccta agrtctcttt     300
cactgggcct gcctcaatga acgtgctgcc cagctacccc gaaacacggc anctgccggc    360
tatcaatgcc ccagctgcaa tgcccatct tccccaacc aacctggctg ggcccgtggg     420
ctccgcactg agararaaas ttggcacart caactgggcc cgggcaggac tgggccyccc    480
tctgatcgat gaagktggtg arcccagagc ccgagcccct caacacgtct gacttctctg    540
actggtctag tttaatgcc agcagtaccc ctggaccaga ggaggtagac agcgcctctg     600
ctgccccagc cttctacagc cgagccccc ggccccagc ttcccaggc cggcccgagc      660
agcacacagt gatccacatg ggcaatcctg agcccttgac tcacgcccct aggaaggtgt    720
atgatacgcg ggatgatgac cggacaccag gcctccatgg agactgtgac gatgacaagt    780
accgacgtcg gccggccttg ggttggctgg cccggctgct aaggagccgg gctgggtctc    840
ggaagcgrcc gctgaccctg ctccagcggg cggggctgct gctactcttg ggactgctgg    900
gcttcctggc cctccttgcc ctcatgtctc gcctaggccg ggccgcagct gacagcgatc    960
ccaacctgga cccactcatg aaccctcaca tccgcgtggg ccctcctga gccccttgc    1020
ttgtggctag gccagcctag gatgtgggtt ctgtggagga gaggcggggt aatgggagg    1080
ctgagggcac ctcttcactg ccctctccc tcaagcctaa gacactaaga ccccagaccc    1140
aaagccaagt ccaccagagt ggctgcaggc caggcctgga gtccccgtgg gtcaagcatt  1200
```

```
tgtcttgact tgctttcctc ccgggtytcc agcctccgac ccctcgcccc atgaaggagc   1260
tggcaggtgg aaataaacaa caactttatt aaaaaaaaaa aaaaaaaaaa aaaaaaaaaa   1320 aaanaa                                                              1326
```

<210> SEQ ID NO 34
<211> LENGTH: 710
<212> TYPE: DNA
<213> ORGANISM: Homo sapiens

<400> SEQUENCE: 34

```
gcgaaagaga aaaggctgg agctcccgcc cccggggctg tcagatggct tgggtttctg    60
cgacgcgatt ggctcgcgga gggcagaaat tactcagcaa acatgactat tattagctgc   120
ttagcaacag ctcaccaaag tagagagacc acccaggtag gcaacccagt gtgtgcatcc   180
tcggcttcgg ggcagcctct gagagcgcca accttctcgc atgcaatact tccattaagg   240
aatgctcccc ctcctttctc tcttattcct tttcttttca acagtgtctt cttttgtgg   300 gatgcctttg cgcgcacaca cgcgcgcgca sgcacacaca cgaacatttg cctcgcggta   360
gacacggggg gaaatgtwat attttttaa gcgcttaaac aatttctgaa attcctcaaa    420
gaaaagcctt tcagargcac cttggcctca agctgcaaca aatactggga rgtccggctc   480
gcattcccag gcctgcacca ataatgacag cgtgctggat artgcgccag tgtgtgccag   540
attttttttt cctcttctct tttcttttat aactaaaggg aagacttagg ctcttgcagg   600
gaacaacgcc tcgcattaag ataaacagaa tggaaagtta aagaggaaag caaggacgtt   660
gggaaaagcc atctttctta aaatccgtct gccccccagc cgctttctcc              710
```

<210> SEQ ID NO 35
<211> LENGTH: 1188
<212> TYPE: DNA
<213> ORGANISM: Homo sapiens

<400> SEQUENCE: 35

```
gatggctttt atatctatta tcgacccaca gacagtgaca atgatagtga ctacaagaag    60
gatatggtgg aagggacaa gtactggcac tccatcagcc acctgcagcc agagacctcc   120
tacgacatta agatgcagtg cttcaatgaa ggaggggaga gcgagttcag caacgtgatg   180
atctgtgaga ccaaagctcg gaagtcttct ggccagcctg gtcgactgcc accccaact   240 ctggccccac cacagccgcc ccttcctgaa accatagagc ggccggtggg cactggggcc   300
atggtggctc gctccagcga cctgccctat ctgattgtcg gggtcgtcct gggctccatc   360
gttctcatca tcgtcacctt catccccttc tgcttgtgga gggcctggtc taagcaaaaa   420
catacaacag acctgggttt tcctcgaagt gcccttccac cctcctgccc gtatactatg   480
gtgccattgg gaggactccc aggccaccag gcagtggaca gccctacctc agtggcatca   540
gtggacgggc ctgtgctaat gggatccaca tgaatagggg ctgcccctcg gctgcagtgg   600
gctacccggg catgaagccc cagcagcact gcccaggcga gcttcagcag cagagtgaca   660
ccagcagcct gctgaggcag acccatcttg gcaatggata tgaccccaa agtcaccaga   720 tcacgagggg tcccaagtct agcccggacg agggctcttt cttatacaca ctgcccgacg   780
actccactca ccagctgctg cagccccatc acgactgctg ccaacgccag gagcagcctg   840
ctgstgtggg ccagtcaggg gtgaggagag ccccgacag tcctgtcctg gaagcagtgt   900
gggaccctcc atttcactca gggccccat gctgcttggg ccttgtgcca gttgaagagg   960
```

-continued

| | |
|---|---|
| tggacagtcc tgactcctgc caagtgagtg gaggagactg gtgtcccag caccccgtag | 1020 |
| gggcctacgt aggacaggaa cctggaatgc agctctcccc ggggccactg gtgcgtgtgt | 1080 |
| cttttgaaac accacctctc acaatttagg cagaagctga tatcccagaa agactatata | 1140 |
| ttgttttttt tttaaaaaaa aaaaaaaaaa awcycggggg ggggcccc | 1188 |

<210> SEQ ID NO 36
<211> LENGTH: 956
<212> TYPE: DNA
<213> ORGANISM: Homo sapiens
<220> FEATURE:
<221> NAME/KEY: SITE
<222> LOCATION: (404)
<223> OTHER INFORMATION: n equals a,t,g, or c

<400> SEQUENCE: 36

| | |
|---|---|
| ggcagagcag tgaaaatgca tcctaaaaat tcaatgttta taccaggctc atgacactaa | 60 |
| gatgtgacat ctggcacacga ggggtcagcc acgtggatac atccctccca gattgcatct | 120 |
| ccaggaatca ctctgctagc agaatgggcg ccccatccct tactatgctg ctcctcctca | 180 |
| aagtgcagcc cagaaggacc caggcctttg atgcacattg gtgggtctc ccactacttt | 240 |
| agttgaaatg ggagcatgct ggagtcggcg ttctgttgct tctggtgaga aggacatccc | 300 |
| attgacccct ggccaccagg tccagtattc catccttcct tctgtcccag cctatcgccc | 360 |
| tccccacyag gcccaccccc acaacttctc ctcaagggag gttntcccgc agctggaggg | 420 |
| cttgcacaga ccagcagtca cagaaatcat tcttcctgct gtactgggcc ttaactgcct | 480 |
| gcaaatgtcc gagcactact gcataggatg ccagagccac cgaagataaa cacagccaag | 540 |
| tttaataata ataaaaggaa aaatctcagc ctgcagaact ctggttttga cccaccatcg | 600 |
| gccagatgca catcttcagg gcctgttgag caccttctga aaagcagggc tcgtaataga | 660 |
| ctccagcaca ttccatcaga gtcaggaaaa ctgcggtgag tcccagagaa tctagggtgc | 720 |
| agggcaggga gcaggagtca taaggagtga taacctaaac tgtgtgtagt cagcggggag | 780 |
| ggtcttatgt tatcaggtga aatgagagcc agtaagttag ttgatcctgt cacagatata | 840 |
| accctgataa cacccccatag atacgcgaca cgtgtgtcct gcccctgctt tccccatcca | 900 |
| acatggttct tctgttccac agacattaaa ggggctttct gcaattactt aaaaaa | 956 |

<210> SEQ ID NO 37
<211> LENGTH: 1603
<212> TYPE: DNA
<213> ORGANISM: Homo sapiens

<400> SEQUENCE: 37

| | |
|---|---|
| tcgacccacg cgtccgctct gccaggaatc tggtctttct gtagacccaa gtcagaaaga | 60 |
| accatttgtg gagttaaatc gaatattaga rgcattaaar gtcagagttc tgagacctgc | 120 |
| tctggaatgg gcagtttcaa accgagagat gcttatagcc caaaacagct ccttggaatt | 180 |
| taaactacac agactgtatt ttattagctt rttaatgggt ggaacacaaa tcagcgagar | 240 |
| gcattacaat atgctaaaaa ttttcagcca tttgccctaa atcatcaaaa agacattcag | 300 |
| gttttgatgg gaagccttgt gtacctgaga caagggattg agaactcacc atatgttcac | 360 |
| ctacttgatg caaccagtg ggctgatatc tgtgacatct ttacgggga tgcttgtgcc | 420 |
| ctcctgggc tctccgtgga gtcccctctc agtgtcagtt tctcagcagg ttgtgtggcg | 480 |
| ctgccagctt taattaacat caaagccgtg attgaacaga ggcagtgtac tggagtttgg | 540 |
| aaccagaaag atgaattacc tattgaagtg gaccttggta aaaagtgctg gtatcactct | 600 |

```
atatttgcct gccccattct tcgtcagcaa acaacagata acaatccacc catgaaattg      660
gtctgtggtc atattatatc aagagatgcc ctgaataaaa tgtttaatgg tagcaaatta      720
aaatgtccct actgtccaat ggaacaaagt ccaggagatg ccaaacagat attttttctga     780 agagataact ttagtttgca atttgtaagt gaaactgaat cgtgggtgca tttcagaaga      840
gaacgttcca tataatgcag ctaaccaagg actcctgtgt ttctataagc taatgctcca      900
gaaactttgc caacctgtta gtgtacacac actgagggga gtgctcccgg tgaatattat      960 cataggctt  tattatattc ttggtcttca tttctgatca agtaaataca ccagcagttg     1020
tcattcaatg caggtttttg tacttaatta tatggtgatt ttttttacttt ttaagagcag    1080 aaacggaaat tgacctcccc gccatgtgtt taatattcct cctgctttta cttttgtcat     1140
tttcttgata atcgtaagcc ttgagagtgt tgtgaaaaa gttttatttc ctgttatgta      1200
tacataatta aatgaaaatt cttcagaaaa agtttgataa attgaattgt ggttatgaaa     1260
ctaatttgca tttttatttg cttaagaaag aaagctgtga tagattccag atatgctttt     1320
tgatgttttc ctctgctcca gctccaagaa gtcagcacac ctgcatttta gctctgcatg     1380
cagccccagc aggctgcgtg tttaagaatt tcattgttta actggctggt gtgagaagtc     1440
ttccgttagc atagagtgga aggagtacta ttgtttggtt gggttttttgt ttgtttgttt     1500 tttgttttttg cttttattgc caagaggtgc ttgttttaaa agtatgttta ataaaatgaa    1560
attctaaagt taaraagtgt tcttaaagtt gatatttaac tct                       1603

<210> SEQ ID NO 38
<211> LENGTH: 1089
<212> TYPE: DNA
<213> ORGANISM: Homo sapiens

<400> SEQUENCE: 38
ggcacgagct acctttctgc ctgctttgct ggctgcaaca gcacgaatct cacgggctgt       60
gcgtgcctca ccaccgtccc tgctgagaac gcaaccgtgg ttcctggaaa atgccccagt      120
cctgggtgcc aagaggcctt cctcactttc tctctgtgtga tgtgtatctg cagcctgatc     180
ggtgccatgg caagacaccc tcagtcatca tcctcatcag acagtcagc cctgaactca       240 agtcttacgc tttgggagtt cttttttctcc tccttcgttt gttgggcttc atccctccac     300
ccctcatctt cggggctggc atcgactcca cctgcctgtt ctggagcacg ttctgtgggg      360
agcaaggcgc ctgcgtcctc tacgacaatg tggtctaccg atacctgtat gtcagcatcg      420
ccatcgcgct caaatccttc gccttcatcc tgtacaccac cacgtggcag tgctgaggaa      480
aaactataaa cgctacatca aaaccacga gggcgggctg agcaccagtg agttctttgc       540
ctctactctg accctagaca acctggggag ggaccctgtg cccgcaaacc agacacatag      600
gacaaagttt atctataacc tggaagacca tgagtggtgt gaaaacatgg agtccgtttt      660
atagtgacta aaggagggct gaactctgta ttagtaatcc aagggtcatt ttttttcttaa     720 aaaagaaaa aaaggttcca aaaaaaacca aaactcagta cacacacaca ggcacagatg       780
cacacacacg cagacagaca caccgacttt gtccttttc tcagcatcag agccagacag       840
gattcagaat aaggagagaa tgacatcgtg cggcagggtc ctggaggcca ctcgcgcggc      900
tgggccacag agtctacttt gaaggcacct catggttttc aggatgctga cagctgcaag      960
caacaggcac tgccaaattc agggaacagt ggtggccagc ttggaggatg gacatttctg     1020
gatacacata cacatacaaa acagaaaaca tttttttaaaa gaagtttcct aaaataaaaa    1080
``` aaaaaaaaa                                                              1089

<210> SEQ ID NO 39
<211> LENGTH: 629
<212> TYPE: DNA
<213> ORGANISM: Homo sapiens

<400> SEQUENCE: 39
agctcagttc ccttagaaat gaaattttaa atgacactac caggtaagcc actgagacca      60
gtggaggtga tagctaagaa cataaggaat taagaatttt taatggagaa aggaggtaat     120
gaataccagt tacatcctaa gactcactgt agtggtgagt gttgtaattt atctcgctat     180
ccatcctctt ttaagttttt ccttagaaag tcctctattg gtaccttgga gggactgctg     240
tcaaaatata tggaaaagtg gtctgtgtg gtacaagagg tggactttgc cacacatgga      300
agtttgctgc caagatcttc actaatgaaa gaaatcacca gtgagctgca cagattagcc     360
aaatactgag ctcattagaa ctactaaggc ctggacattt ctgcctaatc caggactcct     420
gtaattatca gtctttgctt tggagcttcc cattgtgtag ctgaraattt gtcatatctg     480
cattataatc taaggctcca catacttaat cctgcttctc ccccttttc tttcccttc      540
ccagcggtca gctctgctgc atagtctgaa gactttccct gcccaatcct gataaaattc     600
ttgcactcgt aaccccatct cagtgtctg                                       629

<210> SEQ ID NO 40
<211> LENGTH: 1964
<212> TYPE: DNA
<213> ORGANISM: Homo sapiens
<220> FEATURE:
<221> NAME/KEY: SITE
<222> LOCATION: (353)
<223> OTHER INFORMATION: n equals a,t,g, or c
<220> FEATURE:
<221> NAME/KEY: SITE
<222> LOCATION: (476)
<223> OTHER INFORMATION: n equals a,t,g, or c

<400> SEQUENCE: 40
aagaagacat ggaaattgct gaaggatgtt tcaggcatat taagaaaatc tttacgcagc      60
ttgaggaatt cagagcctct gaattgcttc gaagtggact ggacagatct aaatacctt     120
tagtgaaaga agccaaaatt attgctatga cctgtactca tgctgcctta aaacgacatg     180
acttggtcaa gctaggtttc aagtatgaca catttgat ggaagaggct gctcagattc      240
tggagataga aacttttatc cctcttcttc tacagaatcc tcaggatgga tttagccgac     300
taaaacgatg gattatgatt ggcgatcatc accagttacc tccagttatt aangaacatg     360
gccttcaaaa agtactcaaa catggagcag tctctcttca ctcgctttgt tcgcgttgga     420
gttccgactg ttgaccttga tgctcaaggg agagccagag caagcttgtg camctnctac     480
aactggcgat acaagaatct aggaaactta ccccatgtgc agctcttgcc agagtttagt     540
acagcaaatg ctggcttact gtatgacttc cagctcatta atgttgaaga ttttcaagga     600
gtgggagaat ctgaacctaa tccttacttc tatcagaatc ttggagaggc agaatatgta     660
gtagcacttt ttatgtacat gtgtttactt ggttaccctg ctgacaaaat cagtattcta     720
acaacatata atgccaaaaa gcatcttatt cgcgacatca tcaatagacg atgtggaaac     780
aatccattga ttggaagacc aaacaaggtg acaactgttg atagatttca aggtcaacag     840
aatgactata ttcttctttc tctggtacga accaggcag tgggcatct gagggatgtc      900
cgtcgcttgg tagtggccat gtctagagcc agacttggac tttatatctt cgccagagta     960

-continued

```
tccctcttcc aaaactgttt tgaactgact ccagctttca gtcagctcac agctcgcccc    1020
cttcatttgc atataattcc aacagaacct ttcccaacta ctagaaagaa tggagagaga    1080
ccatctcatg aagtacaaat aataaaaaat atgccccaga tggcaaactt tgtatacaac    1140
atgtacatgc atttgataca gactacacat cattatcatc agactttatt acaactacca    1200
cctgctatgg tagaagaggg tgaggaagtt caaaatcaag aaacagaatt ggaaacagaa    1260
gaagaggcca tgactgttca agctgacatc atacccagtc aacagacac cagctgccgt     1320 caagaaactc cagcctttca aactgacacc accccagtg agacaggagc cacttccact     1380
ccagaagcca tccctgcttt atctgagacc accctactg tggtaggagc tgtatctgca     1440
ccggcagaag ctaacacacc tcaggatgcc acatctgccc cagaagagac caagtagcca    1500
aactgtagtc cttctaaagg aggacatggc agtcaaaaag tctgagtaaa gctgttttt     1560 gtattttata tttgcttctg ccatttact gtcactaatt aatgtttagt tcttatattt     1620
gttaactgat ttcggtgtct tgaatatatt tttttaaatt atgtgtatga acaattctag    1680
tttcatttgt tcaatcagaa gagcaaataa ccattccttt catgttttga tcactgagtg    1740
tgtctgtaat catacctaca ttaaaatcat tttctatgaa tatataatat atacttcaca    1800
tttttagtga acttctctaa agaagaggac agaatatact ggacttaacc acgaatacccc   1860 ttgagtgtcc aaattgggaa ggaactkgtt tcttcygtta tactaycaaa tgcttaaatt    1920
ckgtttcctt ttttcttacc tttgtttgct gtctttatgt aaag                     1964
```

<210> SEQ ID NO 41
<211> LENGTH: 1522
<212> TYPE: DNA
<213> ORGANISM: Homo sapiens
<220> FEATURE:
<221> NAME/KEY: SITE
<222> LOCATION: (1282)
<223> OTHER INFORMATION: n equals a,t,g, or c
<220> FEATURE:
<221> NAME/KEY: SITE
<222> LOCATION: (1376)
<223> OTHER INFORMATION: n equals a,t,g, or c
<220> FEATURE:
<221> NAME/KEY: SITE
<222> LOCATION: (1462)
<223> OTHER INFORMATION: n equals a,t,g, or c
<220> FEATURE:
<221> NAME/KEY: SITE
<222> LOCATION: (1492)
<223> OTHER INFORMATION: n equals a,t,g, or c
<220> FEATURE:
<221> NAME/KEY: SITE
<222> LOCATION: (1501)
<223> OTHER INFORMATION: n equals a,t,g, or c

<400> SEQUENCE: 41

```
cgtgtccgcg cgcctgggag acgctgcctc ggcccggacg cgcccgcgcc ccgcggctg      60 gagggtggtc gccactggga cactgtgaac caggagtrag tcggagctgc cgcgctgccc    120
aggccatgga ctgtgaggtc aacaacggtt ccagcctcag ggatgagtgc atcacaaacc    180
tactggtgtt tggcttcctc caaagctgtt ctgacaacag cttccgcaga gagctggacg    240
cactgggcca cgagctgcca gtgctggctc cccagtggga gggctacgat gagctgcaga    300
ctgatggcaa ccgcagcagc cactcccgct gggaagaat agaggcagat tctgaaagtc    360
aagaagacat catccggaat attgccaggc acctcgccca gtcggggac agcatggacc    420 gtagcatccc tccgggcctg gtgaacggcc tggccctgca gctcaggaac accagccggt    480
```

```
cggaggagga  ccggaacagg  gacctggcca  ctgccctgga  gcagctgctg  caggcctacc      540
ctagagacat  ggagaaggag  aagaccatgc  tggtgctggc  cctgctgctg  gccaagaagg      600
tggccagtca  cacgccgtcc  ttgctccgtg  atgtctttca  cacaacagtg  aattttatta      660
accagaacct  acgcacctac  gtgaggagct  tagccagaaa  tgggatggac  tgaacggaca      720
gttccagaag  tgtgactggc  taaagctcga  tgtggtcaca  gctgtatagc  tgcttccagt      780
gtagacggag  ccctggcatg  tcaacagcgt  tcctagagaa  gacaggctgg  aagatagctg      840
tgacttctat  tttaaagaca  atgttaaact  tataacccac  tttaaaatat  ctacattaat      900
atacttgaat  gaaaatgtcc  atttacacgt  atttgaatgg  ccttcatatc  atccacacat      960
gaatctgcac  atctgtaaat  ctacacacgg  tgcctttatt  tccactgtgc  aggttcccac     1020
ttaaaaatta  aattggaaag  caggtttcaa  ggaagtagaa  acaaaataca  attttttttgg    1080 taaaaaaaaa  ttactgttta  ttaaagtaca  accatagagg  atggtcttac  agcaggcagt     1140
atcctgtttg  aggaaagcaa  gaatcagaga  aggaacatac  cccttacaaa  tgaaaaattc     1200
cactcaaaat  agggactatc  yatcttaata  ctaaggaacc  aacaatcttc  ctgtttaaaa     1260
aaccacatgg  cacagagatt  cngaactaaa  gtgctgcact  caaatgatgg  gaagtcccgg     1320
ccccagtaca  ccaggggctt  tggactttt   tcaacttcgt  ttccttttgt  ttggantcca     1380
aaagaaccac  tttgtggttc  ttaaaagggt  gtgaaggtga  tttaagggc   ccaggtcagc     1440 cactggttgg  tttacaaaat  cngggtaact  aactgcatac  aacttttttcc cntttccatg    1500 ncatcaggac  tttgctaaag  ac                                                 1522

<210> SEQ ID NO 42
<211> LENGTH: 875
<212> TYPE: DNA
<213> ORGANISM: Homo sapiens

<400> SEQUENCE: 42
tgggatttcc  ctttatcatg  gaggccttgt  cccacttcct  ctatgtccct  ttccttggtg       60
tctgtgtctg  tggggccatc  tacactggcc  tgttccttcc  tgagaccaaa  ggcaagacct      120
tccaagagat  ctccgaggaa  ttacacagac  tcaacttccc  caggcgggcc  cagggcccca      180
cgtggaggag  cctggaggtt  atccagtcaa  cagaactcta  gtcccaaagg  ggtggccgta      240
gccaaagcca  gctaccgtcc  tgtcctctgc  ttcctgccag  ggccctggtc  ctcamtycct      300
yctgcattcc  tcatttaagg  agtgtttatt  gagcacccct  tgtgtgcaga  catggctcca      360
ggtgcttagc  aatcawtggt  gagcgtggta  tccaggctaa  aggtaattaa  ctgacagraa      420
atcagtaaca  acataattac  aggytggttg  tggcagytca  tgactgtaat  cccagcactt      480
ttgggagcca  aggtgggarg  atcaattgag  gccagagttt  gaaamcagct  aggtaacata      540
gtgagacccc  ctatctctac  aaaaaatttt  aaacattagc  tgggcatggt  ggtatgtgct      600
aacagctcta  gctactcagg  aggctgaggc  agcaggatca  cttgagtcca  agagttcaag      660
gtagcagtaa  gctacaatca  caccactgca  tgccagactg  ggtgacagag  ggagacttca      720
tctctttaaa  acataataat  aataattaca  gactcaggaa  atgcagtgaa  agaaaaatac      780
aggttggcca  ggtgaggtgg  ctgatgcctg  taatcccagc  actttgggag  gccaagatgg      840
gaagattgct  ttgagaccag  aagtttgaga  ccagc                                   875

<210> SEQ ID NO 43
<211> LENGTH: 843
<212> TYPE: DNA
<213> ORGANISM: Homo sapiens
```

```
<220> FEATURE:
<221> NAME/KEY: SITE
<222> LOCATION: (14)
<223> OTHER INFORMATION: n equals a,t,g, or c

<400> SEQUENCE: 43
cccacgcggt ccgnatcgtc cttccctcac ttcagagggt ggccagagct gaatacccag      60
agagggacaa gtaagggtcc agttccaaaa catcatgagg atgtatcatc ccacgtgtct     120
cacctgacag ttacagagga aacccgcacc cagaatgcac gtgctgtctt atgggaacac     180
tcagcgcaga gtgctcaggt ccggccacac tcgggctgtg cttggtcgtg ccatggaatt     240
cctcaggact ttctcagcct ccctaatggc agaagcccct ttacagcaag acatttaccg     300
tttgtctgaa aatagccgaa ctgagctttt cttcaggcta tatgagaagt ctctagacag     360
tgggcaccgt cagaaagccc agagccttgt gatagctccc accctgcctg gctcagatct     420
tcccattttt tttcctctgg cactaacctc accttttgtt tttttgtgtt tgtgtttgtt     480 tttgttttg cagagttgga ttacagaaac tcctatgaaa ttgaatatat ggagaaaatt      540
ggctcctcct tacctgtaag ttcgtctgcc tcgggccact tagggactc gctttcctgc      600 cttcaggggc ctcctcccct gtgcagagtg tctctgggag ctcagacccc aaatcgagtg     660
ttttctgtgt acacagcttc ccgggtgcac agcaatgatg gactgggct gggggttga      720 ggtttgtact caatccactt cgtttgacat tttcaggag aaaatgatag aatacaatta      780
gacgtcctgc agaattactt tcctagactg agaaagagct agagatttct ttaaaaaaaa     840
aaa                                                                   843

<210> SEQ ID NO 44
<211> LENGTH: 489
<212> TYPE: DNA
<213> ORGANISM: Homo sapiens

<400> SEQUENCE: 44
ctcttaggct ttgaagcatt tttgtctgtg ctccctgatc ttcaggtcac caccatgaag      60
ttcttagcag tcctggtact cttgggagtt tccatctttc tggtctctgc ccagaatccg     120
acaacagctg ctccagctga cacgtatcca gctactggtc ctgctgatga tgaagcccct     180
gatgctgaaa ccactgctgc tgcaaccact gcgaccactg ctgctcctac cactgcaacc     240
accgctgctt ctaccactgc tcgtaaagac attccagttt tacccaaatg ggttggggat     300
ctcccgaatg gtagagtgtg tccctgagat ggaatcagct tgagtcttct gcaattggtc     360
acaactattc atgcttcctg tgatttcatc caactactta ccttgcctac gatatcccct     420
ttatctctaa tcagtttatt ttctttcaaa taaaaaataa ctatgagcaa caaaaaaaaa     480
aaaaaaaa                                                              489

<210> SEQ ID NO 45
<211> LENGTH: 534
<212> TYPE: DNA
<213> ORGANISM: Homo sapiens
<220> FEATURE:
<221> NAME/KEY: SITE
<222> LOCATION: (470)
<223> OTHER INFORMATION: n equals a,t,g, or c
<220> FEATURE:
<221> NAME/KEY: SITE
<222> LOCATION: (477)
<223> OTHER INFORMATION: n equals a,t,g, or c

<400> SEQUENCE: 45
```

```
gaagcagtgt gtatctatga ttatatctct gttcatctat atattttga catgtagcaa    60
cacctctcca tcttatcaag gaactcaact cggtctgggt ctccccagtg cccagtggtg   120
gcctttgaca ggtaggagga tgcagtgctg caggctattt tgttttttgt tacaaaactg   180
tcttttccct tttcccctcc acctgattca gcatgatccc tgtgagctgg ttctcacaat   240
ctcctgggac tgggctgagg caggggcttc gctctattct ccctaaccat actgtcttcc   300
tttccccttg ccacttagca gttatccccc agctatgcc ttctccctcc ctcccttgcc    360
ctggcatata ttgtgcctta tttatgctgc aaatataaca ttaaactatc aagtgaaaaa   420
aaaaaaaaaa aaaactccaa ggggggccg gtacccaatt cccctatan tgagtcntat    480
tacaattcac tgggccgtcg ttttacaacg tcgtgaatgg gaaaacctgg gcgt          534
```

<210> SEQ ID NO 46
<211> LENGTH: 1374
<212> TYPE: DNA
<213> ORGANISM: Homo sapiens

<400> SEQUENCE: 46

```
ggcacgagtc cgggatgagc tcagccgcgg ccgaccactg ggcgtggttg ctggtgctca    60
gcttcgtgtt tggatgcaat gttcttagga tcctcctccc gtccttctca tccttcatgt   120
ccagggtgct gcagaaggac gcggagcagg agtcacagat gagagcggag atccaggaca   180
tgaagcagga gctctccaca gtcaacatga tggacgagtt tgccagatat gccaggctgg   240
aaagaaagat caacaagatg acggataagc tcaaaaccca tgtgaaagct cggacagctc   300
aattagccaa gataaaatgg gtgataagtg tcgctttcta cgtattgcag gctgccctga   360
tgatctcact catttggaag tattattctg tccctgtggc tgtcgtgccg agtaaatgga   420
taacccctct agaccgcctg gtagcctttc ctactagagt agcaggtggt gttggaatta   480
cctgttggat tttagtctgt aacaaagttg tcgctattgt gcttcatccg ttcagctgaa   540
caggaggatg gatacagccg cgaggctaaa aaacggattt cctcttccta gcttaaaatc   600
tgatttacac tgttttgttt tttaagaaac aaaagtgcat agtttagatt ttttttttg     660
ttgaatatgt ttgttcttgg actttatgag agagtcttat aagaatcacg attttctaca   720
cctgtcattg agccaagaaa gtccagtttta tgacacgtat gtactagtga acaccgtcct   780
cgatctgtac gaaatgtgaa atgtttaggg acatctccat gctgtcactt gtgatttgcc   840
ctcttatgta ttttggtcat attgccaact ggaaagtcaa aatttttctaa caactttaag   900
taagttcttt gaagacttag tgctgttttt aatccagttt agaaagtaac ttaattttaa   960
taccactact aaaaattcga aaatttcttc tttaatcaca ttcaatatgg ttaaaagaac  1020
aacactaatt gacattgcgt gggcttttttc tcccttttgtt taaaatgtca tttgttgagc  1080
aagagttgta tagtattatc tacttacttg aggctgttaa ttttttcatta cagtgttttg  1140
taaatgtatc cacgagacca tgatgcattg ttttgtgctc aacttgtgtt ttgtatttaa  1200
agcattttga atgaagtgta ttttataagc atttaatatt tatgctcttt agaatggaac  1260
acagaaaaca aaccttataa gtcctgatta atctgaacca ataacctgtg tggcctacaa  1320
agtataattc tattaaatgt tccttaaaac aaaaaaaaaa aaaaaaaaaa aaaa           1374
```

<210> SEQ ID NO 47
<211> LENGTH: 596
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c

<400> SEQUENCE: 47

```
gaattcgnca cgagattact tggacatgaa agaactcagg ttcaagttta ttcatttact    60
aagttagtta aatcatgtgc cttccatgag ccttcatttg gtaacttgga aaatggaaat   120
aataacacta gtcatatata ttctacactg ctaccatatg gaccaaaggg attatagatt   180
acaatcacca tcattcctgc tgacaggtat atagaaaaca atttcattga agaaaagtcc   240
ttacatttat cctttcccta atatctgcat gggtaaacta ataaatatag tcattagaaa   300
accccttatta ttattattag ttcaatgtga gaactgctgc agaaaaaata tgctttataa   360
tattttcttg aatatacata atattcataa attttcaaat cattgaaaat taccttaaaa   420
ttggaaaaaa tgtgcatttc tactcatata acagtataaa attcctatgt caatctcttt   480
tttttttttt tgttttgagt tggagtctcg ctctgtcgcc caggctgggc aacagagcag   540
gaccctgtct taattaaaaa aaaaaaaaaa aaactcgagg ggggcccggt accta        596
```

<210> SEQ ID NO 48
<211> LENGTH: 851
<212> TYPE: DNA
<213> ORGANISM: Homo sapiens

<400> SEQUENCE: 48

```
cacatgaaga cacacagtgg tgagaagccc ttccgctgcg cccgctgtcc ttatgcctct    60
cctcatctgg ataacctgaa acggcaccag cgcgtccata caggagagaa gccctacaag   120
tgccccctct gcccttatgc ctgtggcaat ctggccaacc tcaagcgtca tggtcgcatc   180
cactctggtg acaaaccttt tcggtgtagc cttttgcaact acagctgcaa ccagagcatg   240
aacctcaaac gtcacatgct gcggcacaca ggcgagaagc cttccgctgt gccacctgcg   300
cctataccac gggccactgg gacaactaca agcgccacca gaaggtgcat ggccacggtg   360
gggcaggagg gcctggtctc tctgcctctg agggctgggc cccacctcat agcccaccct   420
ctgttttgag ctctcggggc ccaccagccc tggggactgc tggcagccgg gctgtccaca   480
cagactcatc ctgaactagg tccttcttcc ccatgtttta tacagacgga ccagaagcca   540
cctttttctc ccccgctggc cagggggctcc acacagacta acgtaggcac tataaggacc   600
agcccaaccc catgggcggg ggggcccata tggaccaggg gaccttgcct tgactgaggc   660
acttcacgag ctcagtgaga agggccctgt attcacctcc actgccccca ggggctgtgg   720
acaaaccggc tgggggactg cccagcctcc cacctgttta tttaacttat ttcagtgctt   780
tataataaag gaaacactaa caaagccatg tctatgctga attggcaatg gcaggcaatt   840
tggccttacc c                                                         851
```

<210> SEQ ID NO 49
<211> LENGTH: 2020
<212> TYPE: DNA
<213> ORGANISM: Homo sapiens
<220> FEATURE:
<221> NAME/KEY: SITE
<222> LOCATION: (1239)
<223> OTHER INFORMATION: n equals a,t,g, or c
<220> FEATURE:
<221> NAME/KEY: SITE
<222> LOCATION: (1587)
<223> OTHER INFORMATION: n equals a,t,g, or c

<400> SEQUENCE: 49

```
gtgaaatgaa acagtctttt ttatagcctt tagcttgtga gtttggaagt ttgggggggtc    60
ttatgtttgt tttgcctctt ctgtttcttg gaggagagtt gaggcttttc ttaggtgcat   120
acacagaccc aggtgaacac gctgactgtg aacctgccct gtatccggag ctgtgctggg   180
cactgagggg atgcaacaaa attaggagag gwtccttgct cccaacgtct acttctccta   240
cctcaacagg ggtccagggt gcagtgaact cagttcttgg cccttgggtg aggattcatg   300
gatgaatgaa agctagacct gatggggagg cattatgact aaataggccc agcctccttc   360
ccttccagct ctgtcctagg agcataggcg ggaaatctga gtagagtctg actgcagttt   420
ttgcttatga tttgtaaaag ccgtcatggg gtcaataaga aaatagggggt gatggaggggg   480
gagaagccca ggactgggag aatcgcacgt gccccagggg ttttcaccaa ggattttcaa   540
gacaaactgg agtaagaatt aaagccccag aggatttaat tatcctggtt tgcaaaagag   600
cctcccatgc cagtaccgcc cagccttgga ggccggaatg ctcatggccc ctgtggtctg   660
cttgtccttc agcccatgcc cagcagatac ctctctgact ggagacgggc tcaaagctgg   720
attagaaagg ggagmggcac ttgtgacttt gtttgactct gtgactcact tcctcgctca   780
caccttgttt gaactactgg actttcaact ggctttcctt aggtcaggca agcagacagc   840
tccccactga gaggtctgt acagtgacaa cccgggccgg cagcaaggac acagatgcag   900
ccacagtaag gctccatcag gactgggtca gtgatggcaa caggatggcc aaggatggct   960
ctagaacayt ctgtccatgc gtcactcccc ccagttttrt ttttagcttt ggcttcaggg  1020
agtgacagcc atcacaaata gccacattct gctctactct ccaacatacc agattstaca  1080
ctgttgttat tcatgagac gtgaatgttg cagagagtgg ggggattctg gttgttaagg   1140
aacttacact ggggagcttt actcttccgt gtcaacaatg tgactacatg ttctccagat  1200
tagccacaca tgcaaacatc agtgtccttc tagctttanc cgagaaagaa accagtccca  1260
gggaatgaat ggtggtctcc ccactcccgg cagcacttta gcagcccat aagctatgcg   1320
agaatgtgaa cgctcacctt gctccgtcac ggttctgacc taccacataa acaggaagaa  1380
gccagtgacc ggaacagctc taggaataac aagtcagaat agaagtgtcc tttatattac  1440
cagaaaatat gggcttggcc taagtcgctg tctcctaacc tgccgggggtc attccccacc  1500
aaacaccccca tactaaggag ccatgagcca cctggacatt caccttttct ttgaccatct  1560
ggagtctggg gcaacttaag gaaggcncca cacagtggtg caggcacatt tccaagcgta  1620
ggtgtccctg gcttttgtgg ccaaagctag tgttatggtc aacaacaggc cagggtctgt  1680
ggggcactga ccttgaaagt ggcaaaatgg aggtttcaca ggctgtgcgg gagcaggacg  1740
gcttgcttca tctaacaatc tcagtttcct ttaaaaaaag aaagaaagga aaagatttca  1800
taagcaggtg tcagtggaca gtttaagyac ttaaccattt ctctttcttc ttatggatgt  1860
gaactgtgct gtggataaat catttgtatt tcttgaatgt tctctatgac taacagttat  1920
taagtcggtt gtgtatatgt gtaactaatg taactgcctt ttaaaatttc attacaataa  1980
aaatgacttt gctctgaama aaaaaaaaa aaaaactcga                          2020
```

<210> SEQ ID NO 50
<211> LENGTH: 2432
<212> TYPE: DNA
<213> ORGANISM: Homo sapiens

<400> SEQUENCE: 50

```
atgaagggtc gttggtggga aagatggcgg cgactctggg accccttggg tcgtggcagc    60
```

-continued

```
agtggcggcg atgtttgtcg gctcgggatg ggtccaggat gttactcctt cttcttttgt    120
tggggtctgg gcaggggcca cagcaagtcg gggcgggtca acgttcgag tacttgaaac     180 gggagcactc gctgtcgaag ccctaccagg gtgtgggcac aggcagttcc tcactgtgga    240
atctgatggg caatgccatg gtgatgaccc agtatatccg ccttacccca gatatgcaaa    300
gtaaacaggg tgccttgtgg aaccgggtgc catgtttcct gagagactgg gagttgcagg    360
tgcacttcaa aatccatgga caaggaaaga agaatctgca tggggatggc ttggcaatct    420
ggtacacaag gaatcggatg cagccagggc ctgtgtttgg aaacatggac aaatttgtgg    480
ggctgggagt atttgtagac acctaccca atgaggagaa gcagcaagag cgggtattcc     540
cctacatctc agccatggtg aacaacggct ccctcagcta tgatcatgag cgggatgggc    600
ggcctacaga gctggggagc tgcacagcca ttgtccgcaa tcttcattac gacaccttcc    660
tggtgattcg ctacgtcaag aggcatttga cgataatgat ggatattgat ggcaagcatg    720
agtggaggga ctgcattgaa gtgcccggag tccgcctgcc ccgcggctac tacttcggca    780
cctcctccat cactggggat ctctcagata atcatgatgt catttccttg aagttgtttg    840
aactgacagt ggagagaacc ccagaagagg aaaagctcca tcgagatgtg ttcttgccct    900
cagtggacaa tatgaagctg cctgagatga cagctccact gccgcccctg agtggcctgg    960
ccctcttcct catcgtcttt ttctccctgg tgttttctgt atttgccata gtcattggta    1020
tcatactcta caacaaatgg caggaacaga gccgaaagcg cttctactga gccctcctgc    1080
tgccaccact tttgtgactg tcacccatga ggtatgaag gagcaggcac tggcctgagc     1140
atgcagcctg gagagtgttc ttgtctctag cagctggttg gggactatat tctgtcactg    1200
gagttttgaa tgcagggacc ccgcattccc atggttgtgc atggggacat ctaactctgg    1260
tctgggaagc cacccacccc agggcaatgc tgctgtgatg tgccttccc tgcagtcctt     1320 ccatgtggga gcagaggtgt gaagagaatt tacgtggttg tgatgccaaa atcacagaac    1380
agaatttcat agcccaggct gccgtgttgt ttgactcaga aggcccttct acttcagttt    1440
tgaatccaca aagaattaaa aactggtaac accacaggct ttctgaccat ccattcgttg    1500
ggttttgcat ttgacccaac cctctgccta cctgaggagc tttctttgga aaccaggatg    1560
gaaacttctt ccctgcctta ccttcctttc actccattca ttgtcctctc tgtgtgcaac    1620
ctgagctggg aaaggcattt ggatgcctct ctgttgggc ctgggctgc agaacacacc      1680 tgcgtttcac tggccttcat taggtggccc tagggagatg gctttctgct ttggatcact    1740
gttccctagc atgggtcttg ggtctattgg catgtccatg gccttcccaa tcaagtctct    1800
tcaggccctc agtgaagttt ggctaaaggt tggtgtaaaa atcaagagaa gcctggaaga    1860
catcatggat gccatggatt agctgtgcaa ctgaccagcc ccaggtttga tcaaaccaaa    1920
agcaacattt gtcatgtggt ctgaccatgt ggagatgttt ctggacttgc tagagcctgc    1980
ttagctgcat gttttgtagt tacgattttt ggaatcccac tttgagtgct gaaagtgtaa    2040
ggaagctttc ttcttacacc ttgggcttgg atattgccca gagaagaaat ttggcttttt    2100
ttttcttaat ggacaagaga cagttgctgt tctcatgttc caagtctgag agcaacagac    2160
cctcatcatc tgtgcctgga agagttcact gtcattgagc agcacagcct gagtgctggc    2220
ctctgtcaac ccttattcca ctgccttatt tgacaagggg ttacatgctg ctcacccttac   2280 tgccctggga ttaaatcagt tacaggccag agtctccttg gagggcctgg aactctgagt    2340
cctcctatga acctctgtag cctaaatgaa attcttaaaa tcaccgatgg aaccaaaaaa    2400
aaaaaaaaaa aaaaaaaaaa aaaaaaaaaa aa                                   2432
```

<210> SEQ ID NO 51
<211> LENGTH: 2340
<212> TYPE: DNA
<213> ORGANISM: Homo sapiens
<220> FEATURE:
<221> NAME/KEY: SITE
<222> LOCATION: (96)
<223> OTHER INFORMATION: n equals a,t,g, or c

<400> SEQUENCE: 51

| | | | | | |
|---|---|---|---|---|---|
| gacgctgggg | gcgggtgggg | gcgcggggta | ccgggctgga | cggccggccg | gcgcccctc | 60 |
| attagtatgc | ggacgaagcg | gcgggctgcg | cggagngacg | tccctgcag | ccgcggaccg | 120 |
| aggcagcggc | ggcacctgcc | ggccgagcaa | tgccaagtga | gtacacctat | gtraaactga | 180 |
| gaagtgattg | ctcgaggcct | tccctgcaat | ggtacacccg | agctcaaagc | aagatgagaa | 240 |
| ggcccagctt | gttattaaaa | gacatcctca | aatgtacatt | gcttgtgttt | ggagtgtgga | 300 |
| tcctttatat | cctcaagtta | aattatacta | ctgaagaatg | tgacatgaaa | aaaatgcatt | 360 |
| atgtggaccc | tgaccatgta | aagagagctc | agaaatatgc | tcagcaagtc | ttgcagaagg | 420 |
| aatgtcgtcc | caagtttgcc | aagacatcaa | tggcgctgtt | atttgagcac | aggtatagcg | 480 |
| tggacttact | cccttttgtg | cagaaggscc | ccaaagacag | tgaagctgag | tccaagtacg | 540 |
| atcctccttt | tgggttccgg | aagttctcca | gtaaagtcca | gaccctcttg | gaactcttgc | 600 |
| cagagcacga | cctccctgaa | cacttgaaag | ccaagacctg | tcggcgctgt | gtggttattg | 660 |
| gaagcggagg | aatactgcac | ggattagaac | tgggccacac | cctgaaccag | ttcgatgttg | 720 |
| tgataaggtt | aaacagtgca | ccagttgagg | gatattcaga | acatgttgga | aataaaacta | 780 |
| ctataaggat | gacttatcca | gagggcgcac | cactgtctga | ccttgaatat | tattccaatg | 840 |
| acttatttgt | tgctgtttta | tttaagagtg | ttgatttcaa | ctggcttcaa | gcaatggtaa | 900 |
| aaaggaaac | cctgccattc | tgggtacgac | tcttcttttg | gaagcaggtg | gcagaaaaaa | 960 |
| tcccactgca | gccaaaacat | ttcaggattt | tgaatccagt | tatcatcaaa | gagactgcct | 1020 |
| ttgracatcc | ttcagtactc | agagcctcag | tcaaggttct | gggggccgag | ataagaacgt | 1080 |
| cccccacaatc | ggtgtcattg | ccgttgtctt | agccacacat | ctgtgcgatg | aagtcagttt | 1140 |
| ggcgggtttt | ggatatgacc | tcaatcaacc | cagaacacct | ttgcactact | tcgacagtca | 1200 |
| atgcatggct | gctatgaact | ttcagaccat | gcataatgtg | acaacggaaa | ccaagttcct | 1260 |
| cttaaagctg | gtcaaagagg | gagtggtgaa | agatctcagt | ggaggcattg | atcgtgaatt | 1320 |
| ttgaacacag | aaaacctcag | ttgaaaatgc | aactctaact | ctgagagctg | tttttgacag | 1380 |
| ccttcttgat | gtatttctcc | atcctgcaga | tactttgaag | tgcagctcat | gttttttaact | 1440 |
| tttaatttaa | aaacacaaaa | aaaattttag | ctcttcccac | ttttttttttc | ctatttattt | 1500 |
| gaggtcagtg | tttgttttttg | cacaccattt | tgtaaatgaa | acttaagaat | tgaattggaa | 1560 |
| agacttctca | aagagaattg | tatgtaacga | tgttgtwttg | attttttaaga | aagtaattta | 1620 |
| atttgtaaaa | cttctgctcg | tttacactgc | acattgaata | caggtaacta | attggaagga | 1680 |
| gaggggaggt | cactcttttg | atggtggccc | tgaacctcat | tctggttccc | tgctgcgctg | 1740 |
| cttggtgtga | cccacggagg | atccactccc | aggatgacgt | gctccgtagc | tctgctgctg | 1800 |
| atactgggtc | tgcgatgcag | cggcgtgagg | cctgggctgg | ttgagaagg | tcacaaccct | 1860 |
| tctctgttgg | tctgccttct | gctgaaagac | tcgagaacca | accagggaag | ctgtcctgga | 1920 |
| ggtccctggt | cggagaggga | catagaatct | gtgacctctg | acaactgtga | agccaccctg | 1980 |

| ggctacagaa accacagtct tcccagcaat tattacaatt cttgaattcc ttggggattt | 2040 |
| tttactgccc tttcaaagca cttaagtgtt agatctaacg tgttccagtg tctgtctgag | 2100 |
| gtgacttaaa aaatcagaac aaaacttcta ttatccagag tcatgggaga gtacacccct | 2160 |
| tccaggaata atgttttggg aaacactgaa atgaaatctt cccagtatta taaattgtgt | 2220 |
| atttaaaaaa aagaaacttt tctgaatgcc tactggcggt gtataccagg cagtgtgcca | 2280 |
| gtttaaaaag atgaaaaga ataaaaactt tgaggaama aaaaaaaaaa aaaaactcga | 2340 |

<210> SEQ ID NO 52
<211> LENGTH: 601
<212> TYPE: DNA
<213> ORGANISM: Homo sapiens
<220> FEATURE:
<221> NAME/KEY: SITE
<222> LOCATION: (115)
<223> OTHER INFORMATION: n equals a,t,g, or c
<220> FEATURE:
<221> NAME/KEY: SITE
<222> LOCATION: (184)
<223> OTHER INFORMATION: n equals a,t,g, or c
<220> FEATURE:
<221> NAME/KEY: SITE
<222> LOCATION: (539)
<223> OTHER INFORMATION: n equals a,t,g, or c

<400> SEQUENCE: 52

| agtaggggag actgagactg accggtagcc aggcaggcgg acgacgcacg cccggacaga | 60 |
| ctgagcaggc gccggagaac cactcacagg ttccccccgc ctttcccttt gaaanctagg | 120 |
| cttttgcctt tcccgtggcg cccgagagag aatgctggac tctgccgact tcagcgcaac | 180 |
| taangatttc tcaagctagg ggacaaacga tcagcccaat cctgagaagg ggggaaccaa | 240 |
| gcacccgtc cccatccccc tccctcccc cgactaaact cgggcgccaa acccagccct | 300 |
| tctctaacca ccctacttcc tcctctcctt tctagcatgg tggctgtatg gacagtctga | 360 |
| cagaacagag actgacatct cccaatctgc cggcccccca cctggaacac tacagtgttc | 420 |
| tgcattgcac catgaccctg gatgtgcaaa ctgtagtcgt ttttgccgtg attgtagtcc | 480 |
| tcctgcttgt caatgtcata ctcatgtttt tcctgggaac gcgctgaatg gagtccagnc | 540 |
| acctgagctg tcgcgaactc tcgctttgat ttcatcccga gagccaccga gaagaaaaaa | 600 |
| a | 601 |

<210> SEQ ID NO 53
<211> LENGTH: 359
<212> TYPE: DNA
<213> ORGANISM: Homo sapiens
<220> FEATURE:
<221> NAME/KEY: SITE
<222> LOCATION: (343)
<223> OTHER INFORMATION: n equals a,t,g, or c
<220> FEATURE:
<221> NAME/KEY: SITE
<222> LOCATION: (347)
<223> OTHER INFORMATION: n equals a,t,g, or c
<220> FEATURE:
<221> NAME/KEY: SITE
<222> LOCATION: (349)
<223> OTHER INFORMATION: n equals a,t,g, or c

<400> SEQUENCE: 53

| ctcgtgccga attcggcacg agagatggta cttttaagag gtaattaggt tgctaagatg | 60 |
| gattaacatc tttctcttga cactgagact gggttctcct gggaatggtt agttcccaag | 120 |
| agagtgagtt gttataaaac aatgctgcct cttctatttt gcgcttttg tttgcacaaa | 180 |

```
ctcggtcccc ttctgtttct ctacgatgtt ttgatgcrgc atgaggcagt catgagaacc      240
caccagatac agctgcctga tcctgaattt cccagccaac agaaccaagt gctaaataaa      300 actctttta  ataagttaaa aaaaaaaaaa aaaaaaaaaa aanaaanana aaaaaaaaa       359
```

```
<210> SEQ ID NO 54
<211> LENGTH: 1141
<212> TYPE: DNA
<213> ORGANISM: Homo sapiens

<400> SEQUENCE: 54
```

```
ggcacgagct gctgaggcgt gagaatggcg tcccgcggcc ggcgtccgga gcatggcgga      60
cccccagagc tgttttatga cgagacagaa gcccggaaat acgttcgcaa ctcacggatg      120
attgatatcc agaccaggat ggctgggcga gcattggagc ttctttatct gccagagaat      180
aagccctgtt acctgctgga tattggctgt ggcactgggc tgagtggaag ttatctgtca      240
gatgaagggc actattgggt gggcctggat atcagccctg ccatgctgga tgaggctgtg      300
gaccgagaga tagagggaga cctgctgctg ggggatatgg gccagggcat cccattcaag      360
ccaggcacat ttgatggttg catcagcatt tctgctgtgc agtggctctg taatgctaac      420
aagaagtctg aaaaccctgc caagcgcctg tactgctttt ttgcttctct tttttctgtt      480
ctcgtccggg gatcccgagc tgtcctgcag ctgtaccctg agaactcaga gcagttggag      540
ctgatcacaa cccaggccac aaaggcaggc ttctccggtg gcatggtggt agactaccct      600
aacagtgcca agcaaagaa  attctacctc tgcttgtttt ctgggccttc gacctttata      660
ccagaggggc tgagtgaaaa tcaggatgaa gttgaaccca gggagtctgt gttcaccaat      720
gagaggttcc cattaaggat gtcgaggcgg ggaatggtga ggaagagtcg ggcatgggtg      780
ctggagaaga aggagcggca caggcgccag ggcagggaag tcagacctga cacccagtac      840
accggccgca agcgcaagcc ccgcttctaa gtcaccacgc ggttctggaa aggcacttgc      900
ctctgcactt ttctatattg ttcagctgac aaagtagtat tttagaaaag ttctaaagtt      960
ataaaaatgt tttctgcagt aaaaaaaaag ttctctgggc cgggcgtggt ggctcacacc      1020
tgtaatccca gcaccttggg aggctgaggt gggaggatca tttgaggcca ggagtttgag      1080
acctgcctgg gcaacataat gaaacttcct ttccagggag aaaaaaaaaa aaaaaaaaa      1140 a                                                                     1141
```

```
<210> SEQ ID NO 55
<211> LENGTH: 1560
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c
<220> FEATURE:
<221> NAME/KEY: SITE
<222> LOCATION: (1428)
<223> OTHER INFORMATION: n equals a,t,g, or c

<400> SEQUENCE: 55
```

```
gagagagnga gagaggtatc actgcaaggc tactatgagt attttcaaat caccacatct      60
tatcctgagc aagaggtcac tgttctgtgc tatggtaaga tacaaactat tccttcatat      120
ataataaaat tccaccttt  ttcaaaatta atatagggta agtgaagtct mccaatcatg      180
acrgcaragg aaattagtgt ctaaatgrac tgtgrgttac aggtaccttt cactwagggg      240
```

```
caggcaggtt tttataaaaa accmtgtggt aatcatcmat tgccattaag ctcctattac      300
tagcttttaa gaccatttta taaagattat ctggtgccta attaacaaga aagaaattag      360
actcaggttt aagatgctgc tggtgttctg aaattactct gaaaggtcat tcaaagaact      420
tcaaacttaa aatttttcat tcatgtattt attccacagt caaaataaat caaaatttaa      480
agctataaca ttttttaaaag ataaaggaga atttgtggca cagctgcatt aacaaaacag     540
acaccagtct aaagtgcaac actaaacagg tattctctgt tcccacggtg aataaatac      600 acacaattac acataagatt tcactaaaga taggagatga ggcaaataac cctttgaaat      660
tacctgccca acaaatagag gcaggctaca ttaatttaac attttactgc aaaatggaaa     720
aaatccccga ggtgactaac tcaaactcct catttcatgc acatgacctt ggcttctgtg     780
ttctttccat agccacatcc aaatccagaa aggctcctgc accccatgct caaaaatgca     840
acctcaagtc cctgaggtcc tcagcacaga ctgacattaa caagcctgtg ttcagccttc     900
atccagaacc tccagggaaa tcaggagcac aaacacagag caaagcaccg tttctttaaa    960
caatggcttt aactgtcgaa tgagctctga caagccatat gcatttcata acaaaccaa      1020 aacatcatct tcatatcttc ctattttcct tgcaaaaatg ttaagccatc caagtaaaaa    1080 aaaaattt aatttaacaa tgaaaaagga acttcaaagg gtttatgcca aaaaacaaac       1140
cagtcctctg cagcctaact catttgtttt tgggctgcga agccatgtag agggcgatca    1200
ggcagtagat ggtccctccc acagtcagcg ccatggtggt ccggtaaagc atttggtcag    1260
gcaggcctcg tttcaggtag acgggcacac catcagcttt ctggaaaaac ttttgtagct    1320
ctggaacttt gttttttccca gcataatcat acactgtgga atcggaggtc agtttagttg   1380
gtgtggcaaa tatgataggt ggtgcttctg tggaaaccac aggctttaa tctgcgggct     1440 ataggcctcc gaagcccatg ctcctgccaa cttctgcgtg aagccactaa acttgtagta    1500
catgacgccc agagtccggc ttcccgcatc cgctgccaac gcgaccgccc cagagaagga    1560

<210> SEQ ID NO 56
<211> LENGTH: 1507
<212> TYPE: DNA
<213> ORGANISM: Homo sapiens
<220> FEATURE:
<221> NAME/KEY: SITE
<222> LOCATION: (1047)
<223> OTHER INFORMATION: n equals a,t,g, or c
<220> FEATURE:
<221> NAME/KEY: SITE
<222> LOCATION: (1301)
<223> OTHER INFORMATION: n equals a,t,g, or c
<220> FEATURE:
<221> NAME/KEY: SITE
<222> LOCATION: (1507)
<223> OTHER INFORMATION: n equals a,t,g, or c

<400> SEQUENCE: 56
ggaacgcaga gcggagcgtg gagagcggag cgaagctgga taacagggga ccgatgatgt      60
ggcgaccatc agttctgctg cttctgttgc tactgaggca cggggcccag gggaagccat     120
ccccagacgc aggccctcat ggccagggga gggtgcacca gcggccccc ctgagcgacg      180 ctccccatga tgacgcccac gggaacttcc agtacgacca tgaggctttc ctgggacggg    240
aagtggccaa ggaattcgac caactcaccc cagaggaaag ccaggcccgt ctggggcgga    300
tcgtggaccg catggaccgc gcggggacg gcgacggctg ggtgtcgctg gccgagcttc    360
gcgcgtggat cgcgcacacg cagcagcggc acatacggga ctcggtgagc gcggcctggg    420
acacgtacga cacggaccgc gacgggcgtg tgggttggga ggagctgcgc aacgccacct    480
```

| | |
|---|---:|
| atggccacta cgcgcccggt gaagaatttc atgacgtgga ggatgcagag acctacaaaa | 540 |
| agatgctggc tcgggacgag cggcgtttcc gggtggccga ccaggatggg gactcgatgg | 600 |
| ccactcgaga ggagctgaca gccttcctgc accccgagga gttccctcac atgcgggaca | 660 |
| tcgtgattgc tgaaaccctg gaggacctgg acagaaacaa agatggctat gtccaggtgg | 720 |
| aggagtacat cgcggatctg tactcagccg agcctgggga ggaggagccg gcgtgggtgc | 780 |
| agacggagag gcagcagttc cgggacttcc gggatctgaa caaggatggg cacctggatg | 840 |
| ggagtgaggt gggccactgg gtgctgcccc ctgcccagga ccagcccctg gtggaagcca | 900 |
| accacctgct gcacgaragc gacacggaca aggaygggcg gctgagcaaa gcgsaaatcc | 960 |
| tgggtaattg aacatgtttt gtgggcagtc aggccaccaa ctatggyrag gacctgaccc | 1020 |
| ggcaccacga tgagctgtga gcmccgngca cctgccacag cctcagaggc ccgcacaatg | 1080 |
| accggaggag gggccgctgt ggtctggccc cctccctgtc caggccccgc aggaggcaga | 1140 |
| tgcagtccca ggcatcctcc tkcccctggg ctctcaggga cccctgggt cggcttctgt | 1200 |
| ccctgtcaca cccccaaccc cagggagggg ctgtcatagt cccagaggat aagcaatacc | 1260 |
| tatttctgac tgagtctccc agcccagacc caggaccct nggccccaag ctcagctcta | 1320 |
| agaaccgccc caaccctcc agctccaaat ctgagcctcc accacataga ctgaaactcc | 1380 |
| cctggcccca gccctctcct gcctggcctg gcctgggaca cctcctctct gccaggaggc | 1440 |
| aataaaagcc agcgccggga aaaaaaaaa aaaaaaaaaa aaaaaaaaaa aaaaaaaaaa | 1500 |
| aaaaaan | 1507 |

<210> SEQ ID NO 57
<211> LENGTH: 450
<212> TYPE: DNA
<213> ORGANISM: Homo sapiens

<400> SEQUENCE: 57

| | |
|---|---:|
| tttttttact cgaaaaaatg tttaatagaa tttaaaattt taacttcagg gaatttggaa | 60 |
| gttcaatcat tctcaaagag gctgtaagga tgattaaaat cctgaaggaa gccattgaag | 120 |
| aaacttcctt ctgctctttc tggaggatct cttttcaatt atctattcat catatatttc | 180 |
| ttatcttctg tgcacaattg acaactcttc tttacagcac attcctcty attcccatct | 240 |
| cttggttct gattgttcct ggggctgtgg ataaaaccat tctctgagaa gctgataagc | 300 |
| aattggatga gaaagargga gargaaaact ggcaggarga tctggsccca tgcccgcagc | 360 |
| cagcacatct ctcttcagac ctggtgaccc cagccactgg gaacctggca ggcaccagct | 420 |
| acagtgttgg acactgctcg tgccgaattc | 450 |

<210> SEQ ID NO 58
<211> LENGTH: 1147
<212> TYPE: DNA
<213> ORGANISM: Homo sapiens

<400> SEQUENCE: 58

| | |
|---|---:|
| ggcacgagac ccattgagca gaaggaggcc aggtgggaaa gctcctggga agagcagcca | 60 |
| gactggcacac tgggctgctt gagtcctgag tcacaattca gaattcctgg gctccctggg | 120 |
| tgcattctat cattccagtt gaaagtttgc ttccttccag tcatgtggct cttcattcta | 180 |
| ctctccttgg ctctcatttc agatgccatg tcatggatg aaaaggtcaa gagaagcttt | 240 |
| gtgctggaca cggcttctgc catctgcaac tacaatgccc actacaagaa tcaccccaaa | 300 |

| | |
|---|---|
| tactggtgcc gaggctattt ccgtgactac tgcaacatca tcgccttctc ccctaacagc | 360 |
| accaatcatg tggccctgaa ggacacaggg aaccagctca ttgtcactat gtcctgcctg | 420 |
| aacaaagaag acacgggctg gtactggtgt ggcatccagc gggactttgc cagggatgac | 480 |
| atggatttta cagagctgat tgtaactgac gacaaaggaa cctggccaat gactttggtc | 540 |
| tgggaaagac tatcaggcac aaaaccagaa gctgcaaggc tcccaaagtt gtccgcaagg | 600 |
| ctgaccgctc caggacgtcc attctcatca tttgcatact gatcacgggt ttgggaatca | 660 |
| tctctgtaat cagtcatttg accaaaagga ggagaagtca aggaataga agggtaggca | 720 |
| acactttgaa gcccttctcg cgtgtcctga ctccaaagga aatggctcct actgaacaga | 780 |
| tgtgactgaa gatttttta atttagttca taaagtgatg ctacaacaga ataatcacca | 840 |
| tgacaactgg ccccacacct cagagactga ttctgatctc ccaggaattc tgaaggtccc | 900 |
| tctatccttg acaacaatca tttgcagcca ggtagcaacg gcagtagtca gaggagctat | 960 |
| gatagaccac acccaagcaa ggctgccctc aaataacatc tcaagatctt agttcttatg | 1020 |
| cattccatca gtcagaagtg aagaagaggt ggagaatctg gattggggac caggaaatca | 1080 |
| cttgtatttt gttagccaat aaattcctag ccagtgttga atgaaaaaaa aaaaaaaaa | 1140 |
| aaaaaaa | 1147 |

<210> SEQ ID NO 59
<211> LENGTH: 777
<212> TYPE: DNA
<213> ORGANISM: Homo sapiens

<400> SEQUENCE: 59

| | |
|---|---|
| ggcagaggct cctcagaagg gcgtgggctc tccagtcttc cacagtcccc accatgccct | 60 |
| gttgccttac cgctgacgta gctcacccat cttttacttg cctggctaag atgcatggca | 120 |
| tywcattcc tccttgttgc actgcagtca gtccctcact gccccatct cctggaagag | 180 |
| gagcataagc tttgcaaggt cagccacttc tctggggtca cactagttac atcaagacag | 240 |
| gactccagct catatgtgcc agtgcagaca ctcttcatcc acctgggcc ctgggcttgg | 300 |
| gacctggytc cttgcacagc agargacccg gaggctgaga ggagcttgcg gttgtgtcat | 360 |
| agtcacctgg ccagarggaa cgtgagcccc tcccaagctg cagarggarg garcargcgt | 420 |
| ggctgtcagc accgaggtag cagagaatta acattcttgt cagcagagaa tgaagcagga | 480 |
| atataattaa aactttgccc ttggaatagc tgattcattt gaattttatt ccacacgttt | 540 |
| gaaagaggaa agaaaatgtg aagacttgca gcctggttct cgcctggcct gggctggccc | 600 |
| agctgtcagg cccggttcct ttctgagcat tcagtccact gatgttgact gagggccagg | 660 |
| agagaccctc agcagggtat taccatatca gcctcctatc gctgctggga gaaattacca | 720 |
| tgaattcagt ggcttaaaac aacacacgag cctctctgag cctaccctgg ctcagga | 777 |

<210> SEQ ID NO 60
<211> LENGTH: 1191
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c

<400> SEQUENCE: 60

| | |
|---|---|
| aagantgatt ttccttactc tccaaagcgt cagcattttg aagtttcttt tatgaaagtg | 60 |
| ggggcaagaa tcagggtgaa aatgagtgta aacaaagccc atcctgtggt cagcacccac | 120 |

```
tggaggtggc cagcagagtg gcctcagatg ttcctgcacc tggcccagga gcccaggaca      180
gaggtcaaat ctaggcccct tggtctggct ggattcatca ggcaagattc gaaaacaaga      240
aaacctctag aacaagaaac aatcatgtct gcagcagata cggcactgtg gccctatggc      300
catggcaatc gtgagcacca agagaatgag ttacagaaat atctccaata caaagacatg      360
catctcctgg acagtggaca gtcgctggga cacacacaca cacttcaagg ctcacacaac      420
ctaacagcct taaatatctg aagaaacaga atcacgacat taagtcagca gagggagagg      480
taggctgaag cagcaggagg ccaattttat atcccacaga tttttttaaa aatgactccc      540
cagcaagggg tggggagaaa gccactgatt taggagagtt cttggctcag ccaaccactg      600
cggttatcta cacgttttac aaaggcacrg aagtagagag gggctgcact cacgaccctc      660
cccagggccc gcacagccag acacggtggg ttcttccttt ttcccttctg gccttggtgg      720
aattcctacc acggtggcct ctgcctttgg acaatgcct tcatgctcat ccccgggtca       780
aggatggagt ctgttaccat tttccagggg aaattccaag gaccagcccc gcctcattac      840
gttcacccca caggaaggtg atctggaaag cctgtaaaca cgtactctgg gtggctgagt      900
ggtgtcacca agctgctttt gtgcagggct gaagcacaga caagagggca ggcagctgcc      960
ggaggcctga agtggggaga gatccccgca ggcctgcagg agccaggag aacctccaac       1020
tggatctaaa ctgtgggaca gcccaggcgt gcccctcttc acatggctcc caggctccct      1080
caaagccctt cccaggccct gcaggaagag agggagggtg aggagaggca gggagggcag      1140
aggtcgcctg aaagcctggg ctccgaactc cctcagcaga gctttaaagt g              1191
```

<210> SEQ ID NO 61
<211> LENGTH: 1580
<212> TYPE: DNA
<213> ORGANISM: Homo sapiens
<220> FEATURE:
<221> NAME/KEY: SITE
<222> LOCATION: (1567)
<223> OTHER INFORMATION: n equals a,t,g, or c
<220> FEATURE:
<221> NAME/KEY: SITE
<222> LOCATION: (1575)
<223> OTHER INFORMATION: n equals a,t,g, or c

<400> SEQUENCE: 61

```
ccccgccccc cgcccacgaa ggaagtggct gctgctccgg cgcggaccca gagccggttc      60
ggcgcgtcga ctgcccagag tccgcggccg ggcgcgggag gagccaagcc gccatggcct     120
accacagctt cctggtggag cccatcagct gccacgcctg gaacaaggac cgcacccaga     180
ttgccatctg ccccaacaac catgaggtgc atatctatga aaagagcggt gccaaatgga     240
ccaaggtgca cgagctcaag gagcacaacg ggcaggtgac aggcatcgac tgggcccccg     300
agagtaaccg tattgtgacc tgcggcacag accgcaacgc ctacgtgtgg acgctgaagg     360
gccgcacatg gaagcccacg ctggtcatcc tgcggatcaa ccgggctgcc cgctgcgtgc     420
gctgggcccc caacgagaac aagtttgctg tgggcagcgg ctctcgtgtg atctccatct     480
gttatttcga gcaggagaat gactggtggg tttgcaagca catcaagaag cccatccgct     540
ccaccgtcct cagcctggac tggcacccca caatgtgct gctggctgcc ggctcctgtg      600
acttcaagtg tcggatcttt tcagcctaca tcaaggaggt ggaggaacgg ccggcaccca     660
ccccgtgggg ctccaagatg cccctttggg aactgatgtt cgaatccagc agtagctgcg     720
gctgggtaca tggcgtctgt ttctcagcca gcgggagccg cgtggcctgg gtaagccacg     780
```

| | |
|---|---|
| acagcaccgt ctgcctggct gatgccgaca agaagatggc cgtcgcgact ctggcctctg | 840 |
| aaacactacc actgctggcg ctgaccttca tcacagacaa cagcctggtg gcagcgggcc | 900 |
| acgactgctt cccggtgctg ttcacctatg acgccgccgc ggggatgctg agcttcggcg | 960 |
| ggcggctgga cgttcctaag cagagctcgc agcgtggctt gacggcccgc gagcgcttcc | 1020 |
| agaacctgga caagaaggcg agctccgagg gtggcacggc tgcgggcgcg ggcctagact | 1080 |
| cgctgcacaa gaacagcgtc agccagatct cggtgctcag cggcggcaag gccaagtgct | 1140 |
| cgcagttctg caccactggc atggatggcg gcatgagtat ctgggatgtg aagagcttgg | 1200 |
| agtcagcctt gaaggacctc aagatcaaat gacctgtgag gaatatgttg ccttcatcct | 1260 |
| agctgctggg gaagcgggga gaggggtcag ggaggctaat ggttgctttg ctgaatgttt | 1320 |
| ctggggtacc aatacgagtt cccatagggg ctgctccctc aaaaagggag gggacagatg | 1380 |
| gggagctttt cttacctatt caaggaatac gtgcctttt cttaaatgct ttcatttatt | 1440 |
| gaaaaaaaa aaaaatgccc ccaaagcact atgctggtca tgaactgctt caaaatgtgg | 1500 |
| aggtaataaa atgcaactgt gtaaaaaaaa aaaaaaaaa aaatgaccct cgcgatctag | 1560 |
| aactagncgg acgcntgggt | 1580 |

<210> SEQ ID NO 62
<211> LENGTH: 1117
<212> TYPE: DNA
<213> ORGANISM: Homo sapiens

<400> SEQUENCE: 62

| | |
|---|---|
| ggcacgaggc gcgatgcagc acaggctaga ggctgcgcaa sgcgggggcc cgcccctggg | 60 |
| accctccggg ccgggcggtt tggcccctta gcgcccgggc gtcggggcgg taaaaggccg | 120 |
| gcagaaggga ggcacttgag aaatgtcttt cctccaggac ccaagtttct tcaccatggg | 180 |
| gatgtggtcc attggtgcag gagccctggg ggctgctgcc ttggcattgc tgcttgccaa | 240 |
| cacagacgtg tttctgtcca gccccagaa agcggccctg gagtacctgg aggatataga | 300 |
| cctgaaaaca ctggagaagg aaccaaggac tttcaaagca aaggagctat gggaaaaaaa | 360 |
| tggagctgtg attatggccg tgcggaggcc aggctgtttc ctctgtcgag aggaagctgc | 420 |
| ggatctgtcc tccctgaaaa gcatgttgga ccagctgggc gtcccctct atgcagtggt | 480 |
| aaaggagcac atcaggactg aagtgaagga tttccagcct tatttcaaag gagaaatctt | 540 |
| cctggatgaa agaaaaaagt tctatggtcc acaaaggcgg aagatgatgt ttatgggatt | 600 |
| tatccgtctg ggagtgtggt acaacttctt ccgagcctgg aacggaggct tctctggaaa | 660 |
| cctggaagga gaaggcttca tccttggggg agttttcgtg gtgggatcag gaaagcaggg | 720 |
| cattcttctt gagcaccgag aaaaagaatt tggagacaaa gtaaacctac tttctgttct | 780 |
| ggaagctgct aagatgatca aaccacagac tttggcctca gagaaaaaat gattgtgtga | 840 |
| aactgcccag ctcagggata accagggaca ttcacctgtg ttcatgggat gtattgtttc | 900 |
| cactcgtgtc cctaaggagt gagaaaccca tttatactct actctcagta tggattatta | 960 |
| atgtatttta atattctgtt taggcccact aaggcaaaat agccccaaaa caagactgac | 1020 |
| aaaaatctga aaaactaatg aggattatta agctaaaacc tgggaaatag gaggcttwaa | 1080 |
| atgactgccm gctggtgcrt gctcacactt ggcccac | 1117 |

<210> SEQ ID NO 63
<211> LENGTH: 361
<212> TYPE: DNA
<213> ORGANISM: Homo sapiens

<400> SEQUENCE: 63

```
cccacgcgtg ckggcgcctg gcagccaccg cctgggaggt tactgtaagg cccgcagctc      60
ccgccagctc ccgcggacts ctgccgcctc cttaccatga agccagtaag tcgtcgcacg     120
ctggactgga tttattcagt gttgctgctt gccatcgttt taatctcctg gggctgcatc     180
atctatgctt cgatggtgtc tgcaagacga cagctaagga gaaataccc agacaaaatc     240
tttgggacga atgaaaattt gtaactcttc tggatttaat tatctgaaaa tacagttctt     300
tccctcatgc ttatgtagat ataaaaataa aattcataat gcaaaaaaaa aaaaaaaaa     360
g                                                                    361
```

<210> SEQ ID NO 64
<211> LENGTH: 1668
<212> TYPE: DNA
<213> ORGANISM: Homo sapiens
<220> FEATURE:
<221> NAME/KEY: SITE
<222> LOCATION: (1664)
<223> OTHER INFORMATION: n equals a,t,g, or c

<400> SEQUENCE: 64

```
ggcacgaggt ctgccaagct atagaccatg gctgtgaaca catttgtgtg aacagtgacg      60
actcatacac gtgcgagtgc ttggagggat tccggctcgc tgaggatggg aaacgctgcc     120
gaagaaggat gtctgcaaat caacccacca tggctgcgaa cacatttgtg ttaataatgg     180
gaattcctac atctgcaaat gctcakaggg atttgttcta gctgaggacg gaagacggtg     240
caagaaatgc actgaaggcc caattgacct ggtctttgtg atcgatggat ccaagagtct     300
tggagaagag aattttgagg tcgtgaagca gtttgtcact ggaattatag attccttgac     360
aatttccccc aaagccgctc gagtggggct gctccagtat tccacacagg tccacacaga     420
gttcactctg agaaacttca actcagccaa agacatgaaa aaagccgtgg cccacatgaa     480
atacatggga aagggctcta tgactgggct ggccctgaaa cacatgtttg agagaagttt     540
tacccaagga gaaggggcca ggcccttttcc acaagggtgc ccagagcagc cattgtgttc     600
accgacggac gggctcagga tgacgtctcc gagtgggcca gtaaagccaa ggccaatggt     660
atcactatgt atgctgttgg ggtaggaaaa gccattgagg aggaactaca agagattgcc     720
tctgagccca aaacaagca tctcttctat gccgaagact tcagcacaat ggatgagata     780
agtgaaaaac tcaagaaagg catctgtgaa gctctagaag actccgatgg aagacaggac     840
tctccagcag gggaactgcc aaaaacggtc caacagccaa cagtgcaaca cagatatctg     900
tttgaagaag acaatctttt acggtctaca caaaagcttt cccattcaac aaaaccttca     960
ggaagccctt tggaagaaaa acacgatcaa tgcaaatgtg aaaaccttat aatgttccag    1020
aaccttgcaa acgaagaagt aagaaaatta acacagcgct agaagaaat gacacagaga    1080
atggaagccc tggaaaatcg cctgagatac agatgaagat tagaaatcgc gacacatttg    1140
tagtcattgt atcacggatt acaatgaacg cagtgcagag ccccaaagct caggctattg    1200
ttaaatcaat aatgttgtga agtaaaacaa tcagtactga gaaacctggt ttgccacaga    1260
acaaagacaa gaagtataca ctaacttgta taaatttatc taggaaaaaa atccttcaga    1320
attctaagat gaatttacca ggtgagaatg aataagctat gcaaggtatt ttgtaatata    1380
ctgtggacac aacttgcttc tgcctcatcc tgccttagtg tgcaatctca tttgactata    1440
cgataaagtt tgcacagtct tacttctgta gaacactggc cataggaaat gctgttttt    1500
```

```
tgtaytggac tttaccttga tatatgtata tggatgtatg cataaaatca taggacatat    1560
gtacttgtgg aacaagttgg attttttata caatattaaa attcaccact tcagagraaa    1620
aaaaaaaaaa aaaaaaaaaa aaaaaaaaaa aaaaaaaaaa aaanaaaa                 1668
```

<210> SEQ ID NO 65
<211> LENGTH: 1353
<212> TYPE: DNA
<213> ORGANISM: Homo sapiens
<220> FEATURE:
<221> NAME/KEY: SITE
<222> LOCATION: (1322)
<223> OTHER INFORMATION: n equals a,t,g, or c
<220> FEATURE:
<221> NAME/KEY: SITE
<222> LOCATION: (1341)
<223> OTHER INFORMATION: n equals a,t,g, or c

<400> SEQUENCE: 65

```
gggtcgaccc acgcgtccgc ccacgcgtcc ggatggctgc gctgttgctg agacacgttg      60
gtcgtcattg cctccgagcc cactttagcc ctcagctctg tatcagaaat gctgttcctt     120
tgggaaccac ggccaaagaa gagatggagc ggttctggaa taagaatata ggttcaaacc     180
gtcctctgtc tccccacatt actatctaca gttggtctct tcccatggcg atgtccatct     240
gccaccgtgg cactggtatt gctttgagtg caggggtctc tcttttttggc atgtcggccc    300 tgttactccc tgggaacttt gagtcttatt tggaacttgt gaagtccctg tgtctggggc     360
cagcactgat ccacacagct aagtttgcac ttgtcttccc tctcatgtat catacctgga     420
atgggatccg acacttgatg tgggacctag aaaaggcct gaagattccc cagctatacc      480
agtctggagt ggttgtcctg gttcttactg tgttgtcctc tatggggctg gcagccatgt     540
gaagaaagga ggctcccagc atcatcttcc tacacattat tacattcacc catctttctg     600
tttgtcattc ttatctccag cctgggaaaa gttctcctta tttgtttaga tccttttgta     660
ttttcagatc tccttggagc agtagagtac ctggtagacc ataatagtgg aaaagggtct     720
agttttcccc ttgttttctaa agatgaggtg gctgcaaaaa ctccccttttt ttgcccacag    780 cttgcctact ctcggcctag aagcagttat tctctctcca tattgggctt tgatttgtgc     840
tgagggtcag ctttttggctc cttcttcctg agacagtgga aacaatgcca gctctgtggc    900
ttctgccctg gggatgggcc gggttggggg gtgggttggt gaggctttgg gtgccactgc     960
ctgtgggttg ctggcttaaa ggacaattct cttcattggt gagagcccag gccattaaca    1020
cctacacagt gttattgaaa gaagagaggt gggggtggag gggaattagt ctgtcccagc    1080
tagagggaga taaagagggc tagttagttc ttggagcagc tgcttttgag gagaaaatat    1140
atagctttgg acacgaggaa gatctagaaa attatcattg aacatattaa tggttatttc    1200 ttttctcttgg atttccagaa aagcctctta atttttatgct ttctcatcga agtaatgtac    1260 ccttttttttc tgaaactgaa ttaaatactc attttatctt tgaaaaaaaa aaaaaaaacc   1320
tngggggggg ccccggaccc naattggccc tat                                 1353
```

<210> SEQ ID NO 66
<211> LENGTH: 1011
<212> TYPE: DNA
<213> ORGANISM: Homo sapiens
<220> FEATURE:
<221> NAME/KEY: SITE
<222> LOCATION: (951)
<223> OTHER INFORMATION: n equals a,t,g, or c
<220> FEATURE:
<221> NAME/KEY: SITE

```
<222> LOCATION: (952)
<223> OTHER INFORMATION: n equals a,t,g, or c

<400> SEQUENCE: 66
cggaagaaag cagccatcca gacatttcag aacacgtacc aggtgttagc tgtgaccttc      60
aatgacacaa gtgatcagat tatttctggt ggaatagaca atgatatcaa ggtctgggac     120
tgcgccagaa caagctaacc tacaccatga gaggccatgc agattcagtg actggcctga    180
gtttaagttc tgaaggctct tatcttttgt ccaatgcaat ggacaataca gttcgtgtct     240
gggatgtccg gccatttgcc cccaaagaga gatgtgtaaa gatatttcaa ggaaatgtgc     300
acaactttga aaagaacctt ctgagatgtt cttggtcacc tgatggaagc aaaatagcag     360
ctggctcagc cgacaggttt gtttatgtgt gggataccac aagcaggaga atattgtata     420
agctgcccgg ccatgctggc tccatcaatg aagtggcttt ccaccctgat gagcccatca     480
ttatctcagc atcgagtgac aagagactgt atatgggaga gattcagtga agatatggac     540
tggaagactc caaggccgct tgtctttgag acctcagact gcataagtga tgccaaatgt     600
tggatgtcca ggytagcacc ctcccttcag atgaccattg ctagcaagaa acaggaggcg     660
gtggccatat tccaaaaacc acttctgtcc catttcacca ggatgactaa ggcaagctcc     720
ctgtggcctc taaaaaccac ctgccagatt tcagggactg tttttttttt tcttttcttt    780
ttttcctgtt ttctaatgca ggcccaatgt gacaaatttg ttggttggga tttttttttt    840
tttttgtaac tggcttgtat gatattttct ttctgtattt ctctatatca ttttgtatta    900
aaagccaaat agatgccttt ttacaagarm aaaaaaaaaa aaaaaaaaa nnaaaaaaaa      960
ctgggagggg gggcccggta cccaaatcgc cggatatgat cgtaaacaat c             1011

<210> SEQ ID NO 67
<211> LENGTH: 1193
<212> TYPE: DNA
<213> ORGANISM: Homo sapiens
<220> FEATURE:
<221> NAME/KEY: SITE
<222> LOCATION: (512)
<223> OTHER INFORMATION: n equals a,t,g, or c
<220> FEATURE:
<221> NAME/KEY: SITE
<222> LOCATION: (1167)
<223> OTHER INFORMATION: n equals a,t,g, or c
<220> FEATURE:
<221> NAME/KEY: SITE
<222> LOCATION: (1169)
<223> OTHER INFORMATION: n equals a,t,g, or c
<220> FEATURE:
<221> NAME/KEY: SITE
<222> LOCATION: (1171)
<223> OTHER INFORMATION: n equals a,t,g, or c
<220> FEATURE:
<221> NAME/KEY: SITE
<222> LOCATION: (1185)
<223> OTHER INFORMATION: n equals a,t,g, or c

<400> SEQUENCE: 67
ggccgggcgg tgcgcactgc gggcgcatcc ctgccccggc gccgtccgtg cccgcgggac      60
ctgacagccg ggtcagaggg cgaactgtgc tcaggcccgg gctggacgca gagccagagc    120
tgtcccagca ggagcagagg gtcctggaaa ggaagctgaa aaaggaacgg aagaaagagg     180
agaggcagcg tctgcgggag gcaggccttg tggcccagca cccgcctgcc aggcgctcgg     240
ggccgaaact ggcctgggac tacctctgca gatgggccca aaagcacaag aactggaggt     300
ttcagaagac gaggcagacg tggctcctgc tgcacatgta tgacagtgac aaggttcccg     360
```

```
atgagcactt ctccaccctg ctggcctacc tggaggggct gcaggccgg gcccgagagc      420 tgacggtgca gaaggcggaa gcctgatgcg ggagctggat gaggagggct ctgatccccc      480
cctgccgggg agggcccagc gcatccgaca gntgctgcag ctgctctcct agtgggttca      540
gcgcggggcg gggccgctgc ccagtgcagg gctgcctcag accacacagg gtgcagctcc      600
tccggcggtg ggggccgggt tcaccagcag ggcagcggct gagcaagggc tttcagctcc      660
tccggtggtg ggggccggga tcaccagcac cagagcctcg caagggcccc ttccctcctc      720
cagaccctcc ttggccggtg acgctgtgac agtgatggca ggttcagtgc cttcagcgca      780
gagcgtggat gctctggaat cacccggacc cctggccttg gagggaccct ccagcccag       840 gaatctgctt tggagggaaa tgtctatttt tctaccggga atattttaga gattggggca      900
tgctggctcc tcccgccagc tgcaaacctg caccttccgc ctgattcccg atccccctgc      960
gtgggccgca ttcctggtcc cctgcctgcg tccatcgagg ggcctggctg tggcctgttt     1020
tcctttgacc ccacacagcg tcattgcggg tcatggggag cccctggtgg gagcttgtgg     1080
agtcggatca cgtacctgtg cagaaaccgc ctctgtggct gcatttgaaa taaaacccga     1140
cccagcagca aaaaaaaaaa aaaaaancnc naggggggc ccggnaccca att             1193

<210> SEQ ID NO 68
<211> LENGTH: 560
<212> TYPE: DNA
<213> ORGANISM: Homo sapiens

<400> SEQUENCE: 68
gaattcggca cgagttggca catgatgcaa atgcatttc tcagagtaga ttgcagtcaa        60
aaatgttgga aactactaag catgtgcara tagcatgcat gctgctgctg acctgccaga      120
tatttctccc ttcctccctt tctccctcat ttattcattc attaactgat tcattcatcc      180
cattaaaaaa attatatgta tgttttgtgc aaagcaccct actcaaggct gcggggtaca      240
aaagtatatc agaagccttg ggctttgacm wacttctctg tagtagtgct agatttgtgt      300
ggatctgcca cacttactcc aggcctcttg tgacctgtgc tttgcattaa tctcttaggc      360
taagccacat accttttcat tatacaatct ttgctgatgc taaggacaga ttccaaagtg      420
ccctccttat aatttttgta tttaatgcaa agtgtaatca agaataggcc attgttaggt      480
caattgcttt tctgtattta tcttttcaaa caataaaata tcagtgggat gaaaaagggc      540
cggaaaaaaa aaaaaaaaaa                                                  560

<210> SEQ ID NO 69
<211> LENGTH: 1657
<212> TYPE: DNA
<213> ORGANISM: Homo sapiens
<220> FEATURE:
<221> NAME/KEY: SITE
<222> LOCATION: (6)
<223> OTHER INFORMATION: n equals a,t,g, or c
<220> FEATURE:
<221> NAME/KEY: SITE
<222> LOCATION: (343)
<223> OTHER INFORMATION: n equals a,t,g, or c

<400> SEQUENCE: 69
cggacngagc cgccgccggg cacttcctgt ggaggccgca gcgggtgcgg gcgccgacgg       60
gcgagagcca gcgagcgagc gagcgagccg agccgagcct cccgccgtcg ccatgggcca      120
gaacgacctg atgggcacgg ccgaggactt cgccgaccag ttcctccgtg tcacaaagca      180
gtacctgccc cacgtggcgc gcctctgtct gatcagcacc ttcctggagg acggcatccg      240
```

-continued

```
tatgtggttc cagtggagcg agcagcgcga ctacatcgac accacctgga actgcggcta      300
cctgctggcc tcgtccttcg tcttcctcaa cttgctggga cantgactgg ctgcgtcctg      360
gtgttgagca ggaacttcgt gcagtacgcc tgcttcgggc tctttggaat catagctctg      420
cagacgattg cctacagcat tttatgggac ttgaagtttt tgatgaggaa cctggccctg      480
ggaggaggcc tgttgctgct cctagcagaa tcccgttctg aagggaagag catgtttgcg      540
ggcgtcccca ccatgcgtga gagctccccc aaacagtaca tgcagctcgg aggcagggtc      600
ttgctggttc tgatgttcat gaccctcctt cactttgacg ccagcttctt ttctattgtc      660
cagaacatcg tggggcacag ctctgatgat tttagtggcc attggtttta aaaccaagct      720
ggctgctttg actcttgttg tgtggctctt tgccatcaac gtatatttca acgccttctg      780
gaccattcca gtctacaagc ccatgcatga cttcctgaaa tacgacttct ccagaccat       840
gtcggtgatt gggggcttgc tcctggtggt ggccctgggc cctggggtg tctccatgga       900
tgagaagaag aaggagtggt aacagtcaca gatccctacc tgcctggcta agacccgtgg      960
ccgtcaagga ctggtcgggg gtggattcaa caaaactgcc agcttttatg tatcctcttc     1020
ccttcccctc ccttggtaaa ggcacagatg ttttgagaac tttatttgca gagacacctg     1080
agaatcaatg gcttcaggac atgggttctc ttctcctgtg atcattcaag tgctcactgc     1140
atgaagactg gcttgtctca gtgtttcaac ctcaccaggg ctgtctcttg gtccacacct     1200
cgctccctgt tagtgccgta tgacagcccc catcaaatga ccttggccaa gtcacggttt     1260
ctctgtggtc aaggttggtt ggctgattgg tggaaagtag ggtggaccaa aggaggccac     1320
gtgagcagtc agcaccagtt ctgcaccagc agcgcctccg tcctagtggg tgttcctgtt     1380
tctcctggcc ctgggtgggc tagggcctga ttcgggaaga tgcctttgca gggaggggag     1440
gataagtggg atctaccaat tgattctggc aaaacaattt ctaagatttt tttgctttat     1500
gtgggaaaca gatctaaatc tcattttatg ctgtatttta tatcttagtt gtgtttgaaa     1560
acgttttgat ttttggaaac acatcaaaat aaataatggc gtttgttgta aaaaaaaaa     1620
aaaaaaactc grgggggggc ccggtaccca aatcgcc                              1657
```

<210> SEQ ID NO 70
<211> LENGTH: 711
<212> TYPE: DNA
<213> ORGANISM: Homo sapiens

<400> SEQUENCE: 70

```
ggcacgagcg aagaccctgt tcggaccctg ccccgattcc agactcaggt agatcgtcgg       60
catccctct accgtggaca ccaggcagcc ctgggctga tggagagaga tcaggtatcc      120
cccagggagt aggggctacc ttgaggggat gatagacctc ccccactccc agtgkkactc      180
tggaaatatg aaggaactag ggagtggaag agatttcaga gctggggaga ggagttcctc      240
ccttcaaagc cagcaactgc cttggggaa tgtcgggggg tctctccttt ctcctgcttg      300
tgtkargtgg tacacagtcc ccccttcacc tggcgggaag ctgtcccgga cagactcatc      360
tcagctttcc cttggggcag gatcgggggc agcagctcca gcagaaacag caggatctgg      420
agcaggaagg cctcgaggcc acacaggggc tgctggccgg cgagtgggcc ccacccctct      480
ggragctggg cagcctcttc caggccttcg tgaagaggga gagccaggct tatgcgtaag      540
cttcatagct tctgctggcc tggggtggac ccaggacccc tggggcctgg gtgccctgag      600
tggtggtaaa gtggagcaat cccttcacgc tccttggcca tgttctgagc ggccagcttg      660
```

```
gcctttgcct taataaatgt gctttatttt caaaaaaaaa aaaaaaaaac t           711
```

```
<210> SEQ ID NO 71
<211> LENGTH: 935
<212> TYPE: DNA
<213> ORGANISM: Homo sapiens
<220> FEATURE:
<221> NAME/KEY: SITE
<222> LOCATION: (510)
<223> OTHER INFORMATION: n equals a,t,g, or c

<400> SEQUENCE: 71
ggcacagggt gaaagccagc taaacccccaa gtggagaagt gaaagacatg gttgttccca    60
taagtttatt gctcacatta tgaaagaagc catagtcatg agtgaaccac tccctaggtt   120
gataaggaaa ccaacacgga agatctcttt ctggaagaag cagccagcct cgtgaaggag   180
cggcccagcc gccgggcccg agggtcgcct tttgttcgga gtggcacgat tgtccgttcc   240
cagacattct cgcctggagc acgaagccag tatgtttgca gactttatcg tagtgacagc   300
gacagttcaa cgctgccccg gaagtccccc tttgtccgaa atactttgga aagacgaacc   360
cttcgctata agcagtcatg caggtcttcc ctggctgagc tcatggcccg cacctccctg   420
gacttggagc tggatctcca ggcgtcgaga acacggcaga ggcagctgaa tgaggagctc   480
tgcgccctcc gtgagctgcg gcagcggttn ggaggacgcc cagctccgtg gccagactga   540
cctcccaccc tgggtgcttc gggacgagcg gctccgtggc ctgctgcggg agccgagcgg   600
cagacaagac agaccaaact tgactaccgt catgagcagg cggctgagaa gatgctgaag   660
aaggcctcca aggagatcta ccagctgcgt ggcagagcca caagagccc atccaagtgc    720
agcctttag ggagaagata gcattcttca caaggccaag gatcaacata cctcctctcc   780
cagccgacga cgtctgatgg agtgcattgt gcacatgaag tatttatcca cctgttttat   840
tttcatgaag ttcttagact agctgaattt gtctttaaaa tatttgtgca aagctattaa   900
tatacacatt ttgtaaaaaa aaaaaaaaaa aaact                              935
```

```
<210> SEQ ID NO 72
<211> LENGTH: 504
<212> TYPE: DNA
<213> ORGANISM: Homo sapiens
<220> FEATURE:
<221> NAME/KEY: SITE
<222> LOCATION: (504)
<223> OTHER INFORMATION: n equals a,t,g, or c

<400> SEQUENCE: 72 gcagggcga ggggytgggg accgcggggc ggacgggagc gagtatgtcc gctctgactc     60
ggctggcgtc tttcgctcgc gttggaggcc gccttttcag aagcggctgc gcacggactg   120
ctggagatgg tggagtccgt catgccggtg gtggtgtgca cattgagccc cggtatagac   180
agttccccca gctgaccaga tcccaggtgt tccagagcga gttcttcagc ggactcatgt   240
ggttctggat tctctggcgc ttttggcatg actcagaaga ggtgctgggt cactttccgt   300
atcctgatcc ttcccagtgg acagatgaag aattaggtat ccctcctgat gatgaagact   360
gaaggtgtag actcagcctc actctgtaca agagccaggt gagaatttca aggattatcg   420
acttcatatt gcacattaaa gttacaaatt aaagtggctt ggtcaagaat garaaaaaaa   480
aaaaaaatt gggggggggc cccn                                           504
```

```
<210> SEQ ID NO 73
<211> LENGTH: 620
```

```
<212> TYPE: DNA
<213> ORGANISM: Homo sapiens

<400> SEQUENCE: 73
gaattcggca cgaggaggag gggaggcggg gtaagtttgg tgggaaactc tgtaatttcc    60
wttttttactt tcacagcaat agtgcagaat ccagaatgga tgtcctcttt gtagccatct   120
ttgctgtgcc acttatcctg ggacaagaat atgaggatga agaaagactg ggagaggatg   180
aatattatca ggtggtctat tattatacag tcaccccag ttatgatgac tttagtgcag    240
atttcaccat tgattactcc atatttgagt cagaggacag gctgaacagg ttggataagg   300
acataacaga agcaatagag actaccatta gtcttgaaac agcacgtgca gaccatccga   360
agcctgtaac tgtgaaacca gtaacaacgg aacctcagag tccagatctg aacgatgccg   420
tgtccagttt gcgaagtcct attcccctcc tcctgtcgtg tgcctttgtt caggtgggga   480
tgtatttcat gtagaaggtg gaagaaggct gctatgactc tttggatggg agtctggcaa   540
gaggaaattg gaagataaaa taataataa gtgaaataaa aaaaaaaaaa aaaaactcga    600
gggggggccc ggtacccaat                                               620

<210> SEQ ID NO 74
<211> LENGTH: 581
<212> TYPE: DNA
<213> ORGANISM: Homo sapiens

<400> SEQUENCE: 74
acaaggtgtg tgtaaagttt atgtttgtaa actgaattct atcttaaatc caaaaagaac    60
tcgggagtaa ttcattttg tagcataaag atccctaagt tttatttga aatatctgat     120
ttttacacgt taaaaataa cagggcatcg agaggattcc taggtgacat ccagactcct    180
ttagctttgt gtgtgtggca ccggttagtc tgcttctctc tcctttcttg cactgcttca   240
cacagccatg ccctgccagc ccgggcaggt gccttcctgt caatgtacat ttgggcttct   300
gctcatgctg ccctccctcc cctcccctgc ctcccaaccc cgccccttt gttcctccat    360
ggagtacttc catgggtgtg cctccccag ccaagccata ataggtggtt tcccttcgc     420
ttctgtagcc cttgcagaca tcctctgttt acagtaggtg ttgacttact tccctctcc    480
ccgstaaagc cataaactcc ttaaggacag gtagcattct tagtatcttc gttcttctca   540
atgaccagta gaccattaaa catgtagcaa acaaatgtga a                       581

<210> SEQ ID NO 75
<211> LENGTH: 1843
<212> TYPE: DNA
<213> ORGANISM: Homo sapiens
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (24)
<223> OTHER INFORMATION: n equals a,t,g, or c
<220> FEATURE:
<221> NAME/KEY: SITE
<222> LOCATION: (91)
<223> OTHER INFORMATION: n equals a,t,g, or c
<220> FEATURE:
<221> NAME/KEY: SITE
<222> LOCATION: (213)
<223> OTHER INFORMATION: n equals a,t,g, or c
<220> FEATURE:
<221> NAME/KEY: SITE
<222> LOCATION: (1633)
```

<223> OTHER INFORMATION: n equals a,t,g, or c

<400> SEQUENCE: 75

| | | | | | |
|---|---|---|---|---|---|
| aaacccaacn | ccctccggtc | cccnaaagaa | agcccagccc | aaatcccaag | ccggcagtga | 60 |
| gcccgcgaac | aaggccctca | agacgcccag | ncgaacaagc | agccccagg | aggccccgca | 120 |
| agagaactcc | ctggcggccc | aagcgggcag | cttctgtgcg | gcagaactca | gccaccgaga | 180 |
| gcgcagacag | catcgagatt | tatgtcccgg | agnccccagac | caggctctga | gaccatgcag | 240 |
| gaggaaagaa | acgattttaa | atcattaaaa | acacaaaaac | taagtgcgaa | cggaacagag | 300 |
| ttttctcaac | ctttgctatg | gttattctgt | ctagagaccc | tgagccaact | ttcaaattga | 360 |
| cgcatacaag | ggctcacaat | ttggcttttt | tgggtccctc | ccagctttag | gttatgaaga | 420 |
| ttttactcac | aaaaaaaatc | aacaaaaatc | acgaaactag | aaaacttttt | ttttcctctt | 480 |
| gctggccgtg | gtggactaga | tagatggacg | tcggcaactc | ccggcccagc | ctccatactg | 540 |
| cggtcttttt | actcgttcta | tctgatgaga | actcacacta | gcttgtttac | aagatgacga | 600 |
| cagtccaagg | gcagccttgg | gcacctgcca | tgtccctcct | ttccccagct | atccccgctc | 660 |
| tgaccttgat | tttcattctt | atgttttct | cttttccctt | cagagctcac | acagtggtca | 720 |
| ccattgtggc | aagcggcttt | ctgggtctca | gccctctctg | cggttgaggg | cccagaggac | 780 |
| agagagatgg | acatgcgtcc | cctccctccc | ccgccaagt | gctcacacac | aacctcacgc | 840 |
| gcacacacac | acgcagat | ggaggcgcct | cactgggagg | tgccccgcca | gccctgggca | 900 |
| gtgtcaggca | ggactcactc | accgctgagc | agatgagaga | agttttagtc | ttggcgggtg | 960 |
| gaaatgagac | gaagccacag | ttatcacact | ccagactcct | gcccttttat | tttctccagc | 1020 |
| cccttcttcc | ttcagcaaaa | tctaggactc | ccgagtggct | tccaggggc | cgtcagtcct | 1080 |
| cagccgcgcc | tgtgtccggt | gcccgagggg | cgggcggcgg | tgtctgtatg | tatgtgtaca | 1140 |
| tatgcacata | gaccttagag | tgtatagtta | acaaacgccc | atctgctcac | ccatgcccac | 1200 |
| ccagcgccgc | cgccgctggc | tctcggggca | cctggcagga | ggcgggtgtg | tgaatagcat | 1260 |
| atattttac | atgtactata | tctaggtgtg | tgtacaagtg | tgtgtaaaaa | tatatacctt | 1320 |
| gtgtgtaagc | agccctttt | ttttttggtc | tccaccccc | tcccccgcc | ccgcactcct | 1380 |
| aagggcccat | ctgcccagcc | tctgagtttt | ctgttctatt | ttttttttaa | ccccaattat | 1440 |
| ccttctctct | ctcctgcccc | cgcatcccac | tcccagggtg | tcacgagccc | tgagctgcaa | 1500 |
| tggcccgggc | ctgcagggcg | gggtagggga | gggcarggct | sagccccgaa | gccagctcag | 1560 |
| tacctgaggg | gctgctctat | gctgtgtatg | cgcctctctg | gcatccgaga | catcctcttg | 1620 |
| gtggcgcttg | ctngcagggg | acccccccc | cgtcccagg | tgaaccaagg | gtctgctccg | 1680 |
| gggcccattt | ccagcttggc | cgccgtcgtg | gaccttgggc | aagtcacttg | acctctgtgt | 1740 |
| gcctcaactt | cctcctctgt | aaaacgggga | cagtccctgc | ccctccctac | ctcacaggca | 1800 |
| tgttgtgaga | ataaatgagg | taacgtgtaa | aaaaaaaaaa | aat | | 1843 |

<210> SEQ ID NO 76
<211> LENGTH: 1441
<212> TYPE: DNA
<213> ORGANISM: Homo sapiens
<220> FEATURE:
<221> NAME/KEY: SITE
<222> LOCATION: (1056)
<223> OTHER INFORMATION: n equals a,t,g, or c
<220> FEATURE:
<221> NAME/KEY: SITE
<222> LOCATION: (1081)
<223> OTHER INFORMATION: n equals a,t,g, or c

```
<220> FEATURE:
<221> NAME/KEY: SITE
<222> LOCATION: (1109)
<223> OTHER INFORMATION: n equals a,t,g, or c
<220> FEATURE:
<221> NAME/KEY: SITE
<222> LOCATION: (1328)
<223> OTHER INFORMATION: n equals a,t,g, or c
<220> FEATURE:
<221> NAME/KEY: SITE
<222> LOCATION: (1362)
<223> OTHER INFORMATION: n equals a,t,g, or c
<220> FEATURE:
<221> NAME/KEY: SITE
<222> LOCATION: (1419)
<223> OTHER INFORMATION: n equals a,t,g, or c

<400> SEQUENCE: 76
```

| | | | | | |
|---|---|---|---|---|---|
| tcgacccacg | cgtccggctc | cccgagccct | gccaaccatg | gtgaacttgg | gtctgtcccg | 60 |
| ggtggacgac | gccgtggctg | ccaagcaccc | gggactcggg | gagtatgccg | catgccagtc | 120 |
| acacgccttc | atgaagggcg | ttttcacctt | cgtcacaggc | accggcatgg | cctttggctt | 180 |
| gcagatgttc | attcagagga | agtttccata | ccctttgcag | tggagcctcc | tagtggccgt | 240 |
| ggttgcaggc | tctgtggtca | gctacggggt | gacgagagtg | gagtcggaga | aatgcaacaa | 300 |
| cctctggctc | ttcctggaga | ccgggcagct | ccccaaagac | aggagcacag | atcagagaag | 360 |
| ctaggagagc | tccagcaggg | gcacagagga | ttgggggcag | gaggagtctg | gaacacagcc | 420 |
| ttcatgcccc | ctgaccccag | gccgaccctc | cccacaccct | agggtacccc | agtcgtatcc | 480 |
| tctgtccgca | tgtktggcca | ggcctgacaa | acacctgcag | atggctgctg | ccccaacctg | 540 |
| ggacctgccc | agraggttgg | agcagaaagg | gctctccctg | gggtggtgtt | tctcctctag | 600 |
| ggtattggga | tgcatgttct | gcactgccag | cagagagggt | gtgtctgggg | gccaccacct | 660 |
| atgggacacg | gggtcgaagg | ggcctgtaca | ctctgtcatt | tcctttctag | cccctgcatc | 720 |
| tccaacaagt | ccaaggtgac | agctggtgct | aggggcgtgg | ggttaataaa | tggcttatcc | 780 |
| ttctctccac | ccaagtttcc | acctgaccag | gtgaaaaaca | aatcagaagg | gtaagatgat | 840 |
| gacaggtcac | atgaaaacctt | tattaccccta | cagttgatat | atgaggatca | catgcaagtt | 900 |
| acatactgag | gatgtacagg | gaagttccca | gcgctgaacc | ccagaattag | acgttcgcat | 960 |
| cagccccgta | ggccacgtgg | acaccaccac | agcctctctg | tatggggtc | tgcctctgta | 1020 |
| gcacttggca | tgtaggggca | gagcaaaagg | ggccangctg | gccagagcct | ggctgctggg | 1080 |
| nagargaggg | acttgtgggs | cacgccacnt | gcctatcatt | ccccaytcat | ctattagcca | 1140 |
| aagtcactcc | ccagaggcag | agctagcccg | ttgtagccgt | gtctgtgtgg | agggaaagct | 1200 |
| tctgagtggg | caagcctaca | cacagccccg | agccccaaga | ggaggaagag | gtggagacca | 1260 |
| gacggaacct | ccacaagtcc | atcatggtta | cagctggctt | ccccgcagca | ccgaagaccc | 1320 |
| acagcatngg | ccctgctgcc | cccgacccag | ctcagctgcc | angcctcacc | ttgccaggaa | 1380 |
| ttgaaagaaa | gttattgagt | actaattggc | ctcagagtna | caggaagctc | aagttaaagt | 1440 |
| g | | | | | | 1441 |

```
<210> SEQ ID NO 77
<211> LENGTH: 910
<212> TYPE: DNA
<213> ORGANISM: Homo sapiens

<400> SEQUENCE: 77
```

| | | | | | |
|---|---|---|---|---|---|
| ggcagagctg | gccttcgact | cgctatgtcc | actaacaata | tgtcggaccc | acggaggccg | 60 |

| | |
|---|---:|
| aacaaagtgc tgaggtgagg accccagcgt cgtgggcacg ggttcgggtt gtgggtgtgg | 120 |
| atcggggccc tgggaagcgc ctgtctatcc cgggggcagg acctgagcgc ccctgaccct | 180 |
| cgagcctgtc gcaggtacaa gccccgccg agcgaatgta accggcctt ggacgacccg | 240 |
| acgccggact acatgaacct gctgggcatg atcttcagca tgtgcggcct catgcttaag | 300 |
| ctgaagtggt gtgcttgggt cgctgtctac tgctccttca tcagctttgc caactctcgg | 360 |
| agctcggagg cacgaagca aatgatgagt agcttcatgt gagacttgcc ctacagaaca | 420 |
| agtgactctt gagtaagggg tgggggggacc ccagcctggc catcctagac tgacacctct | 480 |
| ctcctgtctt catgctgtcc atctctgccg tggtgatgtc ctatctgcag aatcctcagc | 540 |
| ccatgacgcc cccatggtga taccagccta gaagggtcac attttggacc ctgtctatcc | 600 |
| actaggcctg ggctttggct gctaaacctg ctgccttcag ctgccatcct ggacttccct | 660 |
| gaatgaggcc gtctcggtgc ccccagctgg atagagggaa cctggccctt tcctagggaa | 720 |
| caccctaggc ttacccctcc tgcctccctt cccctgcctg ctgctggggg atgctgtc | 780 |
| catgtttcta ggggtattca tttgctttct cgttgaaacc tgttgttaat aaagtttttc | 840 |
| actctgaaaa aaaaaaaaaa aaaaaaaaac tygrgggggg gcccggaacc caattcsccg | 900 |
| gatagtgagt | 910 |

```
<210> SEQ ID NO 78
<211> LENGTH: 2776
<212> TYPE: DNA
<213> ORGANISM: Homo sapiens

<400> SEQUENCE: 78
```

| | |
|---|---:|
| tcgacccacg cgtccgggcg ggcagtgatg gcggctggtg atgggacgt gaagctaggc | 60 |
| accctgggga gtggcagcga gagcagcaac gacggcggca gcgagagtcc aggcgacgcg | 120 |
| ggagcggcag cgraaggggg aggctgggcg gcggcggcgt tggcgcttct gacgggggggc | 180 |
| ggggaaatgc tgctgaacgt ggcgctggtg gctctggtgc tgctggggggc ctaccggctg | 240 |
| tgggtgcgct gggggcggcg gggtctgggg gccggggccg gggcgggcga ggagagcccc | 300 |
| gccacctctc tgcctcgcat gaagaagcgg gacttcagct tggagcagct gcgccagtac | 360 |
| gacggctccc gcaacccgcg catcctgctc gcggtcaatg ggaaagtctt cgacgtgacc | 420 |
| aaaggcagca agttctacgg cccggcgggt ccatatggaa tatttgctgg tagggatgcc | 480 |
| tccagaggac tggccacatt tgcctagat aaagatgcac ttagagatga atatgatgat | 540 |
| ctctcagatt tgaatgcagt acaaatggag agtgttcgag aatgggaaat gcagtttaaa | 600 |
| gaaaaatatg attatgtagg cagactccta aaaccaggag aagaaccatc agaatataca | 660 |
| gatgaagaag ataccaagga tcacaataaa caggattgaa ctttgtaaac aaccaaagtc | 720 |
| aggggccttc agaactgcaa ttcttactcc ctttcacaga ctgtccggag tctttgggtt | 780 |
| tgattcacct gctgcgaaaa acattcaaca aattgtgtac aagataaatt aatctcacta | 840 |
| tgaagatttg aataactaga cattatttat gctgccaaac tcatttgttg cagttgtttg | 900 |
| taatgtctag tggggcttca tcatcctgaa agaaggaga cagggattt tttaaagagc | 960 |
| aagaaagtca caatattact tctttccttc cтттттттcст tctttccttt cttctttctc | 1020 |
| tttctttctt tttaaaatat attgaagaca accagatatg таттттgcтac tcaagtgtac | 1080 |
| agatctcctc aagaaacatc aagggactcc tgtgtcacat actgtgtttt tattttaaca | 1140 |
| tgggtgaggg aggcgacctg атcagggggag gtggggggтac acatcaattt gagttgttca | 1200 |
| ggctactgaa acattaaaat gtgaattccc aaacтттттcт тттттggcтттт gtcagggaaa | 1260 |

-continued

```
agaaaaatat ctttataaag aaatctttgg aaattaggag aaggaatttc aggtgggttt       1320
aagtcagagc tagttcccca acagaaagat catttgaaac cagttttat cccttctctt       1380 tccttccctt tccctaaatc aaatcaatat taattgtgcc ttatttcact taacatagac      1440
ttgaattatt tttagggaaa gcccctataa tgaattcaga atcactaca agcagcatta      1500 agactgaagt tggaatattc tgttgaccat aaaaccttga tatcattctg tgtatataga      1560
atgtaaaagg aatattacag tgttaactgc catatatgta atatacacaa actcaattag      1620
cattgtaatg gccaaatgca ttcccccatg cttttctgtt tcaaaaaaa ttgaaaaaca       1680 aatcaactct tatccccaac agctgcctaa ttttaggagt ctgaccctcc acatctcact      1740
ggtgtgggtg catggggctg tggagtgggt gtcagtatgg atgtgtctga atgtgtgagg      1800
ccttggaagg gactctttct gcagatactg taaatacaag taccatttta ataaagcatg      1860
tacaataaac caaataagc ttgagttgga ctttatatac agaactgtaa gccagtgcat       1920
tatgatacag ttgtaagatt gtgcatttga ttcaagataa ggaaaaatct tggaaatgaa      1980
aagcaggcac kggttaacca agttgtacac attgtaccac attcagcata actttaggaa      2040
gaaattccac tttgtgaaca ttctccagaa atccaagatt attcaggtaa gaattggtat      2100
attaaatgta catcttttta ctttctattt tgatgccaac tgattatact agacaattag      2160
cactccaggt ggttattgaa cacaaaacag taaaagaata ttgcactgat agatactaaa      2220
ttattatttt attaggttga aaaagcccct actaaaagcc cctcatatat caattacttt      2280
atttcattat gactacttag gttccgggct ggggacaagt tcacttaaaa aggcaatgtt      2340
atttaacagg tcaccagtta agacttctgc tttgtagata catgcagaag ccatcaaaca      2400
agggggrgct tttaactgca acaataagct aaagtatgta aaatactaca ttctattcag      2460
tcttggagtg ttttgtagaa agttatcttc agccaaatct ttgctgaaga ctggttgtgg      2520
agtgttggta aatgctttgt gtttttatgt aaaatatttt ctaaacaaaa aatgttaaaa      2580
gtacatgtcc tctgtagtaa actgatatct atatatatga atcattcaag cctaaagtct      2640
agtaataaac tgtacttgtg aatagagaaa ccctaaatat tcatgcagwa aaaattatgc      2700
ggtctgttaa gaaaatgag taatttgtgt tttggacttg aaataaacag tgttctgtag       2760
ataattcctc aacttc                                                     2776
```

<210> SEQ ID NO 79
<211> LENGTH: 1487
<212> TYPE: DNA
<213> ORGANISM: Homo sapiens
<220> FEATURE:
<221> NAME/KEY: SITE
<222> LOCATION: (78)
<223> OTHER INFORMATION: n equals a,t,g, or c
<220> FEATURE:
<221> NAME/KEY: SITE
<222> LOCATION: (948)
<223> OTHER INFORMATION: n equals a,t,g, or c

<400> SEQUENCE: 79

```
ccgctgctga taactatggc atcccccggg cctgcaggaa ttcggcacgg agctacggcg        60
ccgcctggct cctgctgnca cctgcaggct cgtcgcgggt ggagcccacc caagacatca      120
gcatcagcga ccagctgggg ggccaggacg tgccgtgtt ccggaacctg tccctgctgg       180
tggtgggtgt cggcgccgtg ttctcactgc tattccacct gggcacccgg gagaggcgcc      240
ggccgcatgc ggasgagcca ggcgagcaca ccccctgtt ggccctgcc acggcccagc       300
```

-continued

| | |
|---|---|
| ccctgctgct ctggaagcac tggctccggg agcsggcttt ctaccaggtg ggcatactgt | 360 |
| acatgaccac caggctcatc gtgaacctgt cccagaccta catggccatg tacctcacct | 420 |
| actcgctcca cctgcccaag aagttcatcg cgaccattcc cctggtgatg tacctcagcg | 480 |
| gcttcttgtc ctccttcctc atgaagccca tcaacaagtg cattgggagg aacatgacct | 540 |
| acttctcagg cctcctggtg atcctggcct ttgccgcctg ggtggcgctg gcggagggac | 600 |
| tgggtgtggc cgtgtacgca gcggctgtgc tgctgggtgc tggctgtgcc accatcctcg | 660 |
| tcacctcgct ggccatgacg gccgacctca tcggtcccca cacgaacagc ggagckttcg | 720 |
| tgtacggctc catgagcttc ttggataagg tggccaatgg gctggcagtc atggccatcc | 780 |
| agagcctgca cccttgcccc tcagagctct gctgcagggc ctgcgtgagc ttttaccact | 840 |
| gggcgatggt ggctgtgacg ggcggcgtgg gcgtggccgc tgccctgtgt ctctgtagcc | 900 |
| tcctgctgtg gccgacccgc ctgcgacgct gatgagacct gcacgcantg gctcacagca | 960 |
| gcacgatttg tgacagcccg aggcggagaa caccgaacac ccagtgaagg tgaggggatc | 1020 |
| agcacggcgc ggccacccac gcacccacgc gctggaatga gactcagcca caggaggtg | 1080 |
| cgaagctctg acccaggcca cagtgcggat gcaccttgag gatgtcacgc tcagtgagag | 1140 |
| acaccagaca cagaagggta cgctgtgatc ccacttctat gaaatgtcca ggacagacca | 1200 |
| atccacagaa tcagggagag gattcgtggg tgccgggact ggggaggggg acctgggggt | 1260 |
| gactaggtga cataatgggg acagggctgc cttctggtg atgagaatgt tctggaatca | 1320 |
| gatgggatgg ctgcacggcg tggtgaaggt actgaacgcc acctcactgt aagacggtag | 1380 |
| attttgtatt ttaccacaat aaacaaaaca aaacaaaacc aaaaaaaaaa aaaaaaaaa | 1440 |
| aaaaaaaagg aattcgatat caagcttatc gataccgtcg acctcga | 1487 |

<210> SEQ ID NO 80
<211> LENGTH: 1563
<212> TYPE: DNA
<213> ORGANISM: Homo sapiens
<220> FEATURE:
<221> NAME/KEY: SITE
<222> LOCATION: (14)
<223> OTHER INFORMATION: n equals a,t,g, or c

<400> SEQUENCE: 80

| | |
|---|---|
| aattcggcac gagncagaaa cctgcggaaa atggtagcga tggcggctgg gccgagtggg | 60 |
| tgtctggtgc cggcgtttgg gctacggttg ttgttggcga ctgtgcttca agcggtgtct | 120 |
| gcttttgggg cagagttttc atcggaggca tgcagagagt taggcttttc tagcaacttg | 180 |
| ctttgcagct cttgtgatct tctcggacag ttcaacctgc ttcagctgga tcctgattgc | 240 |
| agaggatgct gtcaggagga agcacaattt gaaaccaaaa agctgtatgc aggagctatt | 300 |
| cttgaagttt gtggatgaaa attgggaagg ttccctcaag tccaagcttt tgttaggagt | 360 |
| gataaaccca aactgttcag aggactgcaa atcaagtatg tccgtggttc agaccctgta | 420 |
| ttaaagcttt tggacgacaa tgggaacatt gctgaagaac tgagcattct caaatggaac | 480 |
| acagacagtg tagaagaatt cctgagtgaa aagttggaac gcatataaat cttgcttaaa | 540 |
| ttttgtccta tccttttgtt accttatcaa atgaaatatt acagcaccta gaaaataatt | 600 |
| tagttttgct tgcttccatt gatcagtctt ttacttgagg cattaaatat ctaattaaat | 660 |
| cgtgaaatgg cagtatagtc catgatatct aaggagttgg caagcttaac aaaacccatt | 720 |
| ttttataaat gtccatcctc ctgcatttgt tgataccact aacaaaatgc tttgtaacag | 780 |
| acttgcggtt aattatgcaa atgatagttt gtgataattg gtccagtttt acgaacaaca | 840 |

```
gatttctaaa ttagagaggt taacaagaca gatgattact atgcctcatg tgctgtgtgc    900
tctttgaaag gaatgacagc agactacaaa gcaaataaga tatactgagc ctcaacagat    960
tgcctgctcc tcagagtctc tcctattttt gtattaccca gctttctttt taatacaaat   1020
gttatttata gtttacaatg aatgcactgc ataaaaactt tgtagcttca ttattgtaaa   1080
acatattcaa gatcctacag taagagtgaa acattcacaa agatttgcgt taatgaagac   1140
tacacagaaa acctttctag ggatttgtgt ggatcagata catacttggc aaattttttga   1200 gttttacatt cttacagaaa agtccattta aaagtgatca tttgtaagac caaaatataa   1260
ataaaaagtt tcaaaaatct atctgaattt ggaattcttc tggtttgttc tttcatgttt   1320
aaaaatgatg ttttttcaatg catttttttc atgtaagccc ttttttttagc caaaatgtaa   1380 aaatggctgt aatatttaaa acttataaca tcttattgtt ggtaatagtg ctttatattt   1440
gtctgatttt attttttcaaa gttttttcat ttatgaacac attttcattg gtatattatt   1500
taaggaatat ctcttgatat agaatttta tattaaaaat gattttctt tgcttaaaaa    1560 aaa                                                                  1563

<210> SEQ ID NO 81
<211> LENGTH: 1020
<212> TYPE: DNA
<213> ORGANISM: Homo sapiens
<220> FEATURE:
<221> NAME/KEY: SITE
<222> LOCATION: (20)
<223> OTHER INFORMATION: n equals a,t,g, or c

<400> SEQUENCE: 81
tgcacgctgg ccatgtgggn gttgggccac tgcgaccccc ggcgctgcac gggccgcaag     60
ctggcccgcc tggggctggt gcgctgcctg cgcctgggcc acagattcgg cggtctggtg    120
ctgagccccg tgggcaagca gtacgcgtcc cccgcagaca gacagctggt ggcgcagtct    180
ggggtcgccg tcatcgactg ctcctgggcc aggctggacg agacaccgtt tgggaagatg    240
cgagggagcc acttgcgcct gttgccctac ctggtgccg ccaacccccgt gaactatggc    300 cggccctaca gacttttcctg cgtggaagcg tttgctgcca ccttctgcat cgtaggcttt    360
ccagaccttg ctgtcatttt gctgcggaag tttaaatggg gcaagggctt cttggacctg    420
aaccgccagc tcctggacaa gtacgcggcc tgcggcagcc cggaggaggt gctgcaggcg    480
gagcaggagt tcttggccaa tgccaaggag agccccagg aggaggagat cgatcccttc     540
gatgtggatt cagggagaga gtttggaaac cccaacaggc ctgtggccag cacccggctg    600
ccctcggaca ctgatgacag tgatgcgtct gaggacccag ggcctkgcgc cgagcgcgga    660
ggagccagca gcagctgctg tgaagaggag cagacgcagg acgggggggc tgaggccagg    720 gcccccggctg aggtttggaa aggaatcaag aaacggcaga gagactgagg gttgcagaca    780 catatattt tgaggctggg tgacgagaaa atctagagac atgagggaca taaatgggcc    840
tggcagcctc ggctctttgc ggctgctggc aggactgagc tgtccgggtt ctccccacac    900
ttccagcaca gctgtgctct gtgtcctgcc tcggcgctct cgcaaatgaa gctgcaggcc    960
aagaaaaaaa aaaaaaaaaa aaaaaaaaa aaaaaaaaa aaaaaaaag ggggggggc   1020

<210> SEQ ID NO 82
<211> LENGTH: 770
<212> TYPE: DNA
<213> ORGANISM: Homo sapiens
<220> FEATURE:
```

```
<221> NAME/KEY: SITE
<222> LOCATION: (757)
<223> OTHER INFORMATION: n equals a,t,g, or c

<400> SEQUENCE: 82
tcgacccacg cgtccgggcc gccgtagcgc gtcttgggtc tcccggctgc cgctgctgcc      60
gccgccgcct cgggtcgtgg agccaggagc gacgtcaccg ccatggcagg catcaaagct     120
ttgattagtt tgtcctttgg aggagcaatc ggactgatgt ttttratgct tggatgtgcc     180
cttccaatat acaacaaata ctggcccctc tttgttctat ttttttacat cctttcacct     240
attccatact gcatagcaag aagattagtg gatgatacag atgctatgag taacgcttgt     300
aaggaacttg ccatctttct tacaacgggc attgtcgtgt cagcttttgg actccctatt     360
gtatttgcca gagcacatct gattgagtgg ggagcttgtg cacttgttct cacaggaaac     420
acagtcatct ttgcaactat actaggcttt ttcttggtct tggaagcaa tgacgacttc      480 agctggcagc agtggtgaaa agaaattact gaactattgt caaatggact tcctgtcatt     540
tgttggccat tcacgcacac aggagatggg gcagttaatg ctgaatggta tagcaagcct     600
cttgggggta ttttaggtgc tcccttctca cttttattgt aagcatacta ttttcacaga     660
gacttgctga aggattaaaa ggattttctc ttttggaaaa aaaaaaaaa aaaaacycga     720 ggggggccc gtwcccattc scccyatatg aattccnttt ttacaatccc                 770

<210> SEQ ID NO 83
<211> LENGTH: 481
<212> TYPE: DNA
<213> ORGANISM: Homo sapiens
<220> FEATURE:
<221> NAME/KEY: SITE
<222> LOCATION: (322)
<223> OTHER INFORMATION: n equals a,t,g, or c
<220> FEATURE:
<221> NAME/KEY: SITE
<222> LOCATION: (365)
<223> OTHER INFORMATION: n equals a,t,g, or c
<220> FEATURE:
<221> NAME/KEY: SITE
<222> LOCATION: (379)
<223> OTHER INFORMATION: n equals a,t,g, or c
<220> FEATURE:
<221> NAME/KEY: SITE
<222> LOCATION: (390)
<223> OTHER INFORMATION: n equals a,t,g, or c

<400> SEQUENCE: 83
gaattcggca cgagcatagt gttaaccact agaattcact gcccttccta tccaaaaatg      60
acactactga tcattttct tccttttsct tttacaacat tmacaaattc aggtggctct     120
ttcccagtac ggtaggctga ttcgtatgga tgcaccacgg ttggtgactc cccccacccc     180
acagagtttc tggcgttcat tcggttgaac ccaaggccag caagggctga ctgggaacaa     240
accgaacact aggccgtgaa ccaatcgtct ctccgtgccc gggagcgamc ccgggggcct     300
ttcactctcc caaggactcc angggggggc cgggtaccca attccgcccc tatagtgaat     360
ccgtnattac aattccacnt gggccgtccn tttttacaaa cgttccgttg aactgggaaa     420
aaccccttgg cggtttaccc caactttaat ccgcctttgc aagcacatcc ccccccttt     480 c                                                                     481

<210> SEQ ID NO 84
<211> LENGTH: 644
<212> TYPE: DNA
<213> ORGANISM: Homo sapiens
```

<400> SEQUENCE: 84

| | | | | | |
|---|---|---|---|---|---|
| gctgggatag | agcatgaaag | gagaactgct | cccttttctg | tttctcacag | tttggttatg | 60 |
| gctttataaa | cttktatttg | gtgaaagccc | cagatacccca | aatgtcattg | gcaaaactta | 120 |
| ttttttttc | tggacagatc | agatttctag | agagagcaga | tttctagaga | gattagcatt | 180 |
| catagtaagt | gaaaattgtc | taatttttt | aatccatgct | attactgggc | agtaggtcta | 240 |
| atttttttg | acaaaaaata | gatctatttt | ccttatatat | tgatttagaa | tcttaagtta | 300 |
| gaattttata | gaagaaatgt | ctgagcagtt | ctatgtatgg | aggagcaatt | cagcttttca | 360 |
| gcagcaactt | tatcttttgc | cactagaggg | agatctgtgg | ttgctttctc | ctttggagaa | 420 |
| tagctgcttt | gcttttattt | ttaatttcta | aggttggaat | agaacttatt | ctcaaaattc | 480 |
| ctttagtgtt | attaaatatt | tcatttatt | agtcaaaggt | aagttaatta | agcttgttta | 540 |
| atgatgccaa | tcttatgctt | ttctgtaatc | ttcaattttt | aataaatgtg | agttagatac | 600 |
| taagtgaaaa | aaaaaaaaa | aaaaaaaaa | aaaaaaaaa | aaaa | | 644 |

<210> SEQ ID NO 85
<211> LENGTH: 1351
<212> TYPE: DNA
<213> ORGANISM: Homo sapiens
<220> FEATURE:
<221> NAME/KEY: SITE
<222> LOCATION: (133)
<223> OTHER INFORMATION: n equals a,t,g, or c
<220> FEATURE:
<221> NAME/KEY: SITE
<222> LOCATION: (1305)
<223> OTHER INFORMATION: n equals a,t,g, or c
<220> FEATURE:
<221> NAME/KEY: SITE
<222> LOCATION: (1344)
<223> OTHER INFORMATION: n equals a,t,g, or c

<400> SEQUENCE: 85

| | | | | | |
|---|---|---|---|---|---|
| ggcacgagtg | cgcasgcgtg | gggctctctc | cttgtcagtc | ggcgccgcgt | gcgggctggt | 60 |
| ggctctgtgg | cagcggcggc | ggcaggactc | cggcactatg | agcggcttca | gcaccgagga | 120 |
| gcgcgccgcg | ccnttctccc | tggagtaccg | agtcttcctc | aaaaatgaga | aggacaata | 180 |
| tatatctcca | tttcatgata | ttccaattta | tgcagataag | gatgtgtttc | acatggtagt | 240 |
| tgaagtacca | cgctggtcta | atgcaaaaat | ggagattgct | acaaaggacc | ctttaaaccc | 300 |
| tattaaacaa | gatgtgaaaa | aaggaaaact | tcgctatgtt | gcgaatttgt | tcccgtataa | 360 |
| aggatatatc | tggaactatg | gtgccatccc | tcagacttgg | gaagacccag | ggcacaatga | 420 |
| taaacatact | ggctgttgtg | gtgacaatga | cccaattgat | gtgtgtgaaa | ttggaagcaa | 480 |
| ggtatgtgca | agaggtgaaa | taattggcgt | gaaagttcta | ggcatattgg | ctatgattga | 540 |
| cgaaggggaa | accgactgga | aagtcattgc | cattaatgtg | gatgatcctg | atgcagccaa | 600 |
| ttataatgat | atcaatgatg | tcaaacggct | gaaacctggc | tacttagaag | ctactgtgga | 660 |
| ctggtttaga | aggtataagg | ttcctgatgg | aaaaccagaa | aatgagtttg | cgtttaatgc | 720 |
| agaatttaaa | gataaggact | tgccattga | tattattaaa | agcactcatg | accattggaa | 780 |
| agcattagtg | actaagaaaa | cgaatggaaa | aggaatcagt | tgcatgaata | caactttgtc | 840 |
| tgagagcccc | ttcaagtgtg | atcctgatgc | tgccagagcc | attgtggatg | ctttaccacc | 900 |
| accctgtgaa | tctgcctgca | cagtaccaac | agacgtggat | aagtggttcc | atcaccagaa | 960 |
| aaactaatga | gatttctctg | gaatacaagc | tgatattgct | acatcgtgtt | catctggatg | 1020 |

-continued

| | |
|---|---|
| tattagaagt aaaagtagta gcttttcaaa gctttaaatt tgtagaactc atctaactaa | 1080 |
| agtaaattct gctgtgacta atccaatata ctcagaatgt tatccatcta aagcattttt | 1140 |
| catatctcaa ctaagataac ttttagcaca tgcttaaata tcaaagcagt tgtcatttgg | 1200 |
| aagtcacttg tgaatagatg tgcaagggga gcacatattg gatgtatatg ttaccatatg | 1260 |
| ttaggaaata aaattatttt gctgaaaaaa aaaaaaaaa aaccncgggg ggggccccgg | 1320 |
| tccccatttg gcccttTggg gggnggtttt a | 1351 |

<210> SEQ ID NO 86
<211> LENGTH: 2527
<212> TYPE: DNA
<213> ORGANISM: Homo sapiens

<400> SEQUENCE: 86

| | |
|---|---|
| ctcttgctac cttcccggcg cagagaaccc cggctgctca gcgcgctccg gggtcatgga | 60 |
| gatccccggg agcctgtgca agaaagtcaa gctgagcaat aacgcgcaga actgggaat | 120 |
| gcagagagca accaatgtca cctaccaagc ccatcatgtc agcaggaaca agagaggtca | 180 |
| ggtggtgggg accagaggtg gctttcgtgg ttgcacagtt tggctaacag gcttgtctgg | 240 |
| agcgggaaag actactgtga gcatggcctt ggaggagtac ctggtttgtc atggtattcc | 300 |
| atgctacact ctggatggtg acaatattcg tcaaggtctc aataaaaatc ttggctttag | 360 |
| tcctgaagac agagaagaga atgttcgacg catcgcagaa gttgctaaac tgtttgcaga | 420 |
| tgctggctta gtgtgcatca caagtttcat atcaccttac actcaggatc gcaacaatgc | 480 |
| aaggcaaatt catgaaggtg caagtttacc gttttttgaa gtatttgttg atgctcctct | 540 |
| gcatgtttgt gaacagaggg atgtcaaagg actctacaaa aaagcccggg caggagaaat | 600 |
| taaaggtttc actgggatcg attctgaata tgaaaagcca gaggcccctg agttggtgct | 660 |
| gaaaacagac tcctgtgatg taatgactg tgtccagcaa gttgtggaac ttctacagga | 720 |
| acgggatatt gtacctgtgg atgcatctta tgaagtaaaa gaactatatg tgccagaaaa | 780 |
| taaacttcat ttggcaaaaa cagatgcgga acattacca gcactgaaaa ttaataaagt | 840 |
| ggatatgcag tgggtgcagg ttttggcaga aggttgggca acccccattga atggctttat | 900 |
| gagagagagg gagtacttgc agtgccttca ttttgattgt cttctggatg aggtgtcat | 960 |
| taacttgtca gtacctatag ttctgactgc gactcatgaa gataaagaga ggctggacgg | 1020 |
| ctgtacagca tttgctctga tgtatgaggg ccgccgtgtg gccattcttc gcaatccaga | 1080 |
| gttttttgag cacaggaaag aggagcgctg tgccagacag tggggaacga catgcaagaa | 1140 |
| ccaccccctat attaagatgg tgatggaaca aggagattgg ctgattggag gagatcttca | 1200 |
| agtcttggat cgagtttatt ggaatgatgg tcttgatcag tatcgtctta ctcctactga | 1260 |
| gctaaagcag aaatttaaag atatgaatgc tgatgctgtc tttgcatttc aactacgcaa | 1320 |
| cccagtgcac aatggacatg ccctgttaat gcaggatacc cataagcaac ttctagagag | 1380 |
| gggctaccgg cgccctgtcc tcctcctcca ccctctgggt ggctggacaa aggatgacga | 1440 |
| tgttcctttg atgtggcgta tgaagcagca tgctgcagtg ttggaggaag gagttctgaa | 1500 |
| tcctgagacg acagtggtgg ccatcttccc atctcccatg atgtatgctg gaccaactga | 1560 |
| ggtccagtgg cattgcagag cacgatggt tgcaggagcc aacttttaca ttgttggacg | 1620 |
| agaccctgct ggcatgcctc atccagaaac agggaaggat ctttatgagc caagtcatgg | 1680 |
| tgccaaagtg ctgacgatgg cccctggttt aatcactttg gaaatagttc cctttcgagt | 1740 |
| tgcagcttac aacaagaaaa agaagcgtat ggactactat gactctgaac accatgaaga | 1800 |

-continued

```
ctttgaattt atttcaggaa cacgaatgcg caaacttgct cgagaaggcc agaaaccacc    1860
tgaaggtttc atggctccca aggcttggac cgtgctgaca gaatactaca aatccttgga    1920
gaaagcttag gctgttaacc cagtcactcc acctttgaca cattactagt aacaagaggg    1980
gaccacatag tctctgttgg catttctttg tggtgtctgt ctggacatgc ttcctaaaaa    2040
cagaccattt tccttaactt gcatcagttt tggtctgcct tatgagttct gttttgaaca    2100
agtgtaacac actgatggtt ttaatgtatc ttttccactt attatagtta tattcctaca    2160
atacaatttt aaaattgtct ttttatatta tatttatgct tctgtgtcat gattttttca    2220
agctgttata ttagttgtaa ccagtagtat tcacattaaa tcttgctttt tttcccctta    2280
aaaaaagaaa aaaattacca aacaataaac ttggctagac cttgttttga ggattttaca    2340
agacctttgt agcgattaga ttttttttct acattgaaaa tagaaactgc ttcctttctt    2400
ctttccagtc agctattggt ctttccagct gttataatct aaagtattct tatgatctgt    2460
gtaagctctg aatgaacttc tttactcaat aaaattaatt ttttggcttc ttaaaaaaaa    2520
aaaaaaa                                                              2527
```

<210> SEQ ID NO 87
<211> LENGTH: 2566
<212> TYPE: DNA
<213> ORGANISM: Homo sapiens
<220> FEATURE:
<221> NAME/KEY: SITE
<222> LOCATION: (22)
<223> OTHER INFORMATION: n equals a,t,g, or c

<400> SEQUENCE: 87

```
cccaagaatt cggcacgagc gnggcawaak tgggatttct gaaacctgta ggccccaagc     60
ccatcaactt gcccaaagaa gattccaaac ctacatttcc ctggcctsct ggaaacaagc    120
catctcttca cagtgtaaac caagaccatg acttaaagcc actaggccga aatctgggcc    180
tactcctcca acctcagaaa atgaacagaa gcaagcktttt cccaaattga ctggggttaa    240
agggaaattt atgtcagcat cacaagatct tgaacccaag cccctcttcc ccaaacccgc    300
ctttggccag aagccgcccc taagtaccga gaactcccat gaagacgaaa gcccatgaa     360 gaatgtgtct tcatcaaaag ggtccccagc tcccctggga gtcaggtcca aaagcggccc    420
tttaaaacca gcaagggaag actcagaaaa taaagaccat gcaggggaga tttcaagttt    480
gccctttcct ggagtggttt tgaaacctgc tgcgagcagg ggaggcccag gtctctccaa    540
aaatggtgaa gaaaaaagg aagataggaa gatagatgct gctaagaaca cttccagag     600 caaaataaat caggaagagt tggcctcagg gactcctcct gccaggttcc ctaaggcccc    660
ttctaagctg acagtggggg ggccatgggg ccaaagtcag gaaaaggaaa agggagacaa    720
gaattcagcc accccgaaac agaagccatt gcctcccttg tttaccttgg gtccacctcc    780
accaaaaccc aacagaccac caaatgttga cctgacgaaa ttccacaaaa cctcttctgg    840
aaacagtact agcaaaggcc agacgtctta ctcaacaact tccctgccac cacctccacc    900
atcccatccg gccagccaac caccattgcc agcatctcac ccatcacaac caccagtccc    960
aagcctacct cccagaaaca ttaaacctcc gtttgaccta aaaagccctg tcaatgaaga   1020
caatcaagat ggtgtcacgc actctgatgg tgctggaaat ctagatgagg aacaagacag   1080
tgaaggagaa acatatgaag acatagaagc atccaaagaa agagagaaga aagggaaaa    1140 ggaagaaaag aagaggttag agctggagaa aaaggaacag aaagagaaag aaaagaaaga   1200
```

```
acaagaaata aagaagaaat ttaaactaac aggccctatt caagtcatcc atcttgcaaa    1260
agcttgttgt gatgtcaaag gaggaaagaa tgaactgagc ttcaagcaag gagagcaaat    1320
tgaaatcatc cgcatcacag acaacccaga aggaaaatgg ttgggcagaa cagcaagggg    1380
ttcatatggc tatattaaaa caactgctgt agagattgac tatgattctt tgaaactgaa    1440
aaaagactct cttggtgccc cttcaagacc tattgaagat gaccaagaag tatatgatga    1500
tgttgcagag caggatgata ttagcagcca cagtcagagt ggaagtggag ggatattccc    1560
tccaccacca gatgatgaca tttatgatgg gattgaagag aagatgctg atgatggctc     1620 cacactacag gttcaagaga agagtaatac gtggtcctgg gggattttga agatgttaaa    1680
gggaaaagat gacagaaaga aaagtatacg agagaaacct aaagtctctg actcagacaa    1740
taatgaaggt tcatctttcc ctgctcctcc taaacaattg gacatgggag atgaagttta    1800
cgatgatgtg gatacctctg atttccctgt ttcatcagca gagatgagtc aaggaactaa    1860
tgttggaaaa gctaagacag aagaaaagga cctaagaag ctaaaaaagc agraaaaara     1920
araaaaagac ttcaggaaaa aatttaaata tgatggtgaa attagagtcc tatattcaac    1980
taaagttaca acttccataa cttctaaaaa gtggggaacc agagatctac aggtaaaacc    2040
tggtgaatct ctagaagtta tacaaaccac agatgacaca aaagttctct gcagaaatga    2100
agaagggaaa tatggttatg tccttcggag ttacctagcg gacaatgatg gagagatcta    2160
tgatgatatt gctgatggct gcatctatga caatgactag cactcaactt tggtcattct    2220
gctgtgttca ttaggtgcca atgtgaagtc tggattttaa ttggcatgtt attgggtatc    2280
aagaaaatta atgcacaaaa ccacttatta tcatttgtta tgaaatccca attatcttta    2340
caaagtgttt aaagtttgaa catagaaaat aatctctctg cttaattgtt atctcagaag    2400
actacattag tgagatgtaa gaattattaa atattccatt tccgctttgg ctacaattat    2460
gaagaagttg aaggtacttc ttttagacca ccagtaaata atcctccttc aaaaaataaa    2520
aataaaaaaa aaaaaaaaa actcgagggg gggcccggta cccaat                   2566

<210> SEQ ID NO 88
<211> LENGTH: 540
<212> TYPE: DNA
<213> ORGANISM: Homo sapiens

<400> SEQUENCE: 88
gaattcggca cgaggctttc tgtgtcctct gtggctgctt tagtgtgcca ccagggcag      60 acttgggtgg gttgcagcag agatggcatg gccctcaagg tccaagatgt ttactctctt    120
gccggtcctc tgttatctct ggtctttgtg gttgccacag ttttcttgga tccaggagtt    180
aaaggcagtc ctgagggatg atggcctcat ctccgcagtt gcytggaatg ctgaatttca    240
gacgtgctaa aggagggttg cagacattgt gtggwatgca ttcagacccc agatgtgggt    300
gcaggaaggc aggcatggca cagccaggta gagactggtt tccaggccca agcagccttc    360
agcagctgtg cgccttgttt ctgatgttgt ttgggagtaa gaataatgta gacatggggg    420
gtcatgargc tcaataaaaa cttcaaggaa acctcccatg gcatggttgg gcgcagtgac    480
tcatgcctgt aaccccagca ctgtggaatg ccaaggtgga aggatcgctt gaggccaaga    540

<210> SEQ ID NO 89
<211> LENGTH: 1863
<212> TYPE: DNA
<213> ORGANISM: Homo sapiens
<220> FEATURE:
<221> NAME/KEY: SITE
```

<222> LOCATION: (1836)
<223> OTHER INFORMATION: n equals a,t,g, or c

<400> SEQUENCE: 89

```
tcgacccacg cgtccggcga gatccctacc gcagtagccg cctctgccgc cgcggagctt    60
cccgaacctc ttcagccgcc cggagccgct cccggagccc ggccgtagag gctgcaatcg   120
cagccgggag cccgcagccc cgcgcccgag cccgccgccg cccttcgagg gcgcccagg    180
ccgcgccatg gtgaaggtga cgttcaactc cgctctggcc cagaaggagg ccaagaagga   240
cgagcccaag agcggcgagg aggcgctcat catcccccc gacgccgtcg cggtggactg    300
caaggaccca gatgatgtgg taccagttgg ccaaagaaga gcctggtgtt ggtgcatgtg   360
ctttggacta gcatttatgc ttgcaggtgt tattctagga ggagcatact tgtacaaata   420
ttttgcactt caaccagatg acgtgtacta ctgtggaata aagtacatca agatgatgt    480
catcttaaat gagccctctg cagatgcccc agctgctctc taccagacaa ttgaagaaaa   540
tattaaaatc tttgaagaag aagaagttga atttatcagt gtgcctgtcc cagagtttgc   600
agatagtgat cctgccaaca ttgttcatga ctttaacaag aaactacag cctatttaga    660
tcttaacctg gataagtgct atgtgatccc tctgaacact tccattgtta tgccacccag   720
aaacctactg gagttactta ttaacatcaa ggctggaacc tatttgcctc agtcctatct   780
gattcatgag cacatggtta ttactgatcg cattgaaaac attgatcacc tgggtttctt   840
tatttatcga ctgtgtcatg acaaggaaac ttacaaactg caacgcagag aaactattaa   900
aggtattcag aaacgtgaag ccagcaattg tttcgcaatt cggcattttg aaaacaaatt   960
tgccgtggaa actttaattt gttcttgaac agtcaagaaa aacattattg aggaaaatta  1020
atatcacagc ataaccccac cctttacatt ttgtgcagtg attatttttt aaagtcttct  1080
ttcatgtaag tagcaaacag ggctttacta tcttttcatc tcattaattc aattaaaacc  1140
attaccttaa aattttttc tttcgaagtg tggtgtcttt tatatttgaa ttagtaactg   1200
tatgaagtca tagataatag tacatgtcac cttaggtagt aggaagaatt acaatttctt  1260
taaatcattt atctggattt ttatgtttta ttagcatttt caagaagacg gattatctag  1320
agaataatca tatatatgca tacgtaaaaa tggaccacag tgacttattt gtagttgtta  1380
gttgccctgc tacctagttt gttagtgcat ttgagcacac attttaattt tcctctaatt  1440
aaaatgtgca gtattttcag tgtcaaatat atttaactat ttagagaatg atttccacct  1500
ttatgtttta atatcctagg catctgctgt aataatattt tagaaaatgt ttggaattta  1560
agaaataact tgtgttacta atttgtataa cccatatctg tgcaatggaa tataaatatc  1620
acaaagttgt ttaactagac tgcgtgttgt ttttcccgta aataaaacc aaagaatagt   1680
ttggttcttc aaatcttaag agaatccaca taaagaaga actatttttt taaaaattca  1740
cttctatata tacaatgagt aaaatcacag atttttttctt taaataaaaa taagtcattt  1800
taataactaa accagattct ttgtgatact attaangtaa catttagccc caaaaaaaaa  1860
aaa                                                                 1863
```

<210> SEQ ID NO 90
<211> LENGTH: 2478
<212> TYPE: DNA
<213> ORGANISM: Homo sapiens

<400> SEQUENCE: 90

```
ggcacagcgg cacgaggtga gctgagccgg tgggtgagcg gcggccacgg catcctgtgc    60
```

-continued

```
tgtggggct acgaggaaag atctaattat catggacctg cgacagtttc ttatgtgcct    120
gtccctgtgc acagcctttg ccttgagcaa acccacagaa aagaaggacc gtgtacatca    180
tgagcctcag ctcagtgaca aggttcacaa tgatgctcag agttttgatt atgaccatga    240
tgccttcttg ggtgctgaag aagcaaagac ctttgatcag ctgacaccag aagagagcaa    300
ggaaaggctt ggaaagattg taagtaaaat agatggcgac aaggacgggt ttgtcactgt    360
ggatgagctc aaagactgga ttaaatttgc acaaaagcgc tggatttacg aggatgtaga    420
gcgacagtgg aagggcatg acctcaatga ggacggcctc gtttcctggg aggagtataa    480
aaatgccacc tacggctacg ttttagatga tccagatcct gatgatggat ttaactataa    540
acagatgatg gttagagatg agcggaggtt taaaatggca gacaaggatg gagacctcat    600
tgccaccaag gaggagttca cagctttcct gcacctgag gagtatgact acatgaaaga    660
tatagtagta caggaaacaa tggaagatat agataagaat gctgatggtt tcattgatct    720
agaagagtat attggtgaca tgtacagcca tgatgggaat actgatgagc cagaatgggt    780
aaagacagag cgagagcagt tgttgagtt tcgggataag aaccgtgatg ggaagatgga    840
caaggaagag accaaagact ggatccttcc ctcagactat gatcatgcag aggcagaagc    900
caggcacctg gtctatgaat cagaccaaaa caaggatggc aagcttacca aggaggagat    960
cgttgacaag tatgacttat ttgttggcag ccaggccaca gatttgggg aggccttagt    1020
acggcatgat gagttctgag ctrcggagga accctcattt cctcaaaagt aatttatttt    1080
tacagcttct ggtttcacat gaaattgttt gcgctactga gactgttact acaaacttt    1140
taagacatga aaaggcgtaa tgaaaaccat cccgtcccca ttcctcctcc tctctgaggg    1200
actggaggga agccgtgctt ctgaggaaca actctaatta gtacacttgt gtttgtagat    1260
ttacactttg tattatgtat taacatggcg tgtttatttt tgtatttttc tctggtggg    1320
agtatgatat gaaggatcaa gatcctcaac tcacacatgt agacaaacat tagctctta    1380
ctcttttctca acccctttta tgatttaat aattctcact taactaattt tgtaagcctg    1440
agatcaataa gaaatgttca ggagagagga agaaaaaaaa atatatgctc acaattttat    1500
atttagagag agaacactta gtcttgcctg tcaaaaagtc caacatttca taggtagtag    1560
gggccacata ttcacattcag ttgctatagg tccagcaact gaacctgcca ttacctgggc    1620
aaggaaagat cccttttgctc taggaaagct tggcccaaat tgatttcctt cttttttcccc   1680
ctgtaggact gactgttggc taatttttgtc aagcacagct gtggtgggaa gagttagggc   1740
cagtgtcttg aaaatcaatc aagtagtgaa tgtgatctct ttgcagagct atagatagaa   1800
acagctggaa aactaaagga aaaatacaag tgttttcggg gcatacattt tttttctggg   1860
tgtgcatctg ttgaaatgct caagacttaa ttatttgcct tttgaaatca ctgtaaatgc   1920
ccccatccgg ttcctcttct tcccaggtgt gccaaggaat taatcttggt ttcactacaa   1980
ttaaaattca ctcctttcca atcatgtcat tgaaagtgcc tttaacgaaa gaatggtca   2040
ctgaatggga attctcttaa gaaaccctga gattaaaaaa agactatttg gataacttat   2100
aggaaagcct agaacctccc agtagagtgg ggattttttt cttcttcccct ttctcttttg   2160
gacaatagtt aaattagcag tattagttat gagtttggtt gcagtgttct tatcttgtgg   2220
gctgattcc aaaaaccaca tgctgctgaa tttaccaggg atcctcatac ctcacaatgc    2280
aaaccactta ctaccaggcc ttttctgtg tccactggag agcttgagct cacactcaaa    2340
gatcagagga cctacagaga gggctctttg gtttgaggac catggcttac ctttcctgcc    2400
tttgacccat cacaccccat ttcctcctct ttccctctcc ccgctgccaa ttcctgcagc    2460
```

```
<210> SEQ ID NO 91
<211> LENGTH: 2058
<212> TYPE: DNA
<213> ORGANISM: Homo sapiens
<220> FEATURE:
<221> NAME/KEY: SITE
<222> LOCATION: (69)
<223> OTHER INFORMATION: n equals a,t,g, or c
<220> FEATURE:
<221> NAME/KEY: SITE
<222> LOCATION: (161)
<223> OTHER INFORMATION: n equals a,t,g, or c

<400> SEQUENCE: 91
```

| | | | | | |
|---|---|---|---|---|---|
| tcggccttgc | ttttgtggyc | ttcctctgtg | gccagagcgt | ttcatcacc | aagcctcctg | 60 |
| atggcagtnc | cttaccgat | atgttcaaga | tactgacgta | ttcctgctgt | tcccagaagc | 120 |
| gaagtggaga | gcgccagagt | aatggtgaag | gcattggagt | ntttcagcaa | tcttctaaac | 180 |
| aaagtctgtt | tgattcatgt | aagatgtctc | atggtgggcc | atttacagaa | gagaaagtgg | 240 |
| aagatgtgaa | agctctggtc | aagattgtcc | ctgttttctt | ggctttgata | ccttactgga | 300 |
| cagtgtattt | ccaaatgcag | acaacatatg | ttttacagag | tcttcatttg | aggattccag | 360 |
| aaatttcaaa | tattacaacc | actcctcaca | cgctccctgc | agcctggctg | accatgtttg | 420 |
| atgctgtgct | catcctcctg | ctcatccctc | tgaaggacaa | actggtcgat | cccatttga | 480 |
| gaagacatgg | cctgctccca | tcctccctga | agaggatcgc | cgtgggcatg | ttctttgtca | 540 |
| tgtgctcrgc | ctttgctgca | ggaatttttgg | agagtaaaag | gctgaacctt | gttaaagaga | 600 |
| aaaccattaa | tcagaccatc | ggcaacgtcg | tctaccatgc | tgccgatctg | tcgctgtggt | 660 |
| ggcaggtgcc | gcagtacttg | ctgattggga | tcagcgagat | ctttgcaagt | atcgcaggcc | 720 |
| tggaatttgc | atactcagct | gcccccaagt | ccatgcagag | tgccataatg | ggcttgttct | 780 |
| ttttcttctc | tggcgtcggg | tcgttcgtgg | gttctggact | gctggcactg | gtgtctatca | 840 |
| aagccatcgg | atggatgagc | agtcacacag | actttggtaa | tattaacggc | tgctatttga | 900 |
| actattactt | tttccttctg | gctgctattc | aaggagctac | cctcctgctt | tcctcatta | 960 |
| tttctgtgaa | atatgaccat | catcgagacc | atcagcgatc | aagagccaat | ggcgtgccca | 1020 |
| ccagcaggag | ggcctgacct | tcctgaggcc | atgtgcggtt | tctgaggctg | acatgtcagt | 1080 |
| aactgactgg | ggtgcactga | aacaggcaa | gactttaaat | tcccataaaa | tgtctgactt | 1140 |
| cactgaaact | tgcatgttgc | ctggattgat | ttcttctttc | cctctatcca | aaggagcttg | 1200 |
| gtaagtgcct | tactgcagcg | tgtctcctgg | cacgctgggc | cctccgggag | gagagctgca | 1260 |
| gatttcgagt | atgtcgcttg | tcattcaagg | tctctgtgaa | tcctctagct | gggttccctt | 1320 |
| ttttacagaa | actcacaaat | ggagattgca | aagtcttggg | gaactccacg | tgttagttgg | 1380 |
| catcccagtt | tcttaaacaa | atagtatcac | ctgcttccca | tagccatatc | tcactgtaaa | 1440 |
| aaaaaaaatt | aataaactgt | tacttatatt | taagaaagtg | aggattttt | ttttttaaag | 1500 |
| ataaaagcat | ggtcagatgc | tgcaaggatt | ttacataaat | gccatattta | tggtttcctt | 1560 |
| cctgagaaca | atcttgctct | tgccatgttc | tttgatttag | gctggtagta | aacacatttc | 1620 |
| atctgctgct | tcaaaaagta | cttacttttt | aaaccatcaa | cattactttt | ctttcttaag | 1680 |
| gcaaggcatg | cataagagtc | atttgagacc | atgtgtccca | tctcaagcca | cagagcaact | 1740 |
| cacggggtac | ttcacacctt | acctagtcag | agtgcttata | tatagcttta | ttttggtacg | 1800 |

-continued

| | |
|---|---|
| attgagacta aagactgatc atggttgtat gtaaggaaaa cattcttttg aacagaaata | 1860 |
| gtgtaattaa aaataattga aagtgttaaa tgtgaacttg agctgtttga ccagtcacat | 1920 |
| ttttgtattg ttactgtacg tgtatctggg gcttctccgt ttgttaatac tttttctgta | 1980 |
| tttgttgctg tattttttggc ataactttat tataaaaagc atctcaaatg cgaaawaaaa | 2040 |
| aaaaaaaaaa aaaaaaac | 2058 |

<210> SEQ ID NO 92
<211> LENGTH: 1411
<212> TYPE: DNA
<213> ORGANISM: Homo sapiens
<220> FEATURE:
<221> NAME/KEY: SITE
<222> LOCATION: (1391)
<223> OTHER INFORMATION: n equals a,t,g, or c
<220> FEATURE:
<221> NAME/KEY: SITE
<222> LOCATION: (1403)
<223> OTHER INFORMATION: n equals a,t,g, or c

<400> SEQUENCE: 92

| | |
|---|---|
| ggcacaggag cgacccggga gaaggagggc camgakgcgg aagcggagga gtctccagga | 60 |
| gacccgggga cagcatcgcc caggcccctg tttgcaggcc tttcagatat atccatctca | 120 |
| caagacatcc ccgtagaagg agaaatcacc attcctatga gatctcgcat ccggagtttt | 180 |
| gacagctcca cattaaatga atctgttcgc aataccatca tgcgtgatct aaaagctgtt | 240 |
| gggaaaaaat tcatgcatgt tttgtaccca aggaaaagta atactctttt gagagattgg | 300 |
| gatttgtggg gccctttgat cctttgtgtg acactcgcat taatgctgca aagagactct | 360 |
| gcagatagta aaaagatgg agggccccaa tttgcagagg tgtttgtcat tgtctggttt | 420 |
| ggtgcagtta ccatcaccct caactcaaaa cttcttggag ggaacatatc ttttttttcag | 480 |
| agcctctgtg tgctgggtta ctgtatactt cccttgacag tagcaatgct gatttgccgg | 540 |
| ctggtacttt tggctgatcc aggacctgta aacttcatgg ttcggctttt tgtggtgatt | 600 |
| gtgatgtttg cctggtctat agttgcctcc acagctttcc ttgctgatag ccagcctcca | 660 |
| aaccgcagag ccctagctgt ttatcctgtt ttcctgtttt actttgtcat cagttggatg | 720 |
| attctcacct ttactcctca gtaaatcagg aatgggaaat taaaaccag tgaattgaaa | 780 |
| gcacatctga aagatgcaat tcaccatgga gctttgtctc tggcccttat ttgtctaatt | 840 |
| ttggaggtat ttgataactg agtaggtgag gagattaaaa gggagccata tagcactgtc | 900 |
| accccttatt tgaggaactg atgtttgaaa ggctgttctt ttctctctta atgtcatttc | 960 |
| tttaaaaata catgtgcata ctacacacag tatataatgc ctccttaagg catgatggag | 1020 |
| tcaccgtggt ccatttgggt gacaaccagt gacttgggaa gcacatagat acatcttaca | 1080 |
| agttgaatag agttgataac tattttcagt tttgagaata ccagttcagg tgcagctctt | 1140 |
| aaacacattg cctatgact attagaatat gcctctcttt tcataaataa aaatacatgg | 1200 |
| tctatatcca ttttcttta tttctctctc ttaagcttaa aaaggcaatg agagaggtta | 1260 |
| ggagtggggtt catacacgga gaatgagaaa acatgcatta accaatattc agattttgat | 1320 |
| caggggaaat tctayacttg ttgcaaaaaa aaaaaaaaa aaactcgagg ggggcccggt | 1380 |
| acccaatcgc ngtatatgat cgnaaacaat c | 1411 |

<210> SEQ ID NO 93
<211> LENGTH: 2187
<212> TYPE: DNA
<213> ORGANISM: Homo sapiens

<400> SEQUENCE: 93

```
gctttggctt ttttttggcgg actggggcgc cctccggaag cgtttccaac tttccagaag      60
tttctcggga cgggcaggag ggggtgggga ctgccatata tagatcccgg gagcagggga     120
gcgggctaag agtagaatcg tgtcgcgctc gagagcgaga gtcacgtccc ggcgctagcc     180
cagcccgacc caggcccacc gtggtgcacg caaaccactt cctggccatg cgctccctcc     240
tgcttctcag cgccttctgc ctcctggagg cggccctggc cgccgaggtg aagaaacctg     300
cagccgcagc agctcctggc actgcggaga agttgagccc caaggcggcc acgcttgccg     360
agcgcagccg gcctggcctt cagcttgtac caggccatgg ccaaggacca ggcagtggag     420
aacatcctgg tgtcacccgt ggtggtggcc tcgtcgctgg ggctcgtgtc gctgggcggc     480
aaggcgacca cggcgtcgca ggccaaggca gtgctgagcg ccgagcagct gcgcgacgag     540
gaggtgcacg ccggcctggg cgagctgctg cgctcactca gcaactccac ggcgcgcaac     600
gtgacctgga agctgggcag ccgactgtac ggacccagct cagtgagctt cgctgatgac     660
ttcgtgcgca gcagcaagca gcactacaac tgcgagcact ccaagatcaa cttccgcgac     720
aagcgcagcg cgctgcagtc catcaacgag tgggccgcgc agaccaccga cggcaagctg     780
cccgaggtca ccaaggacgt ggagcgcacg gacggcgccc tgttagtcaa cgccatgttc     840
ttcaagccac actgggatga gaaattccac cacaagatgg tggacaaccg tggcttcatg     900
gtgactcggt cctataccgt gggtgtcatg atgatgcacc ggacaggcct ctacaactac     960
tacgacgacg agaaggaaaa gctgcaaatc gtggagatgc ccctggccca caagctctcc    1020
agcctcatca tcctcatgcc ccatcacgtg gagcctctcg agcgccttga aaagctgcta    1080
accaaagagc agctgaagat ctggatgggg aagatgcaga gaaggctgt tgccatctcc    1140
ttgcccaagg gtgtggtgga ggtgacccat gacctgcaga acacctggc tgggctgggc    1200
ctgactgagg ccattgacaa gaacaaggcc gacttgtcac gcatgtcagg caagaaggac    1260
ctgtacctgg ccagcgtgtt ccacgccacc gcctttgagt tggacacaga tggcaaccct    1320
ttgaccagaa ttacgggcgg aggagtgcgc acccaagtgt tctacgccga ccacccttc    1380
atttcctagt gcgggacacc caaagcggtc cctgctattc attgggcgcc tggtccggcc    1440
taagggtgac aagatgcgag acgagttata ggcctcaggg tgcacacagg atggcaggag    1500
gcatccaaag gctcctgaga cacatggtg ctattgggt tgggggggag gtgaggtacc     1560
agccttggat actccatggg gtggggtgga aaagcagacc ggggttcccg tgtgcctgag    1620
cggacttccc agctagaatt cactccactt ggacatgggc cccagatacc atgatgctga    1680
gcccggaaac tccacatcct gtgggacctg ggccatagtc attctgcctg ccctgaaagt    1740
cccagatcaa gcctgcctca atcagtattc atatttatag ccaggtacct tctcacctgt    1800
gagaccaaat tgagctaggg gggtcagcca gccctcttct gacactaaaa cacctcagct    1860
gcctccccag ctctatccca acctctccca actataaaac taggtgctgc agcccctggg    1920
accaggcacc cccagaatga cctggccgca gtgaggcgga ttgagaagga gctcccagga    1980
ggggcttctg ggcagactct ggtcaagaag catcgtgtct ggcgttgtgg ggatgaactt    2040
tttgttttgt ttcttccttt tttagttctt caaagatagg gagggaaggg ggaacatgag    2100
cctttgttgc tatcaatcca agaacttatt tgtacatttt ttttttcaat aaacttttc    2160
caatgacaaa aaaaaaaaaa aaaaaaa                                        2187
```

<210> SEQ ID NO 94

<211> LENGTH: 757
<212> TYPE: DNA
<213> ORGANISM: Homo sapiens
<220> FEATURE:
<221> NAME/KEY: SITE
<222> LOCATION: (756)
<223> OTHER INFORMATION: n equals a,t,g, or c
<220> FEATURE:
<221> NAME/KEY: SITE
<222> LOCATION: (757)
<223> OTHER INFORMATION: n equals a,t,g, or c

<400> SEQUENCE: 94

```
gacagtacgg tcggattccc gggtcgaccc acgcgtccgc ggacggtgaa gaaggtgaag      60
atggcggtgg ccagggccgg ggtcttggga gtccagtggc tgcaaagggc atcccggaac     120
gtgatgccgc tgggcgcacg gacagcctcc cacatgacca aggacatgtt cccgggcccc     180
tatcctagga ccccagaaga acgggccgcc gccgccaaga agtataatat gcgtgtggaa     240
gactacgaac cttaccccga tgatggcatg gggtatggcg actacccgaa gctccctgac     300
cgctcacagc atgagagaga tccatggtat agctgggacc agccgggcct gaggttgaac     360
tggggtgaac cgatgcactg gcacctagac atgtacaaca ggaaccgtgt ggatacatcc     420
cccacacctg tttcttggca tgtcatgtgt atgcagctct tcggtttcct ggctttcatg     480
atattcatgt gctgggtggg ggacgtgtac cctgtctacc agcctgtggg accaaagcag     540
tatccttaca ataatctgta cctggaacga ggcggtgatc cctccaaaga accagagcgg     600
gtggttcact atgagatctg aggaggcttc gtgggctttt gggtcctcta actaggactc     660
cctcattcct agaaatttaa ccttaatgaa atccctaata aaactcagtg ctgtgttaaa     720
aaaaaaaaaa aaaaaaaaaa aaaaggggg gccccnn                              757
```

<210> SEQ ID NO 95
<211> LENGTH: 2394
<212> TYPE: DNA
<213> ORGANISM: Homo sapiens
<220> FEATURE:
<221> NAME/KEY: SITE
<222> LOCATION: (1783)
<223> OTHER INFORMATION: n equals a,t,g, or c

<400> SEQUENCE: 95

```
ggcacgagca ctcctgcact tccccacccc cacgaccgaa cctggcttcg ctaacgccct      60
cccagctccc tcgggcctga cttccggttt cctcgcgcgt ccctggcgcc gagccgcgga     120
cagcagcccc ttttccggct gagagctcat ccacacttcc aatcactttc cggagtgctt     180
ccctccctc cggcccgtgc tggtcccgac ggcgggcctg ggtctcgcgc gcgtattgct     240
gggtaacggg ccttctcycg cgtcggcccg gcccctcctg cctcggctcg tccctccttc     300
cagaacgtcc cgggctcctg ccgagtcaga agaaatggga ctccctccgc gacgtgcccg     360
gagcagctcc cttcgctgtg gaagcggcgg tgtcttcgaa gaaaccggaa gcccgtggtg     420
accctggcg acccggtttg ttttcggtcc gtttccaaac actaaggaat cgaaactcgg     480
cggccttggg ggcggcccta cgtagcctgg cttctggttg tcatggatgc actggtagaa     540
gatgatatct gtattctgaa tcatgaaaaa gcccataaga gagatacagt gactccagtt     600
tcaatatatt caggagatga atctgttgct tcccattttg ctcttgtcac tgcatatgaa     660
gacatcaaaa aacgacttaa ggattcagag aaagagaact cttttgttaaa gaagagaata     720
agattttgg aagaaaagct aatagctcga tttgaagaag aaacaagttc cgtgggacga     780
gaacaagtaa ataaggccta tcatgcatat cgagaggttt gcattgatag agataatttg     840
```

```
aagagcaaac tggacaaaat gaataaagac aactctgaat cttttgaaagt attgaatgag    900
cagctacaat ctaaagaagt agaactcctc cagctgagga cagaggtgga aactcagcag    960
gtgatgagga atttaaatcc accttcatca aactgggagg tggaaaagtt gagctgtgac   1020
ctgaagatcc atggtttgga caagagctg gaactgatga ggaaagaatg tagcgatctc   1080
aaaatagaac tacagaaagc caaacaaacg gatccatatc aggaagacaa tctgaagagc   1140
agagatctcc aaaaactaag catttcaagt gataatatgc agcatgcata ctgggaactg   1200
aagagagaaa tgtctaattt acatctggtg actcaagtac aagctgaact actaagaaaa   1260
ctgaaaacct caactgcaat caagaaagcc tgtgcccctg taggatgcag tgaagacctt   1320
ggaagagaca gcacaaaact gcacttgatg aattttactg caacatacac aagacatccc   1380
cctctcttac caaatggcaa agctctttgt cataccacat cttccccttt accaggagat   1440
gtaaaggttt tatcagagaa agcaatcctc caatcatgga cagacaatga gagatccatt   1500
cctaatgatg gtacatgctt tcaggaacac agttcttatg gcagaaattc tctggaagac   1560
aattcctggg tatttccaag tcctcctaaa tcaagtgaga cagcatttgg ggaaactaaa   1620
actaaaactt tgcctttacc caaccttcca ccactgcatt acttggatca acataatcag   1680
aactgccttt ataagaatta atttggaaga gattcacgat ttcaccatga ggacacttat   1740
ctctttcagt ggtcctccca agaaattatt taacaaactg aaggagatt ttgattaaaa   1800
ttttgcagag gtcttcagta tctatatttg aacacactgt acaatagtac aaaaaccaac   1860
atagttggtt ttctagtatg aaagagcacc ctctagctcc atattctaag aatctgaaat   1920
atgctactat actaattaat aagtaaactt aaggtgttta aaaaactctg ccttctatat   1980
taattgtaaa attttgcctc tcagaagaat ggaattggag attgtagacg tggtttttaca   2040
aaatgtgaaa tgtctaaata tctgttcata aaaataaaag gaaaacatgt ttcttcaaat   2100
tgcataatgg aacaaatggc aatgtgagta ggttacattt ctgttgttat aatgcgtaaa   2160
gatattgaaa atataatgaa ataaaagcat cttaggttat accatcttta tatgctattg   2220
cgtttcaata tttaagattt aaagtgattt ttttggtcaca gtgttttgtt gataaaattt   2280
ttttagaatt gaagtttgaa ttctaagact tgaaacaacc tgatcactga agccaacttt   2340
gtcccagcac attccttaag tcctaattgg ggaaaaaaaa aaaaaaaac tcga           2394
```

<210> SEQ ID NO 96  
<211> LENGTH: 672  
<212> TYPE: DNA  
<213> ORGANISM: Homo sapiens

<400> SEQUENCE: 96

```
agtgctctgt tgcccaggct ggagtgcgtt agtgtaatgt cagtccactg caacctccac     60
ccccaggttc aagcaattct catgcctcag cctcccaagt agctgaaatt actggcatgc    120
accaccacac ccagctgatg tttatttatt tatttatata tttatttatt ttaggtgttt    180
tttttttttt tttttgagac ggagtcttgc tctgttgccc tgggtgtggt tacgtggrat    240
taccatyctg ggtgactcac tgaaatgtac tcmcagtgag tcatgccttc maatgacatc    300
tcaagttctg cctgcttgga gatacatctg gggatcttaa ggggtgaggg actactcaac    360
aagaaggaat ttagcctgtc ttttttaaata aacggcattt cttttttccta kaaaaatggg    420
aaattcttca attctctaat acagggacac tgagataaca aagaggaaag tgtctggttg    480
gaggttggga rgccacccctg gggtctctcc tacaaaaatg gaaagaaaaa gaacggtgar    540
```

-continued

| | | |
|---|---|---|
| aaatcmagca aagcacaara aaktttccct ttgctaaaag ggaaaagatg ccccmcaatg | 600 | |
| cccataaaca tgaactgggg ataaggagga raatgtctct ycttggcacc cccaaacaaa | 660 | |
| cgttaattac cc | 672 | |

<210> SEQ ID NO 97
<211> LENGTH: 1419
<212> TYPE: DNA
<213> ORGANISM: Homo sapiens
<220> FEATURE:
<221> NAME/KEY: SITE
<222> LOCATION: (517)
<223> OTHER INFORMATION: n equals a,t,g, or c
<220> FEATURE:
<221> NAME/KEY: SITE
<222> LOCATION: (539)
<223> OTHER INFORMATION: n equals a,t,g, or c
<220> FEATURE:
<221> NAME/KEY: SITE
<222> LOCATION: (604)
<223> OTHER INFORMATION: n equals a,t,g, or c
<220> FEATURE:
<221> NAME/KEY: SITE
<222> LOCATION: (676)
<223> OTHER INFORMATION: n equals a,t,g, or c
<220> FEATURE:
<221> NAME/KEY: SITE
<222> LOCATION: (912)
<223> OTHER INFORMATION: n equals a,t,g, or c

<400> SEQUENCE: 97

| | | |
|---|---|---|
| taagaacaga acagcaagta tgaaccacat ggaacttaaa acatatgggt gtgaagtcca | 60 | |
| cttatgtaga caaaacttat aatttccaaa ctgttgtcta gtatacagtg atcagttgct | 120 | |
| ctctgttcaa gtcattccac acatttccct attttaggct attataatat agaaagaaaa | 180 | |
| tgggaagcat tagttggagc tagaaaatga actgtatatt attgctatat ttgctaatac | 240 | |
| caactatttc aataagtgtt gtaccatatg tagcattaaa tataaaatac ataaaagaat | 300 | |
| gtacagaaaa tagcttttat tgagtaatat tacatttcat ttatactgta gcaatatatt | 360 | |
| tgtaggtata ctctgtaagg gctttaaata aaagaggtcc attaatactt ccttataaaa | 420 | |
| attctagtct gtttcattac tgcccagatg ttttagagat aaatatttat gcagaaggta | 480 | |
| ttttkgaaag tcyccyttttg tctgatagag tttaacnaga tatttaaatt tagtgcycna | 540 | |
| gaaatcccac aagtcacggt ctaaacacac ttagaatact acagcataaa tctgttagca | 600 | |
| ttanttgcca aataagacag ttgggatccc aaaccccaag tccttgagca atgttttttcc | 660 | |
| tcaaaaagct gctatnccaa tgatatagga aaawacattg tgttttccta aacacacttt | 720 | |
| tcttttttaaa tgtgcttcat tgtttgattt ggtcctgcct aaatttcaca agctaggcca | 780 | |
| atgaaggctg aatcaaagac atttcatcca ccaatatcat gtgtagatat tatgtataga | 840 | |
| aaataaaata aattatggct ctaacttctg tgttgctgtt tatcttgtta ttttttcggcg | 900 | |
| ttatactaat gngtttattg agagcatttt accttccaga cttctcatgg ctaactttttg | 960 | |
| gtctgwattt tgstccttag atgkgaatat ttcttattag tytgctyyct gcwacgcaat | 1020 | |
| gactgcattt ctatcatttc tcagtttgtt agwatatgtg gatagtattc tactgtataa | 1080 | |
| atgattgcaa agtttatcaa aaacaaatta ttatatgtag cttttctaca gtgctttgct | 1140 | |
| aaaccatgta gtactagtta agtsttcctt gaaaataaag atacactctt ataggggaca | 1200 | |
| gttcctgttc actcccagga aacttttttta aaagatgaca ctgaatgttt attgcacttt | 1260 | |
| agtgcagtga agtggcaata aaacctaaca tgaatcaagg ttgttatgg cagatgcatg | 1320 | |
| tgttgcttta cagagtttag caaaagctct taattttatg tcatactgta ttctactgaa | 1380 | |

-continued taataaagct aacattattc aataataaaa tggaaaaaa        1419

<210> SEQ ID NO 98
<211> LENGTH: 1830
<212> TYPE: DNA
<213> ORGANISM: Homo sapiens
<220> FEATURE:
<221> NAME/KEY: SITE
<222> LOCATION: (67)
<223> OTHER INFORMATION: n equals a,t,g, or c
<220> FEATURE:
<221> NAME/KEY: SITE
<222> LOCATION: (97)
<223> OTHER INFORMATION: n equals a,t,g, or c
<220> FEATURE:
<221> NAME/KEY: SITE
<222> LOCATION: (211)
<223> OTHER INFORMATION: n equals a,t,g, or c
<220> FEATURE:
<221> NAME/KEY: SITE
<222> LOCATION: (1813)
<223> OTHER INFORMATION: n equals a,t,g, or c
<220> FEATURE:
<221> NAME/KEY: SITE
<222> LOCATION: (1830)
<223> OTHER INFORMATION: n equals a,t,g, or c

<400> SEQUENCE: 98

| | | | | | |
|---|---|---|---|---|---|
| gcgaccgcgc | ccttcagcta | gctcgctcgc | tcgctctgct | tccctgctgc | cggctgcgca | 60 |
| tggcttnggc | gttggcggcg | ctggcggcgg | tcgagcngcc | tgcgsagccg | gtaccagcag | 120 |
| ttgcagaatg | aagaagagtc | tggagaacct | gaacaggctg | caggtgatgc | tcctccacct | 180 |
| tacagcagca | tttctgcaga | gagcgcacat | nattttgact | acaaggatga | gtctgggttt | 240 |
| ccaaagcccc | catcttacaa | tgtagctaca | acactgccca | gttatgatga | agcggagagg | 300 |
| accaaggctg | aagctactat | cccttttggtt | cctgggagag | atgaggattt | tgtgggtcgg | 360 |
| gatgattttg | atgatgctga | ccagctgagg | ataggaaatg | atgggatttt | catgttaact | 420 |
| tttttcatgg | cattcctctt | taactggatt | gggttttttcc | tgtcttttttg | cctgaccact | 480 |
| tcagctgcag | gaaggtatgg | ggccatttca | ggatttggtc | tctctctaat | taaatggatc | 540 |
| ctgattgtca | ggttttccac | ctatttccct | ggatattttg | atggtcagta | ctggctctgg | 600 |
| tgggtgttcc | ttgttttagg | cttttctcctg | tttctcagag | gatttatcaa | ttatgcaaaa | 660 |
| gttcggaaga | tgccagaaac | tttctcaaat | ctcccccagga | ccagagttct | ctttattttat | 720 |
| taaagatgtt | ttctggcaaa | ggccttcctg | catttatgaa | ttctctctca | agaagcaaga | 780 |
| gaacacctgc | aggaagtgaa | tcaagatgca | gaacacagag | gaataatcac | ctgctttaaa | 840 |
| aaaataaagt | actgttgaaa | agatcatttc | tctctatttg | ttcctaggtg | taaaatttta | 900 |
| atagttaatg | cagaattctg | taatcattga | atcattagtg | gttaatgttt | gaaaaagctc | 960 |
| ttgcaatcaa | gtctgtgatg | tattaataat | gccttatata | ttgtttgtag | tcattttaag | 1020 |
| tagcatgagc | catgtccctg | tagtcggtag | ggggcagtct | tgctttattc | atcctccatc | 1080 |
| tcaaaatgaa | cttggaatta | aatattgtaa | gatatgtata | atgctggcca | ttttaaaggg | 1140 |
| gttttctcaa | aagttaaact | tttgttatga | ctgtgttttt | gcacataatc | catatttgct | 1200 |
| gttcaagtta | atctagaaat | ttattcaatt | ctgtatgaac | acctggaagc | aaaatcatag | 1260 |
| tgcaaaaata | catttaaggt | gtggtcaaaa | ataagtcttt | aattggtaaa | taataagcat | 1320 |
| taatttttta | tagcctgtat | tcacaattct | gcggtacctt | attgtaccta | agggattcta | 1380 |
| aaggtgttgt | cactgtataa | aacagaaagc | actaggatac | aaatgaagct | taattactaa | 1440 |

-continued

```
aatgtaattc ttgacactct ttctataatt agcgttcttc accccccacccc cacccccac    1500 ccccttatt ttccttttgt ctcctggtga ttaggccaaa gtctgggagt aaggagagga    1560
ttaggtactt aggagcaaag aaagaagtag cttggaactt ttgagatgat ccctaacata    1620
ctgtactact tgcttttaca atgtgttagc agaaaccagt gggttataat gtagaatgat    1680 gtgcttctg cccaagtggt aattcatctt ggtttgctat gttaaaactg taaatacaac    1740
agaacattaa taaatatctc ttgtgtagca ccttttaaaa aaaaaaaaa aaaaaaaaa    1800 aaaaaaaaaa aanccgggg ggggccccn                                       1830
```

<210> SEQ ID NO 99
<211> LENGTH: 1145
<212> TYPE: DNA
<213> ORGANISM: Homo sapiens

<400> SEQUENCE: 99

```
tttttttttt tttttttttt ttgactgaac taagtggctt ttttattaga gaaagccaga      60
attacaaaag acttcccttt tcttggggta tggctgtctc agcacaatac tcaacataac     120
tgcagaactg atgtggctca ggcaccctgg ttttaattcc ttgaggatct ggcaattggc     180
ttacgcaaaa ggtcaccatt tgaggtcctg ccttactaat tatgtgctgc ccaacaacta     240
aatttgtaat tgtttttct ctagtttgag caggtctga attttttcat ttatttcctt       300
ttttgccagc agacagactt gagtctgtaa agacaagcaa atacactgac agaagtttac     360
catagtttct aaaatgtaaa aaagaaaacc cccaaaagac tcaagaaaat tagaccacaa     420
attttgcatt gttcattgta gcactattgg taataaaata acaaatgttt gtgcattttt     480
atgtgaagat cccttctcgta tttcatttgg aaagatgagc aagaggtctg cttccttcat    540
tttacttccc cttctgtttt tgaaaggcag tttcgccaag cttaatgcaa gaatatctga    600
ctgtttagaa gaaagatatt gccacaatct ctggatggtt ttccagggtt gtgttattac    660
tgagcttcat cttccagaa tgagcaaaac actgtccagt cttgttacg attttgtaat       720 aaatgtgtac atttttttta aatttttgga catcacatga ataaaggtat gtatgtacga    780
atgtgtatat attatatata tgacatctat tttggaaaat gtttgccctg ctgtacctca    840 ttttaggag gtgtgcatgg atgcaatata tgaaatggg acattctgga actgctggtc    900
agggactttt gtcgccctgt gcactaaaag ggccagattt tcagcagcca aggacatcca    960
tacccaagtg aatgtgatgg gacttaaaag aagtgaactg agacaattca ctctggctgt   1020
ttgaacagca gcgtttcata ggaagagaaa aaaagatcaa tcttgtattt tctgaccaca   1080
taaaggcttc ttctctttgt aataaagtag aaaagctctc ctcaaaaaaa aaaaaaaaa    1140 aaaaa                                                               1145
```

<210> SEQ ID NO 100
<211> LENGTH: 734
<212> TYPE: DNA
<213> ORGANISM: Homo sapiens

<400> SEQUENCE: 100

```
tacccggcgg attccaggaa ggtaaattta gtcctataat tttcagctta attataaaca      60
aaggaacaaa taagtggaag ggcagctatt accattcgct tagtcaaaac attcggttac    120 tgcccttaa tacactccta tcatcagcac ttccaccatg tattacaagt cttgacccat     180
ccctgtcgta actccagtaa aagttactgt tactagaaaa ttttttatcaa ttaactgaca    240 aatagtttct ttttaaagta gtttcttcca tctttattct gactagcttc caaaatgtgt     300
```

```
tcccttttg  aatcgaggtt  tttttgtttt  gttttgtttt  ctgaaaaaat  catacaactt    360
tgtgcttcta  ttgctttttt  gtgttttgtt  aagcatgtcc  cttggcccaa  atggaagagg    420
aaatgtttaa  ttaatgcttt  ttagtttaaa  taaattgaat  catttataat  aatcagtgtt    480
aacaatttag  tgaccccttgg  taggttaaag  gttgcattat  ttatacttga  gattttttc    540 ccctaactat  tctgttttt   gtactttaaa  actatggggg  aaatatcact  ggtctgtcaa    600
gaaacagcag  taattattac  tgagttaaat  tgaaaagtcc  agtggaccag  gcatttctta    660
tataaataaa  attggtggta  ctaatgtgaa  aaaaaaaaa   aaaaaaaact  cgaggggggc    720
ccggtaccct  atta                                                          734

<210> SEQ ID NO 101
<211> LENGTH: 713
<212> TYPE: DNA
<213> ORGANISM: Homo sapiens
<220> FEATURE:
<221> NAME/KEY: SITE
<222> LOCATION: (27)
<223> OTHER INFORMATION: n equals a,t,g, or c

<400> SEQUENCE: 101
ccgcgggaac  gctgtcctgg  ctgccgncac  ccgaacagcc  tgtcctggtg  ccccggctcc     60
ctgccccgcg  cccagtcatg  accctgcgcc  cctcactcct  cccgctccat  ctgctgctgc    120
tgctgctgct  cagtgcggcg  gtgtgccggg  ctgaggctgg  gctcgaaacc  gaaagtcccg    180
tccggaccct  ccaagtggag  accctggtgg  agccccccaga  accatgtgcc  gagcccgctg    240
cttttggaga  cacgcttcac  atacactaca  cgggaagctt  ggtagatgga  cgtattattg    300
acacctccct  gaccagagac  cctctggtta  tagaacttgg  ccaaaagcag  gtgattccag    360
gtctggagca  gagtcttctc  gacatgtgtg  tgggagagaa  gcgaagggca  atcattcctt    420
ctcacttggc  ctatggaaaa  cggggatttc  caccatctgt  cccagcggat  gcagtggtgc    480
agtatgacgt  ggagctgatt  gcactaatcc  gagccaacta  ctggctaaag  ctggtgaagg    540
gcattttgcc  tctggtaggg  atggccatgg  tgccaccctc  ctgggcctca  ttgggtatca    600
cctatacaga  aaggccaata  gacccaaagt  ctccaaaaag  aagctcaagg  aagagaaacg    660
aaacaagagc  aaaaagaaat  aataaataat  aaattttaaa  aaacttaaaa  aaa           713

<210> SEQ ID NO 102
<211> LENGTH: 1080
<212> TYPE: DNA
<213> ORGANISM: Homo sapiens
<220> FEATURE:
<221> NAME/KEY: SITE
<222> LOCATION: (514)
<223> OTHER INFORMATION: n equals a,t,g, or c
<220> FEATURE:
<221> NAME/KEY: SITE
<222> LOCATION: (721)
<223> OTHER INFORMATION: n equals a,t,g, or c

<400> SEQUENCE: 102
ccgatgtgga  catcatcctg  tctatcccca  tgttcctgcg  cctgtacctg  atcgcccgag     60
tcatgctgct  gcacagaagc  tcttcaccga  tgcctcgtcc  cgcagcatcg  gggccctcaa    120
caagatcaac  ttcaacaccc  gctttgtcat  gaagacgctc  atgaccatct  gcctggcac    180 tgtgctgctc  gtgttcagca  tctctctgtg  gatcattgct  gcctggaccg  tccgtgtctg    240
tgaaagtcct  gaatcaccag  cccagccttc  tggctcatca  cttcctgctt  ggtaccatga    300
```

```
ccagcaggac gtaactagta actttctggg tgccatgtgg ctcatctcca tcacattcct    360
ttccattggt tatggggaca tggtgcccca cacatactgt gggaaaggtg tctgtctcct    420
cactggcatc atgggtgcag gctgcactgc ccttgtggtg gccgtggtgg cccgaaagct    480
ggaactcacc aaagcggaga agcacgttca taanttcatg atggacactc agctcaccaa    540
gcggatcaag aatgytgcag ccaatgtcct tsgggaaaca tggttaatct ataaacacac    600
aaagytgyta aagaagattg accatgccaa agtgaggaac accagaggaa gttcytccaa    660
gtatccacca gttgaggagc gtcaagatgg aacagaggaa gctgagtgac caagccaaca    720
ntctggtgga cctttccaag atgcagaatg tcmtgtatga cttaatcaca gaactcaatg    780
accggagcga agacctggag aagcagattg gcagcctgga gtcgaagctg gagcatctca    840
ccgccagctt caactccctg ccgctgctca tcgccgacac cctgcgccag cagcagcagc    900
agctcctgtc tgccatcatc gaggcccggg tgtcagcgt ggcagtgggc accacccaca    960
ccccaatctc cgatagcccc attggggtca gctccacctc cttcccgacc cgtacacaa    1020 gttcaagcag ttgctaaata aatctcccca ctccagaagc attaaaaaaa aaaaaaaaa    1080
```

```
<210> SEQ ID NO 103
<211> LENGTH: 489
<212> TYPE: DNA
<213> ORGANISM: Homo sapiens

<400> SEQUENCE: 103
```

```
ggcacgagag gctttgaagc attttttgtct gtgctccctg atcttcaggt caccaccatg     60
aagttcttag cagtcctggt actcttggga gtttccatct ttctggtctc tgcccagaat    120
ccgacaacag ctgctccagc tgacacgtat ccagctactg gtcctgctga tgatgaagcc    180
cctgatgctg aaaccactgc tgctgcaacc actgcgacca ctgctgctcc taccactgca    240
accaccgctg cttctaccac tgctcgtaaa gacattccag ttttacccaa atgggttggg    300
gatctcccga atggtagagt gtgtccctga gatggaatca gcttgagtct tctgcaattg    360
gtcacaacta ttcatgcttc ctgtgatttc atccaactac ttaccttgcc tacgatatcc    420
cctttatctc taatcagttt attttctttc aaataaaaaa taactatgag caacaaaaaa    480
aaaaaaaaa                                                            489
```

```
<210> SEQ ID NO 104
<211> LENGTH: 1529
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c

<400> SEQUENCE: 104
```

```
gggcacnaga tggagctgcc gtagcggacc cagcacagcc aggagcgtcc gggatgagct     60
cagccgcggc cgaccactgg gcgtggttgc tggtgctcag cttcgtgttt ggatgcaatg    120
ttcttaggat cctcctcccg tccttctcat ccttcatgtc cagggtgctg cagaaggacg    180
cggacaggag tcacagatga gagcggagat ccaggacatg aagcaggagc tctccacagt    240
caacatgatg gacgagtttg ccagatatgc caggctggaa agaaagatca acaagatgac    300
ggataagctc aaaacccatg tgaaagctcg gacagctcaa ttagccaaga taaaatgggt    360
gataagtgtc gctttctacg tattgcaggc tgccctgatg atctcactca tttggaagta    420
ttattctgtc cctgtggctg tcgtgccgag taaatggata cccctctag accgcctggt    480
```

-continued

```
agcctttcct actagagtag caggtggtgt tggaattacc tgttggatt tagtctgtaa      540 caaagttgtc gctattgtgc ttcatccgtt cagctgaaca ggaggatgga tacagccgcg      600
agtaaaaaaa cggatttcct cttcctagct taaaatctga tttacactgt tttgttttt      660 aagaaacaaa agtgcatagt ttagattttt tttttgttga atatgtttgt tcttggactt      720
tatgagatag tcttataaga atcacgattt tctacacctg tcattgagcc aagaaagtcc      780
agtttatgac acgtatgtac tagtgaacac cgtcctcgat ctgtacgaaa tgtgaaatgt      840
ttagggacat ctccatgctg tcacttgtga tttgccctct tatgtatttt ggtcatattg      900
ccaactggaa agtcaaaatt ttctaacaac tttaagtaag ttctttgaag acttagtgct      960 gttttaatc cagtttagaa agtaacttaa ttttaatacc rctactaaaa attcgaaaat     1020
ttcttcttta atcacattca atatggttaa aagaacaaca ctaattgaca ttgcgtgggc     1080
tttttctccc tttgtttaaa atgtcatttg ttgagcaaga gttgtatagt attatctact     1140
tacttgaggc tgttaatttt tcattacagt gttttgtaaa tgtatccacg agaccatgat     1200
gcattgtttt gtgctcaact tgtgttttgt atttaaagca ttttgaatga agtgtatttt     1260
ataagcattt aatatttatg ctctttagaa tggaacacag aaaacaaacc ttataagtcc     1320
tgattaatct gaaccaataa cctgtgtggc ctacaaagta taattctatt aaatgttcct     1380
taaaacactt ttttctaatt aaaatctttg caaatgcttg tgtaacttcc tgccttacag     1440
ctacttgttt gctgtgagcc acccgcaact gacaagtggc tgttaactga gtcaccatat     1500
cccagtaaag ctgaatttc tcactaaaa                                        1529
```

<210> SEQ ID NO 105
<211> LENGTH: 2435
<212> TYPE: DNA
<213> ORGANISM: Homo sapiens
<220> FEATURE:
<221> NAME/KEY: SITE
<222> LOCATION: (455)
<223> OTHER INFORMATION: n equals a,t,g, or c
<220> FEATURE:
<221> NAME/KEY: SITE
<222> LOCATION: (2107)
<223> OTHER INFORMATION: n equals a,t,g, or c
<220> FEATURE:
<221> NAME/KEY: SITE
<222> LOCATION: (2435)
<223> OTHER INFORMATION: n equals a,t,g, or c

<400> SEQUENCE: 105

```
atgaagggtc gttggtggga agatggcgg cgactctggg acccttggt cgtggcagca       60 gtggcgrcga tgtttgtcgg ctcgggatgg gtccaggatg ttactccttc ttcttttgtt     120
ggggtctggg cagggccac agcaagtcgg ggcgggtcaa acgttcgagt acttgaaacg      180
ggagcactcg ctgtcgaagc cctaccaggg tgtgggcaca gcagttcct cactgtggaa      240 tctgatgggc aatgccatgg tgatgaccca gtatatccgc cttaccccag atatgcaaag     300
taaacagggt gccttgtgga accgggtgcc atgtttcctg agagactggg agttgcaggt     360
gcacttcaaa atccatggac aaggaaagaa gaatctgcat ggggatggct tggcaatctg     420
gtacacaaag grwtcggatg cagccagggc ctgtnttgg gaaacatgga caaatttgtg     480
gggctgggag tatttgtaga cacctacccc aatgaggaga agcagcaaga gcgggtattc     540
ccctrcmtct cagccatggt gaacaacggc tccctcagct atgatcatga gcggatggg      600 cggcctacag agctggagg ctgcasagcc attgtccgca atcttcatta cgacaccttc     660
```

```
ctggtgattc gctacgtcaa gaggcattr acgataatga tggatattga tggcaagcat      720
gagtggaggg actgcattga agtgcccgga gtccgcctgc cccgcggcta ctacttcggc      780
acctcctcca tcactgggga tctctcagat aatcatgatg tcatttcctt gaagttgttt      840
gaactgacag tggagagaac cccagaagag gaaaagctcc atcgagatgt gttcttgccc      900
tcagtggaca atatgaagct gcctgagatg acagctccac tgccgcccct gagtggcctg      960
gccctcttcc tcatcgtctt tttctccctg ggtgttttct gtatttgcca tagtcattgg     1020
tatcatactc tacaacaaat ggcaggaaca gagccgaaag cgcttctact gagccctcct     1080
gctgccacca cttttgtgac tgtcacccat gaggtatgga aggagcaggc actggcctga     1140
gcatgcagcc tggagagtgt tcttgtctct agcagctggt tggggactat attctgtcac     1200
tggagttttg aatgcaggga ccccgcattc ccatggttgt gcatgggac atctaactct      1260 ggtctgggaa gccacccacc ccagggcaat gctgctgtga tgtgcctttc cctgcagtcc     1320
ttccatgtgg gagcagaggt gtgaagagaa tttacgtggt tgtgatgcca aaatcacaga     1380
acagaatttc atagcccagg ctgccgtgtt gtttgactca gaaggcccctt ctacttcagt    1440 tttgaatcca caagaatta aaaactggta acaccacagg ctttctgacc atccattcgt      1500
tgggttttgc atttgaccca accctctgcc tacctgagga gctttctttg gaaaccagga     1560
tggaaacttc ttccctgcct taccttcctt tcactccatt cattgtcctc tctgtgtgca     1620
acctgagctg ggaaaggcat ttggatgcct ctctgttggg gcctggggct gcagaacaca     1680
cctgcgtttc actggccttc attaggtggc cctaggggaga tggctttctg ctttggatca    1740 ctgttccccta gcatgggtct tgggtctatt ggcatgtcca tggccttccc aatcaagtct    1800
cttcaggccc tcagtgaagt ttggctaaag gttggtgtaa aaatcaagag aagcctggaa     1860
gacatcatgg atgccatgga ttagctgtgc aactgaccag ctccaggttt gatcaaacca     1920
aaagcaacat ttgtcatgtg gtctgaccat gtggagatgt ttctggactt gctagagcct     1980
gcttagctgc atgttttgta gttacgattt ttggaatccc actttgagtg ctgaaagtgt     2040
aaggaagctt tcttcttaca ccttgggctt ggatattgcc cagagaagaa atttggcttt     2100
ttttttnctt aatggacaag agacagttgc tgttctcatg ttccaagtct gagagcaaca     2160
gaccctcatc atctgtgcct ggaagagttc actgtcattg agcagcacag cctgagtgct     2220
ggcctctgtc aacccttatt ccactgcctt atttgacaag gggttacatg ctgctcacct     2280
tactgccctg ggattaaatc agttacaggc cagagtctcc ttggagggcc tggaactctg     2340
agtcctccta tgaacctctg tagcctaaat gaaattctta aaatcaccga tggaaccaaa     2400
aaaaaaaaaa aaaaaaaaaa aaaaaaaaaa aaaan                                2435
```

<210> SEQ ID NO 106
<211> LENGTH: 805
<212> TYPE: DNA
<213> ORGANISM: Homo sapiens

<400> SEQUENCE: 106

```
atgaaactta agaattgaat tggaaagact tctcaaagag aattgtatgt aacgatgttg       60
tattgatttt taagaaagta atttaatttg taaaacttct gctcgtttac actgcacatt      120
gaatacaggt aactaattgg aaggagaggg gaggtcactc ttttgatggt ggccctgaac      180
ctcattctgg ttccctgctg cgctgcttgg tgtgaccccac ggaggatcca ctcccaggat    240
gacgtgctcc gtagctctgc tgctgatact gggtctgcga tgcagcggcg tgaggcctgg      300
gctggttgga gaaggtcaca acccttctct gttggtctgc cttctgctga aagactcgag      360
```

```
aaccaaccag ggaagctgtc ctggaggtcc ctggtcggag agggacatag aatctgtgac      420
ctctgacaac tgtgaagcca ccctgggcta cagaaaccac agtcttccca gcaattatta      480
caattcttga attccttggg gattttttac tgcccttca aagcacttaa gtgttagatc       540
taacgtgttc cagtgtctgt ctgaggtgac ttaaaaaatc agaacaaaac ttctattatc      600
cagagtcatg ggagagtaca ccctttccag gaataatgtt ttgggaaaca ctgaaatgaa      660
atcttcccag tattataaat tgtgtattta aaaaaagaa acttttctga atgcctactg       720
gcggtgtata ccaggcagtg tgccagttta aaagatgaa aaagaataaa aacttttgag       780
gaacaaaaaa aaaaaaaaaa aaatt                                            805
```

<210> SEQ ID NO 107
<211> LENGTH: 1166
<212> TYPE: DNA
<213> ORGANISM: Homo sapiens
<220> FEATURE:
<221> NAME/KEY: SITE
<222> LOCATION: (1039)
<223> OTHER INFORMATION: n equals a,t,g, or c

<400> SEQUENCE: 107

```
ggcacgagag gcgccagtcg caggtgtgct gctgaggcgt gagaatggcg tcccgcggcc      60
ggcgtccgga gcatggcgga cccccagagc tgttttatga cgagacagaa gcccggaaat     120
acgttcgcaa ctcacggatg attgatatcc agaccaggat ggctgggcga gcattggagc     180
ttctttatct gccagagaat aagccctgtt acctgctgga tattggctgt ggcactgggc     240
tgagtggaag ttatctgtca gatgaagggc actattggt gggcctggat atcagccctg      300
ccatgctgga tgaggctgtg gaccgagaga tagaggaga cctgctgctg ggggatatgg      360
gccagggcat cccattcaag ccaggcacat tgatggttg catcagcatt tctgctgtgc      420
agtggctctg taatgctaac aagaagtctg aaaaccctgc caagcgcctg tactgctttt     480
ttgcttctct ttttttctgtt ctcgtccggg atcccgagc tgtcctgcag ctgtaccctg     540
agaactcaga gcagttggag ctgatcacaa cccaggccac aaaggcaggc ttctccggtg     600
gcatggtggt agactaccct aacagtgcca agcaaagaa attctacctc tgcttgtttt      660
ctgggccttc gacctttata ccagaggggc tgagtgaaaa tcaggatgaa gttgaaccca      720
gggagtctgt gttcaccaat gagaggttcc cattaaggat gtcgaggcgg ggaatggtga      780
ggaagagtcg ggcatgggtg ctggagaaga aggagcggca caggcgccag ggcagggaag     840
tcagacctga cacccagtac accggccgca agcgcaagcc ccgcttctaa gtcaccacgc      900
ggttctggaa aggcacttgc ctctgcactt ttctatattg ttcagctgac aaagtagtat      960
tttagaaaag ttctaaagtt ataaaaatgt tttctgcagt aaaaaaaaag ttctctgggc     1020
cgggcgtggt ggctcacanc tgtaatccca gcaccttggg aggctgaggt gggaggatca     1080
tttgaggcca ggagtttgag acctgcctgg gcaacataat gaaacttcct ttccagggag     1140
aaaaaaaaaa aaaaaaaaaa actcga                                          1166
```

<210> SEQ ID NO 108
<211> LENGTH: 586
<212> TYPE: DNA
<213> ORGANISM: Homo sapiens

<400> SEQUENCE: 108

```
agagcggacg aagctggata acaggggacc gatgatgtgg cgaccatcag ttctgctgct       60
```

| | |
|---|---|
| tctgttgcta ctgaggcacg gggcccaggg gaagccatcc ccagacgcag gccctcatgg | 120 |
| ccaggggagg gtgcaccagg cggcccccct gagcgacgct ccccatgatg acgcccacgg | 180 |
| gaacttccag tacgaccatg aggctttcct gggacgggaa gtggccaagg aattcgacca | 240 |
| actcacccca gaggaaagcc aggcccgtct ggggcggatc gtggaccgca tggaccgcgc | 300 |
| gggggacggc gacggctggg tgtcgctggc cgagcttcgc gcgtggatcg cgcacacgca | 360 |
| gcagcggcac atacgggact cggtgagcgc ggcctgggac acgtacgaca cggaccgcga | 420 |
| cgggcgtgtg ggttgggagg agctgcgcaa cgycacctat ggccactasg sgcccgktga | 480 |
| agaatttcat gacgtggagg atgcagagac ytacaaaaag atgctggytc gggacgagcg | 540 |
| gcgtttccgg gtggccgacc aggatgggga ctcgatggcc actcga | 586 |

<210> SEQ ID NO 109
<211> LENGTH: 1134
<212> TYPE: DNA
<213> ORGANISM: Homo sapiens
<220> FEATURE:
<221> NAME/KEY: SITE
<222> LOCATION: (418)
<223> OTHER INFORMATION: n equals a,t,g, or c
<220> FEATURE:
<221> NAME/KEY: SITE
<222> LOCATION: (803)
<223> OTHER INFORMATION: n equals a,t,g, or c
<220> FEATURE:
<221> NAME/KEY: SITE
<222> LOCATION: (816)
<223> OTHER INFORMATION: n equals a,t,g, or c

<400> SEQUENCE: 109

| | |
|---|---|
| acccattgag cagaaggagg ccaggtggga aagctcctgg gaagagcagc cagactggac | 60 |
| actgggctgc ttgagtcctg agtcacaatt cagaattcct gggctccctg ggtgcattct | 120 |
| atcattccag ttgaaagttt gcttccttcc agtcatgtgg ctcttcattc tactctcctt | 180 |
| ggctctcatt tcagatgcca tggtcatgga tgaaaaggtc aagagaagtt tgtgctggac | 240 |
| acggcttctg ccatctgcaa ctacaatgcc caytacaaga atcacccaa atactggtgc | 300 |
| cgaggytatt tccgtgayta ctgcaacatc atcgccttct ccctaacag caccaatcat | 360 |
| gtggccctga aggacacagg gaaccagctc attgtcacta tgtcctgcct gaacaaanaa | 420 |
| gacacgggct ggtactggtg tggcatccar cgggactttg cmagggatga catggatttt | 480 |
| acagagctga ttgtaactga cgacaaagga accctggcca atgacttttg gtctgggaaa | 540 |
| gacctatcag gcaacaaaac cagaagctgc aaggctccca agttgtccg caagctgacc | 600 |
| gctccaggac gtccattctc atcatttgca tactgatcac gggtttggga atcatctctg | 660 |
| taatcagtca tttgaccaaa aggaggagaa gtcaaaggaa tagaagggta ggcaacactt | 720 |
| tgaagccctt ctcgcgtgtc ctgactccaa aggaaatggc tcctactgaa cagatgtgac | 780 |
| tgaagwtttt tttaatttag ttncataaag tgatgnctac aacagawtaa tcacccatga | 840 |
| caactggccc cacacctcag agactgattc tgatctccca ggaattctga aggaccctct | 900 |
| atccttgaca caatcatttt gcagccaggt agcaacggcr gtagtcagag gagctatgat | 960 |
| agaccacacc caagcaaggc tgccctcaaa taacatctca agatcttagt tcttatgcat | 1020 |
| tccatcagtc agaagtgaag aagaggtgga gaatctkgat tggggaccag gaaatcactt | 1080 |
| gtattttgtt agccaataaa ttcctagcca gtgttgaatg aaaaaaaaaa aaaa | 1134 |

<210> SEQ ID NO 110
<211> LENGTH: 1333

```
<212> TYPE: DNA
<213> ORGANISM: Homo sapiens

<400> SEQUENCE: 110
cactttaaag ctctgctgag ggagttcgga gcccaggctt tcaggcgacc tctgccctcc       60
ctgcctctcc tcaccctccc tctcttcctg cagggcctgg aagggctttt gagggagcct      120
gggagccatg tgaagagggg cacgcctggg ctgtcccaca gtttagatcc agttggaggt      180
tctccctggc tcctgcaggc ctgcggggat ctctccccac ttcaggcctc cggcagctgc      240
ctgccctctt gtctgtgctt cagccctgca caaaagcagc ttggtgacac cactcagcca      300
cccagagtac gtgtttacag gctttccaga tcaccttcct gtggggtgaa cgtaatgagg      360
cggggctggt ccttggaatt tcccctggaa aatggtaaca gactccatcc ttgacccggg      420
gatgagcatg aaggcattgt cccaaaggca gaggccaccg tggtaggaat tccaccaagg      480
ccagaaggga aaaggaaga acccaccgtg tctggctgtg cgggccctgg ggagggtcgt       540
gagtgcagcc cctctctact tcygtgcctt tgtaaaacgt gtagataacc gcagtggttg      600
gctgagccaa gaactctcct aaatcagtgg ctttctcccc accccttgct ggggagtcat      660
ttttaaaaaa atctgtggga tataaaattg gcctcctgct gcttcagcct acctctccct      720
ctgctgactt aatgtcgtga ttctgttct tcagatattt aaggctgtta ggttgtgtga       780
gccttgaagt gtgtgtgtgt gtcccagcga ctgtccactg tccaggagat gcatgtcttt      840
gtattggaga tatttctgta actcattctc ttggtgctca cgattgccat ggccataggg      900
ccacagtgcc gtatctgctg cagacatgat tgtttcttgt tctagaggtt ttcttgtttt      960
cgaatcttgc ctgatgaatc cagccagacc aaggggccta gatttgacct ctgtcctggg     1020
ctcctgggcc aggtgcagga acatctgagg ccactctgct ggccacctcc agtgggtgct     1080
gaccacagga tgggctttgt ttacactcat tttcaccctg attcttgccc ccactttcat     1140
aaaagaaact tcaaaatgct gacgctttgg agagtaagaa aatcaatctt ggctgggcac     1200
ggtggctcct gcctgtgatc ctagcacttt gggaggctga agctgaagga tcacttgagc     1260
tcaggagttg gagaccaacc ctggcaacat aacaagaccc tgtctctaca aaaaaaaaa     1320
aaaaaaaact cga                                                         1333

<210> SEQ ID NO 111
<211> LENGTH: 1015
<212> TYPE: DNA
<213> ORGANISM: Homo sapiens
<220> FEATURE:
<221> NAME/KEY: SITE
<222> LOCATION: (1014)
<223> OTHER INFORMATION: n equals a,t,g, or c

<400> SEQUENCE: 111
ggcacgagcg gcacgagcgg cacgaggtga cttcaagtgt cggatctttt cagcctacat       60
caaggaggtg gaggaacggc cggcacccac cccgtgggct ccaagatgcc ctttggggaa      120
ctgatgttcg aatccagcag tagctgcggc tgggtacatg cgtctgtttt ctcagccagc      180
gggagccgcg tggcctgggt aagccacgac agcaccgtct gcctggctga tgccgacaag      240
aagatgccg tcgcgactct ggcctctgaa acactaccac tgctggcgct gaccttcatc       300
acagacaaca gcctggtggc agcgggccac gactgcttcc cggtgctgtt cacctatgac      360
gccgccgcgg ggatgctgag cttcggcggg cggctggacg ttcctaagca gagctcgcag      420
cgtggcttga cggcccgcga gcgcttccag aacctggaca agaaggcgag ctccgagggt      480
```

-continued

| | |
|---|---|
| ggcacggctg cgggcgcggg cctagactcg ctgcacaaga acagcgtcag ccagatctcg | 540 |
| gtgctcagcg gcggcaaggc caagtgctcg cagttctgca ccactggcat ggatggcggc | 600 |
| atgagtatct gggatgtgaa gagcttggag tcagccttga aggacctcaa gatcaaatga | 660 |
| cctgtgagga atatgttgcc ttcatcctag ctgctgggga agcggggaga ggggtcaggg | 720 |
| aggctaatgg ttgctttgct gaatgtttct ggggtaccaa tacgagttcc cataggggct | 780 |
| gctccctcaa aagggaggg acagatggg gagcttttct tacctattca aggaatacgt | 840 |
| gcctttttct taaatgcttt catttattga aaaaaaaaa aaatgccccc aaagcactat | 900 |
| gctggtcatg aactgcttca aaatgtggag gtaataaaat gcaactgtgt aaaaaaaaaa | 960 |
| aaaaaaaaaa aaaaaaaaaa aaaaaaaaaa aaaaaaaaa aaaaaaaaaa aacnc | 1015 |

<210> SEQ ID NO 112
<211> LENGTH: 711
<212> TYPE: DNA
<213> ORGANISM: Homo sapiens
<220> FEATURE:
<221> NAME/KEY: SITE
<222> LOCATION: (345)
<223> OTHER INFORMATION: n equals a,t,g, or c

<400> SEQUENCE: 112

| | |
|---|---|
| ggcacgagcg aagaccctgt tcggaccctg ccccgattcc agactcaggt agatcgtcgg | 60 |
| cataccctct accgtggaca ccaggcagcc ctggggctga tggagagaga tcaggtatcc | 120 |
| cccagggagt aggggctacc ttgagggat gatagacctc ccccactccc agtgkkactc | 180 |
| tggaaatatg aaggaactag ggagtggaag agatttcaga gctggggaga ggagttcctc | 240 |
| ccttcaaagc cagcaactgc ctttgggaa tgtcgggggg tctctccttt ctcctgcttg | 300 |
| tttraggtgg tacacagtcc ccccttcamc tggsgggaag ctgtnccgga caractcatc | 360 |
| tcagcttttcc cttggggcag gatcggggc agcagctcca gcagaaacag caggatctgg | 420 |
| agcaggaagg cctcgaggcc acacagggc tgctggccgg cgagtgggcc ccaccctct | 480 |
| ggragctggg cagcctcttc caggccttcg tgaagaggga gagccaggct tatgcgtaag | 540 |
| cttcatagct tctgctggcc tggggtggac ccaggacccc tggggcctgg gtgccctgag | 600 |
| tggtggtaaa gtggagcaat cccttcacgc tccttggcca tgttctgagc ggccagcttg | 660 |
| gcctttgcct taataaatgt gctttatttt caaaaaaaaa aaaaaaaaac t | 711 |

<210> SEQ ID NO 113
<211> LENGTH: 1076
<212> TYPE: DNA
<213> ORGANISM: Homo sapiens
<220> FEATURE:
<221> NAME/KEY: SITE
<222> LOCATION: (1029)
<223> OTHER INFORMATION: n equals a,t,g, or c
<220> FEATURE:
<221> NAME/KEY: SITE
<222> LOCATION: (1037)
<223> OTHER INFORMATION: n equals a,t,g, or c
<220> FEATURE:
<221> NAME/KEY: SITE
<222> LOCATION: (1040)
<223> OTHER INFORMATION: n equals a,t,g, or c

<400> SEQUENCE: 113

| | |
|---|---|
| ggcacgaggg gaaagccatg ctcccaggac tccttccttg cagccttaaa tcggtctgta | 60 |
| cggaaaattc cgcgccttag aaacccacgc ttgggtgtaa cttattattg ttcttcctga | 120 |
| cctacttcct gtttatcact tccgggttca tcatttttggc atttcggtga tcgggttgga | 180 |

```
actattgaag cccgctttca ggttcttttc cccatttttcc ctttgaaagg aagacttctg    240
gcttctccta aatctccgtt ctctgggtaa ggggagtcca agcctctgtc atgaggaacg    300
gaaatgcgag ggcctcgggt gttactctaa aatccgccct cagcttgcac gccggaagct    360
gcgattcctg cagcggaaga ggcgtgatct ggccttcgac tcgctatgtc cactaacaat    420
atgtcggacc cacggaggcc gaacaaagtg ctgaggtaca agcccccgcc gagcgaatgt    480
aacccggcct tggacgaccc gacgccggac tacatgaacc tgctgggcat gatcttcagc    540
atgtgcggcc tcatgcttaa gctgaagtgg tgtgcttggg tcgctgtcta ctgctccttc    600
atcagctttg ccaactctcg gagctcggag gacacgaagc aaatgatgag tagcttcatg    660
ctgtccatct ctgccgtggt gatgtcctat ctgcagaatc ctcagcccat gacgccccca    720
tggtgatacc agcctagaag ggtcacattt tggaccctgt ctatccacta ggcctgggct    780
ttggctgcta aacctgctgc cttcagctgc atcctggac ttccctgaat gaggccgtct    840
cggtgccccc agctggatag agggaacctg gcccttttcct agggaacacc ctaggcttac    900
ccctcctgcc tcccttcccc tgcctgctgc tgggggagat gctgtccatg tttctagggg    960
tattcatttg ctttctcgtt gaaacctgtt gttaataaag ttttttcactc tgaaaaaaaa   1020 aaaaaaaana raaaacncgn ggggggggccc ggaacccaat tcsccggata gtgagt       1076
```

<210> SEQ ID NO 114
<211> LENGTH: 1525
<212> TYPE: DNA
<213> ORGANISM: Homo sapiens
<220> FEATURE:
<221> NAME/KEY: SITE
<222> LOCATION: (78)
<223> OTHER INFORMATION: n equals a,t,g, or c

<400> SEQUENCE: 114

```
ccgctgctga taactatggc atcccccggg cctgcaggaa ttcggcacgg agctacggcg     60
ccgcctggct cctgctgnca cctgcaggct cgtcgcgggt ggagcccacc caagacatca    120
gcatcagcga ccagctgggg ggccaggacg tgcccgtgtt ccggaacctg tcccctgctgg   180 tggtgggtgt cggcgccgtg ttctcactgc tattccacct gggcacccgg agaggcgcc    240 ggccgcatgc ggasgagcca ggcgagcaca ccccccctgtt ggcccctgcc acggcccagc    300
ccctgctgct ctggaagcac tggctccggg agcsggcttt ctaccaggtg ggcatactgt    360
acatgaccac caggctcatc gtgaacctgt cccagaccta catggccatg tacctcacct    420
actcgctcca cctgcccaag aagttcatcg cgaccattcc cctggtgatg tacctcagcg    480
gcttcttgtc ctccttcctc atgaagccca tcaacaagtg cattgggagg aacatgacct    540
acttctcagg cctcctggtg atcctggcct ttgccgcctg ggtggcgctg gcggagggac    600
tgggtgtggc cgtgtacgca gcggctgtgc tgctgggtgc tggctgtgcc accatcctcg    660
tcacctcgct ggccatgacg gccgacctca tcggtcccca cacgaacagc ggactktcgt    720
gtacggctcc atgagcttct tggataaggt ggccaatggg ctggcagtca tggccatcca    780
gagcctgcac ccttgcccct cagagctctg ctgcagggcc tgcgtgagct tttaccactg    840
ggcgatggtg gctgtgacgg gcggcgtggg cgtggccgct gccctgtgtc tctgtagcct    900
cctgctgtgg ccgacccgcc tgcgacgctg ggaccgtgat gccggcccct gactcctgac    960
agcctcctgc acctgtgcaa gggaactgtg gggacgcacg aggatgcccc ccarggcctt   1020
ggggaaaagc cccactgcc cctcactctt ctctggaccc ccaccctcca tcctcaccca   1080
```

```
gctcccgggg gtggggtcgg gtgagggcag cagggatgcc cgccagggac ttgcaaggac    1140
cccctgggtt ttgagggtgt cccattctca actctaatcc atcccagccc tctggaggat    1200
ttggggtgcc cctctcggca gggaacagga agtaggaatc ccagaagggt ctgggggaac    1260
cctaaccctg agctcagtcc agttcacccc tcacctccag cctgggggtc tccagacact    1320
gccagggccc cctcaggacg gctggagcct ggaggagaca gccacgggt ggtgggctgg    1380 gcctggaccc caccgtggtg ggcagcaggg ctgcccggca ggcttggtgg actctgctgg    1440
cagcaaataa agagatgacg gcaaaaaaaa aaaaaaaaaa aaaaaaaaaa aaaaaaaaaa    1500
aaaaaaaaaa aaacccaccg tccgc                                          1525
```

<210> SEQ ID NO 115
<211> LENGTH: 1350
<212> TYPE: DNA
<213> ORGANISM: Homo sapiens
<220> FEATURE:
<221> NAME/KEY: SITE
<222> LOCATION: (15)
<223> OTHER INFORMATION: n equals a,t,g, or c
<220> FEATURE:
<221> NAME/KEY: SITE
<222> LOCATION: (1343)
<223> OTHER INFORMATION: n equals a,t,g, or c

<400> SEQUENCE: 115

```
ggcacgagtg cgcangcgtg gggctctctc cttgtcagtc ggcgccgcgt gcgggctggt     60
ggctctgtgg cagcggcggc ggcaggactc cggcactatg agcggcttca gcaccgagga    120
gcgcgccgcg ccttctcct ggagtaccga gtcttcctca aaaatgagaa aggacaatat    180
atatctccat ttcatgatat tccaatttat gcagataagg atgtgtttca catggtagtt    240
gaagtaccac gctggtctaa tgcaaaaatg gagattgcta caaaggaccc tttaaaccct    300
attaaacaag atgtgaaaaa aggaaaactt cgctatgttg cgaatttgtt cccgtataaa    360
ggatatatct ggaactatgg tgccatccct cagacttggg aagacccagg gcacaatgat    420
aaacatactg gctgttgtgg tgacaatgac ccaattgatg tgtgtgaaat tggaagcaag    480
gtatgtgcaa gaggtgaaat aattggcgtg aaagttctag gcatattggc tatgattgac    540 gaagggaaa ccgactggaa agtcattgcc attaatgtgg atgatcctga tgcagccaat    600
tataatgata tcaatgatgt caaacggctg aaacctggct acttagaagc tactgtggac    660
tggtttagaa ggtataaggt tcctgatgga aaaccagaaa atgagtttgc gtttaatgca    720
gaatttaaag ataaggactt tgccattgat attattaaaa gcactcatga ccattggaaa    780
gcattagtga ctaagaaaac gaatggaaaa ggaatcagtt gcatgaatac aactttgtct    840
gagagcccct tcaagtgtga tcctgatgct gccagagcca ttgtggatgc tttaccacca    900
ccctgtgaat ctgcctgcac agtaccaaca gacgtggata agtggttcca tcaccagaaa    960
aactaatgag atttctctgg aatacaagct gatattgcta catcgtgttc atctggatgt   1020
attagaagta aaagtagtag cttttcaaag ctttaaattt gtagaactca tctaactaaa   1080
gtaaattctg ctgtgactaa tccaatatac tcagaatgtt atccatcaa agcattttc    1140 atatctcaac taagataact tttagcacat gcttaaatat caaagcagtt gtcatttgga   1200
agtcacttgt gaatagatgt gcaagggag cacatattgg atgtatatgt taccatatgt   1260
taggaaataa aattattttg ctgaaaaaaa aaaaaaaaa acctsggggg gggscccggt   1320
ccccatttgg ccctttgggg ggnggtttta                                    1350
```

<210> SEQ ID NO 116
<211> LENGTH: 2527
<212> TYPE: DNA
<213> ORGANISM: Homo sapiens

<400> SEQUENCE: 116

| | | | | | |
|---|---|---|---|---|---|
| ctcttgctac | cttcccggcg | cagagaaccc | cggctgctca | gcgcgctccg | gggtcatgga | 60 |
| gatccccggg | agcctgtgca | agaaagtcaa | gctgagcaat | aacgcgcaga | actgggaat | 120 |
| gcagagagca | accaatgtca | cctaccaagc | ccatcatgtc | agcaggaaca | agagaggtca | 180 |
| ggtggtgggg | accagaggtg | gctttcgtgg | ttgcacagtt | tggctaacag | gcttgtctgg | 240 |
| agcgggaaag | actactgtga | gcatggcctt | ggaggagtac | ctggtttgtc | atggtattcc | 300 |
| atgctacact | ctggatggtg | acaatattcg | tcaaggtctc | aataaaaatc | ttggctttag | 360 |
| tcctgaagac | agagaagaga | atgttcgacg | catcgcagaa | gttgctaaac | tgtttgcaga | 420 |
| tgctggctta | gtgtgcatca | caagtttcat | atcaccttac | actcaggatc | gcaacaatgc | 480 |
| aaggcaaatt | catgaaggtg | caagtttacc | gttttttgaa | gtatttgttg | atgctcctct | 540 |
| gcatgtttgt | gaacagaggg | atgtcaaagg | actctacaaa | aaagcccggg | caggagaaat | 600 |
| taaaggtttc | actgggatcg | attctgaata | tgaaaagcca | gaggcccctg | agttggtgct | 660 |
| gaaaacagac | tcctgtgatg | taaatgactg | tgtccagcaa | gttgtggaac | ttctacagga | 720 |
| acgggatatt | gtacctgtgg | atgcatctta | tgaagtaaaa | gaactatatg | tgccagaaaa | 780 |
| taaacttcat | ttggcaaaaa | cagatgcgga | acattacca | gcactgaaaa | ttaataaagt | 840 |
| ggatatgcag | tgggtgcagg | ttttggcaga | aggttgggca | accccattga | atggcttat | 900 |
| gagagagagg | gagtacttgc | agtgccttca | ttttgattgt | cttctggatg | gaggtgtcat | 960 |
| taacttgtca | gtacctatag | ttctgactgc | gactcatgaa | gataaagaga | ggctggacgg | 1020 |
| ctgtacagca | tttgctctga | tgtatgaggg | ccgccgtgtg | gccattcttc | gcaatccaga | 1080 |
| gttttttgag | cacaggaaag | aggagcgctg | tgccagacag | tggggaacga | catgcaagaa | 1140 |
| ccaccctat | attaagatgg | tgatggaaca | aggagattgg | ctgattggag | gagatcttca | 1200 |
| agtcttggat | cgagtttatt | ggaatgatgg | tcttgatcag | tatcgtctta | ctcctactga | 1260 |
| gctaaagcag | aaatttaaag | atatgaatgc | tgatgctgtc | tttgcatttc | aactacgcaa | 1320 |
| cccagtgcac | aatggacatg | ccctgttaat | gcaggatacc | cataagcaac | ttctagagag | 1380 |
| gggctaccgg | cgccctgtcc | tcctcctcca | ccctctgggt | ggctggacaa | aggatgacga | 1440 |
| tgttcctttg | atgtggcgta | tgaagcagca | tgctgcagtg | ttggaggaag | gagttctgaa | 1500 |
| tcctgagacg | acagtggtgg | ccatcttccc | atctcccatg | atgtatgctg | gaccaactga | 1560 |
| ggtccagtgg | cattgcagag | cacggatggt | tgcaggagcc | aacttttaca | ttgttggacg | 1620 |
| agaccctgct | ggcatgcctc | atccagaaac | agggaaggat | ctttatgagc | caagtcatgg | 1680 |
| tgccaaagtg | ctgacgatgg | cccctggttt | aatcactttg | gaaatagttc | cctttcgagt | 1740 |
| tgcagcttac | aacaagaaaa | agaagcgtat | ggactactat | gactctgaac | accatgaaga | 1800 |
| ctttgaattt | atttcaggaa | cacgaatgcg | caaacttgct | cgagaaggcc | agaaaccacc | 1860 |
| tgaaggtttc | atggctccca | aggcttggac | cgtgctgaca | gaatactaca | aatccttgga | 1920 |
| gaaagcttag | gctgttaacc | cagtcactcc | acctttgaca | cattactagt | aacaagaggg | 1980 |
| gaccacatag | tctctgttgg | catttctttg | tggtgtctgt | ctggacatgc | ttcctaaaaa | 2040 |
| cagaccattt | tccttaactt | gcatcagttt | tggtctgcct | tatgagttct | gttttgaaca | 2100 |
| agtgtaacac | actgatggtt | ttaatgtatc | ttttccactt | attatagtta | tattcctaca | 2160 |

-continued

```
atacaatttt aaaattgtct ttttatatta tatttatgct tctgtgtcat gatttttca    2220 agctgttata ttagttgtaa ccagtagtat tcacattaaa tcttgctttt tttcccctta   2280
aaaaaagaaa aaaattacca aacaataaac ttggctagac cttgttttga ggattttaca   2340
agacctttgt agcgattaga tttttttcct acattgaaaa tagaaactgc ttcctttctt   2400
ctttccagtc agctattggt ctttccagct gttataatct aaagtattct tatgatctgt   2460
gtaagctctg aatgaacttc tttactcaat aaaattaatt ttttggcttc ttaaaaaaaa   2520
aaaaaaa                                                             2527
```

<210> SEQ ID NO 117
<211> LENGTH: 1098
<212> TYPE: DNA
<213> ORGANISM: Homo sapiens
<220> FEATURE:
<221> NAME/KEY: SITE
<222> LOCATION: (88)
<223> OTHER INFORMATION: n equals a,t,g, or c
<220> FEATURE:
<221> NAME/KEY: SITE
<222> LOCATION: (89)
<223> OTHER INFORMATION: n equals a,t,g, or c

<400> SEQUENCE: 117

```
cgcatcacag acaacccaga aggaaaatgg ttgggcagaa cagcaagggg ttcatatggc     60
tatattaaaa caactgctgt agagattnnc tatgattctt tgaaactgaa aaaagactct   120
cttggtgccc cttcaagacc tattgaagat gaccaagaag tatatgatga tgttgcagag   180
caggatgata ttagcagcca cagtcagagt ggaagtggag ggatattccc tccaccacca   240
gatgatgaca tttatgatgg gattgaagag gaagatgctg atgatggttt ccctgctcct   300
cctaaacaat tggacatggg agatgaagtt tacgatgatg tggatacctc tgatttccct   360
gtttcatcag cagagatgag tcaaggaact aatgttggaa aagctaagac agaagaaaag   420
gaccttaaga agctaaaaaa gcagraaaaa gaaraaaaag acttcaggaa aaaatttaaa   480
tatgatggtg aaattagagt cctatattca actaaagtta caacttccat aacttctaaa   540
aagtggggaa ccagagatct acaggtaaaa cctggtgaat ctctagaagt tatacaaacc   600
acagatgaca caaagttct ctgcagaaat gaagaaggga aatatggtta tgtccttcgg   660
agttacctag cggacaatga tggagagatc tatgatgata ttgctgatgg ctgcatctat   720
gacaatgact agcactcaac tttggtcatt ctgctgtgtt cattaggtgc caatgtgaag   780
tctggatttt aattggcatg ttattgggta tcmagaaaat taatgcacar aaccacttat   840
tatcatttgt tatgaaatcc caattatctt tacaaagtgt ttaaagtttg aacatagaaa   900
ataatctctc tgcttaattg ttatctcaga agactacatt agtgagatgt aagaattatt   960
aaatattcca tttccgcttt ggctacaatt atgaagaagt tgaaggtact tcttttagac  1020
caccagtaaa taatcctcct tcaaaaaata aaataaaaa aaaaaaaaa aaactcgagg   1080 gggggcccgg tacccaat                                                1098
```

<210> SEQ ID NO 118
<211> LENGTH: 1679
<212> TYPE: DNA
<213> ORGANISM: Homo sapiens
<220> FEATURE:
<221> NAME/KEY: SITE
<222> LOCATION: (1679)
<223> OTHER INFORMATION: n equals a,t,g, or c

<400> SEQUENCE: 118

-continued

```
tcgacccacg cgtccggcga gatccctacc gcagtagccg cctctgccgc cgcggagctt    60
cccgaacctc ttcagccgcc cggagccgct cccggagccc ggccgtagag gctgcaatcg   120
cagccgggag cccgcagccc gcgccccgag ccgccgccg cccttcgagg gcgccccagg    180
ccgcgccatg gtgaaggtga cgttcaactc cgctctggcc cagaaggagg ccaagaagga   240
cgagcccaag agcggcgagg aggcgctcat catcccccc gacgccgtcg cggtggactg    300
caaggaccca gatgatgtgg taccagttgg ccaaagaaga gcctggtgtt ggtgcatgtg   360
ctttggacta gcatttatgc ttgcaggtgt tattctagga ggagcatact tgtacaaata   420
ttttgcactt caaccagatg acgtgtacta ctgtggaata aagtacatca agatgatgt    480 catcttaaat gagccctctg cagatgcccc agctgctctc taccagacaa ttgaagaaaa   540
tattaaaatc tttgaagaag aagaagttga atttatcagt gtgcctgtcc cagagtttgc   600
agatagtgat cctgccaaca ttgttcatga ctttaacaag aaactacag cctatttaga    660 tcttaacctg gataagtgct atgtgatccc tctgaacact tccattgtta tgccacccag   720
aaacctactg gagttactta ttaacatcaa ggctggaacc tatttgcctc agtcctatct   780
gattcatgag cacatggtta ttactgatcg cattgaaaac attgatcacc tgggtttctt   840
tatttatcga ctgtgtcatg acaaggaaac ttacaaactg caacgcagag aaactattaa   900
aggtattcag aaacgtgaag ccagcaattg tttcgcaatt cggcattttg aaaacaaatt   960
tgccgtggaa actttaattt gttcttgaac agtcaagaaa aacattattg aggaaaatta  1020
atatcacagc ataaccccac cctttacatt ttgtgcagtg attattttt aaagtcttct   1080 ttcatgtaag tagcaaacag ggctttacta tctttcatc tcattaattc aattaaaacc   1140
attaccttaa aatttttttc tttcgaagtg tggtgtcttt tatatttgaa ttagtaactg   1200
tatgaagtca tagataatag tacatgtcac cttaggtagt aggaagaatt acaatttctt   1260
taaatcattt atctggattt ttatgtttta ttagcatttt caagaagacg gattatctag   1320
agaataatca tatatatgca tacgtaaaaa tggaccacag tgacttattt gtagttgtta   1380
gttgccctgc tacctagttt gttagtgcat ttgagcacac atttttaattt tcctctaatt  1440 aaaatgtgca gtattttcag tgtcaaatat atttaactat ttagagaatg atttccacct   1500
ttatgtttta atatcctagg catctgctgt aataatattt tagaaaatgt ttggaattta   1560
agaaataact tgtgttacta atttgtataa cccatatctg tgcaatggaa tataaatatc   1620
acaaagttgt ttaamwaaaa aaaaaaaaaa aaaaaaaaaa aaaaaaaaa aaaaaaaan   1679
```

<210> SEQ ID NO 119
<211> LENGTH: 1411
<212> TYPE: DNA
<213> ORGANISM: Homo sapiens
<220> FEATURE:
<221> NAME/KEY: SITE
<222> LOCATION: (1391)
<223> OTHER INFORMATION: n equals a,t,g, or c
<220> FEATURE:
<221> NAME/KEY: SITE
<222> LOCATION: (1403)
<223> OTHER INFORMATION: n equals a,t,g, or c

<400> SEQUENCE: 119

```
ggcacaggag cgacccggga gaaggagggc camgakgcgg aagcggagga gtctccagga    60
gacccgggga cagcatcgcc caggcccctg tttgcaggcc tttcagatat atccatctca   120
caagacatcc ccgtagaagg agaaatcacc attcctatga gatctcgcat ccgggagttt   180
```

-continued

| | |
|---|---|
| gacagctcca cattaaatga atctgttcgc aataccatca tgcgtgatct aaaagctgtt | 240 |
| gggaaaaaat tcatgcatgt tttgtaccca aggaaaagta atactctttt gagagattgg | 300 |
| gatttgtggg gcccttttgat cctttgtgtg cactcgcat taatgctgca aagagactct | 360 |
| gcagatagtg aaaagatgg agggcccaa tttgcagagg tgtttgtcat tgtctggttt | 420 |
| ggtgcagtta ccatcaccct caactcaaaa cttcttggag ggaacatatc ttttttcag | 480 |
| agcctctgtg tgctgggtta ctgtatactt cccttgacag tagcaatgct gatttgccgg | 540 |
| ctggtacttt tggctgatcc aggacctgta aacttcatgg ttcggctttt tgtggtgatt | 600 |
| gtgatgtttg cctggtctat agttgcctcc acagctttcc ttgctgatag ccagcctcca | 660 |
| aaccgcagag ccctagctgt ttatcctgtt ttcctgtttt actttgtcat cagttggatg | 720 |
| attctcacct ttactcctca gtaaatcagg aatgggaaat taaaaaccag tgaattgaaa | 780 |
| gcacatctga agatgcaat tcaccatgga gctttgtctc tggcccttat ttgtctaatt | 840 |
| ttggaggtat ttgataactg agtaggtgag gagattaaaa gggagccata tagcactgtc | 900 |
| accccttatt tgaggaactg atgtttgaaa ggctgttctt ttctctctta atgtcatttc | 960 |
| tttaaaaata catgtgcata ctacacacag tatataatgc ctccttaagg catgatggag | 1020 |
| tcaccgtggt ccatttgggt gacaaccagt gacttgggaa gcacatagat acatcttaca | 1080 |
| agttgaatag agttgataac tattttcagt tttgagaata ccagtcagg tgcagctctt | 1140 |
| aaacacattg ccttatgact attagaatat gcctctcttt tcataaataa aaatacatgg | 1200 |
| tctatatcca ttttctttta tttctctctc ttaagcttaa aaaggcaatg agagaggtta | 1260 |
| ggagtgggtt catacacgga gaatgagaaa acatgcatta accaatattc agattttgat | 1320 |
| cagggggaaat tctayacttg ttgcaaaaaa aaaaaaaaaa aaactcgagg ggggcccggt | 1380 |
| acccaatcgc ngtatatgat cgnaaacaat c | 1411 |

<210> SEQ ID NO 120
<211> LENGTH: 2223
<212> TYPE: DNA
<213> ORGANISM: Homo sapiens
<220> FEATURE:
<221> NAME/KEY: SITE
<222> LOCATION: (338)
<223> OTHER INFORMATION: n equals a,t,g, or c
<220> FEATURE:
<221> NAME/KEY: SITE
<222> LOCATION: (2206)
<223> OTHER INFORMATION: n equals a,t,g, or c
<220> FEATURE:
<221> NAME/KEY: SITE
<222> LOCATION: (2209)
<223> OTHER INFORMATION: n equals a,t,g, or c

<400> SEQUENCE: 120

| | |
|---|---|
| cctccggaag cgtttccaac tttccagaag tttctcggga cgggcaggag ggggtgggga | 60 |
| ctgccatata tagatcccgg gagcagggga gcgggctaag agtagaatcg tgtcgcggct | 120 |
| cgagagcgag agtcacgtcc cggcgctagc cagcccgacc caggcccacc gtggtgcacg | 180 |
| caaaccactt cctggccatg cgctcccctcc tgcttctcag cgccttctgc ctcctggagg | 240 |
| cggccctggc cgccgaggtg aagaaacctg cagccgcagc agctcctggc actgcggaga | 300 |
| agttgagccc caaggcggcc acgcttgccg agcgcagncg gcctggcctt cagcttgtac | 360 |
| caggccatgg ccaaggacca ggcagtggag aacatcctgg tgtcacccgt ggtggtggcc | 420 |
| tcgtcgctgg ggctcgtgtc gctgggcgga aaggcgacca cggcgtcgca ggccaaggca | 480 |
| gtgctgagcg ccgagcagct gcgcgacgag gaggtgcacg ccggcctggg cgagctgctg | 540 |

-continued

```
cgctcactca gcaactcsac ggcgcgcaac gtgacctgga agctgggcag ccgactgtac      600
ggacccagct cagtgagctt cgctgatgac ttcgtgcgca cagcaagcag cactacaact      660
gcgagcactc caagatcaac ttccgcgaca agcgcacgcg ctgcagtcca tcaacgagtg      720
ggccgcgcag accaccgacg gcaagctgcc cgaggtcacc aaggacgtgg agcgcacgga      780
cggcgccctg ytagtcaacg ccatgttctt caagccacac tgggatgaga aattccacca      840
caagatggtg gacaaccgtg gcttcatggt gactcggtcc tatacygtgg gtgtcatgat      900
gatgcaccgg acaggcctct acaactacta cgacgacgag aaggaaaagc tgcaaatcgt      960
ggagatgccc ctggcccaca gctctccag cctcatcatc ctcatgcccc atcacgtgga      1020
gcctctcgag cgccttgaaa agctgctaac caaagagcag ctgaagatct ggatggggaa      1080
gatgcagaag aaggctgttg ccatctcctt gcccaagggt gtggtggagg tgacccatga      1140
cctgcagaaa cacctggctg ggctgggcct gactgaggcc attgacaaga acaaggccga      1200
cttrtcacgc atgtcaggca agaaggacct gtacctggcc agcgtgttcc acgccaccgc      1260
ctttgagttg gacacagatg caacccctt tgaccaggac atctacgggc gcgaggagct      1320
gcgcascccca agctgttcta cgccgaccac cccttcatct tcctagtgcg ggacacccaa      1380
agcggctccc tgctattcat tgggcgcctg gtccggccta agggtgacaa gatgcgagac      1440
gagttatagg gcctcagggt gcacacagga tggcaggagg catccaaagg ctcctgagac      1500
acatgggtgc tattgggtt ggggggagg tgaggtacca gccttggata ctccatgggg      1560
tgggggtgga aaarcagacc ggggttcccg tgtgcctgag cggaccttcc cagctagaat      1620
tcactccact tggacatggg ccccagatac catgatgctg agcccggaaa ctccacatcc      1680
tgtgggacct gggccatagt cattctgcct gccctgaaag tcccagatca agcctgcctc      1740
aatcagtatt catatttata gccaggtacc ttctcacctg tgagaccaaa ttgagctagg      1800
ggggtcagcc agccctcttc tgacactaaa acacctcagc tgcctcccca gctctatccc      1860
aacctctccc aactataaaa ctaggtgctg cagcccctgg gaccaggcac cccagaatg      1920
acctggccgc agtgaggcgg attgagaagg agctcccagg aggggcttct gggcagactc      1980
tggtcaagaa gcatcgtgtc tggcgttgtg gggatgaact ttttgttttg tttcttcctt      2040
ttttagttct tcaaagatag ggagggaagg gggaacatga gcctttgttg ctatcaatcc      2100
aagaacttat ttgtacattt ttttttttcaa taaaactttt ccaatgacaa aaaaaaaaa      2160
aaaaaaaaaa mwmggggsgg gccgctccta gagggatccc tccganggng cccaatcgaa      2220
aat                                                                   2223
```

<210> SEQ ID NO 121
<211> LENGTH: 31
<212> TYPE: PRT
<213> ORGANISM: Homo sapiens

<400> SEQUENCE: 121

Met Lys Lys Gln Ser Lys Arg Cys Leu Trp Lys Pro Pro Gly Ser Leu
1               5                   10                  15

Arg Arg Leu Trp Trp Met Arg Ala Leu Leu Ile Leu Lys Tyr Ile
            20                  25                  30

<210> SEQ ID NO 122
<211> LENGTH: 198
<212> TYPE: PRT
<213> ORGANISM: Homo sapiens
<220> FEATURE:

```
<221> NAME/KEY: SITE
<222> LOCATION: (29)
<223> OTHER INFORMATION: Xaa equals any of the naturally occurring
      L-amino acids

<400> SEQUENCE: 122

Met Lys Lys Ser Leu Glu Asn Leu Asn Arg Leu Gln Val Met Leu Leu
 1               5                   10                  15

His Leu Thr Ala Ala Phe Leu Gln Arg Ala Gln His Xaa Phe Asp Tyr
            20                  25                  30

Lys Asp Glu Ser Gly Phe Pro Lys Pro Pro Ser Tyr Asn Val Ala Thr
        35                  40                  45

Thr Leu Pro Ser Tyr Asp Glu Ala Glu Arg Thr Lys Ala Glu Ala Thr
    50                  55                  60

Ile Pro Leu Val Pro Gly Arg Asp Glu Asp Phe Val Gly Arg Asp Asp
65                  70                  75                  80

Phe Asp Asp Ala Asp Gln Leu Arg Ile Gly Asn Asp Gly Ile Phe Met
                85                  90                  95

Leu Thr Phe Phe Met Ala Phe Leu Phe Asn Trp Ile Gly Phe Phe Leu
            100                 105                 110

Ser Phe Cys Leu Thr Thr Ser Ala Ala Gly Arg Tyr Gly Ala Ile Ser
        115                 120                 125

Gly Phe Gly Leu Ser Leu Ile Lys Trp Ile Leu Ile Val Arg Phe Ser
130                 135                 140

Thr Tyr Phe Pro Gly Tyr Phe Asp Gly Gln Tyr Trp Leu Trp Trp Val
145                 150                 155                 160

Phe Leu Val Leu Gly Phe Leu Leu Phe Leu Arg Gly Phe Ile Asn Tyr
                165                 170                 175

Ala Lys Val Arg Lys Met Pro Glu Thr Phe Ser Asn Leu Pro Arg Thr
            180                 185                 190

Arg Val Leu Phe Ile Tyr
        195

<210> SEQ ID NO 123
<211> LENGTH: 39
<212> TYPE: PRT
<213> ORGANISM: Homo sapiens

<400> SEQUENCE: 123

Met His Asn Gln Arg Gln Val Phe Leu Phe His Leu Phe Ser Asn Tyr
 1               5                   10                  15

Leu Leu Ser Ile Asn Ser Val Pro Gly Thr Leu Leu Ala Ala Thr Tyr
            20                  25                  30

Cys Leu Asn Met Thr Tyr Gly
            35

<210> SEQ ID NO 124
<211> LENGTH: 23
<212> TYPE: PRT
<213> ORGANISM: Homo sapiens

<400> SEQUENCE: 124

Met Arg Lys Lys Phe Leu Leu Ala Gln Val Phe Leu Ser Leu Ser Val
 1               5                   10                  15

Met Pro Ser Met Pro Val Thr
            20

<210> SEQ ID NO 125
```

```
<211> LENGTH: 110
<212> TYPE: PRT
<213> ORGANISM: Homo sapiens

<400> SEQUENCE: 125

Met Val Leu Leu Cys Leu Leu Leu Val Pro Leu Leu Leu Ser Leu Phe
 1               5                  10                  15

Val Leu Gly Leu Phe Leu Trp Phe Leu Lys Arg Glu Arg Gln Glu Glu
            20                  25                  30

Tyr Ile Glu Glu Lys Lys Arg Val Asp Ile Cys Arg Glu Thr Pro Asn
        35                  40                  45

Ile Cys Pro His Ser Gly Glu Asn Thr Glu Tyr Asp Thr Ile Pro His
    50                  55                  60

Thr Asn Arg Thr Ile Leu Lys Glu Asp Pro Ala Asn Thr Val Tyr Ser
65                  70                  75                  80

Thr Val Glu Ile Pro Lys Lys Met Glu Asn Pro His Ser Leu Leu Thr
                85                  90                  95

Met Pro Asp Thr Pro Arg Leu Phe Ala Tyr Glu Asn Val Ile
            100                 105                 110

<210> SEQ ID NO 126
<211> LENGTH: 63
<212> TYPE: PRT
<213> ORGANISM: Homo sapiens

<400> SEQUENCE: 126

Met Leu Leu Leu Phe Ile Tyr Phe Tyr Ser His Pro Ala Pro Val Pro
 1               5                  10                  15

Ala Gly Ala Thr Ser Lys Pro Arg Tyr Arg Val Ile Thr Cys Gly Pro
            20                  25                  30

Ala Ser Val Phe Ser Thr Ser Phe Ser His Ser Pro Pro Ala Arg Cys
        35                  40                  45

Leu Gly Arg Leu Glu Gln Met Phe His Phe Gly Leu Ala Ser Gly
    50                  55                  60

<210> SEQ ID NO 127
<211> LENGTH: 30
<212> TYPE: PRT
<213> ORGANISM: Homo sapiens

<400> SEQUENCE: 127

Met Pro Phe Pro Ile Ser Ile Leu Gln Leu Cys Leu Gln Ile Ser Asn
 1               5                  10                  15

Leu Ser Phe Cys Leu Gln Lys Ile Tyr Lys Ile Pro Phe Val
            20                  25                  30

<210> SEQ ID NO 128
<211> LENGTH: 53
<212> TYPE: PRT
<213> ORGANISM: Homo sapiens

<400> SEQUENCE: 128

Met Ala Ala Ala Cys Arg Ser Val Lys Gly Leu Val Ala Val Ile Thr
 1               5                  10                  15

Gly Gly Ala Ser Gly Leu Gly Leu Ala Thr Ala Asp Asp Leu Trp Gly
            20                  25                  30

Arg Glu Pro Leu Leu Cys Phe Trp Thr Cys Pro Thr Arg Val Gly Arg
        35                  40                  45

Pro Lys Pro Arg Ser
    50
```

<210> SEQ ID NO 129
<211> LENGTH: 57
<212> TYPE: PRT
<213> ORGANISM: Homo sapiens
<220> FEATURE:
<221> NAME/KEY: SITE
<222> LOCATION: (10)
<223> OTHER INFORMATION: Xaa equals any of the naturally occurring
      L-amino acids
<220> FEATURE:
<221> NAME/KEY: SITE
<222> LOCATION: (28)
<223> OTHER INFORMATION: Xaa equals any of the naturally occurring
      L-amino acids

<400> SEQUENCE: 129

Met Leu Leu Val Tyr Asp Leu Tyr Leu Xaa Pro Lys Leu Trp Ala Leu
 1               5                  10                  15

Ala Thr Pro Gln Lys Asn Gly Lys Gly Ala Arg Xaa Gly Asp Gly Thr
            20                  25                  30

Pro Ala Gln Ala Phe Trp Asp Phe Trp Ser His Leu Ile Ser Ala Asp
        35                  40                  45

Pro Gln Thr Trp Glu Arg Ala Ala Pro
    50                  55

<210> SEQ ID NO 130
<211> LENGTH: 216
<212> TYPE: PRT
<213> ORGANISM: Homo sapiens

<400> SEQUENCE: 130

Met Arg Leu Ser Ala Leu Leu Ala Leu Ser Lys Val Thr Leu Pro
 1               5                  10                  15

Pro His Tyr Arg Tyr Gly Met Ser Pro Pro Gly Ser Val Ala Asp Lys
            20                  25                  30

Arg Lys Asn Pro Pro Trp Ile Arg Arg Arg Pro Val Val Glu Pro
        35                  40                  45

Ile Ser Asp Glu Asp Trp Tyr Leu Phe Cys Gly Asp Thr Val Glu Ile
 50                  55                  60

Leu Glu Gly Lys Asp Ala Gly Lys Gln Gly Lys Val Val Gln Val Ile
 65                  70                  75                  80

Arg Gln Arg Asn Trp Val Val Val Gly Gly Leu Asn Thr His Tyr Arg
                 85                  90                  95

Tyr Ile Gly Lys Thr Met Asp Tyr Arg Gly Thr Met Ile Pro Ser Glu
            100                 105                 110

Ala Pro Leu Leu His Arg Gln Val Lys Leu Val Asp Pro Met Asp Arg
        115                 120                 125

Lys Pro Thr Glu Ile Glu Trp Arg Phe Thr Glu Ala Gly Glu Arg Val
    130                 135                 140

Arg Val Ser Thr Arg Ser Gly Arg Ile Ile Pro Lys Pro Glu Phe Pro
145                 150                 155                 160

Arg Ala Asp Gly Ile Val Pro Glu Thr Trp Ile Asp Gly Pro Lys Asp
                165                 170                 175

Thr Ser Val Glu Asp Ala Leu Glu Arg Thr Tyr Val Pro Cys Leu Lys
            180                 185                 190

Thr Leu Gln Glu Glu Val Met Glu Ala Met Gly Ile Lys Glu Thr Arg
        195                 200                 205

```
Lys Tyr Lys Lys Val Tyr Trp Tyr
    210             215
```

<210> SEQ ID NO 131
<211> LENGTH: 49
<212> TYPE: PRT
<213> ORGANISM: Homo sapiens

<400> SEQUENCE: 131

```
Met Ser Leu Arg Gln Lys Ser Ser Phe Arg Leu Met Val Met Ser Leu
 1               5                  10                  15

Thr Ile Leu Lys Leu Ser Lys Thr Thr Val Leu Cys Leu Arg Cys Leu
            20                  25                  30

His Ser Leu Lys Leu Thr Trp Arg Asp Gly Ala Arg Cys Ile Asn Ala
        35                  40                  45

Glu
```

<210> SEQ ID NO 132
<211> LENGTH: 68
<212> TYPE: PRT
<213> ORGANISM: Homo sapiens

<400> SEQUENCE: 132

```
Met Ser Gly Ser Phe Ile Leu Cys Leu Ala Leu Val Thr Arg Trp Ser
 1               5                  10                  15

Pro Gln Ala Ser Ser Val Pro Leu Ala Val Tyr Glu Ser Lys Thr Arg
            20                  25                  30

Lys Ser Tyr Arg Ser Gln Arg Asp Arg Asp Gly Lys Asp Arg Ser Gln
        35                  40                  45

Gly Met Gly Leu Ser Leu Leu Val Glu Thr Arg Lys Leu Leu Leu Ser
    50                  55                  60

Ala Asn Gln Gly
 65
```

<210> SEQ ID NO 133
<211> LENGTH: 52
<212> TYPE: PRT
<213> ORGANISM: Homo sapiens

<400> SEQUENCE: 133

```
Met Cys Phe Arg Phe Phe Leu Phe Cys Ser Arg Ile Leu Leu Lys Leu
 1               5                  10                  15

Phe Phe Leu Leu Phe Pro Ala Ser Ala Phe Pro Leu Ser Thr Arg Ser
            20                  25                  30

Ser Leu Ser Val Asn Glu His Val Val Val Ser Pro Arg Ser Thr Val
        35                  40                  45

Ser Ile Ser Arg
    50
```

<210> SEQ ID NO 134
<211> LENGTH: 540
<212> TYPE: PRT
<213> ORGANISM: Homo sapiens
<220> FEATURE:
<221> NAME/KEY: SITE
<222> LOCATION: (137)
<223> OTHER INFORMATION: Xaa equals any of the naturally occurring
      L-amino acids

<400> SEQUENCE: 134

```
Met Val Arg Thr Asp Gly His Thr Leu Ser Glu Lys Arg Asn Tyr Gln
```

```
         1               5                 10                15
Val Thr Asn Ser Met Phe Gly Ala Ser Arg Lys Lys Phe Val Glu Gly
                20                  25                  30

Val Asp Ser Asp Tyr His Asp Glu Asn Met Tyr Tyr Ser Gln Ser Ser
                35                  40                  45

Met Phe Pro His Arg Ser Glu Lys Asp Met Leu Ala Ser Pro Ser Thr
                50                  55                  60

Ser Gly Gln Leu Ser Gln Phe Gly Ala Ser Leu Tyr Gly Gln Gln Ser
 65                  70                  75                  80

Ala Leu Gly Leu Pro Met Arg Gly Met Ser Asn Asn Thr Pro Gln Leu
                85                  90                  95

Asn Arg Ser Leu Ser Gln Gly Thr Gln Leu Pro Ser His Val Thr Pro
                100                 105                 110

Thr Thr Gly Val Pro Thr Met Ser Leu His Thr Pro Ser Pro Ser
                115                 120                 125

Arg Gly Ile Leu Pro Met Asn Pro Xaa Asn Met Met Asn His Ser Gln
 130                 135                 140

Val Gly Gln Gly Ile Gly Ile Pro Ser Arg Thr Asn Ser Met Ser Ser
145                  150                 155                 160

Ser Gly Leu Gly Ser Pro Asn Arg Ser Ser Pro Ser Ile Ile Cys Met
                165                 170                 175

Pro Lys Gln Gln Pro Ser Arg Gln Pro Phe Thr Val Asn Ser Met Ser
                180                 185                 190

Gly Phe Gly Met Asn Arg Asn Gln Ala Phe Gly Met Asn Asn Ser Leu
                195                 200                 205

Ser Ser Asn Ile Phe Asn Gly Thr Asp Gly Ser Glu Asn Val Thr Gly
 210                 215                 220

Leu Asp Leu Ser Asp Phe Pro Ala Leu Ala Asp Arg Asn Arg Arg Glu
225                  230                 235                 240

Gly Ser Gly Asn Pro Thr Pro Leu Ile Asn Pro Leu Ala Gly Arg Ala
                245                 250                 255

Pro Tyr Val Gly Met Val Thr Lys Pro Ala Asn Glu Gln Ser Gln Asp
                260                 265                 270

Phe Ser Ile His Asn Glu Asp Phe Pro Ala Leu Pro Gly Ser Ser Tyr
                275                 280                 285

Lys Asp Pro Thr Ser Ser Asn Asp Asp Ser Lys Ser Asn Leu Asn Thr
                290                 295                 300

Ser Gly Lys Thr Thr Ser Ser Thr Asp Gly Pro Lys Phe Pro Gly Asp
305                  310                 315                 320

Lys Ser Ser Thr Thr Gln Asn Asn Asn Gln Gln Lys Lys Gly Ile Gln
                325                 330                 335

Val Leu Pro Asp Gly Arg Val Thr Asn Ile Pro Gln Gly Met Val Thr
                340                 345                 350

Asp Gln Phe Gly Met Ile Gly Leu Leu Thr Phe Ile Arg Ala Ala Glu
                355                 360                 365

Thr Asp Pro Gly Met Val His Leu Ala Leu Gly Ser Asp Leu Thr Thr
                370                 375                 380

Leu Gly Leu Asn Leu Asn Ser Pro Glu Asn Leu Tyr Pro Lys Phe Ala
385                  390                 395                 400

Ser Pro Trp Ala Ser Pro Cys Arg Pro Gln Asp Ile Asp Phe His
                405                 410                 415

Val Pro Ser Glu Tyr Leu Thr Asn Ile His Ile Arg Asp Lys Leu Ala
                420                 425                 430
```

```
Ala Ile Lys Leu Gly Arg Tyr Gly Glu Asp Leu Leu Phe Tyr Leu Tyr
            435                 440                 445

Tyr Met Asn Gly Gly Asp Val Leu Gln Leu Leu Ala Ala Val Glu Leu
        450                 455                 460

Phe Asn Arg Asp Trp Arg Tyr His Lys Glu Glu Arg Val Trp Ile Thr
465                 470                 475                 480

Arg Ala Pro Gly Met Glu Pro Thr Met Lys Thr Asn Thr Tyr Glu Arg
                485                 490                 495

Gly Thr Tyr Tyr Phe Phe Asp Cys Leu Asn Trp Arg Lys Val Ala Lys
                500                 505                 510

Glu Phe His Leu Glu Tyr Asp Lys Leu Glu Glu Arg Pro His Leu Pro
            515                 520                 525

Ser Thr Phe Asn Tyr Asn Pro Ala Gln Gln Ala Phe
            530                 535                 540

<210> SEQ ID NO 135
<211> LENGTH: 57
<212> TYPE: PRT
<213> ORGANISM: Homo sapiens

<400> SEQUENCE: 135

Met Ile Cys Pro Gln Cys Pro Leu Ser Leu Leu Cys Leu Ile Ser Ser
1               5                   10                  15

Leu Cys Ser Leu Val Ile Gln Ile Ser Leu Lys Thr Ile Arg Asp Ile
                20                  25                  30

Thr Leu Leu Asn Met Val Gly Ile Lys Phe Ser Ile Ser Leu Ser Asn
            35                  40                  45

Lys Ile Asn Ile Asn Ser Arg Thr Trp
        50                  55

<210> SEQ ID NO 136
<211> LENGTH: 201
<212> TYPE: PRT
<213> ORGANISM: Homo sapiens

<400> SEQUENCE: 136

Met Thr Leu Arg Pro Ser Leu Pro Leu His Leu Leu Leu Leu Leu Leu
1               5                   10                  15

Leu Leu Ser Ala Ala Val Cys Arg Ala Glu Ala Gly Leu Glu Thr Glu
                20                  25                  30

Ser Pro Val Arg Thr Leu Gln Val Glu Thr Leu Val Glu Pro Pro Glu
            35                  40                  45

Pro Cys Ala Glu Pro Ala Ala Phe Gly Asp Thr Leu His Ile His Tyr
        50                  55                  60

Thr Gly Ser Leu Val Asp Gly Arg Ile Ile Asp Thr Ser Leu Thr Arg
65                  70                  75                  80

Asp Pro Leu Val Ile Glu Leu Gly Gln Lys Gln Val Ile Pro Gly Leu
                85                  90                  95

Glu Gln Ser Leu Leu Asp Met Cys Val Gly Glu Lys Arg Arg Ala Ile
            100                 105                 110

Ile Pro Ser His Leu Ala Tyr Gly Lys Arg Gly Phe Pro Pro Ser Val
        115                 120                 125

Pro Ala Asp Ala Val Val Gln Tyr Asp Val Glu Leu Ile Ala Leu Ile
    130                 135                 140

Arg Ala Asn Tyr Trp Leu Lys Leu Val Lys Gly Ile Leu Pro Leu Val
145                 150                 155                 160
```

```
Gly Met Ala Met Val Pro Ala Leu Leu Gly Leu Ile Gly Tyr His Leu
                165                 170                 175

Tyr Arg Lys Ala Asn Arg Pro Lys Val Ser Lys Lys Leu Lys Glu
            180                 185                 190

Glu Lys Arg Asn Lys Ser Lys Lys Lys
            195                 200

<210> SEQ ID NO 137
<211> LENGTH: 216
<212> TYPE: PRT
<213> ORGANISM: Homo sapiens

<400> SEQUENCE: 137

Met Phe Leu Arg Leu Tyr Leu Ile Ala Arg Val Met Leu Leu His Ser
  1               5                  10                  15

Lys Leu Phe Thr Asp Ala Ser Ser Arg Ser Ile Gly Ala Leu Asn Lys
                20                  25                  30

Ile Asn Phe Asn Thr Arg Phe Val Met Lys Thr Leu Met Thr Ile Cys
            35                  40                  45

Pro Gly Thr Val Leu Val Phe Ser Ile Ser Leu Trp Ile Ile Ala
 50                  55                  60

Ala Trp Thr Val Arg Val Cys Glu Ser Pro Glu Ser Pro Ala Gln Pro
 65                  70                  75                  80

Ser Gly Ser Ser Leu Pro Ala Trp Tyr His Asp Gln Gln Asp Val Thr
                85                  90                  95

Ser Asn Phe Leu Gly Ala Met Trp Leu Ile Ser Ile Thr Phe Leu Ser
            100                 105                 110

Ile Gly Tyr Gly Asp Met Val Pro His Thr Tyr Cys Gly Lys Gly Val
        115                 120                 125

Cys Leu Leu Thr Gly Ile Met Gly Ala Gly Cys Thr Ala Leu Val Val
    130                 135                 140

Ala Val Val Ala Arg Lys Leu Glu Leu Thr Lys Ala Glu Lys His Val
145                 150                 155                 160

His Asn Phe Met Met Asp Thr Gln Leu Thr Lys Arg Ile Lys Asn Ala
                165                 170                 175

Ala Ala Asn Val Leu Arg Glu Thr Trp Leu Ile Tyr Lys His Thr Lys
            180                 185                 190

Leu Leu Lys Lys Ile Asp His Ala Lys Val Arg Lys His Gln Arg Lys
        195                 200                 205

Phe Leu Pro Ser Tyr Pro Pro Val
    210                 215

<210> SEQ ID NO 138
<211> LENGTH: 102
<212> TYPE: PRT
<213> ORGANISM: Homo sapiens

<400> SEQUENCE: 138

Met Ser Asn Thr Thr Val Pro Asn Ala Pro Gln Ala Asn Ser Asp Ser
  1               5                  10                  15

Met Val Gly Tyr Val Leu Gly Pro Phe Phe Leu Ile Thr Leu Val Gly
                20                  25                  30

Val Val Val Ala Val Val Met Tyr Val Gln Lys Lys Lys Arg Val Asp
            35                  40                  45

Arg Leu Arg His His Leu Leu Pro Met Tyr Ser Tyr Asp Pro Ala Glu
 50                  55                  60
```

-continued

```
Glu Leu His Glu Ala Glu Gln Glu Leu Leu Ser Asp Met Gly Asp Pro
 65                  70                  75                  80

Lys Val Val His Gly Trp Gln Ser Gly Tyr Gln His Lys Arg Met Pro
                 85                  90                  95

Leu Leu Asp Val Lys Thr
            100

<210> SEQ ID NO 139
<211> LENGTH: 112
<212> TYPE: PRT
<213> ORGANISM: Homo sapiens

<400> SEQUENCE: 139

Met Arg Glu Cys Gln Glu Ser Phe Trp Lys Arg Ala Leu Pro Phe
  1               5                  10                  15

Ser Leu Val Ser Met Leu Val Thr Gln Gly Leu Val Tyr Gln Gly Tyr
                 20                  25                  30

Leu Ala Ala Asn Ser Arg Phe Gly Ser Leu Pro Lys Val Ala Leu Ala
             35                  40                  45

Gly Leu Leu Gly Phe Gly Leu Gly Lys Val Ser Tyr Ile Gly Val Cys
 50                  55                  60

Gln Ser Lys Phe His Phe Phe Glu Asp Gln Leu Arg Gly Ala Gly Phe
 65                  70                  75                  80

Gly Pro Gln His Asn Arg His Cys Leu Leu Thr Cys Glu Glu Cys Lys
                 85                  90                  95

Ile Lys His Gly Leu Ser Glu Lys Gly Asp Ser Gln Pro Ser Ala Ser
            100                 105                 110

<210> SEQ ID NO 140
<211> LENGTH: 20
<212> TYPE: PRT
<213> ORGANISM: Homo sapiens

<400> SEQUENCE: 140

Met Lys Asn Asp Arg Asn Gln Gly Phe Ser Leu Leu Gln Leu Ile Asp
  1               5                  10                  15

Trp Asn Lys Pro
            20

<210> SEQ ID NO 141
<211> LENGTH: 30
<212> TYPE: PRT
<213> ORGANISM: Homo sapiens

<400> SEQUENCE: 141

Met Gly Thr Gln Pro Pro Val Val Ala Gly Phe Thr Ile Pro Met Leu
  1               5                  10                  15

Gly Tyr Thr Val Arg Val Leu Thr Phe His Leu Ser Cys Ser
                 20                  25                  30

<210> SEQ ID NO 142
<211> LENGTH: 99
<212> TYPE: PRT
<213> ORGANISM: Homo sapiens

<400> SEQUENCE: 142

Met Lys Ile Pro Val Leu Pro Ala Val Val Leu Leu Ser Leu Leu Val
  1               5                  10                  15

Leu His Ser Ala Gln Gly Ala Thr Leu Gly Gly Pro Glu Glu Glu Ser
```

```
                    20                  25                  30
Thr Ile Glu Asn Tyr Ala Ser Arg Pro Glu Ala Phe Asn Thr Pro Phe
        35                  40                  45

Leu Asn Ile Asp Lys Leu Arg Ser Ala Phe Lys Ala Asp Glu Phe Leu
    50                  55                  60

Asn Trp His Ala Leu Phe Glu Ser Ile Lys Arg Lys Leu Pro Phe Leu
65                  70                  75                  80

Asn Trp Asp Ala Phe Pro Lys Leu Lys Gly Leu Arg Ser Ala Thr Pro
                85                  90                  95

Asp Ala Gln

<210> SEQ ID NO 143
<211> LENGTH: 8
<212> TYPE: PRT
<213> ORGANISM: Homo sapiens

<400> SEQUENCE: 143

Met Val Trp Gly Leu Leu Leu Gly
1               5

<210> SEQ ID NO 144
<211> LENGTH: 39
<212> TYPE: PRT
<213> ORGANISM: Homo sapiens
<220> FEATURE:
<221> NAME/KEY: SITE
<222> LOCATION: (30)
<223> OTHER INFORMATION: Xaa equals any of the naturally occurring
      L-amino acids

<400> SEQUENCE: 144

Met Leu Pro Leu Leu Ser Leu Leu Phe Leu Phe Ser Thr Val Ser
1               5                   10                  15

Ser Phe Cys Gly Met Pro Leu Arg Ala His Thr Arg Ala Xaa Ala His
                20                  25                  30

Thr Arg Thr Phe Ala Ser Arg
        35

<210> SEQ ID NO 145
<211> LENGTH: 131
<212> TYPE: PRT
<213> ORGANISM: Homo sapiens

<400> SEQUENCE: 145

Met Ile Cys Glu Thr Lys Ala Arg Lys Ser Ser Gly Gln Pro Gly Arg
1               5                   10                  15

Leu Pro Pro Pro Thr Leu Ala Pro Pro Gln Pro Pro Leu Pro Glu Thr
                20                  25                  30

Ile Glu Arg Pro Val Gly Thr Gly Ala Met Val Ala Arg Ser Ser Asp
            35                  40                  45

Leu Pro Tyr Leu Ile Val Gly Val Val Leu Gly Ser Ile Val Leu Ile
    50                  55                  60

Ile Val Thr Phe Ile Pro Phe Cys Leu Trp Arg Ala Trp Ser Lys Gln
65                  70                  75                  80

Lys His Thr Thr Asp Leu Gly Phe Pro Arg Ser Ala Leu Pro Pro Ser
                85                  90                  95

Cys Pro Tyr Thr Met Val Pro Leu Gly Gly Leu Pro Gly His Gln Ala
                100                 105                 110

Val Asp Ser Pro Thr Ser Val Ala Ser Val Asp Gly Pro Val Leu Met
```

Gly Ser Thr
    130

<210> SEQ ID NO 146
<211> LENGTH: 32
<212> TYPE: PRT
<213> ORGANISM: Homo sapiens

<400> SEQUENCE: 146

Met Gly Ala Pro Ser Leu Thr Met Leu Leu Leu Lys Val Gln Pro
  1               5                  10                  15

Arg Arg Thr Gln Ala Phe Asp Ala His Trp Val Gly Leu Pro Leu Leu
            20                  25                  30

<210> SEQ ID NO 147
<211> LENGTH: 14
<212> TYPE: PRT
<213> ORGANISM: Homo sapiens

<400> SEQUENCE: 147

Met Cys Leu Ile Phe Leu Leu Leu Leu Leu Ser Phe Ser
  1               5                  10

<210> SEQ ID NO 148
<211> LENGTH: 8
<212> TYPE: PRT
<213> ORGANISM: Homo sapiens

<400> SEQUENCE: 148

His Pro His Gln Asp Ser Gln Pro
  1               5

<210> SEQ ID NO 149
<211> LENGTH: 68
<212> TYPE: PRT
<213> ORGANISM: Homo sapiens

<400> SEQUENCE: 149

Met Asn Thr Ser Tyr Ile Leu Arg Leu Thr Val Val Ser Val Val
  1               5                  10                  15

Ile Tyr Leu Ala Ile His Pro Leu Leu Ser Phe Ser Leu Glu Ser Pro
            20                  25                  30

Leu Leu Val Pro Trp Arg Asp Cys Cys Gln Asn Ile Trp Lys Ser Gly
        35                  40                  45

Ser Val Trp Tyr Lys Arg Trp Thr Leu Pro His Met Glu Val Cys Cys
    50                  55                  60

Gln Asp Leu His
 65

<210> SEQ ID NO 150
<211> LENGTH: 26
<212> TYPE: PRT
<213> ORGANISM: Homo sapiens

<400> SEQUENCE: 150

Met Leu Lys Ile Phe Lys Glu Trp Glu Asn Leu Asn Leu Ile Leu Thr
  1               5                  10                  15

Ser Ile Arg Ile Leu Glu Arg Gln Asn Met
            20                  25

-continued

```
<210> SEQ ID NO 151
<211> LENGTH: 195
<212> TYPE: PRT
<213> ORGANISM: Homo sapiens

<400> SEQUENCE: 151

Met Asp Cys Glu Val Asn Asn Gly Ser Ser Leu Arg Asp Glu Cys Ile
 1               5                  10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
     50                  55                  60

Ser His Ser Arg Leu Gly Arg Ile Glu Ala Asp Ser Glu Ser Gln Glu
 65                  70                  75                  80

Asp Ile Ile Arg Asn Ile Ala Arg His Leu Ala Gln Val Gly Asp Ser
                 85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
            180                 185                 190

Gly Met Asp
        195

<210> SEQ ID NO 152
<211> LENGTH: 91
<212> TYPE: PRT
<213> ORGANISM: Homo sapiens
<220> FEATURE:
<221> NAME/KEY: SITE
<222> LOCATION: (85)
<223> OTHER INFORMATION: Xaa equals any of the naturally occurring
      L-amino acids
<220> FEATURE:
<221> NAME/KEY: SITE
<222> LOCATION: (87)
<223> OTHER INFORMATION: Xaa equals any of the naturally occurring
      L-amino acids

<400> SEQUENCE: 152

Met Ser Leu Ser Leu Val Ser Val Ser Val Gly Pro Ser Thr Leu Ala
 1               5                  10                  15

Cys Ser Phe Leu Arg Pro Lys Ala Arg Pro Ser Lys Arg Ser Pro Arg
            20                  25                  30

Asn Tyr Thr Asp Ser Thr Ser Pro Gly Gly Pro Arg Ala Pro Arg Gly
        35                  40                  45

Gly Ala Trp Arg Leu Ser Ser Gln Gln Asn Ser Ser Pro Lys Gly Val
     50                  55                  60

Ala Val Ala Lys Ala Ser Tyr Arg Pro Val Leu Cys Phe Leu Pro Gly
 65                  70                  75                  80
```

```
Pro Trp Ser Ser Xaa Pro Xaa Ala Phe Leu Ile
                85              90

<210> SEQ ID NO 153
<211> LENGTH: 31
<212> TYPE: PRT
<213> ORGANISM: Homo sapiens

<400> SEQUENCE: 153

Met Gly Thr Leu Ser Ala Glu Cys Ser Gly Pro Ala Thr Leu Gly Leu
  1               5                  10                  15

Cys Leu Val Val Pro Trp Asn Ser Ser Gly Leu Ser Gln Pro Pro
             20                  25                  30

<210> SEQ ID NO 154
<211> LENGTH: 90
<212> TYPE: PRT
<213> ORGANISM: Homo sapiens

<400> SEQUENCE: 154

Met Lys Phe Leu Ala Val Leu Val Leu Leu Gly Val Ser Ile Phe Leu
  1               5                  10                  15

Val Ser Ala Gln Asn Pro Thr Thr Ala Ala Pro Ala Asp Thr Tyr Pro
             20                  25                  30

Ala Thr Gly Pro Ala Asp Asp Glu Ala Pro Asp Ala Glu Thr Thr Ala
         35                  40                  45

Ala Ala Thr Thr Ala Thr Thr Ala Ala Pro Thr Thr Ala Thr Thr Ala
     50                  55                  60

Ala Ser Thr Thr Ala Arg Lys Asp Ile Pro Val Leu Pro Lys Trp Val
 65                  70                  75                  80

Gly Asp Leu Pro Asn Gly Arg Val Cys Pro
                 85                  90

<210> SEQ ID NO 155
<211> LENGTH: 89
<212> TYPE: PRT
<213> ORGANISM: Homo sapiens

<400> SEQUENCE: 155

Met Ile Ile Ser Leu Phe Ile Tyr Ile Phe Leu Thr Cys Ser Asn Thr
  1               5                  10                  15

Ser Pro Ser Tyr Gln Gly Thr Gln Leu Gly Leu Gly Leu Pro Ser Ala
             20                  25                  30

Gln Trp Trp Pro Leu Thr Gly Arg Arg Met Gln Cys Cys Arg Leu Phe
         35                  40                  45

Cys Phe Leu Leu Gln Asn Cys Leu Phe Pro Phe Pro Leu His Leu Ile
     50                  55                  60

Gln His Asp Pro Cys Glu Leu Val Leu Thr Ile Ser Trp Asp Trp Ala
 65                  70                  75                  80

Glu Ala Gly Ala Ser Leu Tyr Ser Pro
                 85

<210> SEQ ID NO 156
<211> LENGTH: 174
<212> TYPE: PRT
<213> ORGANISM: Homo sapiens

<400> SEQUENCE: 156

Met Ser Ser Ala Ala Ala Asp His Trp Ala Trp Leu Leu Val Leu Ser
  1               5                  10                  15
```

-continued

```
Phe Val Phe Gly Cys Asn Val Leu Arg Ile Leu Leu Pro Ser Phe Ser
             20                  25                  30

Ser Phe Met Ser Arg Val Leu Gln Lys Asp Ala Glu Gln Glu Ser Gln
         35                  40                  45

Met Arg Ala Glu Ile Gln Asp Met Lys Gln Glu Leu Ser Thr Val Asn
     50                  55                  60

Met Met Asp Glu Phe Ala Arg Tyr Ala Arg Leu Glu Arg Lys Ile Asn
 65                  70                  75                  80

Lys Met Thr Asp Lys Leu Lys Thr His Val Lys Ala Arg Thr Ala Gln
                 85                  90                  95

Leu Ala Lys Ile Lys Trp Val Ile Ser Val Ala Phe Tyr Val Leu Gln
             100                 105                 110

Ala Ala Leu Met Ile Ser Leu Ile Trp Lys Tyr Tyr Ser Val Pro Val
         115                 120                 125

Ala Val Val Pro Ser Lys Trp Ile Thr Pro Leu Asp Arg Leu Val Ala
     130                 135                 140

Phe Pro Thr Arg Val Ala Gly Gly Val Gly Ile Thr Cys Trp Ile Leu
145                 150                 155                 160

Val Cys Asn Lys Val Val Ala Ile Val Leu His Pro Phe Ser
                 165                 170

<210> SEQ ID NO 157
<211> LENGTH: 45
<212> TYPE: PRT
<213> ORGANISM: Homo sapiens

<400> SEQUENCE: 157

Met Gly Lys Leu Ile Asn Ile Val Ile Arg Lys Pro Leu Leu Leu Leu
  1               5                  10                  15

Leu Val Gln Cys Glu Asn Cys Cys Arg Lys Asn Met Leu Tyr Asn Ile
             20                  25                  30

Phe Leu Asn Ile His Asn Ile His Lys Phe Ser Asn His
         35                  40                  45

<210> SEQ ID NO 158
<211> LENGTH: 23
<212> TYPE: PRT
<213> ORGANISM: Homo sapiens

<400> SEQUENCE: 158

Met Val Ala Ser Thr Leu Val Thr Asn Leu Phe Gly Val Ala Phe Ala
  1               5                  10                  15

Thr Thr Ala Ala Thr Arg Ala
             20

<210> SEQ ID NO 159
<211> LENGTH: 70
<212> TYPE: PRT
<213> ORGANISM: Homo sapiens
<220> FEATURE:
<221> NAME/KEY: SITE
<222> LOCATION: (33)
<223> OTHER INFORMATION: Xaa equals any of the naturally occurring
      L-amino acids

<400> SEQUENCE: 159

Met Leu Met Ala Pro Val Val Cys Leu Ser Phe Ser Pro Cys Pro Ala
  1               5                  10                  15

Asp Thr Ser Leu Thr Gly Asp Gly Leu Lys Ala Gly Leu Glu Arg Gly
```

```
                    20                  25                  30
Xaa Ala Leu Val Thr Leu Phe Asp Ser Val Thr His Phe Leu Ala His
                35                  40                  45

Thr Leu Phe Glu Leu Leu Asp Phe Gln Leu Ala Phe Leu Arg Ser Gly
    50                  55                  60

Lys Gln Thr Ala Pro His
65                  70

<210> SEQ ID NO 160
<211> LENGTH: 323
<212> TYPE: PRT
<213> ORGANISM: Homo sapiens

<400> SEQUENCE: 160

Met Leu Leu Leu Leu Leu Leu Gly Ser Gly Gln Gly Pro Gln Gln
1               5                   10                  15

Val Gly Ala Gly Gln Thr Phe Glu Tyr Leu Lys Arg Glu His Ser Leu
                20                  25                  30

Ser Lys Pro Tyr Gln Gly Val Gly Thr Gly Ser Ser Leu Trp Asn
        35                  40                  45

Leu Met Gly Asn Ala Met Val Met Thr Gln Tyr Ile Arg Leu Thr Pro
    50                  55                  60

Asp Met Gln Ser Lys Gln Gly Ala Leu Trp Asn Arg Val Pro Cys Phe
65                  70                  75                  80

Leu Arg Asp Trp Glu Leu Gln Val His Phe Lys Ile His Gly Gln Gly
                85                  90                  95

Lys Lys Asn Leu His Gly Asp Gly Leu Ala Ile Trp Tyr Thr Arg Asn
            100                 105                 110

Arg Met Gln Pro Gly Pro Val Phe Gly Asn Met Asp Lys Phe Val Gly
        115                 120                 125

Leu Gly Val Phe Val Asp Thr Tyr Pro Asn Glu Glu Lys Gln Gln Glu
    130                 135                 140

Arg Val Phe Pro Tyr Ile Ser Ala Met Val Asn Asn Gly Ser Leu Ser
145                 150                 155                 160

Tyr Asp His Glu Arg Asp Gly Arg Pro Thr Glu Leu Gly Gly Cys Thr
                165                 170                 175

Ala Ile Val Arg Asn Leu His Tyr Asp Thr Phe Leu Val Ile Arg Tyr
            180                 185                 190

Val Lys Arg His Leu Thr Ile Met Met Asp Ile Asp Gly Lys His Glu
        195                 200                 205

Trp Arg Asp Cys Ile Glu Val Pro Gly Val Arg Leu Pro Arg Gly Tyr
    210                 215                 220

Tyr Phe Gly Thr Ser Ser Ile Thr Gly Asp Leu Ser Asp Asn His Asp
225                 230                 235                 240

Val Ile Ser Leu Lys Leu Phe Glu Leu Thr Val Glu Arg Thr Pro Glu
                245                 250                 255

Glu Glu Lys Leu His Arg Asp Val Phe Leu Pro Ser Val Asp Asn Met
            260                 265                 270

Lys Leu Pro Glu Met Thr Ala Pro Leu Pro Pro Leu Ser Gly Leu Ala
        275                 280                 285

Leu Phe Leu Ile Val Phe Phe Ser Leu Val Phe Ser Val Phe Ala Ile
    290                 295                 300

Val Ile Gly Ile Ile Leu Tyr Asn Lys Trp Gln Glu Gln Ser Arg Lys
305                 310                 315                 320
```

Arg Phe Tyr

<210> SEQ ID NO 161
<211> LENGTH: 320
<212> TYPE: PRT
<213> ORGANISM: Homo sapiens
<220> FEATURE:
<221> NAME/KEY: SITE
<222> LOCATION: (120)
<223> OTHER INFORMATION: Xaa equals any of the naturally occurring
      L-amino acids
<220> FEATURE:
<221> NAME/KEY: SITE
<222> LOCATION: (292)
<223> OTHER INFORMATION: Xaa equals any of the naturally occurring
      L-amino acids

<400> SEQUENCE: 161

```
Met Pro Ser Glu Tyr Thr Tyr Val Lys Leu Arg Ser Asp Cys Ser Arg
 1               5                  10                  15

Pro Ser Leu Gln Trp Tyr Thr Arg Ala Gln Ser Lys Met Arg Arg Pro
            20                  25                  30

Ser Leu Leu Leu Lys Asp Ile Leu Lys Cys Thr Leu Leu Val Phe Gly
        35                  40                  45

Val Trp Ile Leu Tyr Ile Leu Lys Leu Asn Tyr Thr Thr Glu Glu Cys
50                  55                  60

Asp Met Lys Lys Met His Tyr Val Asp Pro Asp His Val Lys Arg Ala
65                  70                  75                  80

Gln Lys Tyr Ala Gln Gln Val Leu Gln Lys Glu Cys Arg Pro Lys Phe
                85                  90                  95

Ala Lys Thr Ser Met Ala Leu Leu Phe Glu His Arg Tyr Ser Val Asp
            100                 105                 110

Leu Leu Pro Phe Val Gln Lys Xaa Pro Lys Asp Ser Glu Ala Glu Ser
        115                 120                 125

Lys Tyr Asp Pro Pro Phe Gly Phe Arg Lys Phe Ser Ser Lys Val Gln
    130                 135                 140

Thr Leu Glu Leu Leu Pro Glu His Asp Leu Pro Glu His Leu Lys
145                 150                 155                 160

Ala Lys Thr Cys Arg Arg Cys Val Val Ile Gly Ser Gly Ile Leu
                165                 170                 175

His Gly Leu Glu Leu Gly His Thr Leu Asn Gln Phe Asp Val Val Ile
            180                 185                 190

Arg Leu Asn Ser Ala Pro Val Glu Gly Tyr Ser Glu His Val Gly Asn
        195                 200                 205

Lys Thr Thr Ile Arg Met Thr Tyr Pro Glu Gly Ala Pro Leu Ser Asp
    210                 215                 220

Leu Glu Tyr Tyr Ser Asn Asp Leu Phe Val Ala Val Leu Phe Lys Ser
225                 230                 235                 240

Val Asp Phe Asn Trp Leu Gln Ala Met Val Lys Lys Glu Thr Leu Pro
                245                 250                 255

Phe Trp Val Arg Leu Phe Phe Trp Lys Gln Val Ala Glu Lys Ile Pro
            260                 265                 270

Leu Gln Pro Lys His Phe Arg Ile Leu Asn Pro Val Ile Ile Lys Glu
        275                 280                 285

Thr Ala Phe Xaa His Pro Ser Val Leu Arg Ala Ser Val Lys Val Leu
    290                 295                 300

Gly Ala Glu Ile Arg Thr Ser Pro Gln Ser Val Ser Leu Pro Leu Ser
305                 310                 315                 320
```

```
<210> SEQ ID NO 162
<211> LENGTH: 31
<212> TYPE: PRT
<213> ORGANISM: Homo sapiens

<400> SEQUENCE: 162

Met Thr Leu Asp Val Gln Thr Val Val Phe Ala Val Ile Val Val
 1               5                  10                  15

Leu Leu Leu Val Asn Val Ile Leu Met Phe Phe Leu Gly Thr Arg
            20                  25                  30

<210> SEQ ID NO 163
<211> LENGTH: 72
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring
      L-amino acids
<220> FEATURE:
<221> NAME/KEY: SITE
<222> LOCATION: (68)
<223> OTHER INFORMATION: Xaa equals any of the naturally occurring
      L-amino acids
<220> FEATURE:
<221> NAME/KEY: SITE
<222> LOCATION: (69)
<223> OTHER INFORMATION: Xaa equals any of the naturally occurring
      L-amino acids
<220> FEATURE:
<221> NAME/KEY: SITE
<222> LOCATION: (70)
<223> OTHER INFORMATION: Xaa equals any of the naturally occurring
      L-amino acids

<400> SEQUENCE: 163

Met Leu Pro Leu Leu Phe Cys Ala Phe Cys Leu His Lys Leu Gly Pro
 1               5                  10                  15

Leu Leu Phe Leu Tyr Asp Val Leu Met Xaa His Glu Ala Val Met Arg
            20                  25                  30

Thr His Gln Ile Gln Leu Pro Asp Pro Glu Phe Pro Ser Gln Gln Asn
        35                  40                  45

Gln Val Leu Asn Lys Thr Leu Phe Asn Lys Leu Lys Lys Lys Lys Lys
    50                  55                  60

Lys Lys Lys Xaa Xaa Xaa Lys Lys
 65                  70

<210> SEQ ID NO 164
<211> LENGTH: 281
<212> TYPE: PRT
<213> ORGANISM: Homo sapiens

<400> SEQUENCE: 164

Met Ala Ser Arg Gly Arg Arg Pro Glu His Gly Gly Pro Pro Glu Leu
 1               5                  10                  15

Phe Tyr Asp Glu Thr Glu Ala Arg Lys Tyr Val Arg Asn Ser Arg Met
            20                  25                  30

Ile Asp Ile Gln Thr Arg Met Ala Gly Arg Ala Leu Glu Leu Leu Tyr
        35                  40                  45

Leu Pro Glu Asn Lys Pro Cys Tyr Leu Leu Asp Ile Gly Cys Gly Thr
    50                  55                  60

Gly Leu Ser Gly Ser Tyr Leu Ser Asp Glu Gly His Tyr Trp Val Gly
```

```
                65                  70                  75                  80
Leu Asp Ile Ser Pro Ala Met Leu Asp Glu Ala Val Asp Arg Glu Ile
                        85                  90                  95

Glu Gly Asp Leu Leu Leu Gly Asp Met Gly Gln Gly Ile Pro Phe Lys
                100                 105                 110

Pro Gly Thr Phe Asp Gly Cys Ile Ser Ile Ser Ala Val Gln Trp Leu
            115                 120                 125

Cys Asn Ala Asn Lys Lys Ser Glu Asn Pro Ala Lys Arg Leu Tyr Cys
        130                 135                 140

Phe Phe Ala Ser Leu Phe Ser Val Leu Val Arg Gly Ser Arg Ala Val
145                 150                 155                 160

Leu Gln Leu Tyr Pro Glu Asn Ser Glu Gln Leu Glu Leu Ile Thr Thr
                165                 170                 175

Gln Ala Thr Lys Ala Gly Phe Ser Gly Gly Met Val Val Asp Tyr Pro
            180                 185                 190

Asn Ser Ala Lys Ala Lys Lys Phe Tyr Leu Cys Leu Phe Ser Gly Pro
        195                 200                 205

Ser Thr Phe Ile Pro Glu Gly Leu Ser Glu Asn Gln Asp Glu Val Glu
    210                 215                 220

Pro Arg Glu Ser Val Phe Thr Asn Glu Arg Phe Pro Leu Arg Met Ser
225                 230                 235                 240

Arg Arg Gly Met Val Arg Lys Ser Arg Ala Trp Val Leu Glu Lys Lys
                245                 250                 255

Glu Arg His Arg Arg Gln Gly Arg Glu Val Arg Pro Asp Thr Gln Tyr
            260                 265                 270

Thr Gly Arg Lys Arg Lys Pro Arg Phe
        275                 280

<210> SEQ ID NO 165
<211> LENGTH: 81
<212> TYPE: PRT
<213> ORGANISM: Homo sapiens

<400> SEQUENCE: 165

Met Glu Lys Ile Pro Glu Val Thr Asn Ser Asn Ser Ser Phe His Ala
1               5                   10                  15

His Asp Leu Gly Phe Cys Val Leu Ser Ile Ala Thr Ser Lys Ser Arg
            20                  25                  30

Lys Ala Pro Ala Pro His Ala Gln Lys Cys Asn Leu Lys Ser Leu Arg
        35                  40                  45

Ser Ser Ala Gln Thr Asp Ile Asn Lys Pro Val Phe Ser Leu His Pro
    50                  55                  60

Glu Pro Pro Gly Lys Ser Gly Ala Gln Thr Gln Ser Lys Ala Pro Phe
65                  70                  75                  80

Leu

<210> SEQ ID NO 166
<211> LENGTH: 327
<212> TYPE: PRT
<213> ORGANISM: Homo sapiens
<220> FEATURE:
<221> NAME/KEY: SITE
<222> LOCATION: (300)
<223> OTHER INFORMATION: Xaa equals any of the naturally occurring
      L-amino acids

<400> SEQUENCE: 166
```

```
Met Trp Arg Pro Ser Val Leu Leu Leu Leu Leu Arg His Gly
  1               5                  10                  15

Ala Gln Gly Lys Pro Ser Pro Asp Ala Gly Pro His Gly Gln Gly Arg
             20                  25                  30

Val His Gln Ala Ala Pro Leu Ser Asp Ala Pro His Asp Asp Ala His
         35                  40                  45

Gly Asn Phe Gln Tyr Asp His Glu Ala Phe Leu Gly Arg Glu Val Ala
     50                  55                  60

Lys Glu Phe Asp Gln Leu Thr Pro Glu Glu Ser Gln Ala Arg Leu Gly
 65                  70                  75                  80

Arg Ile Val Asp Arg Met Asp Arg Ala Gly Asp Gly Asp Gly Trp Val
                 85                  90                  95

Ser Leu Ala Glu Leu Arg Ala Trp Ile Ala His Thr Gln Gln Arg His
             100                 105                 110

Ile Arg Asp Ser Val Ser Ala Ala Trp Asp Thr Tyr Asp Thr Asp Arg
         115                 120                 125

Asp Gly Arg Val Gly Trp Glu Glu Leu Arg Asn Ala Thr Tyr Gly His
     130                 135                 140

Tyr Ala Pro Gly Glu Glu Phe His Asp Val Asp Ala Glu Thr Tyr
145                 150                 155                 160

Lys Lys Met Leu Ala Arg Asp Glu Arg Arg Phe Arg Val Ala Asp Gln
                 165                 170                 175

Asp Gly Asp Ser Met Ala Thr Arg Glu Glu Leu Thr Ala Phe Leu His
             180                 185                 190

Pro Glu Glu Phe Pro His Met Arg Asp Ile Val Ile Ala Glu Thr Leu
         195                 200                 205

Glu Asp Leu Asp Arg Asn Lys Asp Gly Tyr Val Gln Val Glu Glu Tyr
     210                 215                 220

Ile Ala Asp Leu Tyr Ser Ala Glu Pro Gly Glu Glu Pro Ala Trp
225                 230                 235                 240

Val Gln Thr Glu Arg Gln Gln Phe Arg Asp Phe Arg Asp Leu Asn Lys
                 245                 250                 255

Asp Gly His Leu Asp Gly Ser Glu Val Gly His Trp Val Leu Pro Pro
             260                 265                 270

Ala Gln Asp Gln Pro Leu Val Glu Ala Asn His Leu Leu His Glu Ser
         275                 280                 285

Asp Thr Asp Lys Asp Gly Arg Leu Ser Lys Ala Xaa Ile Leu Gly Asn
     290                 295                 300

Trp Asn Met Phe Val Gly Ser Gln Ala Thr Asn Tyr Gly Glu Asp Leu
305                 310                 315                 320

Thr Arg His His Asp Glu Leu
                 325

<210> SEQ ID NO 167
<211> LENGTH: 65
<212> TYPE: PRT
<213> ORGANISM: Homo sapiens

<400> SEQUENCE: 167

Met Ile Lys Ile Leu Lys Glu Ala Ile Glu Glu Thr Ser Phe Cys Ser
  1               5                  10                  15

Phe Trp Arg Ile Ser Phe Gln Leu Ser Ile His His Ile Phe Leu Ile
                 20                  25                  30

Phe Cys Ala Gln Leu Thr Thr Leu Leu Tyr Ser Thr Phe Leu Phe Ile
             35                  40                  45
```

```
Pro Ile Ser Trp Phe Leu Ile Val Pro Gly Ala Val Asp Lys Thr Ile
        50                  55                  60

Leu
 65

<210> SEQ ID NO 168
<211> LENGTH: 159
<212> TYPE: PRT
<213> ORGANISM: Homo sapiens

<400> SEQUENCE: 168

Met Trp Leu Phe Ile Leu Leu Ser Leu Ala Leu Ile Ser Asp Ala Met
 1               5                  10                  15

Val Met Asp Glu Lys Val Lys Arg Ser Phe Val Leu Asp Thr Ala Ser
            20                  25                  30

Ala Ile Cys Asn Tyr Asn Ala His Tyr Lys Asn His Pro Lys Tyr Trp
        35                  40                  45

Cys Arg Gly Tyr Phe Arg Asp Tyr Cys Asn Ile Ile Ala Phe Ser Pro
    50                  55                  60

Asn Ser Thr Asn His Val Ala Leu Lys Asp Thr Gly Asn Gln Leu Ile
 65                  70                  75                  80

Val Thr Met Ser Cys Leu Asn Lys Glu Asp Thr Gly Trp Tyr Trp Cys
                85                  90                  95

Gly Ile Gln Arg Asp Phe Ala Arg Asp Asp Met Asp Phe Thr Glu Leu
            100                 105                 110

Ile Val Thr Asp Asp Lys Gly Thr Trp Pro Met Thr Leu Val Trp Glu
        115                 120                 125

Arg Leu Ser Gly Thr Lys Pro Glu Ala Ala Arg Leu Pro Lys Leu Ser
    130                 135                 140

Ala Arg Leu Thr Ala Pro Gly Arg Pro Phe Ser Ser Phe Ala Tyr
145                 150                 155

<210> SEQ ID NO 169
<211> LENGTH: 123
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring
      L-amino acids
<220> FEATURE:
<221> NAME/KEY: SITE
<222> LOCATION: (65)
<223> OTHER INFORMATION: Xaa equals any of the naturally occurring
      L-amino acids
<220> FEATURE:
<221> NAME/KEY: SITE
<222> LOCATION: (88)
<223> OTHER INFORMATION: Xaa equals any of the naturally occurring
      L-amino acids
<220> FEATURE:
<221> NAME/KEY: SITE
<222> LOCATION: (99)
<223> OTHER INFORMATION: Xaa equals any of the naturally occurring
      L-amino acids
<220> FEATURE:
<221> NAME/KEY: SITE
<222> LOCATION: (100)
<223> OTHER INFORMATION: Xaa equals any of the naturally occurring
      L-amino acids
<220> FEATURE:
<221> NAME/KEY: SITE
<222> LOCATION: (101)
<223> OTHER INFORMATION: Xaa equals any of the naturally occurring
```

L-amino acids

<400> SEQUENCE: 169

Met Ala Xaa His Phe Leu Leu Val Ala Leu Gln Ser Val Pro His Cys
1               5                   10                  15

Pro His Leu Leu Glu Glu His Lys Leu Cys Lys Val Ser His Phe
            20                  25                  30

Ser Gly Val Thr Leu Val Thr Ser Arg Gln Asp Ser Ser Tyr Val
        35                  40                  45

Pro Val Gln Thr Leu Phe Ile His Leu Gly Pro Trp Ala Trp Asp Leu
    50                  55                  60

Xaa Pro Cys Thr Ala Glu Asp Pro Glu Ala Glu Arg Ser Leu Arg Leu
65                  70                  75                  80

Cys His Ser His Leu Ala Arg Xaa Asn Val Ser Pro Ser Gln Ala Ala
                85                  90                  95

Glu Gly Xaa Xaa Xaa Arg Gly Cys Gln His Arg Gly Ser Arg Glu Leu
            100                 105                 110

Thr Phe Leu Ser Ala Glu Asn Glu Ala Gly Ile
        115                 120

<210> SEQ ID NO 170
<211> LENGTH: 129
<212> TYPE: PRT
<213> ORGANISM: Homo sapiens

<400> SEQUENCE: 170

Met Lys Val Gly Ala Arg Ile Arg Val Lys Met Ser Val Asn Lys Ala
1               5                   10                  15

His Pro Val Ser Thr His Trp Arg Trp Pro Ala Glu Trp Pro Gln
            20                  25                  30

Met Phe Leu His Leu Ala Gln Glu Pro Arg Thr Glu Val Lys Ser Arg
        35                  40                  45

Pro Leu Gly Leu Ala Gly Phe Ile Arg Gln Asp Ser Lys Thr Arg Lys
    50                  55                  60

Pro Leu Glu Gln Glu Thr Ile Met Ser Ala Ala Asp Thr Ala Leu Trp
65                  70                  75                  80

Pro Tyr Gly His Gly Asn Arg Glu His Gln Glu Asn Glu Leu Gln Lys
                85                  90                  95

Tyr Leu Gln Tyr Lys Asp Met His Leu Leu Asp Ser Gly Gln Ser Leu
            100                 105                 110

Gly His Thr His Thr Leu Gln Gly Ser His Asn Leu Thr Ala Leu Asn
        115                 120                 125

Ile

<210> SEQ ID NO 171
<211> LENGTH: 372
<212> TYPE: PRT
<213> ORGANISM: Homo sapiens

<400> SEQUENCE: 171

Met Ala Tyr His Ser Phe Leu Val Glu Pro Ile Ser Cys His Ala Trp
1               5                   10                  15

Asn Lys Asp Arg Thr Gln Ile Ala Ile Cys Pro Asn Asn His Glu Val
            20                  25                  30

His Ile Tyr Glu Lys Ser Gly Ala Lys Trp Thr Lys Val His Glu Leu
        35                  40                  45

```
Lys Glu His Asn Gly Gln Val Thr Gly Ile Asp Trp Ala Pro Glu Ser
     50                  55                  60

Asn Arg Ile Val Thr Cys Gly Thr Asp Arg Asn Ala Tyr Val Trp Thr
 65                  70                  75                  80

Leu Lys Gly Arg Thr Trp Lys Pro Thr Leu Val Ile Leu Arg Ile Asn
                 85                  90                  95

Arg Ala Ala Arg Cys Val Arg Trp Ala Pro Asn Glu Asn Lys Phe Ala
                100                 105                 110

Val Gly Ser Gly Ser Arg Val Ile Ser Ile Cys Tyr Phe Glu Gln Glu
            115                 120                 125

Asn Asp Trp Trp Val Cys Lys His Ile Lys Lys Pro Ile Arg Ser Thr
    130                 135                 140

Val Leu Ser Leu Asp Trp His Pro Asn Asn Val Leu Leu Ala Ala Gly
145                 150                 155                 160

Ser Cys Asp Phe Lys Cys Arg Ile Phe Ser Ala Tyr Ile Lys Glu Val
                165                 170                 175

Glu Glu Arg Pro Ala Pro Thr Pro Trp Gly Ser Lys Met Pro Phe Gly
                180                 185                 190

Glu Leu Met Phe Glu Ser Ser Ser Cys Gly Trp Val His Gly Val
                195                 200                 205

Cys Phe Ser Ala Ser Gly Ser Arg Val Ala Trp Val Ser His Asp Ser
    210                 215                 220

Thr Val Cys Leu Ala Asp Ala Asp Lys Lys Met Ala Val Ala Thr Leu
225                 230                 235                 240

Ala Ser Glu Thr Leu Pro Leu Leu Ala Leu Thr Phe Ile Thr Asp Asn
                245                 250                 255

Ser Leu Val Ala Ala Gly His Asp Cys Phe Pro Val Leu Phe Thr Tyr
            260                 265                 270

Asp Ala Ala Gly Met Leu Ser Phe Gly Gly Arg Leu Asp Val Pro
            275                 280                 285

Lys Gln Ser Ser Gln Arg Gly Leu Thr Ala Arg Glu Arg Phe Gln Asn
290                 295                 300

Leu Asp Lys Lys Ala Ser Ser Glu Gly Gly Thr Ala Ala Gly Ala Gly
305                 310                 315                 320

Leu Asp Ser Leu His Lys Asn Ser Val Ser Gln Ile Ser Val Leu Ser
                325                 330                 335

Gly Gly Lys Ala Lys Cys Ser Gln Phe Cys Thr Thr Gly Met Asp Gly
            340                 345                 350

Gly Met Ser Ile Trp Asp Val Lys Ser Leu Glu Ser Ala Leu Lys Asp
        355                 360                 365

Leu Lys Ile Lys
    370

<210> SEQ ID NO 172
<211> LENGTH: 216
<212> TYPE: PRT
<213> ORGANISM: Homo sapiens

<400> SEQUENCE: 172

Met Trp Ser Ile Gly Ala Gly Ala Leu Gly Ala Ala Leu Ala Leu
 1               5                  10                  15

Leu Leu Ala Asn Thr Asp Val Phe Leu Ser Lys Pro Gln Lys Ala Ala
                20                  25                  30

Leu Glu Tyr Leu Glu Asp Ile Asp Leu Lys Thr Leu Glu Lys Glu Pro
            35                  40                  45
```

```
Arg Thr Phe Lys Ala Lys Glu Leu Trp Glu Lys Asn Gly Ala Val Ile
         50                  55                  60

Met Ala Val Arg Arg Pro Gly Cys Phe Leu Cys Arg Glu Glu Ala Ala
 65                  70                  75                  80

Asp Leu Ser Ser Leu Lys Ser Met Leu Asp Gln Leu Gly Val Pro Leu
                 85                  90                  95

Tyr Ala Val Val Lys Glu His Ile Arg Thr Glu Val Lys Asp Phe Gln
            100                 105                 110

Pro Tyr Phe Lys Gly Glu Ile Phe Leu Asp Glu Lys Lys Lys Phe Tyr
            115                 120                 125

Gly Pro Gln Arg Arg Lys Met Met Phe Met Gly Phe Ile Arg Leu Gly
            130                 135                 140

Val Trp Tyr Asn Phe Phe Arg Ala Trp Asn Gly Phe Ser Gly Asn
145                 150                 155                 160

Leu Glu Gly Glu Gly Phe Ile Leu Gly Gly Val Phe Val Gly Ser
                165                 170                 175

Gly Lys Gln Gly Ile Leu Leu Glu His Arg Glu Lys Glu Phe Gly Asp
            180                 185                 190

Lys Val Asn Leu Leu Ser Val Leu Glu Ala Ala Lys Met Ile Lys Pro
            195                 200                 205

Gln Thr Leu Ala Ser Glu Lys Lys
        210                 215

<210> SEQ ID NO 173
<211> LENGTH: 55
<212> TYPE: PRT
<213> ORGANISM: Homo sapiens

<400> SEQUENCE: 173

Met Lys Pro Val Ser Arg Arg Thr Leu Asp Trp Ile Tyr Ser Val Leu
  1               5                  10                  15

Leu Leu Ala Ile Val Leu Ile Ser Trp Gly Cys Ile Ile Tyr Ala Ser
             20                  25                  30

Met Val Ser Ala Arg Arg Gln Leu Arg Lys Lys Tyr Pro Asp Lys Ile
         35                  40                  45

Phe Gly Thr Asn Glu Asn Leu
         50              55

<210> SEQ ID NO 174
<211> LENGTH: 23
<212> TYPE: PRT
<213> ORGANISM: Homo sapiens
<220> FEATURE:
<221> NAME/KEY: SITE
<222> LOCATION: (19)
<223> OTHER INFORMATION: Xaa equals any of the naturally occurring
      L-amino acids

<400> SEQUENCE: 174

Met Ala Ala Asn Thr Phe Val Leu Ile Met Gly Ile Pro Thr Ser Ala
  1               5                  10                  15

Asn Ala Xaa Arg Asp Leu Phe
             20

<210> SEQ ID NO 175
<211> LENGTH: 103
<212> TYPE: PRT
<213> ORGANISM: Homo sapiens
```

-continued

```
<400> SEQUENCE: 175

Met Ser Ile Cys His Arg Gly Thr Gly Ile Ala Leu Ser Ala Gly Val
1               5                   10                  15

Ser Leu Phe Gly Met Ser Ala Leu Leu Leu Pro Gly Asn Phe Glu Ser
            20                  25                  30

Tyr Leu Glu Leu Val Lys Ser Leu Cys Leu Gly Pro Ala Leu Ile His
        35                  40                  45

Thr Ala Lys Phe Ala Leu Val Phe Pro Leu Met Tyr His Thr Trp Asn
    50                  55                  60

Gly Ile Arg His Leu Met Trp Asp Leu Gly Lys Gly Leu Lys Ile Pro
65                  70                  75                  80

Gln Leu Tyr Gln Ser Gly Val Val Leu Val Leu Thr Val Leu Ser
                85                  90                  95

Ser Met Gly Leu Ala Ala Met
            100

<210> SEQ ID NO 176
<211> LENGTH: 48
<212> TYPE: PRT
<213> ORGANISM: Homo sapiens

<400> SEQUENCE: 176

Met Thr Lys Ala Ser Ser Leu Trp Pro Leu Lys Thr Thr Cys Gln Ile
1               5                   10                  15

Ser Gly Thr Val Phe Phe Phe Leu Phe Leu Phe Ser Cys Phe Leu Met
            20                  25                  30

Gln Ala Gln Cys Asp Lys Phe Val Gly Trp Asp Phe Phe Phe Leu
        35                  40                  45

<210> SEQ ID NO 177
<211> LENGTH: 96
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids

<400> SEQUENCE: 177

Met Arg Arg Ala Leu Ile Pro Pro Cys Arg Gly Pro Ser Ala Ser
1               5                   10                  15

Asp Xaa Cys Cys Ser Cys Ser Pro Ser Gly Phe Ser Ala Gly Arg Gly
            20                  25                  30

Arg Cys Pro Val Gln Gly Cys Leu Arg Pro His Arg Val Gln Leu Leu
        35                  40                  45

Arg Arg Trp Gly Pro Gly Ser Pro Ala Gly Gln Arg Leu Ser Lys Gly
    50                  55                  60

Phe Gln Leu Leu Arg Trp Trp Gly Pro Gly Ser Pro Ala Pro Glu Pro
65                  70                  75                  80

Arg Lys Gly Pro Phe Pro Pro Pro Asp Pro Pro Trp Pro Val Thr Leu
                85                  90                  95

<210> SEQ ID NO 178
<211> LENGTH: 95
<212> TYPE: PRT
<213> ORGANISM: Homo sapiens
<220> FEATURE:
<221> NAME/KEY: SITE
<222> LOCATION: (70)
```

-continued

<223> OTHER INFORMATION: Xaa equals any of the naturally occurring
     L-amino acids

<400> SEQUENCE: 178

Met Leu Glu Thr Thr Lys His Val Gln Ile Ala Cys Met Leu Leu Leu
1               5                   10                  15

Thr Cys Gln Ile Phe Leu Pro Ser Ser Leu Ser Pro Ser Phe Ile His
            20                  25                  30

Ser Leu Thr Asp Ser Phe Ile Pro Leu Lys Leu Tyr Val Cys Phe
        35                  40                  45

Val Gln Ser Thr Leu Leu Lys Ala Ala Gly Tyr Lys Ser Ile Ser Glu
    50                  55                  60

Ala Leu Gly Phe Asp Xaa Leu Leu Cys Ser Ser Ala Arg Phe Val Trp
65                  70                  75                  80

Ile Cys His Thr Tyr Ser Arg Pro Leu Val Thr Cys Ala Leu His
                85                  90                  95

<210> SEQ ID NO 179
<211> LENGTH: 27
<212> TYPE: PRT
<213> ORGANISM: Homo sapiens

<400> SEQUENCE: 179

Met Ser Val Ile Gly Gly Leu Leu Val Val Ala Leu Gly Pro Gly
1               5                   10                  15

Gly Val Ser Met Asp Glu Lys Lys Glu Trp
            20                  25

<210> SEQ ID NO 180
<211> LENGTH: 89
<212> TYPE: PRT
<213> ORGANISM: Homo sapiens
<220> FEATURE:
<221> NAME/KEY: SITE
<222> LOCATION: (12)
<223> OTHER INFORMATION: Xaa equals any of the naturally occurring
     L-amino acids
<220> FEATURE:
<221> NAME/KEY: SITE
<222> LOCATION: (13)
<223> OTHER INFORMATION: Xaa equals any of the naturally occurring
     L-amino acids
<220> FEATURE:
<221> NAME/KEY: SITE
<222> LOCATION: (72)
<223> OTHER INFORMATION: Xaa equals any of the naturally occurring
     L-amino acids

<400> SEQUENCE: 180

Met Ser Gly Gly Leu Ser Phe Leu Leu Leu Val Xaa Xaa Gly Thr Gln
1               5                   10                  15

Ser Pro Leu His Leu Ala Gly Ser Cys Pro Gly Gln Thr His Leu Ser
            20                  25                  30

Phe Pro Leu Gly Gln Asp Arg Gly Gln Gln Leu Gln Gln Lys Gln Gln
        35                  40                  45

Asp Leu Glu Gln Glu Gly Leu Glu Ala Thr Gln Gly Leu Leu Ala Gly
    50                  55                  60

Glu Trp Ala Pro Pro Leu Trp Xaa Leu Gly Ser Leu Phe Gln Ala Phe
65                  70                  75                  80

Val Lys Arg Glu Ser Gln Ala Tyr Ala
                85

```
<210> SEQ ID NO 181
<211> LENGTH: 65
<212> TYPE: PRT
<213> ORGANISM: Homo sapiens

<400> SEQUENCE: 181

Met Phe Ala Asp Phe Ile Val Val Thr Ala Thr Val Gln Arg Cys Pro
1               5                   10                  15

Gly Ser Pro Pro Leu Ser Glu Ile Leu Trp Lys Asp Glu Pro Phe Ala
            20                  25                  30

Ile Ser Ser His Ala Gly Leu Pro Trp Leu Ser Ser Trp Pro Ala Pro
        35                  40                  45

Pro Trp Thr Trp Ser Trp Ile Ser Arg Arg Arg Glu His Gly Arg Gly
    50                  55                  60

Ser
65

<210> SEQ ID NO 182
<211> LENGTH: 105
<212> TYPE: PRT
<213> ORGANISM: Homo sapiens

<400> SEQUENCE: 182

Met Ser Ala Leu Thr Arg Leu Ala Ser Phe Ala Arg Val Gly Gly Arg
1               5                   10                  15

Leu Phe Arg Ser Gly Cys Ala Arg Thr Ala Gly Asp Gly Val Arg
            20                  25                  30

His Ala Gly Gly Gly Val His Ile Glu Pro Arg Tyr Arg Gln Phe Pro
        35                  40                  45

Gln Leu Thr Arg Ser Gln Val Phe Gln Ser Glu Phe Phe Ser Gly Leu
    50                  55                  60

Met Trp Phe Trp Ile Leu Trp Arg Phe Trp His Asp Ser Glu Glu Val
65                  70                  75                  80

Leu Gly His Phe Pro Tyr Pro Asp Pro Ser Gln Trp Thr Asp Glu Glu
                85                  90                  95

Leu Gly Ile Pro Pro Asp Asp Glu Asp
            100                 105

<210> SEQ ID NO 183
<211> LENGTH: 132
<212> TYPE: PRT
<213> ORGANISM: Homo sapiens

<400> SEQUENCE: 183

Met Asp Val Leu Phe Val Ala Ile Phe Ala Val Pro Leu Ile Leu Gly
1               5                   10                  15

Gln Glu Tyr Glu Asp Glu Glu Arg Leu Gly Glu Asp Glu Tyr Tyr Gln
            20                  25                  30

Val Val Tyr Tyr Tyr Thr Val Thr Pro Ser Tyr Asp Phe Ser Ala
        35                  40                  45

Asp Phe Thr Ile Asp Tyr Ser Ile Phe Glu Ser Glu Asp Arg Leu Asn
    50                  55                  60

Arg Leu Asp Lys Asp Ile Thr Glu Ala Ile Glu Thr Thr Ile Ser Leu
65                  70                  75                  80

Glu Thr Ala Arg Ala Asp His Pro Lys Pro Val Thr Val Lys Pro Val
                85                  90                  95

Thr Thr Glu Pro Gln Ser Pro Asp Leu Asn Asp Ala Val Ser Ser Leu
            100                 105                 110
```

```
Arg Ser Pro Ile Pro Leu Leu Leu Ser Cys Ala Phe Val Gln Val Gly
        115                 120                 125

Met Tyr Phe Met
    130

<210> SEQ ID NO 184
<211> LENGTH: 69
<212> TYPE: PRT
<213> ORGANISM: Homo sapiens

<400> SEQUENCE: 184

Met Pro Cys Gln Pro Gly Gln Val Pro Ser Cys Gln Cys Thr Phe Gly
 1               5                  10                  15

Leu Leu Leu Met Leu Pro Ser Leu Pro Ser Pro Ala Ser Gln Pro Arg
            20                  25                  30

Pro Phe Cys Ser Ser Met Glu Tyr Phe His Gly Cys Ala Ser Pro Ser
        35                  40                  45

Gln Ala Ile Ile Gly Gly Phe Pro Phe Ala Ser Val Ala Leu Ala Asp
    50                  55                  60

Ile Leu Cys Leu Gln
 65

<210> SEQ ID NO 185
<211> LENGTH: 45
<212> TYPE: PRT
<213> ORGANISM: Homo sapiens

<400> SEQUENCE: 185

Met Ser Leu Leu Ser Pro Ala Ile Pro Ala Leu Thr Leu Ile Phe Ile
 1               5                  10                  15

Leu Met Phe Phe Ser Phe Pro Phe Arg Ala His Thr Val Val Thr Ile
            20                  25                  30

Val Ala Ser Gly Phe Leu Gly Leu Ser Pro Leu Cys Gly
        35                  40                  45

<210> SEQ ID NO 186
<211> LENGTH: 65
<212> TYPE: PRT
<213> ORGANISM: Homo sapiens

<400> SEQUENCE: 186

Met Ala Phe Gly Leu Gln Met Phe Ile Gln Arg Lys Phe Pro Tyr Pro
 1               5                  10                  15

Leu Gln Trp Ser Leu Leu Val Ala Val Val Ala Gly Ser Val Val Ser
            20                  25                  30

Tyr Gly Val Thr Arg Val Glu Ser Glu Lys Cys Asn Asn Leu Trp Leu
        35                  40                  45

Phe Leu Glu Thr Gly Gln Leu Pro Lys Asp Arg Ser Thr Asp Gln Arg
    50                  55                  60

Ser
 65

<210> SEQ ID NO 187
<211> LENGTH: 49
<212> TYPE: PRT
<213> ORGANISM: Homo sapiens

<400> SEQUENCE: 187

Met Asn Leu Leu Gly Met Ile Phe Ser Met Cys Gly Leu Met Leu Lys
```

-continued

```
                1               5              10              15
Leu Lys Trp Cys Ala Trp Val Ala Val Tyr Cys Ser Phe Ile Ser Phe
                        20                  25                  30

Ala Asn Ser Arg Ser Ser Glu Asp Thr Lys Gln Met Met Ser Ser Phe
                35                  40                  45

Met
```

<210> SEQ ID NO 188
<211> LENGTH: 170
<212> TYPE: PRT
<213> ORGANISM: Homo sapiens

<400> SEQUENCE: 188

```
Met Leu Leu Asn Val Ala Leu Val Ala Leu Val Leu Gly Ala Tyr
 1               5                  10                  15

Arg Leu Trp Val Arg Trp Gly Arg Arg Gly Leu Gly Ala Gly Ala Gly
                20                  25                  30

Ala Gly Glu Glu Ser Pro Ala Thr Ser Leu Pro Arg Met Lys Lys Arg
                35                  40                  45

Asp Phe Ser Leu Glu Gln Leu Arg Gln Tyr Asp Gly Ser Arg Asn Pro
        50                  55                  60

Arg Ile Leu Leu Ala Val Asn Gly Lys Val Phe Asp Val Thr Lys Gly
65                  70                  75                  80

Ser Lys Phe Tyr Gly Pro Ala Gly Pro Tyr Gly Ile Phe Ala Gly Arg
                    85                  90                  95

Asp Ala Ser Arg Gly Leu Ala Thr Phe Cys Leu Asp Lys Asp Ala Leu
                100                 105                 110

Arg Asp Glu Tyr Asp Asp Leu Ser Asp Leu Asn Ala Val Gln Met Glu
            115                 120                 125

Ser Val Arg Glu Trp Glu Met Gln Phe Lys Glu Lys Tyr Asp Tyr Val
        130                 135                 140

Gly Arg Leu Leu Lys Pro Gly Glu Glu Pro Ser Glu Tyr Thr Asp Glu
145                 150                 155                 160

Glu Asp Thr Lys Asp His Asn Lys Gln Asp
                165                 170
```

<210> SEQ ID NO 189
<211> LENGTH: 132
<212> TYPE: PRT
<213> ORGANISM: Homo sapiens

<400> SEQUENCE: 189

```
Met Thr Tyr Phe Ser Gly Leu Leu Val Ile Leu Ala Phe Ala Ala Trp
 1               5                  10                  15

Val Ala Leu Ala Glu Gly Leu Gly Val Ala Val Tyr Ala Ala Ala Val
                20                  25                  30

Leu Leu Gly Ala Gly Cys Ala Thr Ile Leu Val Thr Ser Leu Ala Met
            35                  40                  45

Thr Ala Asp Leu Ile Gly Pro His Thr Asn Ser Gly Ala Phe Val Tyr
        50                  55                  60

Gly Ser Met Ser Phe Leu Asp Lys Val Ala Asn Gly Leu Ala Val Met
65                  70                  75                  80

Ala Ile Gln Ser Leu His Pro Cys Pro Ser Glu Leu Cys Cys Arg Ala
                    85                  90                  95

Cys Val Ser Phe Tyr His Trp Ala Met Val Ala Val Thr Gly Gly Val
                100                 105                 110
```

-continued

Gly Val Ala Ala Ala Leu Cys Leu Cys Ser Leu Leu Leu Trp Pro Thr
        115                 120                 125

Arg Leu Arg Arg
    130

<210> SEQ ID NO 190
<211> LENGTH: 92
<212> TYPE: PRT
<213> ORGANISM: Homo sapiens

<400> SEQUENCE: 190

Met Ala Ala Gly Pro Ser Gly Cys Leu Val Pro Ala Phe Gly Leu Arg
1               5                   10                  15

Leu Leu Leu Ala Thr Val Leu Gln Ala Val Ser Ala Phe Gly Ala Glu
            20                  25                  30

Phe Ser Ser Glu Ala Cys Arg Glu Leu Gly Phe Ser Ser Asn Leu Leu
        35                  40                  45

Cys Ser Ser Cys Asp Leu Leu Gly Gln Phe Asn Leu Leu Gln Leu Asp
    50                  55                  60

Pro Asp Cys Arg Gly Cys Cys Gln Glu Glu Ala Gln Phe Glu Thr Lys
65                  70                  75                  80

Lys Leu Tyr Ala Gly Ala Ile Leu Glu Val Cys Gly
            85                  90

<210> SEQ ID NO 191
<211> LENGTH: 176
<212> TYPE: PRT
<213> ORGANISM: Homo sapiens
<220> FEATURE:
<221> NAME/KEY: SITE
<222> LOCATION: (137)
<223> OTHER INFORMATION: Xaa equals any of the naturally occurring
      L-amino acids

<400> SEQUENCE: 191

Met Arg Gly Ser His Leu Arg Leu Pro Tyr Leu Val Ala Ala Asn
1               5                   10                  15

Pro Val Asn Tyr Gly Arg Pro Tyr Arg Leu Ser Cys Val Glu Ala Phe
            20                  25                  30

Ala Ala Thr Phe Cys Ile Val Gly Phe Pro Asp Leu Ala Val Ile Leu
        35                  40                  45

Leu Arg Lys Phe Lys Trp Gly Lys Gly Phe Leu Asp Leu Asn Arg Gln
    50                  55                  60

Leu Leu Asp Lys Tyr Ala Ala Cys Gly Ser Pro Glu Glu Val Leu Gln
65                  70                  75                  80

Ala Glu Gln Glu Phe Leu Ala Asn Ala Lys Glu Ser Pro Gln Glu Glu
            85                  90                  95

Glu Ile Asp Pro Phe Asp Val Asp Ser Gly Arg Glu Phe Gly Asn Pro
        100                 105                 110

Asn Arg Pro Val Ala Ser Thr Arg Leu Pro Ser Asp Thr Asp Asp Ser
    115                 120                 125

Asp Ala Ser Glu Asp Pro Gly Pro Xaa Ala Glu Arg Gly Gly Ala Ser
130                 135                 140

Ser Ser Cys Cys Glu Glu Glu Gln Thr Gln Gly Arg Gly Ala Glu Ala
145                 150                 155                 160

Arg Ala Pro Ala Glu Val Trp Lys Gly Ile Lys Lys Arg Gln Arg Asp
            165                 170                 175

<210> SEQ ID NO 192
<211> LENGTH: 70
<212> TYPE: PRT
<213> ORGANISM: Homo sapiens

<400> SEQUENCE: 192

Met Ser Asn Ala Cys Lys Glu Leu Ala Ile Phe Leu Thr Thr Gly Ile
 1               5                  10                  15

Val Val Ser Ala Phe Gly Leu Pro Ile Val Phe Ala Arg Ala His Leu
            20                  25                  30

Ile Glu Trp Gly Ala Cys Ala Leu Val Leu Thr Gly Asn Thr Val Ile
        35                  40                  45

Phe Ala Thr Ile Leu Gly Phe Phe Leu Val Gly Ser Asn Asp Asp
    50                  55                  60

Phe Ser Trp Gln Gln Trp
65                  70

<210> SEQ ID NO 193
<211> LENGTH: 25
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring
      L-amino acids
<220> FEATURE:
<221> NAME/KEY: SITE
<222> LOCATION: (15)
<223> OTHER INFORMATION: Xaa equals any of the naturally occurring
      L-amino acids

<400> SEQUENCE: 193

Met Thr Leu Leu Ile Ile Phe Leu Pro Phe Xaa Phe Thr Thr Xaa Thr
 1               5                  10                  15

Asn Ser Gly Gly Ser Phe Pro Val Arg
            20                  25

<210> SEQ ID NO 194
<211> LENGTH: 73
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring
      L-amino acids

<400> SEQUENCE: 194

Met Lys Gly Glu Leu Leu Pro Phe Leu Phe Leu Thr Val Trp Leu Trp
 1               5                  10                  15

Leu Tyr Lys Leu Xaa Phe Gly Glu Ser Pro Arg Tyr Pro Asn Val Ile
            20                  25                  30

Gly Lys Thr Tyr Phe Phe Phe Trp Thr Asp Gln Ile Ser Arg Glu Ser
        35                  40                  45

Arg Phe Leu Glu Arg Leu Ala Phe Ile Val Ser Glu Asn Cys Leu Ile
    50                  55                  60

Phe Leu Ile His Ala Ile Thr Gly Gln
65                  70

<210> SEQ ID NO 195
<211> LENGTH: 289
<212> TYPE: PRT

<210> SEQ ID NO 195
<211> LENGTH: 289 (implied)
<212> TYPE: PRT
<213> ORGANISM: Homo sapiens

<400> SEQUENCE: 195

```
Met Ser Gly Phe Ser Thr Glu Glu Arg Ala Ala Pro Phe Ser Leu Glu
 1               5                  10                  15

Tyr Arg Val Phe Leu Lys Asn Glu Lys Gly Gln Tyr Ile Ser Pro Phe
            20                  25                  30

His Asp Ile Pro Ile Tyr Ala Asp Lys Asp Val Phe His Met Val Val
        35                  40                  45

Glu Val Pro Arg Trp Ser Asn Ala Lys Met Glu Ile Ala Thr Lys Asp
    50                  55                  60

Pro Leu Asn Pro Ile Lys Gln Asp Val Lys Lys Gly Lys Leu Arg Tyr
65                  70                  75                  80

Val Ala Asn Leu Phe Pro Tyr Lys Gly Tyr Ile Trp Asn Tyr Gly Ala
                85                  90                  95

Ile Pro Gln Thr Trp Glu Asp Pro Gly His Asn Asp Lys His Thr Gly
            100                 105                 110

Cys Cys Gly Asp Asn Asp Pro Ile Asp Val Cys Glu Ile Gly Ser Lys
        115                 120                 125

Val Cys Ala Arg Gly Glu Ile Ile Gly Val Lys Val Leu Gly Ile Leu
    130                 135                 140

Ala Met Ile Asp Glu Gly Glu Thr Asp Trp Lys Val Ile Ala Ile Asn
145                 150                 155                 160

Val Asp Asp Pro Asp Ala Ala Asn Tyr Asn Asp Ile Asn Asp Val Lys
                165                 170                 175

Arg Leu Lys Pro Gly Tyr Leu Glu Ala Thr Val Asp Trp Phe Arg Arg
            180                 185                 190

Tyr Lys Val Pro Asp Gly Lys Pro Glu Asn Glu Phe Ala Phe Asn Ala
        195                 200                 205

Glu Phe Lys Asp Lys Asp Phe Ala Ile Asp Ile Lys Ser Thr His
    210                 215                 220

Asp His Trp Lys Ala Leu Val Thr Lys Thr Asn Gly Lys Gly Ile
225                 230                 235                 240

Ser Cys Met Asn Thr Thr Leu Ser Glu Ser Pro Phe Lys Cys Asp Pro
                245                 250                 255

Asp Ala Ala Arg Ala Ile Val Asp Ala Leu Pro Pro Pro Cys Glu Ser
            260                 265                 270

Ala Cys Thr Val Pro Thr Asp Val Asp Lys Trp Phe His His Gln Lys
        275                 280                 285

Asn
```

<210> SEQ ID NO 196
<211> LENGTH: 624
<212> TYPE: PRT
<213> ORGANISM: Homo sapiens

<400> SEQUENCE: 196

```
Met Glu Ile Pro Gly Ser Leu Cys Lys Lys Val Lys Leu Ser Asn Asn
 1               5                  10                  15

Ala Gln Asn Trp Gly Met Gln Arg Ala Thr Asn Val Thr Tyr Gln Ala
            20                  25                  30

His His Val Ser Arg Asn Lys Arg Gly Gln Val Val Gly Thr Arg Gly
        35                  40                  45

Gly Phe Arg Gly Cys Thr Val Trp Leu Thr Gly Leu Ser Gly Ala Gly
    50                  55                  60
```

```
Lys Thr Thr Val Ser Met Ala Leu Glu Glu Tyr Leu Val Cys His Gly
 65                  70                  75                  80

Ile Pro Cys Tyr Thr Leu Asp Gly Asp Asn Ile Arg Gln Gly Leu Asn
                 85                  90                  95

Lys Asn Leu Gly Phe Ser Pro Glu Asp Arg Glu Asn Val Arg Arg
            100                 105                 110

Ile Ala Glu Val Ala Lys Leu Phe Ala Asp Ala Gly Leu Val Cys Ile
            115                 120                 125

Thr Ser Phe Ile Ser Pro Tyr Thr Gln Asp Arg Asn Asn Ala Arg Gln
130                 135                 140

Ile His Glu Gly Ala Ser Leu Pro Phe Phe Glu Val Phe Val Asp Ala
145                 150                 155                 160

Pro Leu His Val Cys Glu Gln Arg Asp Val Lys Gly Leu Tyr Lys Lys
                165                 170                 175

Ala Arg Ala Gly Glu Ile Lys Gly Phe Thr Gly Ile Asp Ser Glu Tyr
            180                 185                 190

Glu Lys Pro Glu Ala Pro Glu Leu Val Leu Lys Thr Asp Ser Cys Asp
            195                 200                 205

Val Asn Asp Cys Val Gln Gln Val Glu Leu Leu Gln Glu Arg Asp
210                 215                 220

Ile Val Pro Val Asp Ala Ser Tyr Glu Val Lys Glu Leu Tyr Val Pro
225                 230                 235                 240

Glu Asn Lys Leu His Leu Ala Lys Thr Asp Ala Glu Thr Leu Pro Ala
                245                 250                 255

Leu Lys Ile Asn Lys Val Asp Met Gln Trp Val Gln Val Leu Ala Glu
                260                 265                 270

Gly Trp Ala Thr Pro Leu Asn Gly Phe Met Arg Glu Arg Glu Tyr Leu
            275                 280                 285

Gln Cys Leu His Phe Asp Cys Leu Leu Asp Gly Gly Val Ile Asn Leu
            290                 295                 300

Ser Val Pro Ile Val Leu Thr Ala Thr His Glu Asp Lys Glu Arg Leu
305                 310                 315                 320

Asp Gly Cys Thr Ala Phe Ala Leu Met Tyr Glu Gly Arg Arg Val Ala
                325                 330                 335

Ile Leu Arg Asn Pro Glu Phe Phe Glu His Arg Lys Glu Glu Arg Cys
            340                 345                 350

Ala Arg Gln Trp Gly Thr Thr Cys Lys Asn His Pro Tyr Ile Lys Met
            355                 360                 365

Val Met Glu Gln Gly Asp Trp Leu Ile Gly Gly Asp Leu Gln Val Leu
370                 375                 380

Asp Arg Val Tyr Trp Asn Asp Gly Leu Asp Gln Tyr Arg Leu Thr Pro
385                 390                 395                 400

Thr Glu Leu Lys Gln Lys Phe Lys Asp Met Asn Ala Asp Ala Val Phe
                405                 410                 415

Ala Phe Gln Leu Arg Asn Pro Val His Asn Gly His Ala Leu Leu Met
                420                 425                 430

Gln Asp Thr His Lys Gln Leu Leu Glu Arg Gly Tyr Arg Arg Pro Val
            435                 440                 445

Leu Leu Leu His Pro Leu Gly Gly Trp Thr Lys Asp Asp Val Pro
            450                 455                 460

Leu Met Trp Arg Met Lys Gln His Ala Ala Val Leu Glu Glu Gly Val
465                 470                 475                 480
```

```
Leu Asn Pro Glu Thr Thr Val Val Ala Ile Phe Pro Ser Pro Met Met
                485                 490                 495

Tyr Ala Gly Pro Thr Glu Val Gln Trp His Cys Arg Ala Arg Met Val
            500                 505                 510

Ala Gly Ala Asn Phe Tyr Ile Val Gly Arg Asp Pro Ala Gly Met Pro
        515                 520                 525

His Pro Glu Thr Gly Lys Asp Leu Tyr Glu Pro Ser His Gly Ala Lys
    530                 535                 540

Val Leu Thr Met Ala Pro Gly Leu Ile Thr Leu Glu Ile Val Pro Phe
545                 550                 555                 560

Arg Val Ala Ala Tyr Asn Lys Lys Lys Arg Met Asp Tyr Tyr Asp
                565                 570                 575

Ser Glu His His Glu Asp Phe Glu Phe Ile Ser Gly Thr Arg Met Arg
            580                 585                 590

Lys Leu Ala Arg Glu Gly Gln Lys Pro Pro Glu Gly Phe Met Ala Pro
        595                 600                 605

Lys Ala Trp Thr Val Leu Thr Glu Tyr Tyr Lys Ser Leu Glu Lys Ala
    610                 615                 620

<210> SEQ ID NO 197
<211> LENGTH: 649
<212> TYPE: PRT
<213> ORGANISM: Homo sapiens
<220> FEATURE:
<221> NAME/KEY: SITE
<222> LOCATION: (555)
<223> OTHER INFORMATION: Xaa equals any of the naturally occurring
      L-amino acids
<220> FEATURE:
<221> NAME/KEY: SITE
<222> LOCATION: (557)
<223> OTHER INFORMATION: Xaa equals any of the naturally occurring
      L-amino acids
<220> FEATURE:
<221> NAME/KEY: SITE
<222> LOCATION: (558)
<223> OTHER INFORMATION: Xaa equals any of the naturally occurring
      L-amino acids

<400> SEQUENCE: 197

Met Ser Ala Ser Gln Asp Leu Glu Pro Lys Pro Leu Phe Pro Lys Pro
  1               5                  10                  15

Ala Phe Gly Gln Lys Pro Pro Leu Ser Thr Glu Asn Ser His Glu Asp
             20                  25                  30

Glu Ser Pro Met Lys Asn Val Ser Ser Lys Gly Ser Pro Ala Pro
         35                  40                  45

Leu Gly Val Arg Ser Lys Ser Gly Pro Leu Lys Pro Ala Arg Glu Asp
     50                  55                  60

Ser Glu Asn Lys Asp His Ala Gly Glu Ile Ser Ser Leu Pro Phe Pro
 65                  70                  75                  80

Gly Val Val Leu Lys Pro Ala Ala Ser Arg Gly Gly Pro Gly Leu Ser
                 85                  90                  95

Lys Asn Gly Glu Glu Lys Lys Glu Asp Arg Lys Ile Asp Ala Ala Lys
            100                 105                 110

Asn Thr Phe Gln Ser Lys Ile Asn Gln Glu Glu Leu Ala Ser Gly Thr
        115                 120                 125

Pro Pro Ala Arg Phe Pro Lys Ala Pro Ser Lys Leu Thr Val Gly Gly
    130                 135                 140

Pro Trp Gly Gln Ser Gln Glu Lys Glu Lys Gly Asp Lys Asn Ser Ala
145                 150                 155                 160
```

-continued

```
Thr Pro Lys Gln Lys Pro Leu Pro Pro Leu Phe Thr Leu Gly Pro Pro
                165                 170                 175
Pro Pro Lys Pro Asn Arg Pro Pro Asn Val Asp Leu Thr Lys Phe His
            180                 185                 190
Lys Thr Ser Ser Gly Asn Ser Thr Ser Lys Gly Gln Thr Ser Tyr Ser
        195                 200                 205
Thr Thr Ser Leu Pro Pro Pro Pro Ser His Pro Ala Ser Gln Pro
    210                 215                 220
Pro Leu Pro Ala Ser His Pro Ser Gln Pro Pro Val Pro Ser Leu Pro
225                 230                 235                 240
Pro Arg Asn Ile Lys Pro Pro Phe Asp Leu Lys Ser Pro Val Asn Glu
                245                 250                 255
Asp Asn Gln Asp Gly Val Thr His Ser Asp Gly Ala Gly Asn Leu Asp
            260                 265                 270
Glu Glu Gln Asp Ser Glu Gly Glu Thr Tyr Glu Asp Ile Glu Ala Ser
        275                 280                 285
Lys Glu Arg Glu Lys Lys Arg Glu Lys Glu Lys Lys Arg Leu Glu
    290                 295                 300
Leu Glu Lys Lys Glu Gln Lys Glu Lys Glu Lys Lys Glu Gln Glu Ile
305                 310                 315                 320
Lys Lys Lys Phe Lys Leu Thr Gly Pro Ile Gln Val Ile His Leu Ala
                325                 330                 335
Lys Ala Cys Cys Asp Val Lys Gly Gly Lys Asn Glu Leu Ser Phe Lys
            340                 345                 350
Gln Gly Glu Gln Ile Glu Ile Ile Arg Ile Thr Asp Asn Pro Glu Gly
        355                 360                 365
Lys Trp Leu Gly Arg Thr Ala Arg Gly Ser Tyr Gly Tyr Ile Lys Thr
    370                 375                 380
Thr Ala Val Glu Ile Asp Tyr Asp Ser Leu Lys Leu Lys Lys Asp Ser
385                 390                 395                 400
Leu Gly Ala Pro Ser Arg Pro Ile Glu Asp Asp Gln Glu Val Tyr Asp
                405                 410                 415
Asp Val Ala Glu Gln Asp Asp Ile Ser Ser His Ser Gln Ser Gly Ser
            420                 425                 430
Gly Gly Ile Phe Pro Pro Pro Asp Asp Ile Tyr Asp Gly Ile
        435                 440                 445
Glu Glu Glu Asp Ala Asp Asp Gly Ser Thr Leu Gln Val Gln Glu Lys
    450                 455                 460
Ser Asn Thr Trp Ser Trp Gly Ile Leu Lys Met Leu Lys Gly Lys Asp
465                 470                 475                 480
Asp Arg Lys Lys Ser Ile Arg Glu Lys Pro Lys Val Ser Asp Ser Asp
                485                 490                 495
Asn Asn Glu Gly Ser Ser Phe Pro Ala Pro Lys Gln Leu Asp Met
            500                 505                 510
Gly Asp Glu Val Tyr Asp Val Asp Thr Ser Asp Phe Pro Val Ser
    515                 520                 525
Ser Ala Glu Met Ser Gln Gly Thr Asn Val Gly Lys Ala Lys Thr Glu
530                 535                 540
Glu Lys Asp Leu Lys Lys Leu Lys Lys Gln Xaa Lys Xaa Xaa Lys Asp
545                 550                 555                 560
Phe Arg Lys Lys Phe Lys Tyr Asp Gly Glu Ile Arg Val Leu Tyr Ser
                565                 570                 575
```

```
Thr Lys Val Thr Thr Ser Ile Thr Ser Lys Lys Trp Gly Thr Arg Asp
            580                 585                 590

Leu Gln Val Lys Pro Gly Glu Ser Leu Glu Val Ile Gln Thr Thr Asp
        595                 600                 605

Asp Thr Lys Val Leu Cys Arg Asn Glu Glu Gly Lys Tyr Gly Tyr Val
    610                 615                 620

Leu Arg Ser Tyr Leu Ala Asp Asn Asp Gly Glu Ile Tyr Asp Asp Ile
625                 630                 635                 640

Ala Asp Gly Cys Ile Tyr Asp Asn Asp
                645

<210> SEQ ID NO 198
<211> LENGTH: 55
<212> TYPE: PRT
<213> ORGANISM: Homo sapiens

<400> SEQUENCE: 198

Met Ala Trp Pro Ser Arg Ser Lys Met Phe Thr Leu Pro Val Leu
 1               5                  10                  15

Cys Tyr Leu Trp Ser Leu Trp Leu Pro Gln Phe Ser Trp Ile Gln Glu
                20                  25                  30

Leu Lys Ala Val Leu Arg Asp Asp Gly Leu Ile Ser Ala Val Ala Trp
            35                  40                  45

Asn Ala Glu Phe Gln Thr Cys
        50                  55

<210> SEQ ID NO 199
<211> LENGTH: 266
<212> TYPE: PRT
<213> ORGANISM: Homo sapiens

<400> SEQUENCE: 199

Met Val Lys Val Thr Phe Asn Ser Ala Leu Ala Gln Lys Glu Ala Lys
 1               5                  10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Phe Glu Glu Glu Val Glu
        115                 120                 125

Phe Ile Ser Val Pro Val Pro Glu Phe Ala Asp Ser Asp Pro Ala Asn
    130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190
```

```
Leu Pro Gln Ser Tyr Leu Ile His Glu His Met Val Ile Thr Asp Arg
        195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Ser
                260                 265

<210> SEQ ID NO 200
<211> LENGTH: 315
<212> TYPE: PRT
<213> ORGANISM: Homo sapiens

<400> SEQUENCE: 200

Met Asp Leu Arg Gln Phe Leu Met Cys Leu Ser Leu Cys Thr Ala Phe
 1               5                  10                  15

Ala Leu Ser Lys Pro Thr Glu Lys Lys Asp Arg Val His His Glu Pro
                20                  25                  30

Gln Leu Ser Asp Lys Val His Asn Asp Ala Gln Ser Phe Asp Tyr Asp
            35                  40                  45

His Asp Ala Phe Leu Gly Ala Glu Glu Ala Lys Thr Phe Asp Gln Leu
        50                  55                  60

Thr Pro Glu Glu Ser Lys Glu Arg Leu Gly Lys Ile Val Ser Lys Ile
65                  70                  75                  80

Asp Gly Asp Lys Asp Gly Phe Val Thr Val Asp Glu Leu Lys Asp Trp
                85                  90                  95

Ile Lys Phe Ala Gln Lys Arg Trp Ile Tyr Glu Asp Val Glu Arg Gln
                100                 105                 110

Trp Lys Gly His Asp Leu Asn Glu Asp Gly Leu Val Ser Trp Glu Glu
            115                 120                 125

Tyr Lys Asn Ala Thr Tyr Gly Tyr Val Leu Asp Asp Pro Asp Pro Asp
    130                 135                 140

Asp Gly Phe Asn Tyr Lys Gln Met Met Val Arg Asp Glu Arg Arg Phe
145                 150                 155                 160

Lys Met Ala Asp Lys Asp Gly Asp Leu Ile Ala Thr Lys Glu Glu Phe
                165                 170                 175

Thr Ala Phe Leu His Pro Glu Glu Tyr Asp Tyr Met Lys Asp Ile Val
            180                 185                 190

Val Gln Glu Thr Met Glu Asp Ile Asp Lys Asn Ala Asp Gly Phe Ile
        195                 200                 205

Asp Leu Glu Glu Tyr Ile Gly Asp Met Tyr Ser His Asp Gly Asn Thr
    210                 215                 220

Asp Glu Pro Glu Trp Val Lys Thr Glu Arg Glu Gln Phe Val Glu Phe
225                 230                 235                 240

Arg Asp Lys Asn Arg Asp Gly Lys Met Asp Lys Glu Glu Thr Lys Asp
                245                 250                 255

Trp Ile Leu Pro Ser Asp Tyr Asp His Ala Glu Ala Glu Ala Arg His
            260                 265                 270

Leu Val Tyr Glu Ser Asp Gln Asn Lys Asp Gly Lys Leu Thr Lys Glu
        275                 280                 285

Glu Ile Val Asp Lys Tyr Asp Leu Phe Val Gly Ser Gln Ala Thr Asp
    290                 295                 300
```

```
Phe Gly Glu Ala Leu Val Arg His Asp Glu Phe
305                 310                 315

<210> SEQ ID NO 201
<211> LENGTH: 207
<212> TYPE: PRT
<213> ORGANISM: Homo sapiens

<400> SEQUENCE: 201

Met Phe Asp Ala Val Leu Ile Leu Leu Ile Pro Leu Lys Asp Lys
  1               5                  10                  15

Leu Val Asp Pro Ile Leu Arg Arg His Gly Leu Leu Pro Ser Ser Leu
                 20                  25                  30

Lys Arg Ile Ala Val Gly Met Phe Phe Val Met Cys Ser Ala Phe Ala
             35                  40                  45

Ala Gly Ile Leu Glu Ser Lys Arg Leu Asn Leu Val Lys Glu Lys Thr
         50                  55                  60

Ile Asn Gln Thr Ile Gly Asn Val Val Tyr His Ala Ala Asp Leu Ser
 65                  70                  75                  80

Leu Trp Trp Gln Val Pro Gln Tyr Leu Leu Ile Gly Ile Ser Glu Ile
                 85                  90                  95

Phe Ala Ser Ile Ala Gly Leu Glu Phe Ala Tyr Ser Ala Ala Pro Lys
            100                 105                 110

Ser Met Gln Ser Ala Ile Met Gly Leu Phe Phe Phe Ser Gly Val
            115                 120                 125

Gly Ser Phe Val Gly Ser Gly Leu Leu Ala Leu Val Ser Ile Lys Ala
        130                 135                 140

Ile Gly Trp Met Ser Ser His Thr Asp Phe Gly Asn Ile Asn Gly Cys
145                 150                 155                 160

Tyr Leu Asn Tyr Phe Phe Leu Leu Ala Ala Ile Gln Gly Ala Thr
                165                 170                 175

Leu Leu Leu Phe Leu Ile Ile Ser Val Lys Tyr Asp His His Arg Asp
            180                 185                 190

His Gln Arg Ser Arg Ala Asn Gly Val Pro Thr Ser Arg Arg Ala
        195                 200                 205

<210> SEQ ID NO 202
<211> LENGTH: 195
<212> TYPE: PRT
<213> ORGANISM: Homo sapiens

<400> SEQUENCE: 202

Met Arg Ser Arg Ile Arg Glu Phe Asp Ser Ser Thr Leu Asn Glu Ser
  1               5                  10                  15

Val Arg Asn Thr Ile Met Arg Asp Leu Lys Ala Val Gly Lys Lys Phe
                 20                  25                  30

Met His Val Leu Tyr Pro Arg Lys Ser Asn Thr Leu Leu Arg Asp Trp
             35                  40                  45

Asp Leu Trp Gly Pro Leu Ile Leu Cys Val Thr Leu Ala Leu Met Leu
         50                  55                  60

Gln Arg Asp Ser Ala Asp Ser Glu Lys Asp Gly Gly Pro Gln Phe Ala
 65                  70                  75                  80

Glu Val Phe Val Ile Val Trp Phe Gly Ala Val Thr Ile Thr Leu Asn
                 85                  90                  95

Ser Lys Leu Leu Gly Gly Asn Ile Ser Phe Phe Gln Ser Leu Cys Val
            100                 105                 110
```

```
Leu Gly Tyr Cys Ile Leu Pro Leu Thr Val Ala Met Leu Ile Cys Arg
            115                 120                 125

Leu Val Leu Leu Ala Asp Pro Gly Pro Val Asn Phe Met Val Arg Leu
        130                 135                 140

Phe Val Val Ile Val Met Phe Ala Trp Ser Ile Val Ala Ser Thr Ala
145                 150                 155                 160

Phe Leu Ala Asp Ser Gln Pro Pro Asn Arg Arg Ala Leu Ala Val Tyr
                165                 170                 175

Pro Val Phe Leu Phe Tyr Phe Val Ile Ser Trp Met Ile Leu Thr Phe
            180                 185                 190

Thr Pro Gln
        195

<210> SEQ ID NO 203
<211> LENGTH: 330
<212> TYPE: PRT
<213> ORGANISM: Homo sapiens

<400> SEQUENCE: 203

Met Ala Lys Asp Gln Ala Val Glu Asn Ile Leu Val Ser Pro Val Val
  1               5                  10                  15

Val Ala Ser Ser Leu Gly Leu Val Ser Leu Gly Gly Lys Ala Thr Thr
                 20                  25                  30

Ala Ser Gln Ala Lys Ala Val Leu Ser Ala Glu Gln Leu Arg Asp Glu
             35                  40                  45

Glu Val His Ala Gly Leu Gly Glu Leu Leu Arg Ser Leu Ser Asn Ser
         50                  55                  60

Thr Ala Arg Asn Val Thr Trp Lys Leu Gly Ser Arg Leu Tyr Gly Pro
 65                  70                  75                  80

Ser Ser Val Ser Phe Ala Asp Asp Phe Val Arg Ser Ser Lys Gln His
                 85                  90                  95

Tyr Asn Cys Glu His Ser Lys Ile Asn Phe Arg Asp Lys Arg Ser Ala
            100                 105                 110

Leu Gln Ser Ile Asn Glu Trp Ala Ala Gln Thr Thr Asp Gly Lys Leu
        115                 120                 125

Pro Glu Val Thr Lys Asp Val Glu Arg Thr Asp Gly Ala Leu Leu Val
    130                 135                 140

Asn Ala Met Phe Phe Lys Pro His Trp Asp Glu Lys Phe His His Lys
145                 150                 155                 160

Met Val Asp Asn Arg Gly Phe Met Val Thr Arg Ser Tyr Thr Val Gly
                165                 170                 175

Val Met Met Met His Arg Thr Gly Leu Tyr Asn Tyr Tyr Asp Asp Glu
            180                 185                 190

Lys Glu Lys Leu Gln Ile Val Glu Met Pro Leu Ala His Lys Leu Ser
        195                 200                 205

Ser Leu Ile Ile Leu Met Pro His His Val Glu Pro Leu Glu Arg Leu
    210                 215                 220

Glu Lys Leu Leu Thr Lys Glu Gln Leu Lys Ile Trp Met Gly Lys Met
225                 230                 235                 240

Gln Lys Lys Ala Val Ala Ile Ser Leu Pro Lys Gly Val Val Glu Val
                245                 250                 255

Thr His Asp Leu Gln Lys His Leu Ala Gly Leu Gly Leu Thr Glu Ala
            260                 265                 270

Ile Asp Lys Asn Lys Ala Asp Leu Ser Arg Met Ser Gly Lys Lys Asp
```

```
                        275                 280                 285
Leu Tyr Leu Ala Ser Val Phe His Ala Thr Ala Phe Glu Leu Asp Thr
    290                 295                 300

Asp Gly Asn Pro Leu Thr Arg Ile Thr Gly Gly Val Arg Thr Gln
305                 310                 315                 320

Val Phe Tyr Ala Asp His Pro Phe Ile Ser
                325                 330

<210> SEQ ID NO 204
<211> LENGTH: 58
<212> TYPE: PRT
<213> ORGANISM: Homo sapiens

<400> SEQUENCE: 204

Met Cys Met Gln Leu Phe Gly Phe Leu Ala Phe Met Ile Phe Met Cys
  1               5                  10                  15

Trp Val Gly Asp Val Tyr Pro Val Tyr Gln Pro Val Gly Pro Lys Gln
                 20                  25                  30

Tyr Pro Tyr Asn Asn Leu Tyr Leu Glu Arg Gly Gly Asp Pro Ser Lys
             35                  40                  45

Glu Pro Glu Arg Val Val His Tyr Glu Ile
     50                  55

<210> SEQ ID NO 205
<211> LENGTH: 392
<212> TYPE: PRT
<213> ORGANISM: Homo sapiens

<400> SEQUENCE: 205

Met Asp Ala Leu Val Glu Asp Ile Cys Ile Leu Asn His Glu Lys
  1               5                  10                  15

Ala His Lys Arg Asp Thr Val Thr Pro Val Ser Ile Tyr Ser Gly Asp
                 20                  25                  30

Glu Ser Val Ala Ser His Phe Ala Leu Val Thr Ala Tyr Glu Asp Ile
             35                  40                  45

Lys Lys Arg Leu Lys Asp Ser Glu Lys Glu Asn Ser Leu Leu Lys Lys
     50                  55                  60

Arg Ile Arg Phe Leu Glu Glu Lys Leu Ile Ala Arg Phe Glu Glu Glu
 65                  70                  75                  80

Thr Ser Ser Val Gly Arg Glu Gln Val Asn Lys Ala Tyr His Ala Tyr
                 85                  90                  95

Arg Glu Val Cys Ile Asp Arg Asp Asn Leu Lys Ser Lys Leu Asp Lys
                100                 105                 110

Met Asn Lys Asp Asn Ser Glu Ser Leu Lys Val Leu Asn Glu Gln Leu
            115                 120                 125

Gln Ser Lys Glu Val Glu Leu Leu Gln Leu Arg Thr Glu Val Glu Thr
130                 135                 140

Gln Gln Val Met Arg Asn Leu Asn Pro Pro Ser Ser Asn Trp Glu Val
145                 150                 155                 160

Glu Lys Leu Ser Cys Asp Leu Lys Ile His Gly Leu Glu Gln Glu Leu
                165                 170                 175

Glu Leu Met Arg Lys Glu Cys Ser Asp Leu Lys Ile Glu Leu Gln Lys
            180                 185                 190

Ala Lys Gln Thr Asp Pro Tyr Gln Glu Asp Asn Leu Lys Ser Arg Asp
        195                 200                 205

Leu Gln Lys Leu Ser Ile Ser Ser Asp Asn Met Gln His Ala Tyr Trp
```

```
                210                 215                 220
Glu Leu Lys Arg Glu Met Ser Asn Leu His Leu Val Thr Gln Val Gln
225                 230                 235                 240

Ala Glu Leu Leu Arg Lys Leu Lys Thr Ser Thr Ala Ile Lys Lys Ala
                245                 250                 255

Cys Ala Pro Val Gly Cys Ser Glu Asp Leu Gly Arg Asp Ser Thr Lys
                260                 265                 270

Leu His Leu Met Asn Phe Thr Ala Thr Tyr Thr Arg His Pro Pro Leu
            275                 280                 285

Leu Pro Asn Gly Lys Ala Leu Cys His Thr Thr Ser Ser Pro Leu Pro
        290                 295                 300

Gly Asp Val Lys Val Leu Ser Glu Lys Ala Ile Leu Gln Ser Trp Thr
305                 310                 315                 320

Asp Asn Glu Arg Ser Ile Pro Asn Asp Gly Thr Cys Phe Gln Glu His
                325                 330                 335

Ser Ser Tyr Gly Arg Asn Ser Leu Glu Asp Asn Ser Trp Val Phe Pro
                340                 345                 350

Ser Pro Pro Lys Ser Ser Glu Thr Ala Phe Gly Glu Thr Lys Thr Lys
                355                 360                 365

Thr Leu Pro Leu Pro Asn Leu Pro Pro Leu His Tyr Leu Asp Gln His
370                 375                 380

Asn Gln Asn Cys Leu Tyr Lys Asn
385                 390

<210> SEQ ID NO 206
<211> LENGTH: 26
<212> TYPE: PRT
<213> ORGANISM: Homo sapiens

<400> SEQUENCE: 206

Met His His His Thr Gln Leu Met Phe Ile Tyr Leu Phe Ile Tyr Leu
  1               5                  10                  15

Phe Ile Leu Gly Val Phe Phe Phe Phe
             20                  25

<210> SEQ ID NO 207
<211> LENGTH: 38
<212> TYPE: PRT
<213> ORGANISM: Homo sapiens

<400> SEQUENCE: 207

Met Asn Cys Ile Leu Leu Leu Tyr Leu Leu Ile Pro Thr Ile Ser Ile
  1               5                  10                  15

Ser Val Val Pro Tyr Val Ala Leu Asn Ile Lys Tyr Ile Lys Glu Cys
                 20                  25                  30

Thr Glu Asn Ser Phe Tyr
            35

<210> SEQ ID NO 208
<211> LENGTH: 45
<212> TYPE: PRT
<213> ORGANISM: Homo sapiens
<220> FEATURE:
<221> NAME/KEY: SITE
<222> LOCATION: (28)
<223> OTHER INFORMATION: Xaa equals any of the naturally occurring
      L-amino acids

<400> SEQUENCE: 208
```

```
Met Lys Lys Ser Leu Glu Asn Leu Asn Arg Leu Gln Val Met Leu Leu
 1               5                  10                  15

His Leu Thr Ala Ala Phe Leu Gln Arg Ala His Xaa Ile Leu Thr Thr
                20                  25                  30

Arg Met Ser Leu Gly Phe Gln Ser Pro His Leu Thr Met
        35                  40                  45
```

<210> SEQ ID NO 209
<211> LENGTH: 81
<212> TYPE: PRT
<213> ORGANISM: Homo sapiens

<400> SEQUENCE: 209

```
Met Ser Lys Arg Ser Ala Ser Phe Ile Leu Leu Pro Leu Leu Phe Leu
 1               5                  10                  15

Lys Gly Ser Phe Ala Lys Leu Asn Ala Arg Ile Ser Asp Cys Leu Glu
                20                  25                  30

Glu Arg Tyr Cys His Asn Leu Trp Met Val Phe Gln Gly Cys Val Ile
            35                  40                  45

Thr Glu Leu His Leu Ser Arg Met Ser Lys Thr Leu Ser Ser Leu Cys
     50                  55                  60

Tyr Asp Phe Val Ile Asn Val Tyr Ile Phe Phe Lys Phe Leu Asp Ile
 65                  70                  75                  80

Thr
```

<210> SEQ ID NO 210
<211> LENGTH: 49
<212> TYPE: PRT
<213> ORGANISM: Homo sapiens

<400> SEQUENCE: 210

```
Met Cys Ser Leu Phe Glu Ser Arg Phe Phe Cys Phe Val Leu Phe Ser
 1               5                  10                  15

Glu Lys Ile Ile Gln Leu Cys Ala Ser Ile Ala Phe Leu Cys Phe Val
                20                  25                  30

Lys His Val Pro Trp Pro Lys Trp Lys Arg Lys Cys Leu Ile Asn Ala
            35                  40                  45

Phe
```

<210> SEQ ID NO 211
<211> LENGTH: 203
<212> TYPE: PRT
<213> ORGANISM: Homo sapiens

<400> SEQUENCE: 211

```
Met Thr Leu Arg Pro Ser Leu Pro Leu His Leu Leu Leu Leu Leu Leu
 1               5                  10                  15

Leu Leu Ser Ala Ala Val Cys Arg Ala Glu Ala Gly Leu Glu Thr Glu
                20                  25                  30

Ser Pro Val Arg Thr Leu Gln Val Glu Thr Leu Val Glu Pro Pro Glu
            35                  40                  45

Pro Cys Ala Glu Pro Ala Ala Phe Gly Asp Thr Leu His Ile His Tyr
     50                  55                  60

Thr Gly Ser Leu Val Asp Gly Arg Ile Ile Asp Thr Ser Leu Thr Arg
 65                  70                  75                  80

Asp Pro Leu Val Ile Glu Leu Gly Gln Lys Gln Val Ile Pro Gly Leu
                 85                  90                  95
```

-continued

```
Glu Gln Ser Leu Leu Asp Met Cys Val Gly Glu Lys Arg Arg Ala Ile
            100                 105                 110

Ile Pro Ser His Leu Ala Tyr Gly Lys Arg Gly Phe Pro Pro Ser Val
            115                 120                 125

Pro Ala Asp Ala Val Val Gln Tyr Asp Val Glu Leu Ile Ala Leu Ile
        130                 135                 140

Arg Ala Asn Tyr Trp Leu Lys Leu Val Lys Gly Ile Leu Pro Leu Val
145                 150                 155                 160

Gly Met Ala Met Val Pro Pro Ser Trp Ala Ser Leu Gly Ile Thr Tyr
                165                 170                 175

Thr Glu Arg Pro Ile Asp Pro Lys Ser Pro Lys Arg Ser Ser Arg Lys
            180                 185                 190

Arg Asn Glu Thr Arg Ala Lys Arg Asn Asn Lys
            195                 200
```

<210> SEQ ID NO 212
<211> LENGTH: 186
<212> TYPE: PRT
<213> ORGANISM: Homo sapiens
<220> FEATURE:
<221> NAME/KEY: SITE
<222> LOCATION: (122)
<223> OTHER INFORMATION: Xaa equals any of the naturally occurring
      L-amino acids
<220> FEATURE:
<221> NAME/KEY: SITE
<222> LOCATION: (136)
<223> OTHER INFORMATION: Xaa equals any of the naturally occurring
      L-amino acids
<220> FEATURE:
<221> NAME/KEY: SITE
<222> LOCATION: (142)
<223> OTHER INFORMATION: Xaa equals any of the naturally occurring
      L-amino acids

<400> SEQUENCE: 212

```
Met Lys Thr Leu Met Thr Ile Cys Pro Gly Thr Val Leu Leu Val Phe
1               5                   10                  15

Ser Ile Ser Leu Trp Ile Ile Ala Ala Trp Thr Val Arg Val Cys Glu
            20                  25                  30

Ser Pro Glu Ser Pro Ala Gln Pro Ser Gly Ser Ser Leu Pro Ala Trp
        35                  40                  45

Tyr His Asp Gln Gln Asp Val Thr Ser Asn Phe Leu Gly Ala Met Trp
    50                  55                  60

Leu Ile Ser Ile Thr Phe Leu Ser Ile Gly Tyr Gly Asp Met Val Pro
65                  70                  75                  80

His Thr Tyr Cys Gly Lys Gly Val Cys Leu Leu Thr Gly Ile Met Gly
                85                  90                  95

Ala Gly Cys Thr Ala Leu Val Val Ala Val Val Ala Arg Lys Leu Glu
            100                 105                 110

Leu Thr Lys Ala Glu Lys His Val His Xaa Phe Met Met Asp Thr Gln
        115                 120                 125

Leu Thr Lys Arg Ile Lys Asn Xaa Ala Ala Asn Val Leu Xaa Glu Thr
    130                 135                 140

Trp Leu Ile Tyr Lys His Thr Lys Leu Leu Lys Lys Ile Asp His Ala
145                 150                 155                 160

Lys Val Arg Asn Thr Arg Gly Ser Ser Ser Lys Tyr Pro Pro Val Glu
                165                 170                 175

Glu Arg Gln Asp Gly Thr Glu Glu Ala Glu
            180                 185
```

<210> SEQ ID NO 213
<211> LENGTH: 90
<212> TYPE: PRT
<213> ORGANISM: Homo sapiens

<400> SEQUENCE: 213

Met Lys Phe Leu Ala Val Leu Val Leu Gly Val Ser Ile Phe Leu
1               5                   10                  15

Val Ser Ala Gln Asn Pro Thr Thr Ala Ala Pro Ala Asp Thr Tyr Pro
            20                  25                  30

Ala Thr Gly Pro Ala Asp Asp Glu Ala Pro Asp Ala Glu Thr Thr Ala
        35                  40                  45

Ala Ala Thr Thr Ala Thr Thr Ala Ala Pro Thr Thr Ala Thr Thr Ala
    50                  55                  60

Ala Ser Thr Thr Ala Arg Lys Asp Ile Pro Val Leu Pro Lys Trp Val
65                  70                  75                  80

Gly Asp Leu Pro Asn Gly Arg Val Cys Pro
                85                  90

<210> SEQ ID NO 214
<211> LENGTH: 48
<212> TYPE: PRT
<213> ORGANISM: Homo sapiens

<400> SEQUENCE: 214

Met Ser Ser Ala Ala Ala Asp His Trp Ala Trp Leu Leu Val Leu Ser
1               5                   10                  15

Phe Val Phe Gly Cys Asn Val Leu Arg Ile Leu Leu Pro Ser Phe Ser
            20                  25                  30

Ser Phe Met Ser Arg Val Leu Gln Lys Asp Ala Asp Arg Ser His Arg
        35                  40                  45

<210> SEQ ID NO 215
<211> LENGTH: 70
<212> TYPE: PRT
<213> ORGANISM: Homo sapiens

<400> SEQUENCE: 215

Met Thr Ala Pro Leu Pro Pro Leu Ser Gly Leu Ala Leu Phe Leu Ile
1               5                   10                  15

Val Phe Phe Ser Leu Gly Val Phe Cys Ile Cys His Ser His Trp Tyr
            20                  25                  30

His Thr Leu Gln Gln Met Ala Gly Thr Glu Pro Lys Ala Leu Leu Leu
        35                  40                  45

Ser Pro Pro Ala Ala Thr Thr Phe Val Thr Val Thr His Glu Val Trp
    50                  55                  60

Lys Glu Gln Ala Leu Ala
65                  70

<210> SEQ ID NO 216
<211> LENGTH: 83
<212> TYPE: PRT
<213> ORGANISM: Homo sapiens

<400> SEQUENCE: 216

Met Thr Cys Ser Val Ala Leu Leu Leu Ile Leu Gly Leu Arg Cys Ser
1               5                   10                  15

Gly Val Arg Pro Gly Leu Val Gly Glu Gly His Asn Pro Ser Leu Leu

```
                    20                  25                  30

Val Cys Leu Leu Lys Asp Ser Arg Thr Asn Gln Gly Ser Cys Pro
         35                  40                  45

Gly Gly Pro Trp Ser Glu Arg Asp Ile Glu Ser Val Thr Ser Asp Asn
 50                  55                  60

Cys Glu Ala Thr Leu Gly Tyr Arg Asn His Ser Leu Pro Ser Asn Tyr
 65                  70                  75                  80

Tyr Asn Ser

<210> SEQ ID NO 217
<211> LENGTH: 43
<212> TYPE: PRT
<213> ORGANISM: Homo sapiens

<400> SEQUENCE: 217

Met Leu Thr Arg Ser Leu Lys Thr Leu Pro Ser Ala Cys Thr Ala Phe
 1               5                  10                  15

Leu Leu Leu Phe Phe Leu Phe Ser Ser Gly Asp Pro Glu Leu Ser Cys
                 20                  25                  30

Ser Cys Thr Leu Arg Thr Gln Ser Ser Trp Ser
         35                  40

<210> SEQ ID NO 218
<211> LENGTH: 184
<212> TYPE: PRT
<213> ORGANISM: Homo sapiens
<220> FEATURE:
<221> NAME/KEY: SITE
<222> LOCATION: (140)
<223> OTHER INFORMATION: Xaa equals any of the naturally occurring
      L-amino acids
<220> FEATURE:
<221> NAME/KEY: SITE
<222> LOCATION: (145)
<223> OTHER INFORMATION: Xaa equals any of the naturally occurring
      L-amino acids
<220> FEATURE:
<221> NAME/KEY: SITE
<222> LOCATION: (146)
<223> OTHER INFORMATION: Xaa equals any of the naturally occurring
      L-amino acids
<220> FEATURE:
<221> NAME/KEY: SITE
<222> LOCATION: (148)
<223> OTHER INFORMATION: Xaa equals any of the naturally occurring
      L-amino acids
<220> FEATURE:
<221> NAME/KEY: SITE
<222> LOCATION: (165)
<223> OTHER INFORMATION: Xaa equals any of the naturally occurring
      L-amino acids

<400> SEQUENCE: 218

Met Trp Arg Pro Ser Val Leu Leu Leu Leu Leu Leu Arg His Gly
 1               5                  10                  15

Ala Gln Gly Lys Pro Ser Pro Asp Ala Gly Pro His Gly Gln Gly Arg
                 20                  25                  30

Val His Gln Ala Ala Pro Leu Ser Asp Ala Pro His Asp Ala His
         35                  40                  45

Gly Asn Phe Gln Tyr Asp His Glu Ala Phe Leu Gly Arg Glu Val Ala
 50                  55                  60

Lys Glu Phe Asp Gln Leu Thr Pro Glu Glu Ser Gln Ala Arg Leu Gly
 65                  70                  75                  80

Arg Ile Val Asp Arg Met Asp Arg Ala Gly Asp Gly Asp Gly Trp Val
```

-continued

```
                    85                  90                  95
Ser Leu Ala Glu Leu Arg Ala Trp Ile Ala His Thr Gln Gln Arg His
                100                 105                 110

Ile Arg Asp Ser Val Ser Ala Ala Trp Asp Thr Tyr Asp Thr Asp Arg
            115                 120                 125

Asp Gly Arg Val Gly Trp Glu Glu Leu Arg Asn Xaa Thr Tyr Gly His
        130                 135                 140

Xaa Xaa Pro Xaa Glu Glu Phe His Asp Val Glu Asp Ala Glu Thr Tyr
145                 150                 155                 160

Lys Lys Met Leu Xaa Arg Asp Glu Arg Arg Phe Arg Val Ala Asp Gln
                165                 170                 175

Asp Gly Asp Ser Met Ala Thr Arg
            180

<210> SEQ ID NO 219
<211> LENGTH: 71
<212> TYPE: PRT
<213> ORGANISM: Homo sapiens
<220> FEATURE:
<221> NAME/KEY: SITE
<222> LOCATION: (40)
<223> OTHER INFORMATION: Xaa equals any of the naturally occurring
      L-amino acids
<220> FEATURE:
<221> NAME/KEY: SITE
<222> LOCATION: (51)
<223> OTHER INFORMATION: Xaa equals any of the naturally occurring
      L-amino acids
<220> FEATURE:
<221> NAME/KEY: SITE
<222> LOCATION: (55)
<223> OTHER INFORMATION: Xaa equals any of the naturally occurring
      L-amino acids

<400> SEQUENCE: 219

Met Trp Leu Phe Ile Leu Leu Ser Leu Ala Leu Ile Ser Asp Ala Met
 1               5                  10                  15

Val Met Asp Glu Lys Val Lys Arg Ser Leu Cys Trp Thr Arg Leu Leu
                20                  25                  30

Pro Ser Ala Thr Thr Met Pro Xaa Thr Arg Ile Thr Pro Asn Thr Gly
            35                  40                  45

Ala Glu Xaa Ile Ser Val Xaa Thr Ala Thr Ser Ser Pro Ser Pro Leu
        50                  55                  60

Thr Ala Pro Ile Met Trp Pro
 65                  70

<210> SEQ ID NO 220
<211> LENGTH: 10
<212> TYPE: PRT
<213> ORGANISM: Homo sapiens

<400> SEQUENCE: 220

Met His Val Phe Val Leu Glu Ile Phe Leu
 1               5                  10

<210> SEQ ID NO 221
<211> LENGTH: 138
<212> TYPE: PRT
<213> ORGANISM: Homo sapiens

<400> SEQUENCE: 221

Met Ala Val Ala Thr Leu Ala Ser Glu Thr Leu Pro Leu Leu Ala Leu
 1               5                  10                  15
```

```
Thr Phe Ile Thr Asp Asn Ser Leu Val Ala Ala Gly His Asp Cys Phe
             20                  25                  30

Pro Val Leu Phe Thr Tyr Asp Ala Ala Gly Met Leu Ser Phe Gly
         35                  40                  45

Gly Arg Leu Asp Val Pro Lys Gln Ser Ser Gln Arg Gly Leu Thr Ala
     50                  55                  60

Arg Glu Arg Phe Gln Asn Leu Asp Lys Lys Ala Ser Glu Gly Gly
 65                  70                  75                  80

Thr Ala Ala Gly Ala Gly Leu Asp Ser Leu His Lys Asn Ser Val Ser
                 85                  90                  95

Gln Ile Ser Val Leu Ser Gly Gly Lys Ala Lys Cys Ser Gln Phe Cys
            100                 105                 110

Thr Thr Gly Met Asp Gly Gly Met Ser Ile Trp Asp Val Lys Ser Leu
        115                 120                 125

Glu Ser Ala Leu Lys Asp Leu Lys Ile Lys
            130                 135
```

<210> SEQ ID NO 222
<211> LENGTH: 11
<212> TYPE: PRT
<213> ORGANISM: Homo sapiens

<400> SEQUENCE: 222

```
Met Ser Gly Gly Leu Ser Phe Leu Leu Leu Val
 1               5                  10
```

<210> SEQ ID NO 223
<211> LENGTH: 23
<212> TYPE: PRT
<213> ORGANISM: Homo sapiens

<400> SEQUENCE: 223

```
Leu Gly Ser Leu Ser Thr Ala Pro Ser Ser Ala Leu Pro Thr Leu Gly
 1               5                  10                  15

Ala Arg Arg Thr Arg Ser Lys
             20
```

<210> SEQ ID NO 224
<211> LENGTH: 66
<212> TYPE: PRT
<213> ORGANISM: Homo sapiens

<400> SEQUENCE: 224

```
Met Thr Tyr Phe Ser Gly Leu Leu Val Ile Leu Ala Phe Ala Ala Trp
 1               5                  10                  15

Val Ala Leu Ala Glu Gly Leu Gly Val Ala Val Tyr Ala Ala Ala Val
             20                  25                  30

Leu Leu Gly Ala Gly Cys Ala Thr Ile Leu Val Thr Ser Leu Ala Met
         35                  40                  45

Thr Ala Asp Leu Ile Gly Pro His Thr Asn Ser Gly Leu Ser Cys Thr
     50                  55                  60

Ala Pro
 65
```

<210> SEQ ID NO 225
<211> LENGTH: 28
<212> TYPE: PRT
<213> ORGANISM: Homo sapiens

```
<400> SEQUENCE: 225

Gly Lys Pro Thr Gly Lys Ser Leu Pro Leu Met Trp Met Ile Leu Met
1               5                   10                  15

Gln Pro Ile Ile Met Ile Ser Met Met Ser Asn Gly
            20                  25

<210> SEQ ID NO 226
<211> LENGTH: 61
<212> TYPE: PRT
<213> ORGANISM: Homo sapiens

<400> SEQUENCE: 226

Met Gln Gly Lys Phe Met Lys Val Gln Val Tyr Arg Phe Leu Lys Tyr
1               5                   10                  15

Leu Leu Met Leu Cys Met Phe Val Asn Arg Gly Met Ser Lys Asp
            20                  25                  30

Ser Thr Lys Lys Pro Gly Gln Glu Lys Leu Lys Val Ser Leu Gly Ser
        35                  40                  45

Ile Leu Asn Met Lys Ser Gln Arg Pro Leu Ser Trp Cys
    50                  55                  60

<210> SEQ ID NO 227
<211> LENGTH: 29
<212> TYPE: PRT
<213> ORGANISM: Homo sapiens

<400> SEQUENCE: 227

Met Met Glu Arg Ser Met Met Ile Leu Leu Met Ala Ala Ser Met Thr
1               5                   10                  15

Met Thr Ser Thr Gln Leu Trp Ser Phe Cys Cys Val His
            20                  25

<210> SEQ ID NO 228
<211> LENGTH: 18
<212> TYPE: PRT
<213> ORGANISM: Homo sapiens

<400> SEQUENCE: 228

Met Trp Tyr Gln Leu Ala Lys Glu Glu Pro Gly Val Gly Ala Cys Ala
1               5                   10                  15

Leu Asp

<210> SEQ ID NO 229
<211> LENGTH: 72
<212> TYPE: PRT
<213> ORGANISM: Homo sapiens

<400> SEQUENCE: 229

Met Leu Ile Cys Arg Leu Val Leu Leu Ala Asp Pro Gly Pro Val Asn
1               5                   10                  15

Phe Met Val Arg Leu Phe Val Val Ile Val Met Phe Ala Trp Ser Ile
            20                  25                  30

Val Ala Ser Thr Ala Phe Leu Ala Asp Ser Gln Pro Pro Asn Arg Arg
        35                  40                  45

Ala Leu Ala Val Tyr Pro Val Phe Leu Phe Tyr Phe Val Ile Ser Trp
    50                  55                  60

Met Ile Leu Thr Phe Thr Pro Gln
65                  70
```

```
<210> SEQ ID NO 230
<211> LENGTH: 142
<212> TYPE: PRT
<213> ORGANISM: Homo sapiens
<220> FEATURE:
<221> NAME/KEY: SITE
<222> LOCATION: (47)
<223> OTHER INFORMATION: Xaa equals any of the naturally occurring
      L-amino acids
<220> FEATURE:
<221> NAME/KEY: SITE
<222> LOCATION: (121)
<223> OTHER INFORMATION: Xaa equals any of the naturally occurring
      L-amino acids

<400> SEQUENCE: 230

Met Arg Ser Leu Leu Leu Ser Ala Phe Cys Leu Leu Glu Ala Ala
 1               5                  10                  15

Leu Ala Ala Glu Val Lys Lys Pro Ala Ala Ala Ala Pro Gly Thr
                20                  25                  30

Ala Glu Lys Leu Ser Pro Lys Ala Ala Thr Leu Ala Glu Arg Xaa Arg
            35                  40                  45

Pro Gly Leu Gln Leu Val Pro Gly His Gly Gln Gly Pro Gly Ser Gly
        50                  55                  60

Glu His Pro Gly Val Thr Arg Gly Gly Gly Leu Val Ala Gly Ala Arg
65                  70                  75                  80

Val Ala Gly Arg Gln Gly Asp His Gly Val Ala Gly Gln Gly Ser Ala
                85                  90                  95

Glu Arg Arg Ala Ala Ala Arg Arg Gly Gly Ala Arg Pro Gly Arg
            100                 105                 110

Ala Ala Ala Leu Thr Gln Gln Leu Xaa Gly Ala Gln Arg Asp Leu Glu
        115                 120                 125

Ala Gly Gln Pro Thr Val Arg Thr Gln Leu Ser Glu Leu Arg
    130                 135                 140

<210> SEQ ID NO 231
<211> LENGTH: 54
<212> TYPE: PRT
<213> ORGANISM: Homo sapiens

<400> SEQUENCE: 231

Asp Pro Glu Ala Ala Asp Ser Gly Glu Pro Gln Asn Lys Arg Thr Pro
 1               5                  10                  15

Asp Leu Pro Glu Glu Glu Tyr Val Lys Glu Glu Ile Gln Glu Asn Glu
                20                  25                  30

Glu Ala Val Lys Lys Met Leu Val Glu Ala Thr Arg Glu Phe Glu Glu
            35                  40                  45

Val Val Val Asp Glu Ser
    50

<210> SEQ ID NO 232
<211> LENGTH: 63
<212> TYPE: PRT
<213> ORGANISM: Homo sapiens

<400> SEQUENCE: 232

Gln Lys Leu Lys Arg Lys Ala Glu Glu Asp Pro Glu Ala Ala Asp Ser
 1               5                  10                  15

Gly Glu Pro Gln Asn Lys Arg Thr Pro Asp Leu Pro Glu Glu Glu Tyr
                20                  25                  30

Val Lys Glu Glu Ile Gln Glu Asn Glu Glu Ala Val Lys Lys Met Leu
```

```
                35                  40                  45
Val Glu Ala Thr Arg Glu Phe Glu Glu Val Val Asp Glu Ser
        50                  55                  60

<210> SEQ ID NO 233
<211> LENGTH: 113
<212> TYPE: PRT
<213> ORGANISM: Homo sapiens

<400> SEQUENCE: 233

Lys Ala Met Glu Lys Ser Ser Leu Thr Gln His Ser Trp Gln Ser Leu
 1               5                  10                  15

Lys Asp Arg Tyr Leu Lys His Leu Arg Gly Gln Glu His Lys Tyr Leu
            20                  25                  30

Leu Gly Asp Ala Pro Val Ser Pro Ser Ser Gln Lys Leu Lys Arg Lys
        35                  40                  45

Ala Glu Glu Asp Pro Glu Ala Ala Asp Ser Gly Glu Pro Gln Asn Lys
    50                  55                  60

Arg Thr Pro Asp Leu Pro Glu Glu Tyr Val Lys Glu Glu Ile Gln
 65                  70                  75                  80

Glu Asn Glu Glu Ala Val Lys Lys Met Leu Val Glu Ala Thr Arg Glu
                85                  90                  95

Phe Glu Glu Val Val Asp Glu Ser Pro Pro Asp Phe Glu Ile His
            100                 105                 110

Ile

<210> SEQ ID NO 234
<211> LENGTH: 148
<212> TYPE: PRT
<213> ORGANISM: Homo sapiens

<400> SEQUENCE: 234

Leu Pro Ser Tyr Asp Glu Ala Glu Arg Thr Lys Ala Glu Ala Thr Ile
 1               5                  10                  15

Pro Leu Val Pro Gly Arg Asp Glu Asp Phe Val Gly Arg Asp Asp Phe
            20                  25                  30

Asp Asp Ala Asp Gln Leu Arg Ile Gly Asn Asp Gly Ile Phe Met Leu
        35                  40                  45

Thr Phe Phe Met Ala Phe Leu Phe Asn Trp Ile Gly Phe Phe Leu Ser
    50                  55                  60

Phe Cys Leu Thr Thr Ser Ala Ala Gly Arg Tyr Gly Ala Ile Ser Gly
 65                  70                  75                  80

Phe Gly Leu Ser Leu Ile Lys Trp Ile Leu Ile Val Arg Phe Ser Thr
                85                  90                  95

Tyr Phe Pro Gly Tyr Phe Asp Gly Gln Tyr Trp Leu Trp Trp Val Phe
            100                 105                 110

Leu Val Leu Gly Phe Leu Leu Phe Arg Gly Phe Ile Asn Tyr Ala
        115                 120                 125

Lys Val Arg Lys Met Pro Glu Thr Phe Ser Asn Leu Pro Arg Thr Arg
    130                 135                 140

Val Leu Phe Ile
145

<210> SEQ ID NO 235
<211> LENGTH: 24
<212> TYPE: PRT
<213> ORGANISM: Homo sapiens
```

```
<400> SEQUENCE: 235

Ala Gly Arg Tyr Gly Ala Ile Ser Gly Phe Gly Leu Ser Leu Ile Lys
 1               5                  10                  15
Trp Ile Leu Ile Val Arg Phe Ser
            20

<210> SEQ ID NO 236
<211> LENGTH: 51
<212> TYPE: PRT
<213> ORGANISM: Homo sapiens

<400> SEQUENCE: 236

Met Lys His Leu Ser Ala Trp Asn Phe Thr Lys Leu Thr Phe Leu Gln
 1               5                  10                  15
Leu Trp Glu Ile Phe Glu Gly Ser Val Glu Asn Cys Gln Thr Leu Thr
            20                  25                  30
Ser Tyr Ser Lys Leu Gln Ile Lys Tyr Thr Phe Ser Arg Gly Ser Thr
        35                  40                  45
Phe Tyr Ile
    50

<210> SEQ ID NO 237
<211> LENGTH: 213
<212> TYPE: PRT
<213> ORGANISM: Homo sapiens

<400> SEQUENCE: 237

Phe Ser Ser Asp Phe Arg Thr Ser Pro Trp Glu Ser Arg Arg Val Glu
 1               5                  10                  15
Ser Lys Ala Thr Ser Ala Arg Cys Gly Leu Trp Gly Ser Gly Pro Arg
            20                  25                  30
Arg Arg Pro Ala Ser Gly Met Phe Arg Gly Leu Ser Ser Trp Leu Gly
        35                  40                  45
Leu Gln Gln Pro Val Ala Gly Gly Gln Pro Asn Gly Asp Ala Pro
    50                  55                  60
Pro Glu Gln Pro Ser Glu Thr Val Ala Glu Ser Ala Glu Glu Leu
65                  70                  75              80
Gln Gln Ala Gly Asp Gln Glu Leu Leu His Gln Ala Lys Asp Phe Gly
                85                  90                  95
Asn Tyr Leu Phe Asn Phe Ala Ser Ala Ala Thr Lys Lys Ile Thr Glu
                100                 105                 110
Ser Val Ala Glu Thr Ala Gln Thr Ile Lys Lys Ser Val Glu Glu Gly
            115                 120                 125
Lys Ile Asp Gly Ile Ile Asp Lys Thr Ile Ile Gly Asp Phe Gln Lys
    130                 135                 140
Glu Gln Lys Lys Phe Val Glu Gln His Thr Lys Ser Glu Ala
145                 150                 155             160
Ala Val Pro Pro Trp Val Asp Thr Asn Asp Glu Glu Thr Ile Gln Gln
                165                 170                 175
Gln Ile Leu Ala Leu Ser Ala Asp Lys Arg Asn Phe Leu Arg Asp Pro
            180                 185                 190
Pro Ala Gly Val Gln Phe Asn Phe Asp Phe Asp Gln Met Tyr Pro Val
        195                 200                 205
Ala Leu Val Met Leu
    210
```

```
<210> SEQ ID NO 238
<211> LENGTH: 49
<212> TYPE: PRT
<213> ORGANISM: Homo sapiens

<400> SEQUENCE: 238

Met Arg Phe Ala Leu Val Pro Lys Leu Val Lys Glu Val Phe Trp
 1               5                  10                  15

Arg Asn Tyr Phe Tyr Arg Val Ser Leu Ile Lys Gln Ser Ala Gln Leu
                20                  25                  30

Thr Ala Leu Ala Ala Gln Gln Gln Ala Ala Gly Lys Gly Gly Glu Glu
            35                  40                  45

Gln

<210> SEQ ID NO 239
<211> LENGTH: 76
<212> TYPE: PRT
<213> ORGANISM: Homo sapiens

<400> SEQUENCE: 239

Ser Thr Ser Pro Gly Val Ser Glu Phe Val Ser Asp Ala Phe Asp Ala
 1               5                  10                  15

Cys Asn Leu Asn Gln Glu Asp Leu Arg Lys Glu Met Glu Gln Leu Val
                20                  25                  30

Leu Asp Lys Lys Gln Glu Glu Thr Ala Val Leu Glu Glu Asp Ser Ala
            35                  40                  45

Asp Trp Glu Lys Glu Leu Gln Gln Glu Leu Gln Glu Tyr Glu Val Val
        50                  55                  60

Thr Glu Ser Glu Lys Arg Asp Glu Asn Trp Asp Lys
    65                  70                  75

<210> SEQ ID NO 240
<211> LENGTH: 62
<212> TYPE: PRT
<213> ORGANISM: Homo sapiens

<400> SEQUENCE: 240

Ser Pro Trp Glu Ser Arg Arg Val Glu Ser Lys Ala Thr Ser Ala Arg
 1               5                  10                  15

Cys Gly Leu Trp Gly Ser Gly Pro Arg Arg Pro Ala Ser Gly Met
                20                  25                  30

Phe Arg Gly Leu Ser Ser Trp Leu Gly Leu Gln Gln Pro Val Ala Gly
            35                  40                  45

Gly Gly Gln Pro Asn Gly Asp Ala Pro Pro Glu Gln Pro Ser
        50                  55                  60

<210> SEQ ID NO 241
<211> LENGTH: 65
<212> TYPE: PRT
<213> ORGANISM: Homo sapiens

<400> SEQUENCE: 241

Pro Val Ala Gly Gly Gly Gln Pro Asn Gly Asp Ala Pro Pro Glu Gln
 1               5                  10                  15

Pro Ser Glu Thr Val Ala Glu Ser Ala Glu Glu Leu Gln Gln Ala
                20                  25                  30

Gly Asp Gln Glu Leu Leu His Gln Ala Lys Asp Phe Gly Asn Tyr Leu
            35                  40                  45
```

```
Phe Asn Phe Ala Ser Ala Ala Thr Lys Lys Ile Thr Glu Ser Val Ala
 50                  55                  60
Glu
 65

<210> SEQ ID NO 242
<211> LENGTH: 72
<212> TYPE: PRT
<213> ORGANISM: Homo sapiens

<400> SEQUENCE: 242

Phe Gln Lys Glu Gln Lys Lys Phe Val Glu Glu Gln His Thr Lys Lys
  1               5                  10                  15

Ser Glu Ala Ala Val Pro Pro Trp Val Asp Thr Asn Asp Glu Glu Thr
                 20                  25                  30

Ile Gln Gln Gln Ile Leu Ala Leu Ser Ala Asp Lys Arg Asn Phe Leu
             35                  40                  45

Arg Asp Pro Pro Ala Gly Val Gln Phe Asn Phe Asp Phe Asp Gln Met
 50                  55                  60

Tyr Pro Val Ala Leu Val Met Leu
 65                  70

<210> SEQ ID NO 243
<211> LENGTH: 28
<212> TYPE: PRT
<213> ORGANISM: Homo sapiens

<400> SEQUENCE: 243

Pro Phe Ile Cys Val Ala Arg Asn Pro Val Ser Arg Asn Phe Ser Ser
  1               5                  10                  15

Pro Ile Leu Ala Arg Lys Leu Cys Glu Gly Ala Ala
                 20                  25

<210> SEQ ID NO 244
<211> LENGTH: 33
<212> TYPE: PRT
<213> ORGANISM: Homo sapiens

<400> SEQUENCE: 244

Lys Glu Asp Pro Ala Asn Thr Val Tyr Ser Thr Val Glu Ile Pro Lys
  1               5                  10                  15

Lys Met Glu Asn Pro His Ser Leu Leu Thr Met Pro Asp Thr Pro Arg
                 20                  25                  30

Leu

<210> SEQ ID NO 245
<211> LENGTH: 227
<212> TYPE: PRT
<213> ORGANISM: Homo sapiens

<400> SEQUENCE: 245

Ala Ser Ala Val Leu Leu Asp Leu Pro Asn Ser Gly Gly Glu Ala Gln
  1               5                  10                  15

Ala Lys Lys Leu Gly Asn Asn Cys Val Phe Ala Pro Ala Asp Val Thr
                 20                  25                  30

Ser Glu Lys Asp Val Gln Thr Ala Leu Ala Leu Ala Lys Gly Lys Phe
             35                  40                  45

Gly Arg Val Asp Val Ala Val Asn Cys Ala Gly Ile Ala Val Ala Ser
 50                  55                  60
```

-continued

```
Lys Thr Tyr Asn Leu Lys Lys Gly Gln Thr His Thr Leu Glu Asp Phe
 65                  70                  75                  80

Gln Arg Val Leu Asp Val Asn Leu Met Gly Thr Phe Asn Val Ile Arg
                 85                  90                  95

Leu Val Ala Gly Glu Met Gly Gln Asn Glu Pro Asp Gln Gly Gly Gln
            100                 105                 110

Arg Gly Val Ile Ile Asn Thr Ala Ser Val Ala Ala Phe Glu Gly Gln
        115                 120                 125

Val Gly Gln Ala Ala Tyr Ser Ala Ser Lys Gly Gly Ile Val Gly Met
    130                 135                 140

Thr Leu Pro Ile Ala Arg Asp Leu Ala Pro Ile Gly Ile Arg Val Met
145                 150                 155                 160

Thr Ile Ala Pro Gly Leu Phe Gly Thr Pro Leu Leu Thr Ser Leu Pro
                165                 170                 175

Glu Lys Val Cys Asn Phe Leu Ala Ser Gln Val Pro Phe Pro Ser Arg
            180                 185                 190

Leu Gly Asp Pro Ala Glu Tyr Ala His Leu Val Gln Ala Ile Ile Glu
        195                 200                 205

Asn Pro Phe Leu Asn Gly Glu Val Ile Arg Leu Asp Gly Ala Ile Arg
    210                 215                 220

Met Gln Pro
225

<210> SEQ ID NO 246
<211> LENGTH: 29
<212> TYPE: PRT
<213> ORGANISM: Homo sapiens

<400> SEQUENCE: 246

Ser Val Ala Ala Phe Glu Gly Gln Val Gly Gln Ala Ala Tyr Ser Ala
  1               5                  10                  15

Ser Lys Gly Gly Ile Val Gly Met Thr Leu Pro Ile Ala
             20                  25

<210> SEQ ID NO 247
<211> LENGTH: 29
<212> TYPE: PRT
<213> ORGANISM: Homo sapiens

<400> SEQUENCE: 247

Ser Val Ala Ala Phe Glu Gly Gln Val Gly Gln Ala Ala Tyr Ser Ala
  1               5                  10                  15

Ser Lys Gly Gly Ile Val Gly Met Thr Leu Pro Ile Ala
             20                  25

<210> SEQ ID NO 248
<211> LENGTH: 22
<212> TYPE: PRT
<213> ORGANISM: Homo sapiens

<400> SEQUENCE: 248

His Pro Ile Glu Trp Ala Ile Asn Ala Ala Thr Leu Ser Gln Phe Tyr
  1               5                  10                  15

Ile Asn Lys Leu Cys Phe
             20

<210> SEQ ID NO 249
<211> LENGTH: 22
<212> TYPE: PRT
```

```
<213> ORGANISM: Homo sapiens

<400> SEQUENCE: 249

Cys Trp Ile Lys Tyr Cys Leu Thr Leu Met Gln Asn Ala Gln Leu Ser
 1               5                  10                  15

Met Gln Asp Asn Ile Gly
            20

<210> SEQ ID NO 250
<211> LENGTH: 25
<212> TYPE: PRT
<213> ORGANISM: Homo sapiens

<400> SEQUENCE: 250

Lys Val Ser Tyr Leu Arg Pro Leu Asp Phe Glu Glu Ala Arg Glu Leu
 1               5                  10                  15

Phe Leu Leu Gly Gln His Tyr Val Phe
            20                  25

<210> SEQ ID NO 251
<211> LENGTH: 25
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring
      L-amino acids

<400> SEQUENCE: 251

Met Glu Arg Arg Cys Lys Met His Lys Arg Xaa Ile Ala Met Leu Glu
 1               5                  10                  15

Pro Leu Thr Val Asp Leu Asn Pro Gln
            20                  25

<210> SEQ ID NO 252
<211> LENGTH: 23
<212> TYPE: PRT
<213> ORGANISM: Homo sapiens

<400> SEQUENCE: 252

Ser His Ile Val Lys Lys Ile Asn Asn Leu Asn Lys Ser Ala Leu Lys
 1               5                  10                  15

Tyr Tyr Gln Leu Phe Leu Asp
            20

<210> SEQ ID NO 253
<211> LENGTH: 64
<212> TYPE: PRT
<213> ORGANISM: Homo sapiens

<400> SEQUENCE: 253

Phe Thr His Leu Ser Thr Cys Leu Leu Ser Leu Leu Leu Val Arg Met
 1               5                  10                  15

Ser Gly Phe Leu Leu Leu Ala Arg Ala Ser Pro Ser Ile Cys Ala Leu
            20                  25                  30

Asp Ser Ser Cys Phe Val Gln Glu Tyr Cys Ser Ser Tyr Ser Ser Ser
        35                  40                  45

Cys Phe Leu His Gln His Phe Pro Ser Leu Leu Asp His Leu Cys Gln
    50                  55                  60

<210> SEQ ID NO 254
```

```
<211> LENGTH: 23
<212> TYPE: PRT
<213> ORGANISM: Homo sapiens

<400> SEQUENCE: 254

Phe Leu Leu Leu Ala Arg Ala Ser Pro Ser Ile Cys Ala Leu Asp Ser
 1               5                  10                  15

Ser Cys Phe Val Gln Glu Tyr
            20

<210> SEQ ID NO 255
<211> LENGTH: 53
<212> TYPE: PRT
<213> ORGANISM: Homo sapiens

<400> SEQUENCE: 255

Pro Asp Gly Arg Val Thr Asn Ile Pro Gln Gly Met Val Thr Asp Gln
 1               5                  10                  15

Phe Gly Met Ile Gly Leu Leu Thr Phe Ile Arg Ala Ala Glu Thr Asp
            20                  25                  30

Pro Gly Met Val His Leu Ala Leu Gly Ser Asp Leu Thr Thr Leu Gly
        35                  40                  45

Leu Asn Leu Asn Ser
    50

<210> SEQ ID NO 256
<211> LENGTH: 41
<212> TYPE: PRT
<213> ORGANISM: Homo sapiens

<400> SEQUENCE: 256

Glu Asp Leu Leu Phe Tyr Leu Tyr Tyr Met Asn Gly Gly Asp Val Leu
 1               5                  10                  15

Gln Leu Leu Ala Ala Val Glu Leu Phe Asn Arg Asp Trp Arg Tyr His
            20                  25                  30

Lys Glu Glu Arg Val Trp Ile Thr Arg
        35                  40

<210> SEQ ID NO 257
<211> LENGTH: 24
<212> TYPE: PRT
<213> ORGANISM: Homo sapiens

<400> SEQUENCE: 257

Val His Leu Ala Leu Gly Ser Asp Leu Thr Thr Leu Gly Leu Asn Leu
 1               5                  10                  15

Asn Ser Pro Glu Asn Leu Tyr Pro
            20

<210> SEQ ID NO 258
<211> LENGTH: 41
<212> TYPE: PRT
<213> ORGANISM: Homo sapiens

<400> SEQUENCE: 258

Glu Asp Leu Leu Phe Tyr Leu Tyr Tyr Met Asn Gly Gly Asp Val Leu
 1               5                  10                  15

Gln Leu Leu Ala Ala Val Glu Leu Phe Asn Arg Asp Trp Arg Tyr His
            20                  25                  30

Lys Glu Glu Arg Val Trp Ile Thr Arg
        35                  40
```

<210> SEQ ID NO 259
<211> LENGTH: 11
<212> TYPE: PRT
<213> ORGANISM: Homo sapiens

<400> SEQUENCE: 259

His Asn Glu Asp Phe Pro Ala Leu Pro Gly Ser
1               5                   10

<210> SEQ ID NO 260
<211> LENGTH: 75
<212> TYPE: PRT
<213> ORGANISM: Homo sapiens

<400> SEQUENCE: 260

Gly Arg Ile Ile Asp Thr Ser Leu Thr Arg Asp Pro Leu Val Ile Glu
1               5                   10                  15

Leu Gly Gln Lys Gln Val Ile Pro Gly Leu Glu Gln Ser Leu Leu Asp
                20                  25                  30

Met Cys Val Gly Glu Lys Arg Arg Ala Ile Ile Pro Ser His Leu Ala
            35                  40                  45

Tyr Gly Lys Arg Gly Phe Pro Pro Ser Val Pro Ala Asp Ala Val Val
        50                  55                  60

Gln Tyr Asp Val Glu Leu Ile Ala Leu Ile Arg
65                  70                  75

<210> SEQ ID NO 261
<211> LENGTH: 16
<212> TYPE: PRT
<213> ORGANISM: Homo sapiens

<400> SEQUENCE: 261

Ile His Tyr Thr Gly Ser Leu Val Asp Gly Arg Ile Ile Asp Thr Ser
1               5                   10                  15

<210> SEQ ID NO 262
<211> LENGTH: 20
<212> TYPE: PRT
<213> ORGANISM: Homo sapiens

<400> SEQUENCE: 262

Cys Glu Ser Pro Glu Ser Pro Ala Gln Pro Ser Gly Ser Ser Leu Pro
1               5                   10                  15

Ala Trp Tyr His
            20

<210> SEQ ID NO 263
<211> LENGTH: 95
<212> TYPE: PRT
<213> ORGANISM: Homo sapiens

<400> SEQUENCE: 263

Glu Glu Ala Gly Ala Gly Arg Arg Cys Ser His Gly Gly Ala Arg Pro
1               5                   10                  15

Ala Gly Leu Gly Asn Glu Gly Leu Gly Leu Gly Gly Asp Pro Asp His
                20                  25                  30

Thr Asp Thr Gly Ser Arg Ser Lys Gln Arg Ile Asn Asn Trp Lys Glu
            35                  40                  45

Ser Lys His Lys Val Ile Met Ala Ser Ala Ser Ala Arg Gly Asn Gln
        50                  55                  60

```
Asp Lys Asp Ala His Phe Pro Pro Ser Lys Gln Ser Leu Leu Phe
 65                  70                  75                  80

Cys Pro Lys Ser Lys Leu His Ile His Arg Ala Glu Ile Ser Lys
                 85                  90                  95
```

<210> SEQ ID NO 264
<211> LENGTH: 23
<212> TYPE: PRT
<213> ORGANISM: Homo sapiens

<400> SEQUENCE: 264

```
Ser Lys Gln Arg Ile Asn Asn Trp Lys Glu Ser Lys His Lys Val Ile
 1               5                  10                  15

Met Ala Ser Ala Ser Ala Arg
                20
```

<210> SEQ ID NO 265
<211> LENGTH: 32
<212> TYPE: PRT
<213> ORGANISM: Homo sapiens
<220> FEATURE:
<221> NAME/KEY: SITE
<222> LOCATION: (20)
<223> OTHER INFORMATION: Xaa equals any of the naturally occurring
      L-amino acids

<400> SEQUENCE: 265

```
Leu Phe His Trp Ala Cys Leu Asn Glu Arg Ala Ala Gln Leu Pro Arg
 1               5                  10                  15

Asn Thr Ala Xaa Ala Gly Tyr Gln Cys Pro Ser Cys Asn Gly Pro Ser
                20                  25                  30
```

<210> SEQ ID NO 266
<211> LENGTH: 185
<212> TYPE: PRT
<213> ORGANISM: Homo sapiens

<400> SEQUENCE: 266

```
Phe Tyr Ile Tyr Tyr Arg Pro Thr Asp Ser Asp Asn Asp Ser Asp Tyr
 1               5                  10                  15

Lys Lys Asp Met Val Glu Gly Asp Lys Tyr Trp His Ser Ile Ser His
                20                  25                  30

Leu Gln Pro Glu Thr Ser Tyr Asp Ile Lys Met Gln Cys Phe Asn Glu
             35                  40                  45

Gly Gly Glu Ser Glu Phe Ser Asn Val Met Ile Cys Glu Thr Lys Ala
     50                  55                  60

Arg Lys Ser Ser Gly Gln Pro Gly Arg Leu Pro Pro Thr Leu Ala
 65                  70                  75                  80

Pro Pro Gln Pro Pro Leu Pro Glu Thr Ile Glu Arg Pro Val Gly Thr
                 85                  90                  95

Gly Ala Met Val Ala Arg Ser Ser Asp Leu Pro Tyr Leu Ile Val Gly
                100                 105                 110

Val Val Leu Gly Ser Ile Val Leu Ile Val Thr Phe Ile Pro Phe
            115                 120                 125

Cys Leu Trp Arg Ala Trp Ser Lys Gln Lys His Thr Asp Leu Gly
            130                 135                 140

Phe Pro Arg Ser Ala Leu Pro Pro Ser Cys Pro Tyr Thr Met Val Pro
145                 150                 155                 160

Leu Gly Gly Leu Pro Gly His Gln Ala Val Asp Ser Pro Thr Ser Val
```

```
                165                 170                 175
Ala Ser Val Asp Gly Pro Val Leu Met
        180                 185

<210> SEQ ID NO 267
<211> LENGTH: 66
<212> TYPE: PRT
<213> ORGANISM: Homo sapiens

<400> SEQUENCE: 267

Tyr Ile Tyr Tyr Arg Pro Thr Asp Ser Asp Asn Asp Ser Asp Tyr Lys
 1               5                  10                  15

Lys Asp Met Val Glu Gly Asp Lys Tyr Trp His Ser Ile Ser His Leu
            20                  25                  30

Gln Pro Glu Thr Ser Tyr Asp Ile Lys Met Gln Cys Phe Asn Glu Gly
        35                  40                  45

Gly Glu Ser Glu Phe Ser Asn Val Met Ile Cys Glu Thr Lys Ala Arg
    50                  55                  60

Lys Ser
 65

<210> SEQ ID NO 268
<211> LENGTH: 30
<212> TYPE: PRT
<213> ORGANISM: Homo sapiens

<400> SEQUENCE: 268

Asn Val Arg Ala Leu Leu His Arg Met Pro Glu Pro Lys Ile Asn
 1               5                  10                  15

Thr Ala Lys Phe Asn Asn Asn Lys Arg Lys Asn Leu Ser Leu
            20                  25                  30

<210> SEQ ID NO 269
<211> LENGTH: 185
<212> TYPE: PRT
<213> ORGANISM: Homo sapiens

<400> SEQUENCE: 269

Asn Thr Asn Gln Arg Glu Ala Leu Gln Tyr Ala Lys Asn Phe Gln Pro
 1               5                  10                  15

Phe Ala Leu Asn His Gln Lys Asp Ile Gln Val Leu Met Gly Ser Leu
            20                  25                  30

Val Tyr Leu Arg Gln Gly Ile Glu Asn Ser Pro Tyr Val His Leu Leu
        35                  40                  45

Asp Ala Asn Gln Trp Ala Asp Ile Cys Asp Ile Phe Thr Arg Asp Ala
    50                  55                  60

Cys Ala Leu Leu Gly Leu Ser Val Glu Ser Pro Leu Ser Val Ser Phe
65                  70                  75                  80

Ser Ala Gly Cys Val Ala Leu Pro Ala Leu Ile Asn Ile Lys Ala Val
                85                  90                  95

Ile Glu Gln Arg Gln Cys Thr Gly Val Trp Asn Gln Lys Asp Glu Leu
            100                 105                 110

Pro Ile Glu Val Asp Leu Gly Lys Lys Cys Trp Tyr His Ser Ile Phe
        115                 120                 125

Ala Cys Pro Ile Leu Arg Gln Gln Thr Thr Asp Asn Asn Pro Pro Met
    130                 135                 140

Lys Leu Val Cys Gly His Ile Ile Ser Arg Asp Ala Leu Asn Lys Met
145                 150                 155                 160
```

```
Phe Asn Gly Ser Lys Leu Lys Cys Pro Tyr Cys Pro Met Glu Gln Ser
                165                 170                 175

Pro Gly Asp Ala Lys Gln Ile Phe Phe
            180                 185

<210> SEQ ID NO 270
<211> LENGTH: 65
<212> TYPE: PRT
<213> ORGANISM: Homo sapiens

<400> SEQUENCE: 270

Ser Tyr Leu Ser Ala Cys Phe Ala Gly Cys Asn Ser Thr Asn Leu Thr
  1               5                  10                  15

Gly Cys Ala Cys Leu Thr Thr Val Pro Ala Glu Asn Ala Thr Val Val
                 20                  25                  30

Pro Gly Lys Cys Pro Ser Pro Gly Cys Gln Glu Ala Phe Leu Thr Phe
                 35                  40                  45

Leu Cys Val Met Cys Ile Cys Ser Leu Ile Gly Ala Met Ala Arg His
     50                  55                  60

Pro
 65

<210> SEQ ID NO 271
<211> LENGTH: 84
<212> TYPE: PRT
<213> ORGANISM: Homo sapiens

<400> SEQUENCE: 271

Pro Ser Val Ile Ile Leu Ile Arg Thr Val Ser Pro Glu Leu Lys Ser
  1               5                  10                  15

Tyr Ala Leu Gly Val Leu Phe Leu Leu Arg Leu Leu Gly Phe Ile
                 20                  25                  30

Pro Pro Pro Leu Ile Phe Gly Ala Gly Ile Asp Ser Thr Cys Leu Phe
                 35                  40                  45

Trp Ser Thr Phe Cys Gly Glu Gln Gly Ala Cys Val Leu Tyr Asp Asn
     50                  55                  60

Val Val Tyr Arg Tyr Leu Tyr Val Ser Ile Ala Ile Ala Leu Lys Ser
 65                  70                  75                  80

Phe Ala Phe Ile

<210> SEQ ID NO 272
<211> LENGTH: 182
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids
<220> FEATURE:
<221> NAME/KEY: SITE
<222> LOCATION: (30)
<223> OTHER INFORMATION: Xaa equals any of the naturally occurring
      L-amino acids

<400> SEQUENCE: 272

Gln Ser Leu Phe Thr Arg Phe Val Arg Val Gly Val Pro Thr Val Asp
  1               5                  10                  15

Leu Asp Ala Gln Gly Arg Ala Arg Ala Ser Leu Cys Xaa Xaa Tyr Asn
                 20                  25                  30
```

```
Trp Arg Tyr Lys Asn Leu Gly Asn Leu Pro His Val Gln Leu Leu Pro
            35                  40                  45

Glu Phe Ser Thr Ala Asn Ala Gly Leu Leu Tyr Asp Phe Gln Leu Ile
 50                  55                  60

Asn Val Glu Asp Phe Gln Gly Val Gly Glu Ser Glu Pro Asn Pro Tyr
 65                  70                  75                  80

Phe Tyr Gln Asn Leu Gly Glu Ala Glu Tyr Val Val Ala Leu Phe Met
                85                  90                  95

Tyr Met Cys Leu Leu Gly Tyr Pro Ala Asp Lys Ile Ser Ile Leu Thr
            100                 105                 110

Thr Tyr Asn Gly Gln Lys His Leu Ile Arg Asp Ile Asn Arg Arg
            115                 120                 125

Cys Gly Asn Asn Pro Leu Ile Gly Arg Pro Asn Lys Val Thr Thr Val
            130                 135                 140

Asp Arg Phe Gln Gly Gln Gln Asn Asp Tyr Ile Leu Leu Ser Leu Val
145                 150                 155                 160

Arg Thr Arg Ala Val Gly His Leu Arg Asp Val Arg Arg Leu Val Val
                165                 170                 175

Ala Met Ser Arg Ala Arg
            180

<210> SEQ ID NO 273
<211> LENGTH: 77
<212> TYPE: PRT
<213> ORGANISM: Homo sapiens

<400> SEQUENCE: 273

Leu Val Lys Glu Ala Lys Ile Ile Ala Met Thr Cys Thr His Ala Ala
 1               5                   10                  15

Leu Lys Arg His Asp Leu Val Lys Leu Gly Phe Lys Tyr Asp Asn Ile
                20                  25                  30

Leu Met Glu Glu Ala Ala Gln Ile Leu Glu Ile Glu Thr Phe Ile Pro
            35                  40                  45

Leu Leu Leu Gln Asn Pro Gln Asp Gly Phe Ser Arg Leu Lys Arg Trp
 50                  55                  60

Ile Met Ile Gly Asp His His Gln Leu Pro Pro Val Ile
 65                  70                  75

<210> SEQ ID NO 274
<211> LENGTH: 125
<212> TYPE: PRT
<213> ORGANISM: Homo sapiens
<220> FEATURE:
<221> NAME/KEY: SITE
<222> LOCATION: (16)
<223> OTHER INFORMATION: Xaa equals any of the naturally occurring
      L-amino acids
<220> FEATURE:
<221> NAME/KEY: SITE
<222> LOCATION: (17)
<223> OTHER INFORMATION: Xaa equals any of the naturally occurring
      L-amino acids
<220> FEATURE:
<221> NAME/KEY: SITE
<222> LOCATION: (43)
<223> OTHER INFORMATION: Xaa equals any of the naturally occurring
      L-amino acids

<400> SEQUENCE: 274

Asp Thr Tyr Pro Asn Glu Glu Lys Gln Gln Glu Arg Val Phe Pro Xaa
 1               5                   10                  15
```

```
Xaa Ser Ala Met Val Asn Asn Gly Ser Leu Ser Tyr Asp His Glu Arg
         20                  25                  30

Asp Gly Arg Pro Thr Glu Leu Gly Gly Cys Xaa Ala Ile Val Arg Asn
             35                  40                  45

Leu His Tyr Asp Thr Phe Leu Val Ile Arg Tyr Val Lys Arg His Leu
     50                  55                  60

Thr Ile Met Met Asp Ile Asp Gly Lys His Glu Trp Arg Asp Cys Ile
 65                  70                  75                  80

Glu Val Pro Gly Val Arg Leu Pro Arg Gly Tyr Tyr Phe Gly Thr Ser
                 85                  90                  95

Ser Ile Thr Gly Asp Leu Ser Asp Asn His Asp Val Ile Ser Leu Lys
            100                 105                 110

Leu Phe Glu Leu Thr Val Glu Arg Thr Pro Glu Glu Glu
        115                 120                 125

<210> SEQ ID NO 275
<211> LENGTH: 85
<212> TYPE: PRT
<213> ORGANISM: Homo sapiens

<400> SEQUENCE: 275

Leu Lys Arg Glu His Ser Leu Ser Lys Pro Tyr Gln Gly Val Gly Thr
  1               5                  10                  15

Gly Ser Ser Ser Leu Trp Asn Leu Met Gly Asn Ala Met Val Met Thr
             20                  25                  30

Gln Tyr Ile Arg Leu Thr Pro Asp Met Gln Ser Lys Gln Gly Ala Leu
         35                  40                  45

Trp Asn Arg Val Pro Cys Phe Leu Arg Asp Trp Glu Leu Gln Val His
     50                  55                  60

Phe Lys Ile His Gly Gln Gly Lys Lys Asn Leu His Gly Asp Gly Leu
 65                  70                  75                  80

Ala Ile Trp Tyr Thr
             85

<210> SEQ ID NO 276
<211> LENGTH: 32
<212> TYPE: PRT
<213> ORGANISM: Homo sapiens

<400> SEQUENCE: 276

Pro Gly Thr Leu Gln Cys Ser Ala Leu His His Asp Pro Gly Cys Ala
  1               5                  10                  15

Asn Cys Ser Arg Phe Cys Arg Asp Cys Ser Pro Pro Ala Cys Gln Cys
             20                  25                  30

<210> SEQ ID NO 277
<211> LENGTH: 27
<212> TYPE: PRT
<213> ORGANISM: Homo sapiens
<220> FEATURE:
<221> NAME/KEY: SITE
<222> LOCATION: (8)
<223> OTHER INFORMATION: Xaa equals any of the naturally occurring
      L-amino acids

<400> SEQUENCE: 277

Phe Leu Tyr Asp Val Leu Met Xaa His Glu Ala Val Met Arg Thr His
  1               5                  10                  15

Gln Ile Gln Leu Pro Asp Pro Glu Phe Pro Ser
             20                  25
```

<210> SEQ ID NO 278
<211> LENGTH: 92
<212> TYPE: PRT
<213> ORGANISM: Homo sapiens
<220> FEATURE:
<221> NAME/KEY: SITE
<222> LOCATION: (4)
<223> OTHER INFORMATION: Xaa equals any of the naturally occurring
      L-amino acids

<400> SEQUENCE: 278

Pro Ala Asp Xaa Lys Pro Val Val Ser Thr Glu Ala Pro Pro Ile Ile
1               5                   10                  15

Phe Ala Thr Pro Thr Lys Leu Thr Ser Asp Ser Thr Val Tyr Asp Tyr
            20                  25                  30

Ala Gly Lys Asn Lys Val Pro Glu Leu Gln Lys Phe Phe Gln Lys Ala
        35                  40                  45

Asp Gly Val Pro Val Tyr Leu Lys Arg Gly Leu Pro Asp Gln Met Leu
    50                  55                  60

Tyr Arg Thr Thr Met Ala Leu Thr Val Gly Gly Thr Ile Tyr Cys Leu
65                  70                  75                  80

Ile Ala Leu Tyr Met Ala Ser Gln Pro Lys Asn Lys
                85                  90

<210> SEQ ID NO 279
<211> LENGTH: 63
<212> TYPE: PRT
<213> ORGANISM: Homo sapiens
<220> FEATURE:
<221> NAME/KEY: SITE
<222> LOCATION: (45)
<223> OTHER INFORMATION: Xaa equals any of the naturally occurring
      L-amino acids

<400> SEQUENCE: 279

Ser Phe Ser Gly Ala Val Ala Leu Ala Ala Asp Ala Gly Ser Arg Thr
1               5                   10                  15

Leu Gly Val Met Tyr Tyr Lys Phe Ser Gly Phe Thr Gln Lys Leu Ala
            20                  25                  30

Gly Ala Trp Ala Ser Glu Ala Tyr Ser Pro Gln Ile Xaa Ser Leu Trp
        35                  40                  45

Phe Pro Gln Lys His His Leu Ser Tyr Leu Pro His Gln Leu Asn
    50                  55                  60

<210> SEQ ID NO 280
<211> LENGTH: 6
<212> TYPE: PRT
<213> ORGANISM: Homo sapiens

<400> SEQUENCE: 280

Gly Trp Tyr Trp Cys Gly
1               5

<210> SEQ ID NO 281
<211> LENGTH: 129
<212> TYPE: PRT
<213> ORGANISM: Homo sapiens

<400> SEQUENCE: 281

Met Lys Val Gly Ala Arg Ile Arg Val Lys Met Ser Val Asn Lys Ala
1               5                   10                  15

```
His Pro Val Val Ser Thr His Trp Arg Trp Pro Ala Glu Trp Pro Gln
            20                  25                  30

Met Phe Leu His Leu Ala Gln Glu Pro Arg Thr Glu Val Lys Ser Arg
        35                  40                  45

Pro Leu Gly Leu Ala Gly Phe Ile Arg Gln Asp Ser Lys Thr Arg Lys
    50                  55                  60

Pro Leu Glu Gln Glu Thr Ile Met Ser Ala Ala Asp Thr Ala Leu Trp
65                  70                  75                  80

Pro Tyr Gly His Gly Asn Arg Glu His Gln Glu Asn Glu Leu Gln Lys
                85                  90                  95

Tyr Leu Gln Tyr Lys Asp Met His Leu Leu Asp Ser Gly Gln Ser Leu
            100                 105                 110

Gly His Thr His Thr Leu Gln Gly Ser His Asn Leu Thr Ala Leu Asn
        115                 120                 125

Ile

<210> SEQ ID NO 282
<211> LENGTH: 49
<212> TYPE: PRT
<213> ORGANISM: Homo sapiens

<400> SEQUENCE: 282

Ser Leu His Lys Asn Ser Val Ser Gln Ile Ser Val Leu Ser Gly Gly
1               5                   10                  15

Lys Ala Lys Cys Ser Gln Phe Cys Thr Thr Gly Met Asp Gly Gly Met
            20                  25                  30

Ser Ile Trp Asp Val Lys Ser Leu Glu Ser Ala Leu Lys Asp Leu Lys
        35                  40                  45

Ile

<210> SEQ ID NO 283
<211> LENGTH: 21
<212> TYPE: PRT
<213> ORGANISM: Homo sapiens

<400> SEQUENCE: 283

Glu Ala Ser Lys Ser Ser His Ala Gly Leu Asp Leu Phe Ser Val Ala
1               5                   10                  15

Ala Cys His Arg Phe
            20

<210> SEQ ID NO 284
<211> LENGTH: 21
<212> TYPE: PRT
<213> ORGANISM: Homo sapiens

<400> SEQUENCE: 284

Tyr Met Gly Lys Gly Ser Met Thr Gly Leu Ala Leu Lys His Met Phe
1               5                   10                  15

Glu Arg Ser Phe Thr
            20

<210> SEQ ID NO 285
<211> LENGTH: 27
<212> TYPE: PRT
<213> ORGANISM: Homo sapiens

<400> SEQUENCE: 285

Val Thr Gly Ile Ile Asp Ser Leu Thr Ile Ser Pro Lys Ala Ala Arg
```

```
                1               5                  10                 15
Val Gly Leu Leu Gln Tyr Ser Thr Gln Val His
                20                  25
```

<210> SEQ ID NO 286
<211> LENGTH: 24
<212> TYPE: PRT
<213> ORGANISM: Homo sapiens

<400> SEQUENCE: 286

```
Thr Glu Phe Thr Leu Arg Asn Phe Asn Ser Ala Lys Asp Met Lys Lys
 1               5                  10                  15
Ala Val Ala His Met Lys Tyr Met
                20
```

<210> SEQ ID NO 287
<211> LENGTH: 27
<212> TYPE: PRT
<213> ORGANISM: Homo sapiens

<400> SEQUENCE: 287

```
Gly Lys Gly Ser Met Thr Gly Leu Ala Leu Lys His Met Phe Glu Arg
 1               5                  10                  15
Ser Phe Thr Gln Gly Glu Gly Ala Arg Pro Phe
                20                  25
```

<210> SEQ ID NO 288
<211> LENGTH: 44
<212> TYPE: PRT
<213> ORGANISM: Homo sapiens

<400> SEQUENCE: 288

```
Ser Thr Arg Val Pro Arg Ala Ala Ile Val Phe Thr Asp Gly Arg Ala
 1               5                  10                  15
Gln Asp Asp Val Ser Glu Trp Ala Ser Lys Ala Lys Ala Asn Gly Ile
                20                  25                  30
Thr Met Tyr Ala Val Gly Val Gly Lys Ala Ile Glu
            35                  40
```

<210> SEQ ID NO 289
<211> LENGTH: 42
<212> TYPE: PRT
<213> ORGANISM: Homo sapiens

<400> SEQUENCE: 289

```
Glu Glu Leu Gln Glu Ile Ala Ser Glu Pro Thr Asn Lys His Leu Phe
 1               5                  10                  15
Tyr Ala Glu Asp Phe Ser Thr Met Asp Glu Ile Ser Glu Lys Leu Lys
                20                  25                  30
Lys Gly Ile Cys Glu Ala Leu Glu Asp Ser
            35                  40
```

<210> SEQ ID NO 290
<211> LENGTH: 11
<212> TYPE: PRT
<213> ORGANISM: Homo sapiens

<400> SEQUENCE: 290

```
Thr Gln Arg Leu Glu Glu Met Thr Gln Arg Met
 1               5                  10
```

-continued

```
<210> SEQ ID NO 291
<211> LENGTH: 10
<212> TYPE: PRT
<213> ORGANISM: Homo sapiens

<400> SEQUENCE: 291

Pro Gln Gly Cys Pro Glu Gln Pro Leu His
 1               5                  10

<210> SEQ ID NO 292
<211> LENGTH: 33
<212> TYPE: PRT
<213> ORGANISM: Homo sapiens

<400> SEQUENCE: 292

Arg Cys Lys Lys Cys Thr Glu Gly Pro Ile Asp Leu Val Phe Val Ile
 1               5                  10                  15

Asp Gly Ser Lys Ser Leu Gly Glu Glu Asn Phe Glu Val Val Lys Gln
                20                  25                  30

Phe

<210> SEQ ID NO 293
<211> LENGTH: 193
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids

<400> SEQUENCE: 293

Gly Trp Glu Thr Leu Pro Lys Lys Asp Val Cys Lys Ser Thr His His
 1               5                  10                  15

Gly Cys Glu His Ile Cys Val Asn Asn Gly Asn Ser Tyr Ile Cys Lys
                20                  25                  30

Cys Ser Xaa Gly Phe Val Leu Ala Glu Asp Gly Arg Arg Cys Lys Lys
            35                  40                  45

Cys Thr Glu Gly Pro Ile Asp Leu Val Phe Val Ile Asp Gly Ser Lys
 50                  55                  60

Ser Leu Gly Glu Glu Asn Phe Glu Val Val Lys Gln Phe Val Thr Gly
 65                  70                  75                  80

Ile Ile Asp Ser Leu Thr Ile Ser Pro Lys Ala Ala Arg Val Gly Leu
                85                  90                  95

Leu Gln Tyr Ser Thr Gln Val His Thr Glu Phe Thr Leu Arg Asn Phe
            100                 105                 110

Asn Ser Ala Lys Asp Met Lys Lys Ala Val Ala His Met Lys Tyr Met
            115                 120                 125

Gly Lys Gly Ser Met Thr Gly Leu Ala Leu Lys His Met Phe Glu Arg
        130                 135                 140

Ser Phe Thr Gln Gly Glu Gly Ala Arg Pro Phe Pro Gln Gly Cys Pro
145                 150                 155                 160

Glu Gln Pro Leu Cys Ser Pro Thr Asp Gly Leu Arg Met Thr Ser Pro
                165                 170                 175

Ser Gly Pro Val Lys Pro Arg Pro Met Val Ser Leu Cys Met Leu Leu
                180                 185                 190

Gly

<210> SEQ ID NO 294
```

-continued

```
<211> LENGTH: 193
<212> TYPE: PRT
<213> ORGANISM: Homo sapiens

<400> SEQUENCE: 294

Lys Phe Tyr Pro Arg Arg Gly Gln Ala Leu Ser Thr Arg Val Pro
 1               5                  10                  15

Arg Ala Ala Ile Val Phe Thr Asp Gly Arg Ala Gln Asp Val Ser
                20                  25                  30

Glu Trp Ala Ser Lys Ala Lys Ala Asn Gly Ile Thr Met Tyr Ala Val
            35                  40                  45

Gly Val Gly Lys Ala Ile Glu Glu Leu Gln Ile Ala Ser Glu
        50                  55                  60

Pro Thr Asn Lys His Leu Phe Tyr Ala Glu Asp Phe Ser Thr Met Asp
 65                  70                  75                  80

Glu Ile Ser Glu Lys Leu Lys Lys Gly Ile Cys Glu Ala Leu Glu Asp
                85                  90                  95

Ser Asp Gly Arg Gln Asp Ser Pro Ala Gly Glu Leu Pro Lys Thr Val
                100                 105                 110

Gln Gln Pro Thr Val Gln His Arg Tyr Leu Phe Glu Gly Asp Asn Leu
            115                 120                 125

Leu Arg Ser Thr Gln Lys Leu Ser His Ser Thr Lys Pro Ser Gly Ser
130                 135                 140

Pro Leu Glu Glu Lys His Asp Gln Cys Lys Cys Glu Asn Leu Ile Met
145                 150                 155                 160

Phe Gln Asn Leu Ala Asn Glu Glu Val Arg Lys Leu Thr Gln Arg Leu
                165                 170                 175

Glu Glu Met Thr Gln Arg Met Glu Ala Leu Glu Asn Arg Leu Arg Tyr
            180                 185                 190

Arg

<210> SEQ ID NO 295
<211> LENGTH: 60
<212> TYPE: PRT
<213> ORGANISM: Homo sapiens

<400> SEQUENCE: 295

Met Ala Ala Leu Leu Arg His Val Gly Arg His Cys Leu Arg Ala
 1               5                  10                  15

His Phe Ser Pro Gln Leu Cys Ile Arg Asn Ala Val Pro Leu Gly Thr
                20                  25                  30

Thr Ala Lys Glu Glu Met Glu Arg Phe Trp Asn Lys Asn Ile Gly Ser
            35                  40                  45

Asn Arg Pro Leu Ser Pro His Ile Thr Ile Tyr Ser
        50                  55                  60

<210> SEQ ID NO 296
<211> LENGTH: 32
<212> TYPE: PRT
<213> ORGANISM: Homo sapiens

<400> SEQUENCE: 296

Val Phe Pro Leu Met Tyr His Thr Trp Asn Gly Ile Arg His Leu Met
 1               5                  10                  15

Trp Asp Leu Gly Lys Gly Leu Lys Ile Pro Gln Leu Tyr Gln Ser Gly
                20                  25                  30
```

```
<210> SEQ ID NO 297
<211> LENGTH: 17
<212> TYPE: PRT
<213> ORGANISM: Homo sapiens

<400> SEQUENCE: 297

Met Ala Ala Leu Leu Arg His Val Gly Arg His Cys Leu Arg Ala
 1               5                  10                  15

His

<210> SEQ ID NO 298
<211> LENGTH: 18
<212> TYPE: PRT
<213> ORGANISM: Homo sapiens

<400> SEQUENCE: 298

Val Lys Ser Leu Cys Leu Gly Pro Ala Leu Ile His Thr Ala Lys Phe
 1               5                  10                  15

Ala Leu

<210> SEQ ID NO 299
<211> LENGTH: 23
<212> TYPE: PRT
<213> ORGANISM: Homo sapiens

<400> SEQUENCE: 299

Val Phe Pro Leu Met Tyr His Thr Trp Asn Gly Ile Arg His Leu Met
 1               5                  10                  15

Trp Asp Leu Gly Lys Gly Leu
                20

<210> SEQ ID NO 300
<211> LENGTH: 22
<212> TYPE: PRT
<213> ORGANISM: Homo sapiens

<400> SEQUENCE: 300

Arg Val Trp Asp Val Arg Pro Phe Ala Pro Lys Glu Arg Cys Val Lys
 1               5                  10                  15

Ile Phe Gln Gly Asn Val
                20

<210> SEQ ID NO 301
<211> LENGTH: 30
<212> TYPE: PRT
<213> ORGANISM: Homo sapiens

<400> SEQUENCE: 301

His Asn Phe Glu Lys Asn Leu Leu Arg Cys Ser Trp Ser Pro Asp Gly
 1               5                  10                  15

Ser Lys Ile Ala Ala Gly Ser Ala Asp Arg Phe Val Tyr Val
                20                  25                  30

<210> SEQ ID NO 302
<211> LENGTH: 30
<212> TYPE: PRT
<213> ORGANISM: Homo sapiens

<400> SEQUENCE: 302

Trp Asp Thr Thr Ser Arg Arg Ile Leu Tyr Lys Leu Pro Gly His Ala
 1               5                  10                  15

Gly Ser Ile Asn Glu Val Ala Phe His Pro Asp Glu Pro Ile
```

```
                  20                  25                  30
```

<210> SEQ ID NO 303
<211> LENGTH: 141
<212> TYPE: PRT
<213> ORGANISM: Homo sapiens

<400> SEQUENCE: 303

```
Tyr Gln Gly Leu Gly Leu Arg Gln Asn Lys Leu Thr Tyr Thr Met Arg
  1               5                  10                  15

Gly His Ala Asp Ser Val Thr Gly Leu Ser Leu Ser Ser Glu Gly Ser
                 20                  25                  30

Tyr Leu Leu Ser Asn Ala Met Asp Asn Thr Val Arg Val Trp Asp Val
             35                  40                  45

Arg Pro Phe Ala Pro Lys Glu Arg Cys Val Lys Ile Phe Gln Gly Asn
         50                  55                  60

Val His Asn Phe Glu Lys Asn Leu Leu Arg Cys Ser Trp Ser Pro Asp
 65                  70                  75                  80

Gly Ser Lys Ile Ala Ala Gly Ser Ala Asp Arg Phe Val Tyr Val Trp
                 85                  90                  95

Asp Thr Thr Ser Arg Arg Ile Leu Tyr Lys Leu Pro Gly His Ala Gly
            100                 105                 110

Ser Ile Asn Glu Val Ala Phe His Pro Asp Glu Pro Ile Ile Ile Ser
        115                 120                 125

Ala Ser Ser Asp Lys Arg Leu Tyr Met Gly Glu Ile Gln
    130                 135                 140
```

<210> SEQ ID NO 304
<211> LENGTH: 45
<212> TYPE: PRT
<213> ORGANISM: Homo sapiens

<400> SEQUENCE: 304

```
Arg Lys Lys Ala Ala Ile Gln Thr Phe Gln Asn Thr Tyr Gln Val Leu
  1               5                  10                  15

Ala Val Thr Phe Asn Asp Thr Ser Asp Gln Ile Ile Ser Gly Gly Ile
                 20                  25                  30

Asp Asn Asp Ile Lys Val Trp Asp Cys Ala Arg Thr Ser
             35                  40                  45
```

<210> SEQ ID NO 305
<211> LENGTH: 20
<212> TYPE: PRT
<213> ORGANISM: Homo sapiens

<400> SEQUENCE: 305

```
Val Arg Gly Arg Thr Val Leu Arg Pro Gly Leu Asp Ala Glu Pro Glu
  1               5                  10                  15

Leu Ser Pro Glu
                 20
```

<210> SEQ ID NO 306
<211> LENGTH: 19
<212> TYPE: PRT
<213> ORGANISM: Homo sapiens

<400> SEQUENCE: 306

```
Glu Gln Arg Val Leu Glu Arg Lys Leu Lys Lys Glu Arg Lys Lys Glu
  1               5                  10                  15
```

-continued

Glu Arg Gln

<210> SEQ ID NO 307
<211> LENGTH: 13
<212> TYPE: PRT
<213> ORGANISM: Homo sapiens

<400> SEQUENCE: 307

Arg Leu Arg Glu Ala Gly Leu Val Ala Gln His Pro Pro
 1               5                  10

<210> SEQ ID NO 308
<211> LENGTH: 17
<212> TYPE: PRT
<213> ORGANISM: Homo sapiens

<400> SEQUENCE: 308

Gly Arg Ile Pro Ala Pro Ala Pro Ser Val Pro Ala Gly Pro Asp Ser
 1               5                  10                  15

Arg

<210> SEQ ID NO 309
<211> LENGTH: 61
<212> TYPE: PRT
<213> ORGANISM: Homo sapiens

<400> SEQUENCE: 309

Ala Arg Arg Ser Gly Ala Glu Leu Ala Trp Asp Tyr Leu Cys Arg Trp
 1               5                  10                  15

Ala Gln Lys His Lys Asn Trp Arg Phe Gln Lys Thr Arg Gln Thr Trp
             20                  25                  30

Leu Leu Leu His Met Tyr Asp Ser Asp Lys Val Pro Asp Glu His Phe
         35                  40                  45

Ser Thr Leu Leu Ala Tyr Leu Glu Gly Leu Gln Gly Arg
     50                  55                  60

<210> SEQ ID NO 310
<211> LENGTH: 42
<212> TYPE: PRT
<213> ORGANISM: Homo sapiens

<400> SEQUENCE: 310

Thr Gly Cys Val Leu Val Leu Ser Arg Asn Phe Val Gln Tyr Ala Cys
 1               5                  10                  15

Phe Gly Leu Phe Gly Ile Ile Ala Leu Gln Thr Ile Ala Tyr Ser Ile
             20                  25                  30

Leu Trp Asp Leu Lys Phe Leu Met Arg Asn
         35                  40

<210> SEQ ID NO 311
<211> LENGTH: 55
<212> TYPE: PRT
<213> ORGANISM: Homo sapiens

<400> SEQUENCE: 311

Ser Arg Ser Glu Gly Lys Ser Met Phe Ala Gly Val Pro Thr Met Arg
 1               5                  10                  15

Glu Ser Ser Pro Lys Gln Tyr Met Gln Leu Gly Gly Arg Val Leu Leu
             20                  25                  30

Val Leu Met Phe Met Thr Leu Leu His Phe Asp Ala Ser Phe Phe Ser
         35                  40                  45

```
Ile Val Gln Asn Ile Val Gly
        50              55

<210> SEQ ID NO 312
<211> LENGTH: 60
<212> TYPE: PRT
<213> ORGANISM: Homo sapiens

<400> SEQUENCE: 312

Gly Thr Ala Glu Asp Phe Ala Asp Gln Phe Leu Arg Val Thr Lys Gln
 1               5                  10                  15

Tyr Leu Pro His Val Ala Arg Leu Cys Leu Ile Ser Thr Phe Leu Glu
             20                  25                  30

Asp Gly Ile Arg Met Trp Phe Gln Trp Ser Glu Gln Arg Asp Tyr Ile
         35                  40                  45

Asp Thr Thr Trp Asn Cys Gly Tyr Leu Leu Ala Ser
     50                  55                  60

<210> SEQ ID NO 313
<211> LENGTH: 17
<212> TYPE: PRT
<213> ORGANISM: Homo sapiens

<400> SEQUENCE: 313

Ala Ser Phe Leu Leu Ser Arg Thr Ser Trp Gly Thr Ala Leu Met Ile
 1               5                  10                  15

Leu

<210> SEQ ID NO 314
<211> LENGTH: 8
<212> TYPE: PRT
<213> ORGANISM: Homo sapiens

<400> SEQUENCE: 314

Leu Met Arg Asn Glu Ser Arg Ser
 1               5

<210> SEQ ID NO 315
<211> LENGTH: 13
<212> TYPE: PRT
<213> ORGANISM: Homo sapiens

<400> SEQUENCE: 315

Ala Ser Phe Leu Leu Ser Arg Thr Ser Trp Gly Thr Ala
 1               5                  10

<210> SEQ ID NO 316
<211> LENGTH: 17
<212> TYPE: PRT
<213> ORGANISM: Homo sapiens

<400> SEQUENCE: 316

Ala Ser Phe Leu Leu Ser Arg Thr Ser Trp Gly Thr Ala Leu Met Ile
 1               5                  10                  15

Leu

<210> SEQ ID NO 317
<211> LENGTH: 72
<212> TYPE: PRT
<213> ORGANISM: Homo sapiens

<400> SEQUENCE: 317
```

```
Pro Ser Phe Thr Leu Thr Pro Ala Ser Phe Leu Ser Arg Thr Ser
  1               5                  10                  15

Trp Gly Thr Ala Leu Met Ile Leu Val Ala Ile Gly Phe Lys Thr Lys
                20                  25                  30

Leu Ala Ala Leu Thr Leu Val Val Trp Leu Phe Ala Ile Asn Val Tyr
            35                  40                  45

Phe Asn Ala Phe Trp Thr Ile Pro Val Tyr Lys Pro Met His Asp Phe
        50                  55                  60

Leu Lys Tyr Asp Phe Phe Gln Thr
 65              70
```

<210> SEQ ID NO 318
<211> LENGTH: 236
<212> TYPE: PRT
<213> ORGANISM: Homo sapiens
<220> FEATURE:
<221> NAME/KEY: SITE
<222> LOCATION: (115)
<223> OTHER INFORMATION: Xaa equals any of the naturally occurring
    L-amino acids

<400> SEQUENCE: 318

```
Arg Thr Glu Pro Pro Gly Thr Ser Cys Gly Gly Arg Ser Gly Cys
  1               5                  10                  15

Gly Arg Arg Arg Ala Arg Ala Ser Glu Arg Ala Ser Glu Pro Ser Arg
                20                  25                  30

Ala Ser Arg Arg His Gly Pro Glu Arg Pro Asp Gly His Gly Arg
            35                  40                  45

Gly Leu Arg Arg Pro Val Pro Pro Cys His Lys Ala Val Pro Ala Pro
        50                  55                  60

Arg Gly Ala Pro Leu Ser Asp Gln His Leu Pro Gly Gly Arg His Pro
 65                  70                  75                  80

Tyr Val Val Pro Val Glu Arg Ala Ala Arg Leu His Arg His His Leu
                85                  90                  95

Glu Leu Arg Leu Pro Ala Gly Leu Val Leu Arg Leu Pro Gln Leu Ala
            100                 105                 110

Gly Thr Xaa Thr Gly Cys Val Leu Val Leu Ser Arg Asn Phe Val Gln
        115                 120                 125

Tyr Ala Cys Phe Gly Leu Phe Gly Ile Ile Ala Leu Gln Thr Ile Ala
    130                 135                 140

Tyr Ser Ile Leu Trp Asp Leu Lys Phe Leu Met Arg Asn Leu Ala Leu
145                 150                 155                 160

Gly Gly Gly Leu Leu Leu Leu Ala Glu Ser Arg Ser Glu Gly Lys
                165                 170                 175

Ser Met Phe Ala Gly Val Pro Thr Met Arg Glu Ser Ser Pro Lys Gln
            180                 185                 190

Tyr Met Gln Leu Gly Arg Val Leu Leu Val Leu Met Phe Met Thr
        195                 200                 205

Leu Leu His Phe Asp Ala Ser Phe Phe Ser Ile Val Gln Asn Ile Val
    210                 215                 220

Gly His Ser Ser Asp Asp Phe Ser Gly His Trp Phe
225                 230                 235
```

<210> SEQ ID NO 319
<211> LENGTH: 114
<212> TYPE: PRT
<213> ORGANISM: Homo sapiens -continued

```
<220> FEATURE:
<221> NAME/KEY: SITE
<222> LOCATION: (2)
<223> OTHER INFORMATION: Xaa equals any of the naturally occurring
      L-amino acids
<220> FEATURE:
<221> NAME/KEY: SITE
<222> LOCATION: (114)
<223> OTHER INFORMATION: Xaa equals any of the naturally occurring
      L-amino acids

<400> SEQUENCE: 319
```

Gly Xaa Ser Arg Arg Arg Ala Leu Pro Val Glu Ala Ala Gly Ala
1               5                   10                  15

Gly Ala Asp Gly Arg Glu Pro Ala Ser Glu Arg Ala Ser Arg Ala Glu
            20                  25                  30

Pro Pro Ala Val Ala Met Gly Gln Asn Asp Leu Met Gly Thr Ala Glu
        35                  40                  45

Asp Phe Ala Asp Gln Phe Leu Arg Val Thr Lys Gln Tyr Leu Pro His
    50                  55                  60

Val Ala Arg Leu Cys Leu Ile Ser Thr Phe Leu Glu Asp Gly Ile Arg
65                  70                  75                  80

Met Trp Phe Gln Trp Ser Glu Gln Arg Asp Tyr Ile Asp Thr Thr Trp
                85                  90                  95

Asn Cys Gly Tyr Leu Leu Ala Ser Phe Val Phe Leu Asn Leu Leu
            100                 105                 110

Gly Xaa

```
<210> SEQ ID NO 320
<211> LENGTH: 63
<212> TYPE: PRT
<213> ORGANISM: Homo sapiens

<400> SEQUENCE: 320
```

Trp Val Phe Leu Phe Leu Leu Ala Leu Gly Leu Gly Pro Asp Ser
1               5                   10                  15

Gly Arg Cys Leu Cys Arg Glu Gly Arg Ile Ser Gly Ile Tyr Gln Leu
            20                  25                  30

Ile Leu Ala Lys Gln Phe Leu Arg Phe Phe Cys Phe Met Trp Glu Thr
        35                  40                  45

Asp Leu Asn Leu Ile Leu Cys Cys Ile Leu Tyr Leu Ser Cys Val
    50                  55                  60

```
<210> SEQ ID NO 321
<211> LENGTH: 106
<212> TYPE: PRT
<213> ORGANISM: Homo sapiens

<400> SEQUENCE: 321
```

Ser Met Ser Ala Leu Thr Arg Leu Ala Ser Phe Ala Arg Val Gly Gly
1               5                   10                  15

Arg Leu Phe Arg Ser Gly Cys Ala Arg Thr Ala Gly Asp Gly Gly Val
            20                  25                  30

Arg His Ala Gly Gly Gly Val His Ile Glu Pro Arg Tyr Arg Gln Phe
        35                  40                  45

Pro Gln Leu Thr Arg Ser Gln Val Phe Gln Ser Glu Phe Phe Ser Gly
    50                  55                  60

Leu Met Trp Phe Trp Ile Leu Trp Arg Phe Trp His Asp Ser Glu Glu
65                  70                  75                  80

-continued

```
Val Leu Gly His Phe Pro Tyr Pro Asp Pro Ser Gln Trp Thr Asp Glu
              85                  90                  95

Glu Leu Gly Ile Pro Pro Asp Asp Glu Asp
            100                 105

<210> SEQ ID NO 322
<211> LENGTH: 20
<212> TYPE: PRT
<213> ORGANISM: Homo sapiens

<400> SEQUENCE: 322

Phe Ile Ser Phe Ala Asn Ser Arg Ser Ser Glu Asp Thr Lys Gln Met
 1               5                  10                  15

Met Ser Ser Phe
            20

<210> SEQ ID NO 323
<211> LENGTH: 27
<212> TYPE: PRT
<213> ORGANISM: Homo sapiens

<400> SEQUENCE: 323

Asp Pro Arg Arg Pro Asn Lys Val Leu Arg Tyr Lys Pro Pro Pro Ser
 1               5                  10                  15

Glu Cys Asn Pro Ala Leu Asp Asp Pro Thr Pro
            20                  25

<210> SEQ ID NO 324
<211> LENGTH: 30
<212> TYPE: PRT
<213> ORGANISM: Homo sapiens

<400> SEQUENCE: 324

Asp Tyr Met Asn Leu Leu Gly Met Ile Phe Ser Met Cys Gly Leu Met
 1               5                  10                  15

Leu Lys Leu Lys Trp Cys Ala Trp Val Ala Val Tyr Cys Ser
            20                  25                  30

<210> SEQ ID NO 325
<211> LENGTH: 22
<212> TYPE: PRT
<213> ORGANISM: Homo sapiens

<400> SEQUENCE: 325

Met Leu Ser Ile Ser Ala Val Val Met Ser Tyr Leu Gln Asn Pro Gln
 1               5                  10                  15

Pro Met Thr Pro Pro Trp
            20

<210> SEQ ID NO 326
<211> LENGTH: 52
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids

<400> SEQUENCE: 326

Ala Ala Gly Asp Gly Asp Val Lys Leu Gly Thr Leu Gly Ser Gly Ser
 1               5                  10                  15

Glu Ser Ser Asn Asp Gly Gly Ser Glu Ser Pro Gly Asp Ala Gly Ala
```

```
                    20                  25                  30

Ala Ala Xaa Gly Gly Gly Trp Ala Ala Ala Leu Ala Leu Leu Thr
            35                  40                  45

Gly Gly Gly Glu
        50

<210> SEQ ID NO 327
<211> LENGTH: 62
<212> TYPE: PRT
<213> ORGANISM: Homo sapiens
<220> FEATURE:
<221> NAME/KEY: SITE
<222> LOCATION: (45)
<223> OTHER INFORMATION: Xaa equals any of the naturally occurring
      L-amino acids

<400> SEQUENCE: 327

Ser Thr His Ala Ser Gly Arg Ala Val Met Ala Ala Gly Asp Gly Asp
  1               5                  10                  15

Val Lys Leu Gly Thr Leu Gly Ser Gly Ser Glu Ser Ser Asn Asp Gly
                 20                  25                  30

Gly Ser Glu Ser Pro Gly Asp Ala Gly Ala Ala Ala Xaa Gly Gly Gly
            35                  40                  45

Trp Ala Ala Ala Ala Leu Ala Leu Leu Thr Gly Gly Gly Glu
    50                  55                  60

<210> SEQ ID NO 328
<211> LENGTH: 177
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring
      L-amino acids
<220> FEATURE:
<221> NAME/KEY: SITE
<222> LOCATION: (84)
<223> OTHER INFORMATION: Xaa equals any of the naturally occurring
      L-amino acids
<220> FEATURE:
<221> NAME/KEY: SITE
<222> LOCATION: (111)
<223> OTHER INFORMATION: Xaa equals any of the naturally occurring
      L-amino acids

<400> SEQUENCE: 328

Ala Ala Asp Asn Tyr Gly Ile Pro Arg Ala Cys Arg Asn Ser Ala Arg
  1               5                  10                  15

Ser Tyr Gly Ala Ala Trp Leu Leu Leu Xaa Pro Ala Gly Ser Ser Arg
                 20                  25                  30

Val Glu Pro Thr Gln Asp Ile Ser Ile Ser Asp Gln Leu Gly Gly Gln
            35                  40                  45

Asp Val Pro Val Phe Arg Asn Leu Ser Leu Leu Val Gly Val Gly
    50                  55                  60

Ala Val Phe Ser Leu Leu Phe His Leu Gly Thr Arg Glu Arg Arg
 65                  70                  75                  80

Pro His Ala Xaa Glu Pro Gly Glu His Thr Pro Leu Leu Ala Pro Ala
                 85                  90                  95

Thr Ala Gln Pro Leu Leu Leu Trp Lys His Trp Leu Arg Glu Xaa Ala
            100                 105                 110

Phe Tyr Gln Val Gly Ile Leu Tyr Met Thr Thr Arg Leu Ile Val Asn
        115                 120                 125
```

```
Leu Ser Gln Thr Tyr Met Ala Met Tyr Leu Thr Tyr Ser Leu His Leu
        130                 135                 140

Pro Lys Lys Phe Ile Ala Thr Ile Pro Leu Val Met Tyr Leu Ser Gly
145                 150                 155                 160

Phe Leu Ser Ser Phe Leu Met Lys Pro Ile Asn Lys Cys Ile Gly Arg
                165                 170                 175

Asn

<210> SEQ ID NO 329
<211> LENGTH: 79
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids

<400> SEQUENCE: 329

Cys Thr Leu Ala Met Trp Xaa Leu Gly His Cys Asp Pro Arg Arg Cys
  1               5                  10                  15

Thr Gly Arg Lys Leu Ala Arg Leu Gly Leu Val Arg Cys Leu Arg Leu
                 20                  25                  30

Gly His Arg Phe Gly Gly Leu Val Leu Ser Pro Val Gly Lys Gln Tyr
             35                  40                  45

Ala Ser Pro Ala Asp Arg Gln Leu Val Ala Gln Ser Gly Val Ala Val
         50                  55                  60

Ile Asp Cys Ser Trp Ala Arg Leu Asp Glu Thr Pro Phe Gly Lys
 65                  70                  75

<210> SEQ ID NO 330
<211> LENGTH: 72
<212> TYPE: PRT
<213> ORGANISM: Homo sapiens

<400> SEQUENCE: 330

Ser Gly Arg Gly Ala Arg Ser Asp Val Thr Ala Met Ala Gly Ile Lys
  1               5                  10                  15

Ala Leu Ile Ser Leu Ser Phe Gly Gly Ala Ile Gly Leu Met Phe Leu
                 20                  25                  30

Met Leu Gly Cys Ala Leu Pro Ile Tyr Asn Lys Tyr Trp Pro Leu Phe
             35                  40                  45

Val Leu Phe Phe Tyr Ile Leu Ser Pro Ile Pro Tyr Cys Ile Ala Arg
         50                  55                  60

Arg Leu Val Asp Asp Thr Asp Ala
 65                  70

<210> SEQ ID NO 331
<211> LENGTH: 32
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring
      L-amino acids

<400> SEQUENCE: 331

Ala Arg Val Arg Xaa Arg Gly Ala Leu Ser Leu Ser Val Gly Ala Ala
  1               5                  10                  15
```

```
Cys Gly Leu Val Ala Leu Trp Gln Arg Arg Gln Asp Ser Gly Thr
            20                  25                  30
```

<210> SEQ ID NO 332
<211> LENGTH: 45
<212> TYPE: PRT
<213> ORGANISM: Homo sapiens

<400> SEQUENCE: 332

```
Leu Ser Asn Asn Ala Gln Asn Trp Gly Met Gln Arg Ala Thr Asn Val
 1               5                  10                  15

Thr Tyr Gln Ala His His Val Ser Arg Asn Lys Arg Gly Gln Val Val
            20                  25                  30

Gly Thr Arg Gly Gly Phe Arg Gly Cys Thr Val Trp Leu
            35                  40                  45
```

<210> SEQ ID NO 333
<211> LENGTH: 38
<212> TYPE: PRT
<213> ORGANISM: Homo sapiens

<400> SEQUENCE: 333

```
Val Ser Met Ala Leu Glu Glu Tyr Leu Val Cys His Gly Ile Pro Cys
 1               5                  10                  15

Tyr Thr Leu Asp Gly Asp Asn Ile Arg Gln Gly Leu Asn Lys Asn Leu
            20                  25                  30

Gly Phe Ser Pro Glu Asp
            35
```

<210> SEQ ID NO 334
<211> LENGTH: 39
<212> TYPE: PRT
<213> ORGANISM: Homo sapiens

<400> SEQUENCE: 334

```
Thr Gln Asp Arg Asn Asn Ala Arg Gln Ile His Glu Gly Ala Ser Leu
 1               5                  10                  15

Pro Phe Phe Glu Val Phe Val Asp Ala Pro Leu His Val Cys Glu Gln
            20                  25                  30

Arg Asp Val Lys Gly Leu Tyr
            35
```

<210> SEQ ID NO 335
<211> LENGTH: 40
<212> TYPE: PRT
<213> ORGANISM: Homo sapiens

<400> SEQUENCE: 335

```
Phe Thr Gly Ile Asp Ser Glu Tyr Glu Lys Pro Glu Ala Pro Glu Leu
 1               5                  10                  15

Val Leu Lys Thr Asp Ser Cys Asp Val Asn Asp Cys Val Gln Gln Val
            20                  25                  30

Val Glu Leu Leu Gln Glu Arg Asp
            35                  40
```

<210> SEQ ID NO 336
<211> LENGTH: 41
<212> TYPE: PRT
<213> ORGANISM: Homo sapiens

<400> SEQUENCE: 336

-continued

Ala Glu Thr Leu Pro Ala Leu Lys Ile Asn Lys Val Asp Met Gln Trp
1               5                   10                  15

Val Gln Val Leu Ala Glu Gly Trp Ala Thr Pro Leu Asn Gly Phe Met
            20                  25                  30

Arg Glu Arg Glu Tyr Leu Gln Cys Leu
        35                  40

<210> SEQ ID NO 337
<211> LENGTH: 30
<212> TYPE: PRT
<213> ORGANISM: Homo sapiens

<400> SEQUENCE: 337

Val Pro Ile Val Leu Thr Ala Thr His Glu Asp Lys Glu Arg Leu Asp
1               5                   10                  15

Gly Cys Thr Ala Phe Ala Leu Met Tyr Glu Gly Arg Arg Val
            20                  25                  30

<210> SEQ ID NO 338
<211> LENGTH: 39
<212> TYPE: PRT
<213> ORGANISM: Homo sapiens

<400> SEQUENCE: 338

Ile Gly Gly Asp Leu Gln Val Leu Asp Arg Val Tyr Trp Asn Asp Gly
1               5                   10                  15

Leu Asp Gln Tyr Arg Leu Thr Pro Thr Glu Leu Lys Gln Lys Phe Lys
            20                  25                  30

Asp Met Asn Ala Asp Ala Val
            35

<210> SEQ ID NO 339
<211> LENGTH: 37
<212> TYPE: PRT
<213> ORGANISM: Homo sapiens

<400> SEQUENCE: 339

Gly His Ala Leu Leu Met Gln Asp Thr His Lys Gln Leu Leu Glu Arg
1               5                   10                  15

Gly Tyr Arg Arg Pro Val Leu Leu His Pro Leu Gly Gly Trp Thr
            20                  25                  30

Lys Asp Asp Asp Val
            35

<210> SEQ ID NO 340
<211> LENGTH: 41
<212> TYPE: PRT
<213> ORGANISM: Homo sapiens

<400> SEQUENCE: 340

Met Tyr Ala Gly Pro Thr Glu Val Gln Trp His Cys Arg Ala Arg Met
1               5                   10                  15

Val Ala Gly Ala Asn Phe Tyr Ile Val Gly Arg Asp Pro Ala Gly Met
            20                  25                  30

Pro His Pro Glu Thr Gly Lys Asp Leu
        35                  40

<210> SEQ ID NO 341
<211> LENGTH: 34
<212> TYPE: PRT
<213> ORGANISM: Homo sapiens -continued

```
<400> SEQUENCE: 341

Leu Thr Met Ala Pro Gly Leu Ile Thr Leu Glu Ile Val Pro Phe Arg
 1               5                  10                  15

Val Ala Ala Tyr Asn Lys Lys Lys Arg Met Asp Tyr Tyr Asp Ser
                20                  25                  30

Glu His

<210> SEQ ID NO 342
<211> LENGTH: 19
<212> TYPE: PRT
<213> ORGANISM: Homo sapiens

<400> SEQUENCE: 342

Gly Phe Met Ala Pro Lys Ala Trp Thr Val Leu Thr Glu Tyr Tyr Lys
 1               5                  10                  15

Ser Leu Glu

<210> SEQ ID NO 343
<211> LENGTH: 243
<212> TYPE: PRT
<213> ORGANISM: Homo sapiens
<220> FEATURE:
<221> NAME/KEY: SITE
<222> LOCATION: (30)
<223> OTHER INFORMATION: Xaa equals any of the naturally occurring
      L-amino acids
<220> FEATURE:
<221> NAME/KEY: SITE
<222> LOCATION: (149)
<223> OTHER INFORMATION: Xaa equals any of the naturally occurring
      L-amino acids
<220> FEATURE:
<221> NAME/KEY: SITE
<222> LOCATION: (152)
<223> OTHER INFORMATION: Xaa equals any of the naturally occurring
      L-amino acids

<400> SEQUENCE: 343

Arg Ile Thr Asp Asn Pro Glu Gly Lys Trp Leu Gly Arg Thr Ala Arg
 1               5                  10                  15

Gly Ser Tyr Gly Tyr Ile Lys Thr Thr Ala Val Glu Ile Xaa Tyr Asp
                20                  25                  30

Ser Leu Lys Leu Lys Lys Asp Ser Leu Gly Ala Pro Ser Arg Pro Ile
            35                  40                  45

Glu Asp Asp Gln Glu Val Tyr Asp Val Ala Glu Gln Asp Ile
 50                  55                  60

Ser Ser His Ser Gln Ser Gly Ser Gly Gly Ile Phe Pro Pro Pro
 65                  70                  75                  80

Asp Asp Asp Ile Tyr Asp Gly Ile Glu Glu Glu Asp Ala Asp Gly
                    85                  90                  95

Phe Pro Ala Pro Pro Lys Gln Leu Asp Met Gly Asp Glu Val Tyr Asp
                100                 105                 110

Asp Val Asp Thr Ser Asp Phe Pro Val Ser Ser Ala Glu Met Ser Gln
            115                 120                 125

Gly Thr Asn Val Gly Lys Ala Lys Thr Glu Glu Lys Asp Leu Lys Lys
        130                 135                 140

Leu Lys Lys Gln Xaa Lys Glu Xaa Lys Asp Phe Arg Lys Lys Phe Lys
145                 150                 155                 160

Tyr Asp Gly Glu Ile Arg Val Leu Tyr Ser Thr Lys Val Thr Thr Ser
                165                 170                 175
```

```
Ile Thr Ser Lys Lys Trp Gly Thr Arg Asp Leu Gln Val Lys Pro Gly
            180                 185                 190

Glu Ser Leu Glu Val Ile Gln Thr Thr Asp Thr Lys Val Leu Cys
        195                 200                 205

Arg Asn Glu Glu Gly Lys Tyr Gly Tyr Val Leu Arg Ser Tyr Leu Ala
    210                 215                 220

Asp Asn Asp Gly Glu Ile Tyr Asp Asp Ile Ala Asp Gly Cys Ile Tyr
225                 230                 235                 240

Asp Asn Asp
```